United States Patent
Butora et al.

(10) Patent No.: US 12,071,620 B2
(45) Date of Patent: *Aug. 27, 2024

(54) POLYNUCLEOTIDES CONTAINING A MORPHOLINO LINKER

(71) Applicant: ModernaTX, Inc., Cambridge, MA (US)

(72) Inventors: Gabor Butora, Cambridge, MA (US); Andrew W. Fraley, Arlington, MA (US); Edward John Miracco, Cambridge, MA (US); Jennifer Nelson, Brookline, MA (US); Amy Rhoden Smith, Watertown, MA (US); Matthew Stanton, Marlton, NJ (US)

(73) Assignee: ModernaTX, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/929,956

(22) Filed: Sep. 6, 2022

(65) Prior Publication Data

US 2023/0323344 A1 Oct. 12, 2023

Related U.S. Application Data

(63) Continuation of application No. 15/760,667, filed as application No. PCT/US2016/052482 on Sep. 19, 2016, now Pat. No. 11,434,486.

(60) Provisional application No. 62/279,486, filed on Jan. 15, 2016, provisional application No. 62/219,969, filed on Sep. 17, 2015.

(51) Int. Cl.
C12N 15/113 (2010.01)
C12N 15/11 (2006.01)

(52) U.S. Cl.
CPC .......... *C12N 15/113* (2013.01); *C12N 15/111* (2013.01); *C12N 2310/317* (2013.01); *C12N 2310/321* (2013.01); *C12N 2310/3231* (2013.01); *C12N 2310/3233* (2013.01); *C12N 2310/351* (2013.01); *C12N 2320/51* (2013.01)

(58) Field of Classification Search
None
See application file for complete search history.

(56) References Cited

U.S. PATENT DOCUMENTS

| | | |
|---|---|---|
| 5,034,506 A | 7/1991 | Summerton et al. |
| 5,426,180 A | 6/1995 | Kool |
| 5,489,677 A | 2/1996 | Sanghvi et al. |
| 5,512,439 A | 4/1996 | Hornes et al. |
| 5,591,722 A | 1/1997 | Montgomery et al. |
| 5,637,459 A | 6/1997 | Burke et al. |
| 5,639,873 A | 6/1997 | Barascut et al. |
| 5,789,578 A | 8/1998 | Burton et al. |
| 5,808,039 A | 9/1998 | Reddy et al. |
| 5,989,911 A | 11/1999 | Fournier et al. |
| 6,022,715 A | 2/2000 | Merenkova et al. |
| 6,248,268 B1 | 6/2001 | Cook |
| 6,303,378 B1 | 10/2001 | Bridenbaugh et al. |
| 6,423,492 B1 | 7/2002 | Harbron |
| 6,511,832 B1 | 1/2003 | Guarino et al. |
| 6,521,411 B2 | 2/2003 | Hecker et al. |
| 7,582,744 B2 | 9/2009 | Manoharan et al. |
| 7,691,569 B2 | 4/2010 | Wohlgemuth et al. |
| 8,093,367 B2 | 1/2012 | Kore et al. |
| 8,664,194 B2 | 3/2014 | de Fougerolles et al. |
| 8,680,069 B2 | 3/2014 | de Fougerolles et al. |
| 8,691,750 B2 | 4/2014 | Constien et al. |
| 8,710,200 B2 | 4/2014 | Schrum et al. |
| 8,716,465 B2 | 5/2014 | Rossi et al. |
| 8,802,438 B2 | 8/2014 | Rossi et al. |
| 8,822,663 B2 | 9/2014 | Schrum et al. |
| 8,883,506 B2 | 11/2014 | Rossi et al. |
| 8,898,864 B1 | 12/2014 | Porter |
| 8,969,353 B2 | 3/2015 | Mahon et al. |
| 8,980,864 B2 | 3/2015 | Hoge et al. |
| 8,999,380 B2 | 4/2015 | Bancel et al. |
| 9,050,297 B2 | 6/2015 | Chakraborty et al. |
| 9,061,059 B2 | 6/2015 | Chakraborty et al. |
| 9,089,604 B2 | 7/2015 | Chakraborty et al. |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,149,506 B2 | 10/2015 | Chakraborty et al. |
| 9,428,535 B2 | 8/2016 | de Fougerolles et al. |
| 9,533,047 B2 | 1/2017 | de Fougerolles et al. |
| 9,675,668 B2 | 6/2017 | Bancel et al. |
| 9,751,925 B2 | 9/2017 | Hoge et al. |

(Continued)

FOREIGN PATENT DOCUMENTS

| | | |
|---|---|---|
| CA | 2028849 A1 | 9/1991 |
| CA | 2473135 A1 | 6/2003 |

(Continued)

OTHER PUBLICATIONS

Anderson et al., "Incorporation of pseudouridine into mRNA enhances translation by diminishing PKR activation," Nucleic Acids Res. 38(17):5884-92 (2010).

Anderson et al., "Nucleoside modifications in RNA limit activation of 2'-5'-oligoadenylate synthetase and increase resistance to cleavage by RNase L," Nucleic Acids Res. 39(21): 9329-38 (Aug. 2011) (10 pages).

Andries et al., "N1-methylpseudouridine-incorporated mRNA outperforms pseudouridine-incorporated mRNA by providing enhanced protein expression and reduced immunogenicity in mammalian cell lines and mice," J Control Release. 217:337-44 (2015).

Derrigo et al., "RNA-protein interactions in the control of stability and localization of messenger RNA (review)," Int J Mol Med. 5(2):111-23 (2000).

Fath et al., "Multiparameter RNA and codon optimization: a standardized tool to assess and enhance autologous mammalian gene expression," PLoS One. 6(3):e17596 (2011) (14 pages).

(Continued)

*Primary Examiner* — Patrick T Lewis

(74) *Attorney, Agent, or Firm* — Clark & Elbing LLP

(57) ABSTRACT

The disclosure provides polynucleotides encoding a polypeptide including a morpholino linker. In some embodiments, the polynucleotides of the invention have increased stability compared to wild-type polynucleotides.

20 Claims, No Drawings

Specification includes a Sequence Listing.

(56) References Cited

U.S. PATENT DOCUMENTS

| | | | |
|---|---|---|---|
| 9,803,177 B2 | 10/2017 | Rossi et al. |
| 9,872,900 B2 | 1/2018 | Ciaramella et al. |
| 10,022,435 B2 | 7/2018 | Ciaramella et al. |
| 10,064,935 B2 | 9/2018 | Ciaramella et al. |
| 10,072,057 B2 | 9/2018 | Hoge et al. |
| 2001/0025097 A1 | 9/2001 | Sheridan et al. |
| 2002/0001812 A1 | 1/2002 | Smith et al. |
| 2002/0016450 A1 | 2/2002 | Laugharn et al. |
| 2002/0114784 A1 | 8/2002 | Li et al. |
| 2002/0130430 A1 | 9/2002 | Castor |
| 2002/0153312 A1 | 10/2002 | Gjerde et al. |
| 2002/0164635 A1 | 11/2002 | Salerno |
| 2003/0120035 A1 | 6/2003 | Gao et al. |
| 2003/0170876 A1 | 9/2003 | Widner et al. |
| 2003/0170891 A1 | 9/2003 | McSwiggen |
| 2003/0180779 A1 | 9/2003 | Lofton-Day et al. |
| 2004/0038278 A1 | 2/2004 | Tzertzinis et al. |
| 2004/0142433 A1 | 7/2004 | Padgett et al. |
| 2004/0220127 A1 | 11/2004 | Sternberg et al. |
| 2004/0259097 A1 | 12/2004 | De Backer et al. |
| 2005/0003496 A1 | 1/2005 | McGall et al. |
| 2005/0130196 A1 | 6/2005 | Hofstadler et al. |
| 2006/0058266 A1* | 3/2006 | Manoharan .............. A61P 27/02 544/243 |
| 2006/0121441 A1 | 6/2006 | Spira |
| 2006/0223081 A1 | 10/2006 | Jarrell et al. |
| 2007/0020678 A1 | 1/2007 | Ault-Riche et al. |
| 2007/0037148 A1 | 2/2007 | Fong et al. |
| 2007/0037770 A1 | 2/2007 | Gryaznov et al. |
| 2007/0244062 A1 | 10/2007 | Laux et al. |
| 2007/0281336 A1 | 12/2007 | Jendrisak et al. |
| 2008/0076910 A1 | 3/2008 | Takkellapati et al. |
| 2008/0171711 A1 | 7/2008 | Hoerr et al. |
| 2008/0274463 A1 | 11/2008 | Chen et al. |
| 2008/0311140 A1 | 12/2008 | Lee et al. |
| 2009/0264511 A1 | 10/2009 | de Fougerolles et al. |
| 2009/0286852 A1 | 11/2009 | Kariko et al. |
| 2010/0015232 A1 | 1/2010 | Besenbacher et al. |
| 2010/0047261 A1 | 2/2010 | Hoerr et al. |
| 2010/0178272 A1 | 7/2010 | Hartmann et al. |
| 2010/0183639 A1 | 7/2010 | Uhlmann et al. |
| 2010/0261228 A1 | 10/2010 | Gharib et al. |
| 2010/0261231 A1 | 10/2010 | Kore et al. |
| 2010/0317532 A1 | 12/2010 | Liu et al. |
| 2011/0130440 A1 | 6/2011 | Manoharan et al. |
| 2011/0143397 A1 | 6/2011 | Kariko et al. |
| 2011/0218170 A1 | 9/2011 | Thottassery et al. |
| 2011/0244026 A1 | 10/2011 | Guild et al. |
| 2011/0281938 A1 | 11/2011 | Schaub et al. |
| 2012/0046346 A1 | 2/2012 | Rossi et al. |
| 2012/0100136 A1 | 4/2012 | Patel et al. |
| 2012/0129261 A1 | 5/2012 | Eberwine et al. |
| 2012/0251618 A1 | 10/2012 | Schrum et al. |
| 2013/0046083 A1 | 2/2013 | Brown et al. |
| 2013/0046084 A1 | 2/2013 | Brown et al. |
| 2013/0052721 A1 | 2/2013 | Hollander et al. |
| 2013/0058894 A1 | 3/2013 | Maldonado et al. |
| 2013/0115272 A1 | 5/2013 | De Fougerolles et al. |
| 2013/0123481 A1 | 5/2013 | De Fougerolles et al. |
| 2013/0156849 A1 | 6/2013 | De Fougerolles et al. |
| 2013/0165504 A1 | 6/2013 | Bancel et al. |
| 2013/0197068 A1 | 8/2013 | Kariko et al. |
| 2013/0203115 A1 | 8/2013 | Schrum et al. |
| 2013/0244282 A1 | 9/2013 | Schrum et al. |
| 2013/0245103 A1 | 9/2013 | De Fougerolles et al. |
| 2013/0245105 A1 | 9/2013 | De Fougerolles et al. |
| 2013/0245106 A1 | 9/2013 | De Fougerolles et al. |
| 2013/0251618 A1 | 9/2013 | Li et al. |
| 2013/0259923 A1 | 10/2013 | Bancel et al. |
| 2013/0259924 A1 | 10/2013 | Bancel et al. |
| 2014/0010861 A1 | 1/2014 | Bancel et al. |
| 2014/0105964 A1 | 4/2014 | Bancel et al. |
| 2014/0105966 A1 | 4/2014 | Bancel et al. |
| 2014/0147454 A1 | 5/2014 | Chakraborty et al. |
| 2014/0200261 A1 | 7/2014 | Hoge et al. |
| 2014/0206752 A1 | 7/2014 | Afeyan et al. |
| 2014/0206852 A1 | 7/2014 | Hoge et al. |
| 2014/0243399 A1 | 8/2014 | Schrum et al. |
| 2014/0273230 A1 | 9/2014 | Chen et al. |
| 2014/0275227 A1 | 9/2014 | Hoge et al. |
| 2014/0343129 A1 | 11/2014 | de Fougerolles et al. |
| 2014/0371302 A1 | 12/2014 | Afeyan et al. |
| 2015/0005372 A1 | 1/2015 | Hoge et al. |
| 2015/0017211 A1 | 1/2015 | de Fougerolles et al. |
| 2015/0030576 A1 | 1/2015 | Bancel |
| 2015/0050354 A1 | 2/2015 | Bouchon et al. |
| 2015/0050738 A1 | 2/2015 | Ozsolak et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0141269 A1 | 5/2015 | Soldatov et al. |
| 2015/0141499 A1 | 5/2015 | Bancel et al. |
| 2015/0166616 A1 | 6/2015 | Bancel et al. |
| 2015/0167017 A1 | 6/2015 | Roy et al. |
| 2015/0211039 A1 | 7/2015 | Wang et al. |
| 2015/0291678 A1 | 10/2015 | Rudolph et al. |
| 2015/0307542 A1 | 10/2015 | Roy et al. |
| 2016/0017313 A1 | 1/2016 | Spivak et al. |
| 2016/0024140 A1 | 1/2016 | Issa et al. |
| 2016/0024141 A1 | 1/2016 | Issa et al. |
| 2016/0024492 A1 | 1/2016 | Issa et al. |
| 2016/0024547 A1 | 1/2016 | Bancel et al. |
| 2016/0032273 A1 | 2/2016 | Shahrokh et al. |
| 2016/0038612 A1 | 2/2016 | Hoge et al. |
| 2016/0177295 A1 | 6/2016 | Rudolph et al. |
| 2016/0194368 A1 | 7/2016 | Hoge et al. |
| 2016/0194625 A1 | 7/2016 | Hoge et al. |
| 2016/0237108 A1 | 8/2016 | Fraley et al. |
| 2016/0244742 A1 | 8/2016 | Linnarsson et al. |
| 2016/0326575 A1 | 11/2016 | Von Der Mulbe et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2017/0136131 A1 | 5/2017 | Roy et al. |
| 2017/0136132 A1 | 5/2017 | Roy et al. |
| 2017/0175129 A1 | 6/2017 | Roy et al. |

FOREIGN PATENT DOCUMENTS

| | | |
|---|---|---|
| EP | 0366400 A2 | 5/1990 |
| EP | 1083232 B1 | 2/2005 |
| EP | 1619254 A1 | 1/2006 |
| EP | 1383556 B9 | 3/2008 |
| EP | 1831160 B1 | 6/2010 |
| EP | 2092064 B1 | 9/2010 |
| EP | 2377938 A1 | 10/2011 |
| EP | 2484770 A1 | 8/2012 |
| EP | 2188379 B1 | 1/2013 |
| EP | 2548960 A1 | 1/2013 |
| JP | 2011-130725 A | 7/2011 |
| RU | 2540017 C2 | 1/2015 |
| WO | WO-91/05058 A1 | 4/1991 |
| WO | WO-93/03052 A1 | 2/1993 |
| WO | WO-93/13121 A1 | 7/1993 |
| WO | WO-200155306 A2 | 8/2001 |
| WO | WO-02/44399 A2 | 6/2002 |
| WO | WO-2002/098443 A2 | 12/2002 |
| WO | WO-03/039523 A2 | 5/2003 |
| WO | WO-03/051881 A1 | 6/2003 |
| WO | WO-2004/020575 A2 | 3/2004 |
| WO | WO-2004/064782 A2 | 8/2004 |
| WO | WO-2006/015445 A1 | 2/2006 |
| WO | WO-2007/024798 A2 | 3/2007 |
| WO | WO-2007024708 A2 | 3/2007 |
| WO | WO-2007/089607 A2 | 8/2007 |
| WO | WO-2007/120863 A2 | 10/2007 |
| WO | WO-2008/039669 A1 | 4/2008 |
| WO | WO-2008/045505 A2 | 4/2008 |
| WO | WO-2008083949 A2 | 7/2008 |

(56) References Cited

FOREIGN PATENT DOCUMENTS

| | | |
|---|---|---|
| WO | WO-2008/120016 A1 | 10/2008 |
| WO | WO-2009042971 A2 | 4/2009 |
| WO | WO-2009127230 A1 | 10/2009 |
| WO | WO-20090127060 A1 | 10/2009 |
| WO | WO-2009/147519 A1 | 12/2009 |
| WO | WO-2009149253 A2 | 12/2009 |
| WO | WO-2010/014895 A2 | 2/2010 |
| WO | WO-2010/017510 A1 | 2/2010 |
| WO | WO-2010/109289 A1 | 9/2010 |
| WO | WO-2011/005850 A1 | 1/2011 |
| WO | WO-2011068810 A1 | 6/2011 |
| WO | WO-2011071931 A2 | 6/2011 |
| WO | WO-2011/127933 A1 | 10/2011 |
| WO | WO-2011130624 A2 | 10/2011 |
| WO | WO-2011133868 A2 | 10/2011 |
| WO | WO-2011/140627 A1 | 11/2011 |
| WO | WO-2012019168 A2 | 2/2012 |
| WO | WO-2012135805 A2 | 10/2012 |
| WO | WO-2012138530 A1 | 10/2012 |
| WO | WO-2012/158736 A1 | 11/2012 |
| WO | WO-2012/164565 A1 | 12/2012 |
| WO | WO-2013039857 A1 | 3/2013 |
| WO | WO-2013039861 A2 | 3/2013 |
| WO | WO-2013052523 A1 | 4/2013 |
| WO | WO-2013/090186 A1 | 6/2013 |
| WO | WO-2013/096709 A2 | 6/2013 |
| WO | WO-2013090294 A1 | 6/2013 |
| WO | WO-2013090648 A1 | 6/2013 |
| WO | WO-2013090897 A1 | 6/2013 |
| WO | WO-2013/101690 A1 | 7/2013 |
| WO | WO-2013113326 A1 | 8/2013 |
| WO | WO-2013113501 A1 | 8/2013 |
| WO | WO-2013113502 A1 | 8/2013 |
| WO | WO-2013130161 A1 | 9/2013 |
| WO | WO-2013151663 A1 | 10/2013 |
| WO | WO-2013151664 A1 | 10/2013 |
| WO | WO-2013151665 A2 | 10/2013 |
| WO | WO-2013151666 A2 | 10/2013 |
| WO | WO-2013151667 A1 | 10/2013 |
| WO | WO-2013151668 A2 | 10/2013 |
| WO | WO-2013151669 A1 | 10/2013 |
| WO | WO-2013151670 A2 | 10/2013 |
| WO | WO-2013151671 A1 | 10/2013 |
| WO | WO-2013151672 A2 | 10/2013 |
| WO | WO-2013151736 A2 | 10/2013 |
| WO | WO-2013/184976 A2 | 12/2013 |
| WO | WO-2013185069 A1 | 12/2013 |
| WO | WO-2014028429 A2 | 2/2014 |
| WO | WO-2014081507 A1 | 5/2014 |
| WO | WO-2014093574 A1 | 6/2014 |
| WO | WO-2014093924 A1 | 6/2014 |
| WO | WO-2014/113089 A2 | 7/2014 |
| WO | WO-2014/152513 A1 | 9/2014 |
| WO | WO-2014/152659 A1 | 9/2014 |
| WO | WO-2014/152673 A1 | 9/2014 |
| WO | WO-2014144039 A1 | 9/2014 |
| WO | WO-2014144711 A1 | 9/2014 |
| WO | WO-2014144767 A1 | 9/2014 |
| WO | WO-2014152027 A1 | 9/2014 |
| WO | WO-2014152030 A1 | 9/2014 |
| WO | WO-2014152031 A1 | 9/2014 |
| WO | WO-2014152211 A1 | 9/2014 |
| WO | WO-2014152540 A1 | 9/2014 |
| WO | WO-2014/160243 A1 | 10/2014 |
| WO | WO-2014/160284 A1 | 10/2014 |
| WO | WO-2015006747 A2 | 1/2015 |
| WO | WO-2015/023975 A1 | 2/2015 |
| WO | WO-2015034925 A1 | 3/2015 |
| WO | WO-2015034928 A1 | 3/2015 |
| WO | WO-2015038892 A1 | 3/2015 |
| WO | WO-2015/051169 A2 | 4/2015 |
| WO | WO-2015048744 A2 | 4/2015 |
| WO | WO-2015051173 A2 | 4/2015 |
| WO | WO-2015051214 A1 | 4/2015 |
| WO | WO-2015058069 A1 | 4/2015 |
| WO | WO-2015/070413 A1 | 5/2015 |
| WO | WO-2015/085318 A2 | 6/2015 |
| WO | WO-2015/089511 A2 | 6/2015 |
| WO | WO-2015/101416 A1 | 7/2015 |
| WO | WO-2015105926 A1 | 7/2015 |
| WO | WO-2015/196118 A1 | 12/2015 |
| WO | WO-2015/196128 A2 | 12/2015 |
| WO | WO-2015/196130 A2 | 12/2015 |
| WO | WO-2016/010840 A1 | 1/2016 |
| WO | WO-2016/011222 A2 | 1/2016 |
| WO | WO-2016/011226 A1 | 1/2016 |
| WO | WO-2016/034620 A1 | 3/2016 |
| WO | WO-2016/036902 A1 | 3/2016 |
| WO | WO-2016/077125 A1 | 5/2016 |
| WO | WO-2016/118724 A1 | 7/2016 |
| WO | WO-2016/118725 A1 | 7/2016 |

OTHER PUBLICATIONS

Grosjean, Modification and editing of RNA: historical overview and important facts to remember. *Fine-Tuning of RNA Functions by Modification and Editing.* Grosjean H, 1-22 (2005).

Henke et al., "microRNA-122 stimulates translation of hepatitis C virus RNA," EMBO J. 27(24):3300-10 (2008).

Hikishima et al., "Synthesis of 1,8-naphthyridine C-nucleosides and their base-pairing properties in oligodeoxynucleotides: thermally stable naphthyridine:imidazopyridopyrimidine base-pairing motifs," Angew Chem Int Ed. 44:596-8 (2005).

International Search Report and Written Opinion for International Application No. PCT/US2016/052482, mailed Jan. 19, 2017 (13 pages).

Irier et al., "Translational regulation of GluR2 mRNAs in rat hippocampus by alternative 3' untranslated regions," available in PMC Aug. 17, 2009, published in final edited form as: J Neurochem. 109(2):584-594 (2009) (18 pages).

Jani et al., "In vitro transcription and capping of Gaussia luciferase mRNA followed by HeLa cell transfection," J Vis Exp. 61:e3702 (2012) (9 pages).

Karikó et al., "mRNA is an endogenous ligand for Toll-like receptor 3," J Biol Chem. 279(13):12542-50 (2004).

Karikó et al., "Generating the optimal mRNA for therapy: HPLC purification eliminates immune activation and improves translation of nucleoside-modified, protein-encoding mRNA," Nucleic Acids Res. 39(21):e142, DOI: 10.1093/nar/gkr695 (2011) (10 pages).

Karikó et al., "Incorporation of pseudouridine into mRNA yields superior nonimmunogenic vector with increased translational capacity and biological stability." Mol Ther. 16(11):1833-40 (2008).

Karikó et al., "Suppression of RNA recognition by Toll-like receptors: the impact of nucleoside modification and the evolutionary origin of RNA," Immunity. 23(2):165-75 (2005).

Kore et al., "Synthesis and application of 2'-fluoro-substituted cap analogs," Bioorg Med Chem Letters. 17:5295-9 (2007).

Kumar et al., "Template-directed oligonucleotide strand ligation, covalent intramolecular DNA circularization and catenation using click chemistry," J Am Chem Soc. 129(21):6859-64 (2007).

Kuwahara et al., "Molecular evolution of functional nucleic acids with chemical modifications," Molecules. 15(8):5423-44 (2010).

Loomis et al., "Strategies for modulating innate immune activation and protein production of *in vitro* transcribed mRNAs," J Mater Chem B. 4(9):1619-32 (2016).

Melton et al., "Efficient *in vitro* synthesis of biologically active RNA and RNA hybridization probes from plasmids containing a bacteriophage SP6 promoter," Nucleic Acids Res. 12(18):7035-56 (1984).

Nakazato et al., "Purification of messenger RNA and heterogeneous nuclear RNA containing poly(A) sequences," Methods Enzymol. 29:431-43 (1974).

Nielsen et al., "An mRNA is capped by a 2',5' lariat catalyzed by a group I-like ribozyme," Science. 309(5740):1584-7 (2005).

Olesiak et al., "The synthesis of di- and oligo-nucleotides containing a phosphorodithioate internucleotide linkage with one of the sulfur atoms in a 5'-bridging position," Org Biomol Chem. 7(10):2162-9 (2009).

(56) References Cited

OTHER PUBLICATIONS

Pardi et al., "Expression kinetics of nucleoside-modified mRNA delivered in lipid nanoparticles to mice by various routes," available in PMC Nov. 10, 2016, published in final edited form as: J Control Release. 217:345-51 (2015) (18 pages).

Probst et al., "Spontaneous cellular uptake of exogenous messenger RNA in vivo is nucleic acid-specific, saturable and ion dependent," Gene Ther. 14(15):1175-1180 (2007).

Quabius et al., "Synthetic mRNAs for manipulating cellular phenotypes: an overview," N Biotechnol. 32(1):229-35 (2015).

Rodriguez et al., "Magnetic poly (styrene/divinylbenzene/acrylic acid)-based hybrid microspheres for bio-molecular recognition," Micro Nano Lett. 6(6):349-352 (2011).

Semple et al., "Rational design of cationic lipids for siRNA delivery," Nat Biotechnol. 28(2):172-6 (2010) (26 pages).

Stewart et al., "Effect of azide position on the rate of azido glucose-cyclooctyne cycloaddition," Journal of Carbohydrate Chemistry. 33(7-8):408-19 (2014).

Takita et al., "Precise sequential DNA ligation on a solid substrate: solid-based rapid sequential ligation of multiple DNA molecules," DNA Res. 20(6):583-92 (Dec. 2013).

Tavernier et al., "mRNA as gene therapeutic: how to control protein expression," J Control Release. 150(3):238-47 (2011).

Thess et al., "Sequence-engineered mRNA without chemical nucleoside modifications enables an effective protein therapy in large animals," Mol Ther. 23(9):1456-64 (2015).

Thess et al., Supplementary material for "Sequence-engineered mRNA without chemical nucleoside modifications enables an effective protein therapy in large animals," Mol Ther. 23(9):1456-64 (2015), accessed via <https://www.sciencedirect.com/science/article/pii/S1525001616302738#cesec90> (11 Pages).

Valadi et al., "Exosome-mediated transfer of mRNAs and microRNAs is a novel mechanism of genetic exchange between cells," Nat Cell Biol. 9(6):654-9 (2007) (17 pages).

Virnekäs et al., "Trinucleotide phosphoramidites: ideal reagents for the synthesis of mixed oligonucleotides for random mutagenesis," Nucleic Acids Res. 22(25):5600-7 (1994).

Warren et al., "Highly efficient reprogramming to pluripotency and directed differentiation of human cells with synthetic modified mRNA," Cell Stem Cell. 7(5):618-30 (2010).

Weissman et al., "mRNA: Fulfilling the promise of gene therapy," Mol Ther. 23(9):1416-7 (2015).

Yamamoto et al., "Current prospects for mRNA gene delivery," Eur J Pharm Biopharm. 71(3):484-9 (2009).

\* cited by examiner

SEQUENCE LISTING

```
Sequence total quantity: 32
SEQ ID NO: 1                 moltype = AA  length = 13
FEATURE                      Location/Qualifiers
source                       1..13
                             mol_type = protein
                             organism = synthetic construct
                             note = synthetic construct
SITE                         12
                             note = MOD_RES - Lysine is modified with Aoa (2-aminooxy
                              acetic acid)
SITE                         13
                             note = MOD_RES - Glycine is modified with amide
SEQUENCE: 1
PKKKRKVEDP YKG                                                                        13

SEQ ID NO: 2                 moltype = AA  length = 4
FEATURE                      Location/Qualifiers
source                       1..4
                             mol_type = protein
                             organism = synthetic construct
                             note = synthetic construct
SITE                         1
                             note = MOD_RES - Lysine is modified with Aoa (2-aminooxy
                              acetic acid)
SEQUENCE: 2
KDEL                                                                                   4

SEQ ID NO: 3                 moltype = AA  length = 20
FEATURE                      Location/Qualifiers
source                       1..20
                             mol_type = protein
                             organism = synthetic construct
                             note = synthetic construct
SITE                         1
                             note = MOD_RES - Histidine is modified with Aoa (2-aminooxy
                              acetic acid)
SITE                         20
                             note = MOD_RES - Histidine is modified with amide
SEQUENCE: 3
HHHHHHHHHH HHHHHHHHHH                                                                 20

SEQ ID NO: 4                 moltype = DNA  length = 10
FEATURE                      Location/Qualifiers
source                       1..10
                             mol_type = other DNA
                             organism = synthetic construct
                             note = synthetic construct
SEQUENCE: 4
tttttctttt                                                                            10

SEQ ID NO: 5                 moltype = DNA  length = 11
FEATURE                      Location/Qualifiers
source                       1..11
                             mol_type = other DNA
                             organism = synthetic construct
                             note = synthetic construct
SEQUENCE: 5
ttttgctttt t                                                                          11

SEQ ID NO: 6                 moltype = DNA  length = 10
FEATURE                      Location/Qualifiers
source                       1..10
                             mol_type = other DNA
                             organism = synthetic construct
                             note = synthetic construct
SEQUENCE: 6
ttttgctttt                                                                            10

SEQ ID NO: 7                 moltype = DNA  length = 11
FEATURE                      Location/Qualifiers
source                       1..11
                             mol_type = other DNA
                             organism = synthetic construct
                             note = synthetic construct
SEQUENCE: 7
aaaaagcaaa a                                                                          11
```

-continued

```
SEQ ID NO: 8              moltype = DNA  length = 24
FEATURE                   Location/Qualifiers
source                    1..24
                          mol_type = other DNA
                          organism = synthetic construct
                          note = synthetic construct
SEQUENCE: 8
caaaggctct tttcagagcc acca                                              24

SEQ ID NO: 9              moltype = RNA  length = 24
FEATURE                   Location/Qualifiers
source                    1..24
                          mol_type = other RNA
                          organism = synthetic construct
                          note = synthetic construct
SEQUENCE: 9
caaaggctct tttcagagcc acca                                              24

SEQ ID NO: 10             moltype = AA  length = 20
FEATURE                   Location/Qualifiers
source                    1..20
                          mol_type = protein
                          organism = synthetic construct
                          note = synthetic construct
SITE                      1
                          note = MOD_RES - Histidine is modified with Aoa (2-aminooxy
                           acetic acid)
SITE                      20
                          note = MOD_RES - Histidine is modified with amide
SEQUENCE: 10
HHHHHHHHHH HHHHHHHHHH                                                   20

SEQ ID NO: 11             moltype = AA  length = 20
FEATURE                   Location/Qualifiers
source                    1..20
                          mol_type = protein
                          organism = synthetic construct
                          note = synthetic construct
SITE                      1
                          note = MOD_RES - Histidine is modified with Aoa (2-aminooxy
                           acetic acid)
SITE                      1
                          note = D-Histidine
SITE                      2
                          note = D-Histidine
SITE                      3
                          note = D-Histidine
SITE                      4
                          note = D-Histidine
SITE                      5
                          note = D-Histidine
SITE                      6
                          note = D-Histidine
SITE                      7
                          note = D-Histidine
SITE                      8
                          note = D-Histidine
SITE                      9
                          note = D-Histidine
SITE                      10
                          note = D-Histidine
SITE                      11
                          note = D-Histidine
SITE                      12
                          note = D-Histidine
SITE                      13
                          note = D-Histidine
SITE                      14
                          note = D-Histidine
SITE                      15
                          note = D-Histidine
SITE                      16
                          note = D-Histidine
SITE                      17
                          note = D-Histidine
SITE                      18
                          note = D-Histidine
```

```
SITE                       19
                           note = D-Histidine
SITE                       20
                           note = D-Histidine
SITE                       20
                           note = MOD_RES - Histidine is modified with amide
SEQUENCE: 11
HHHHHHHHHH HHHHHHHHHH                                                      20

SEQ ID NO: 12              moltype = AA  length = 5
FEATURE                    Location/Qualifiers
source                     1..5
                           mol_type = protein
                           organism = synthetic construct
                           note = synthetic construct
SITE                       1
                           note = MOD_RES - Histidine is modified with Aoa (2-aminooxy
                            acetic acid)
SEQUENCE: 12
HHHHH                                                                       5

SEQ ID NO: 13              moltype = AA  length = 10
FEATURE                    Location/Qualifiers
source                     1..10
                           mol_type = protein
                           organism = synthetic construct
                           note = synthetic construct
SITE                       1
                           note = MOD_RES - Histidine is modified with Aoa (2-aminooxy
                            acetic acid)
SEQUENCE: 13
HHHHHHHHHH                                                                 10

SEQ ID NO: 14              moltype = AA  length = 15
FEATURE                    Location/Qualifiers
source                     1..15
                           mol_type = protein
                           organism = synthetic construct
                           note = synthetic construct
SITE                       1
                           note = MOD_RES - Histidine is modified with Aoa (2-aminooxy
                            acetic acid)
SEQUENCE: 14
HHHHHHHHHH HHHHH                                                           15

SEQ ID NO: 15              moltype = AA  length = 20
FEATURE                    Location/Qualifiers
source                     1..20
                           mol_type = protein
                           organism = synthetic construct
                           note = synthetic construct
SITE                       1
                           note = MOD_RES - Histidine is modified with Aoa (2-aminooxy
                            acetic acid)
SEQUENCE: 15
HHHHHHHHHH HHHHHHHHHH                                                      20

SEQ ID NO: 16              moltype = AA  length = 13
FEATURE                    Location/Qualifiers
source                     1..13
                           mol_type = protein
                           organism = synthetic construct
                           note = synthetic construct
SITE                       1
                           note = MOD_RES - Proline is modified with Ac -
                            Acetyl-Proline
SITE                       12
                           note = MOD_RES - Lysine is modified with Aoa (2-aminooxy
                            acetic acid)
SITE                       13
                           note = MOD_RES - Glycine is modified with amide
SEQUENCE: 16
PKKKRKVEDP YKG                                                             13
```

```
SEQ ID NO: 17            moltype = AA   length = 4
FEATURE                  Location/Qualifiers
source                   1..4
                         mol_type = protein
                         organism = synthetic construct
                         note = synthetic construct
SITE                     1
                         note = MOD_RES - Lysine is modified with Aoa (2-aminooxy
                           acetic acid)
SEQUENCE: 17
KDEL                                                                           4

SEQ ID NO: 18            moltype = AA   length = 12
FEATURE                  Location/Qualifiers
source                   1..12
                         mol_type = protein
                         organism = synthetic construct
                         note = synthetic construct
SITE                     1
                         note = MOD_RES - Phenylalanine is modified with Aoa
                           (2-aminooxy acetic acid)
SEQUENCE: 18
FFRKSIINFE KL                                                                 12

SEQ ID NO: 19            moltype = AA   length = 5
FEATURE                  Location/Qualifiers
source                   1..5
                         mol_type = protein
                         organism = synthetic construct
                         note = synthetic construct
SITE                     1
                         note = MOD_RES - Lysine is modified with Aoa (2-aminooxy
                           acetic acid)
SEQUENCE: 19
KTKKL                                                                          5

SEQ ID NO: 20            moltype = AA   length = 4
FEATURE                  Location/Qualifiers
source                   1..4
                         mol_type = protein
                         organism = synthetic construct
                         note = synthetic construct
SITE                     1
                         note = MOD_RES - Lysine is modified with Aoa (2-aminooxy
                           acetic acid)
SEQUENCE: 20
KKSL                                                                           4

SEQ ID NO: 21            moltype = AA   length = 5
FEATURE                  Location/Qualifiers
source                   1..5
                         mol_type = protein
                         organism = synthetic construct
                         note = synthetic construct
SITE                     1
                         note = MOD_RES - Lysine is modified with Aoa (2-aminooxy
                           acetic acid)
SEQUENCE: 21
KPRRE                                                                          5

SEQ ID NO: 22            moltype = AA   length = 5
FEATURE                  Location/Qualifiers
source                   1..5
                         mol_type = protein
                         organism = synthetic construct
                         note = synthetic construct
SITE                     1
                         note = MOD_RES - Lysine is modified with Aoa (2-aminooxy
                           acetic acid)
SEQUENCE: 22
KFERQ                                                                          5

SEQ ID NO: 23            moltype = AA   length = 28
FEATURE                  Location/Qualifiers
source                   1..28
                         mol_type = protein
                         organism = synthetic construct
                         note = synthetic construct
```

```
                                  -continued

SITE                    28
                        note = MOD_RES - Lysine is modified with Aoa (2-aminooxy
                         acetic acid)
SITE                    28
                        note = MOD_RES - Lysine is modified with amide
SEQUENCE: 23
MSSESGKPIA KPIRKPGYTN PALKALGK                                              28

SEQ ID NO: 24           moltype = AA  length = 26
FEATURE                 Location/Qualifiers
source                  1..26
                        mol_type = protein
                        organism = synthetic construct
                        note = synthetic construct
SITE                    26
                        note = MOD_RES - Lysine is modified with Aoa (2-aminooxy
                         acetic acid)
SITE                    26
                        note = MOD_RES - Lysine is modified with amide
SEQUENCE: 24
MLSLRQSIRF FKPATRTLCS SRYLLK                                                26

SEQ ID NO: 25           moltype = AA  length = 13
FEATURE                 Location/Qualifiers
source                  1..13
                        mol_type = protein
                        organism = synthetic construct
                        note = synthetic construct
SITE                    13
                        note = MOD_RES - Lysine is modified with Aoa (2-aminooxy
                         acetic acid)
SITE                    13
                        note = MOD_RES - Lysine is modified with amide
SEQUENCE: 25
MLSLRQSIRF FKK                                                              13

SEQ ID NO: 26           moltype = AA  length = 30
FEATURE                 Location/Qualifiers
source                  1..30
                        mol_type = protein
                        organism = synthetic construct
                        note = synthetic construct
SITE                    1
                        note = MOD_RES - Tryptophan is modified with Aoa
                         (2-aminooxy acetic acid)
SITE                    30
                        note = MOD_RES - Alanine is modified with amide
SEQUENCE: 26
WEAKLAKALA KALAKHLAKA LAKALKACEA                                            30

SEQ ID NO: 27           moltype = AA  length = 30
FEATURE                 Location/Qualifiers
source                  1..30
                        mol_type = protein
                        organism = synthetic construct
                        note = synthetic construct
SITE                    1
                        note = MOD_RES - Tryptophan is modified with Aoa
                         (2-aminooxy acetic acid)
SITE                    30
                        note = MOD_RES - Alanine is modified with amide
SEQUENCE: 27
WEAALAEALA EALAEHLAEA LAEALEALAA                                            30

SEQ ID NO: 28           moltype = RNA  length = 845
FEATURE                 Location/Qualifiers
source                  1..845
                        mol_type = other RNA
                        organism = synthetic construct
                        note = synthetic construct
modified_base           1
                        mod_base = OTHER
                        note = 2'-O-methyl-guanosine
misc_feature            1
                        note = MISC_FEATURE - N7mGpppmG - N7-methylguanosine
                         triphosphate attached to guanosine
modified_base           7
                        mod_base = OTHER
                        note = MISC_FEATURE - 5-methoxy-uridine
```

-continued

| | |
|---|---|
| modified_base | 25<br>mod_base = OTHER<br>note = MISC_FEATURE - 5-methoxy-uridine |
| modified_base | 35<br>mod_base = OTHER<br>note = MISC_FEATURE - 5-methoxy-uridine |
| modified_base | 37<br>mod_base = OTHER<br>note = MISC_FEATURE - 5-methoxy-uridine |
| modified_base | 49<br>mod_base = OTHER<br>note = MISC_FEATURE - 5-methoxy-uridine |
| modified_base | 55<br>mod_base = OTHER<br>note = MISC_FEATURE - 5-methoxy-uridine |
| modified_base | 63<br>mod_base = OTHER<br>note = MISC_FEATURE - 5-methoxy-uridine |
| modified_base | 65<br>mod_base = OTHER<br>note = MISC_FEATURE - 5-methoxy-uridine |
| modified_base | 72<br>mod_base = OTHER<br>note = MISC_FEATURE - 5-methoxy-uridine |
| modified_base | 75<br>mod_base = OTHER<br>note = MISC_FEATURE - 5-methoxy-uridine |
| modified_base | 76<br>mod_base = OTHER<br>note = MISC_FEATURE - 5-methoxy-uridine |
| modified_base | 78<br>mod_base = OTHER<br>note = MISC_FEATURE - 5-methoxy-uridine |
| modified_base | 81<br>mod_base = OTHER<br>note = MISC_FEATURE - 5-methoxy-uridine |
| modified_base | 82<br>mod_base = OTHER<br>note = MISC_FEATURE - 5-methoxy-uridine |
| modified_base | 85<br>mod_base = OTHER<br>note = MISC_FEATURE - 5-methoxy-uridine |
| modified_base | 88<br>mod_base = OTHER<br>note = MISC_FEATURE - 5-methoxy-uridine |
| modified_base | 90<br>mod_base = OTHER<br>note = MISC_FEATURE - 5-methoxy-uridine |
| modified_base | 94<br>mod_base = OTHER<br>note = MISC_FEATURE - 5-methoxy-uridine |
| modified_base | 96<br>mod_base = OTHER<br>note = MISC_FEATURE - 5-methoxy-uridine |
| modified_base | 97<br>mod_base = OTHER<br>note = MISC_FEATURE - 5-methoxy-uridine |
| modified_base | 103<br>mod_base = OTHER<br>note = MISC_FEATURE - 5-methoxy-uridine |
| modified_base | 109<br>mod_base = OTHER<br>note = MISC_FEATURE - 5-methoxy-uridine |
| modified_base | 115<br>mod_base = OTHER<br>note = MISC_FEATURE - 5-methoxy-uridine |
| modified_base | 119<br>mod_base = OTHER<br>note = MISC_FEATURE - 5-methoxy-uridine |
| modified_base | 121<br>mod_base = OTHER<br>note = MISC_FEATURE - 5-methoxy-uridine |
| modified_base | 124<br>mod_base = OTHER<br>note = MISC_FEATURE - 5-methoxy-uridine |
| modified_base | 141<br>mod_base = OTHER<br>note = MISC_FEATURE - 5-methoxy-uridine |

-continued

```
modified_base    142
                 mod_base = OTHER
                 note = MISC_FEATURE - 5-methoxy-uridine
modified_base    145
                 mod_base = OTHER
                 note = MISC_FEATURE - 5-methoxy-uridine
modified_base    147
                 mod_base = OTHER
                 note = MISC_FEATURE - 5-methoxy-uridine
modified_base    153
                 mod_base = OTHER
                 note = MISC_FEATURE - 5-methoxy-uridine
modified_base    160
                 mod_base = OTHER
                 note = MISC_FEATURE - 5-methoxy-uridine
modified_base    163
                 mod_base = OTHER
                 note = MISC_FEATURE - 5-methoxy-uridine
modified_base    164
                 mod_base = OTHER
                 note = MISC_FEATURE - 5-methoxy-uridine
modified_base    171
                 mod_base = OTHER
                 note = MISC_FEATURE - 5-methoxy-uridine
modified_base    175
                 mod_base = OTHER
                 note = MISC_FEATURE - 5-methoxy-uridine
modified_base    176
                 mod_base = OTHER
                 note = MISC_FEATURE - 5-methoxy-uridine
modified_base    178
                 mod_base = OTHER
                 note = MISC_FEATURE - 5-methoxy-uridine
modified_base    179
                 mod_base = OTHER
                 note = MISC_FEATURE - 5-methoxy-uridine
modified_base    202
                 mod_base = OTHER
                 note = MISC_FEATURE - 5-methoxy-uridine
modified_base    213
                 mod_base = OTHER
                 note = MISC_FEATURE - 5-methoxy-uridine
modified_base    225
                 mod_base = OTHER
                 note = MISC_FEATURE - 5-methoxy-uridine
modified_base    228
                 mod_base = OTHER
                 note = MISC_FEATURE - 5-methoxy-uridine
modified_base    232
                 mod_base = OTHER
                 note = MISC_FEATURE - 5-methoxy-uridine
modified_base    236
                 mod_base = OTHER
                 note = MISC_FEATURE - 5-methoxy-uridine
modified_base    244
                 mod_base = OTHER
                 note = MISC_FEATURE - 5-methoxy-uridine
modified_base    245
                 mod_base = OTHER
                 note = MISC_FEATURE - 5-methoxy-uridine
modified_base    248
                 mod_base = OTHER
                 note = MISC_FEATURE - 5-methoxy-uridine
modified_base    250
                 mod_base = OTHER
                 note = MISC_FEATURE - 5-methoxy-uridine
modified_base    257
                 mod_base = OTHER
                 note = MISC_FEATURE - 5-methoxy-uridine
modified_base    265
                 mod_base = OTHER
                 note = MISC_FEATURE - 5-methoxy-uridine
modified_base    269
                 mod_base = OTHER
                 note = MISC_FEATURE - 5-methoxy-uridine
modified_base    270
                 mod_base = OTHER
                 note = MISC_FEATURE - 5-methoxy-uridine
```

| | | |
|---|---|---|
| modified_base | 271<br>mod_base = OTHER<br>note = MISC_FEATURE - 5-methoxy-uridine | |
| modified_base | 273<br>mod_base = OTHER<br>note = MISC_FEATURE - 5-methoxy-uridine | |
| modified_base | 275<br>mod_base = OTHER<br>note = MISC_FEATURE - 5-methoxy-uridine | |
| modified_base | 279<br>mod_base = OTHER<br>note = MISC_FEATURE - 5-methoxy-uridine | |
| modified_base | 289<br>mod_base = OTHER<br>note = MISC_FEATURE - 5-methoxy-uridine | |
| modified_base | 295<br>mod_base = OTHER<br>note = MISC_FEATURE - 5-methoxy-uridine | |
| modified_base | 310<br>mod_base = OTHER<br>note = MISC_FEATURE - 5-methoxy-uridine | |
| modified_base | 316<br>mod_base = OTHER<br>note = MISC_FEATURE - 5-methoxy-uridine | |
| modified_base | 318<br>mod_base = OTHER<br>note = MISC_FEATURE - 5-methoxy-uridine | |
| modified_base | 328<br>mod_base = OTHER<br>note = MISC_FEATURE - 5-methoxy-uridine | |
| modified_base | 334<br>mod_base = OTHER<br>note = MISC_FEATURE - 5-methoxy-uridine | |
| modified_base | 335<br>mod_base = OTHER<br>note = MISC_FEATURE - 5-methoxy-uridine | |
| modified_base | 336<br>mod_base = OTHER<br>note = MISC_FEATURE - 5-methoxy-uridine | |
| modified_base | 337<br>mod_base = OTHER<br>note = MISC_FEATURE - 5-methoxy-uridine | |
| modified_base | 339<br>mod_base = OTHER<br>note = MISC_FEATURE - 5-methoxy-uridine | |
| modified_base | 349<br>mod_base = OTHER<br>note = MISC_FEATURE - 5-methoxy-uridine | |
| modified_base | 351<br>mod_base = OTHER<br>note = MISC_FEATURE - 5-methoxy-uridine | |
| modified_base | 352<br>mod_base = OTHER<br>note = MISC_FEATURE - 5-methoxy-uridine | |
| modified_base | 359<br>mod_base = OTHER<br>note = MISC_FEATURE - 5-methoxy-uridine | |
| modified_base | 367<br>mod_base = OTHER<br>note = MISC_FEATURE - 5-methoxy-uridine | |
| modified_base | 370<br>mod_base = OTHER<br>note = MISC_FEATURE - 5-methoxy-uridine | |
| modified_base | 373<br>mod_base = OTHER<br>note = MISC_FEATURE - 5-methoxy-uridine | |
| modified_base | 378<br>mod_base = OTHER<br>note = MISC_FEATURE - 5-methoxy-uridine | |
| modified_base | 381<br>mod_base = OTHER<br>note = MISC_FEATURE - 5-methoxy-uridine | |
| modified_base | 390<br>mod_base = OTHER<br>note = MISC_FEATURE - 5-methoxy-uridine | |
| modified_base | 400<br>mod_base = OTHER<br>note = MISC_FEATURE - 5-methoxy-uridine | |

-continued

| | | |
|---|---|---|
| modified_base | 406 | |
| | mod_base = OTHER | |
| | note = MISC_FEATURE - 5-methoxy-uridine | |
| modified_base | 407 | |
| | mod_base = OTHER | |
| | note = MISC_FEATURE - 5-methoxy-uridine | |
| modified_base | 410 | |
| | mod_base = OTHER | |
| | note = MISC_FEATURE - 5-methoxy-uridine | |
| modified_base | 412 | |
| | mod_base = OTHER | |
| | note = MISC_FEATURE - 5-methoxy-uridine | |
| modified_base | 416 | |
| | mod_base = OTHER | |
| | note = MISC_FEATURE - 5-methoxy-uridine | |
| modified_base | 424 | |
| | mod_base = OTHER | |
| | note = MISC_FEATURE - 5-methoxy-uridine | |
| modified_base | 426 | |
| | mod_base = OTHER | |
| | note = MISC_FEATURE - 5-methoxy-uridine | |
| modified_base | 433 | |
| | mod_base = OTHER | |
| | note = MISC_FEATURE - 5-methoxy-uridine | |
| modified_base | 441 | |
| | mod_base = OTHER | |
| | note = MISC_FEATURE - 5-methoxy-uridine | |
| modified_base | 442 | |
| | mod_base = OTHER | |
| | note = MISC_FEATURE - 5-methoxy-uridine | |
| modified_base | 450 | |
| | mod_base = OTHER | |
| | note = MISC_FEATURE - 5-methoxy-uridine | |
| modified_base | 451 | |
| | mod_base = OTHER | |
| | note = MISC_FEATURE - 5-methoxy-uridine | |
| modified_base | 454 | |
| | mod_base = OTHER | |
| | note = MISC_FEATURE - 5-methoxy-uridine | |
| modified_base | 455 | |
| | mod_base = OTHER | |
| | note = MISC_FEATURE - 5-methoxy-uridine | |
| modified_base | 461 | |
| | mod_base = OTHER | |
| | note = MISC_FEATURE - 5-methoxy-uridine | |
| modified_base | 463 | |
| | mod_base = OTHER | |
| | note = MISC_FEATURE - 5-methoxy-uridine | |
| modified_base | 482 | |
| | mod_base = OTHER | |
| | note = MISC_FEATURE - 5-methoxy-uridine | |
| modified_base | 484 | |
| | mod_base = OTHER | |
| | note = MISC_FEATURE - 5-methoxy-uridine | |
| modified_base | 485 | |
| | mod_base = OTHER | |
| | note = MISC_FEATURE - 5-methoxy-uridine | |
| modified_base | 486 | |
| | mod_base = OTHER | |
| | note = MISC_FEATURE - 5-methoxy-uridine | |
| modified_base | 494 | |
| | mod_base = OTHER | |
| | note = MISC_FEATURE - 5-methoxy-uridine | |
| modified_base | 504 | |
| | mod_base = OTHER | |
| | note = MISC_FEATURE - 5-methoxy-uridine | |
| modified_base | 517 | |
| | mod_base = OTHER | |
| | note = MISC_FEATURE - 5-methoxy-uridine | |
| modified_base | 526 | |
| | mod_base = OTHER | |
| | note = MISC_FEATURE - 5-methoxy-uridine | |
| modified_base | 540 | |
| | mod_base = OTHER | |
| | note = MISC_FEATURE - 5-methoxy-uridine | |
| modified_base | 541 | |
| | mod_base = OTHER | |
| | note = MISC_FEATURE - 5-methoxy-uridine | |

| | | |
|---|---|---|
| modified_base | 542 | |
| | mod_base = OTHER | |
| | note = MISC_FEATURE - 5-methoxy-uridine | |
| modified_base | 550 | |
| | mod_base = OTHER | |
| | note = MISC_FEATURE - 5-methoxy-uridine | |
| modified_base | 551 | |
| | mod_base = OTHER | |
| | note = MISC_FEATURE - 5-methoxy-uridine | |
| modified_base | 552 | |
| | mod_base = OTHER | |
| | note = MISC_FEATURE - 5-methoxy-uridine | |
| modified_base | 553 | |
| | mod_base = OTHER | |
| | note = MISC_FEATURE - 5-methoxy-uridine | |
| modified_base | 554 | |
| | mod_base = OTHER | |
| | note = MISC_FEATURE - 5-methoxy-uridine | |
| modified_base | 559 | |
| | mod_base = OTHER | |
| | note = MISC_FEATURE - 5-methoxy-uridine | |
| modified_base | 561 | |
| | mod_base = OTHER | |
| | note = MISC_FEATURE - 5-methoxy-uridine | |
| modified_base | 569 | |
| | mod_base = OTHER | |
| | note = MISC_FEATURE - 5-methoxy-uridine | |
| modified_base | 570 | |
| | mod_base = OTHER | |
| | note = MISC_FEATURE - 5-methoxy-uridine | |
| modified_base | 571 | |
| | mod_base = OTHER | |
| | note = MISC_FEATURE - 5-methoxy-uridine | |
| modified_base | 574 | |
| | mod_base = OTHER | |
| | note = MISC_FEATURE - 5-methoxy-uridine | |
| modified_base | 586 | |
| | mod_base = OTHER | |
| | note = MISC_FEATURE - 5-methoxy-uridine | |
| modified_base | 591 | |
| | mod_base = OTHER | |
| | note = MISC_FEATURE - 5-methoxy-uridine | |
| modified_base | 592 | |
| | mod_base = OTHER | |
| | note = MISC_FEATURE - 5-methoxy-uridine | |
| modified_base | 594 | |
| | mod_base = OTHER | |
| | note = MISC_FEATURE - 5-methoxy-uridine | |
| modified_base | 596 | |
| | mod_base = OTHER | |
| | note = MISC_FEATURE - 5-methoxy-uridine | |
| modified_base | 599 | |
| | mod_base = OTHER | |
| | note = MISC_FEATURE - 5-methoxy-uridine | |
| modified_base | 602 | |
| | mod_base = OTHER | |
| | note = MISC_FEATURE - 5-methoxy-uridine | |
| modified_base | 609 | |
| | mod_base = OTHER | |
| | note = MISC_FEATURE - 5-methoxy-uridine | |
| modified_base | 611 | |
| | mod_base = OTHER | |
| | note = MISC_FEATURE - 5-methoxy-uridine | |
| modified_base | 623 | |
| | mod_base = OTHER | |
| | note = MISC_FEATURE - 5-methoxy-uridine | |
| modified_base | 627 | |
| | mod_base = OTHER | |
| | note = MISC_FEATURE - 5-methoxy-uridine | |
| modified_base | 630 | |
| | mod_base = OTHER | |
| | note = MISC_FEATURE - 5-methoxy-uridine | |

-continued

| | | |
|---|---|---|
| modified_base | 633 | |
| | mod_base = OTHER | |
| | note = MISC_FEATURE - 5-methoxy-uridine | |
| modified_base | 638 | |
| | mod_base = OTHER | |
| | note = MISC_FEATURE - 5-methoxy-uridine | |
| modified_base | 645 | |
| | mod_base = OTHER | |
| | note = MISC_FEATURE - 5-methoxy-uridine | |
| modified_base | 649 | |
| | mod_base = OTHER | |
| | note = MISC_FEATURE - 5-methoxy-uridine | |
| modified_base | 655 | |
| | mod_base = OTHER | |
| | note = MISC_FEATURE - 5-methoxy-uridine | |
| modified_base | 658 | |
| | mod_base = OTHER | |
| | note = MISC_FEATURE - 5-methoxy-uridine | |
| modified_base | 659 | |
| | mod_base = OTHER | |
| | note = MISC_FEATURE - 5-methoxy-uridine | |
| modified_base | 661 | |
| | mod_base = OTHER | |
| | note = MISC_FEATURE - 5-methoxy-uridine | |
| modified_base | 662 | |
| | mod_base = OTHER | |
| | note = MISC_FEATURE - 5-methoxy-uridine | |
| modified_base | 668 | |
| | mod_base = OTHER | |
| | note = MISC_FEATURE - 5-methoxy-uridine | |
| modified_base | 669 | |
| | mod_base = OTHER | |
| | note = MISC_FEATURE - 5-methoxy-uridine | |
| modified_base | 675 | |
| | mod_base = OTHER | |
| | note = MISC_FEATURE - 5-methoxy-uridine | |
| modified_base | 688 | |
| | mod_base = OTHER | |
| | note = MISC_FEATURE - 5-methoxy-uridine | |
| modified_base | 691 | |
| | mod_base = OTHER | |
| | note = MISC_FEATURE - 5-methoxy-uridine | |
| modified_base | 696 | |
| | mod_base = OTHER | |
| | note = MISC_FEATURE - 5-methoxy-uridine | |
| modified_base | 697 | |
| | mod_base = OTHER | |
| | note = MISC_FEATURE - 5-methoxy-uridine | |
| modified_base | 700 | |
| | mod_base = OTHER | |
| | note = MISC_FEATURE - 5-methoxy-uridine | |
| modified_base | 708 | |
| | mod_base = OTHER | |
| | note = MISC_FEATURE - 5-methoxy-uridine | |
| modified_base | 716 | |
| | mod_base = OTHER | |
| | note = MISC_FEATURE - 5-methoxy-uridine | |
| modified_base | 719 | |
| | mod_base = OTHER | |
| | note = MISC_FEATURE - 5-methoxy-uridine | |
| modified_base | 721 | |
| | mod_base = OTHER | |
| | note = MISC_FEATURE - 5-methoxy-uridine | |
| modified_base | 722 | |
| | mod_base = OTHER | |
| | note = MISC_FEATURE - 5-methoxy-uridine | |
| modified_base | 723 | |
| | mod_base = OTHER | |
| | note = MISC_FEATURE - 5-methoxy-uridine | |

| | | |
|---|---|---|
| modified_base | 727 | |
| | mod_base = OTHER | |
| | note = MISC_FEATURE - 5-methoxy-uridine | |
| modified_base | 732 | |
| | mod_base = OTHER | |
| | note = MISC_FEATURE - 5-methoxy-uridine | |
| modified_base | 734 | |
| | mod_base = OTHER | |
| | note = MISC_FEATURE - 5-methoxy-uridine | |
| modified_base | 738 | |
| | mod_base = OTHER | |
| | note = MISC_FEATURE - 5-methoxy-uridine | |

SEQUENCE: 28
```
gggaaataag agagaaaaga agagtaagaa gaaatataag agccaccatg ggagtgcacg   60
agtgtcccgc gtggttgtgg ttgctgctgt cgctcttgag cctcccactg ggactgcctg  120
tgctgggggc accacccaga ttgatctgcg actcacgggt acttgagagg taccttcttg  180
aagccaaaga agccgaaaac atcacaaccg gatgcgccga gcactgctcc ctcaatgaga  240
acattactgt accggataca aaggtcaatt tctatgcatg gaagagaatg gaagtaggac  300
agcaggccgt cgaagtgtgg caggggctcg cgcttttgtc ggaggcggtg ttgcggggtc  360
aggccctcct cgtcaactca tcacagccgt gggagcccct ccaacttcat gtcgataaag  420
cggtgtcggg gctccgcagc ttgacgacgt tgcttcgggc tctgggcgca caaaggagg   480
ctatttcgcc gcctgacgcg gcctccgcgg caccccctccg aacgatcacc gcggacacgt  540
ttaggaagct ttttagagtg tacagcaatt tcctccgcgg aaagctgaaa ttgtatactg  600
gtgaagcgtg taggacaggg gatcgctgat aataggctgg agcctcggtg gccatgcttc  660
ttgcccccttg ggcctccccc cagccccctcc tccccttcct gcacccgtac ccccgtggtc  720
tttgaataaa gtctgagtgg gcggcaaaaa aaaaaaaaaa aaaaaaaaaa aaaaaaaaaa  780
aaaaaaaaaa aaaaaaaaaa aaaaaaaaaa aaaaaaaaaa aaaaaaaaaa aaaaaaaaaa  840
aaaaa                                                              845
```

| | | |
|---|---|---|
| SEQ ID NO: 29 | moltype = RNA length = 10 | |
| FEATURE | Location/Qualifiers | |
| source | 1..10 | |
| | mol_type = other RNA | |
| | organism = synthetic construct | |

SEQUENCE: 29
```
aaaaaaaaaa                                                          10
```

| | | |
|---|---|---|
| SEQ ID NO: 30 | moltype = RNA length = 120 | |
| FEATURE | Location/Qualifiers | |
| source | 1..120 | |
| | mol_type = other RNA | |
| | organism = synthetic construct | |

SEQUENCE: 30
```
aaaaaaaaaa aaaaaaaaaa aaaaaaaaaa aaaaaaaaaa aaaaaaaaaa aaaaaaaaaa   60
aaaaaaaaaa aaaaaaaaaa aaaaaaaaaa aaaaaaaaaa aaaaaaaaaa aaaaaaaaaa  120
```

| | | |
|---|---|---|
| SEQ ID NO: 31 | moltype = RNA length = 250 | |
| FEATURE | Location/Qualifiers | |
| source | 1..250 | |
| | mol_type = other RNA | |
| | organism = synthetic construct | |
| misc_difference | 1..250 | |
| | note = This sequence may encompass 100-250 nucleotides | |

SEQUENCE: 31
```
aaaaaaaaaa aaaaaaaaaa aaaaaaaaaa aaaaaaaaaa aaaaaaaaaa aaaaaaaaaa   60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa                                                         250
```

| | | |
|---|---|---|
| SEQ ID NO: 32 | moltype = DNA length = 120 | |
| FEATURE | Location/Qualifiers | |
| source | 1..120 | |
| | mol_type = other DNA | |
| | organism = synthetic construct | |

SEQUENCE: 32
```
tttttttttt tttttttttt tttttttttt tttttttttt tttttttttt tttttttttt   60
tttttttttt tttttttttt tttttttttt tttttttttt tttttttttt tttttttttt  120
```

POLYNUCLEOTIDES CONTAINING A MORPHOLINO LINKER

SEQUENCE LISTING

The instant application contains a Sequence Listing which has been submitted electronically in XML format and is hereby incorporated by reference in its entirety. Said XML copy, created on Sep. 21, 2022, is named 50858-068004_SL.xml and is 144,243 bytes in size.

BACKGROUND OF THE INVENTION

There are multiple problems with prior methodologies of effecting protein expression. For example, heterologous DNA introduced into a cell can be inherited by daughter cells (whether or not the heterologous DNA has integrated into the chromosome) or by offspring. Introduced DNA can integrate into host cell genomic DNA at some frequency, resulting in alterations and/or damage to the host cell genomic DNA. In addition, multiple steps must occur before a protein is made. Once inside the cell, DNA must be transported into the nucleus where it is transcribed into RNA. The RNA transcribed from DNA must then enter the cytoplasm where it is translated into protein. This need for multiple processing steps creates lag times before the generation of a protein of interest. Further, it is difficult to obtain DNA expression in cells; frequently DNA enters cells but is not expressed or not expressed at reasonable rates or concentrations. This can be a particular problem when DNA is introduced into cells such as primary cells or modified cell lines.

Naturally occurring RNAs are synthesized from four basic ribonucleotides: ATP, CTP, UTP and GTP, but may contain post-transcriptionally modified nucleotides. Further, approximately one hundred different nucleoside alterations have been identified in RNA (Rozenski, J, Crain, P, and McCloskey, J. (1999). The RNA Modification Database: 1999 update. Nucl Acids Res 27: 196-197).

There is a need in the art for biological modalities to address the modulation of intracellular translation of nucleic acids. The present invention solves this problem by providing new mRNA molecules incorporating chemical alternatives which impart properties which are advantageous to therapeutic development.

SUMMARY OF THE INVENTION

The present disclosure provides, inter alia, polynucleotides including a morpholino linker.

Accordingly, in some aspects, the disclosure provides a compound, or a salt thereof, including:
a) a polynucleotide; and
b) at least one of a nucleotide, a second polynucleotide, (e.g., including 1 to 500 such as 1 to 200, 1 to 400, 1 to 10, 5 to 15, 10 to 20, 15 to 25, 20 to 30, 25 to 35, 30 to 40, 35 to 45, 40 to 50, 45 to 65, 50 to 70, 65 to 85, 70 to 90, 85 to 105, 90 to 110, 105 to 135, 120 to 150, 130 to 170, 150 to 200 or 1, 2, 3, 4, 5, 6, 7, 8, 9, 10, 20, 30, 40, 50, 60, 70, 80, 90, 100, 110, 120, 130, 140, 150, 160, 170, 180, 190, or 200 nucleosides), targeting moiety, small molecule, polypeptide, or polymer,
wherein the polynucleotide of a) is conjugated to the nucleotide, second polynucleotide, targeting moiety, small molecule, polypeptide, or polymer via a linker including the structure of Formula I:

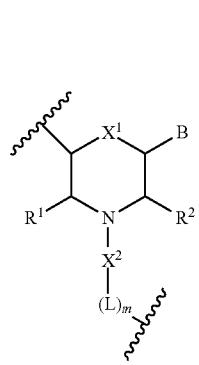

Formula I wherein B is a nucleobase, hydrogen, halo, hydroxy, thiol, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, optionally substituted $C_3$-$C_{10}$ cycloalkyl, optionally substituted $C_6$-$C_{10}$ aryl, or optionally substituted $C_2$-$C_{12}$ heterocycle;
$X^1$ is O, S, $NR^U$, or $C(R^U)_2$, wherein each $R^U$ is, independently, H, halo, or optionally substituted $C_1$-$C_6$ alkyl;
$X^2$ is —O—, —$NR^{N1}$—, —$NR^{N1}NR^{N1}$—, a bond, optionally substituted $C_1$-$C_{10}$ alkylene, optionally substituted $C_2$-$C_{10}$ alkenylene, optionally substituted $C_2$-$C_{10}$ alkynylene, optionally substituted $C_2$-$C_{10}$ heterocyclylene, optionally substituted $C_6$-$C_{12}$ arylene, optionally substituted $C_2$-$C_{100}$ polyethylene glycolene, or optionally substituted $C_1$-$C_{30}$ heteroalkylene, wherein $R^{N1}$ is H, optionally substituted $C_1$-$C_6$ alkyl, optionally substituted $C_2$-$C_6$ alkenyl, optionally substituted $C_2$-$C_6$ alkynyl, or optionally substituted $C_6$-$C_{10}$ aryl;
m is 1, 2, 3, 4, or 5;
each L is, independently, an unbranched or branched linker;
$R^1$ and $R^2$ are each, independently, hydrogen, hydroxyl, or $C_1$-$C_6$ alkoxy, and
wherein if B is a nucleobase, $R^1$ and $R^2$ are hydrogen and the linker conjugates the polynucleotide of a) to the second polynucleotide then $X^2$-$(L)_m$ is not a furanylmethyl moiety, a pyranylmethyl moiety, —P(O)OH—, or —P(O)N($R^N$)$_2$—, wherein $R^N$ is optionally substituted $C_1$-$C_6$ alkyl.

In some embodiments, the compound includes a polynucleotide encoding a polypeptide of interest. In some embodiments, the polynucleotide of a) encodes a polypeptide of interest. In some embodiments, the polynucleotide of a) is conjugated to the nucleotide, second polynucleotide, targeting moiety, small molecule, polypeptide, or polymer via a linker including the structure of Formula I at the 5'-terminus (e.g., the polynucleotide of a) is conjugated to a small molecule connected to an inverted 5' cap structure). In some embodiments, the polynucleotide of a) is conjugated to the nucleotide, second polynucleotide, targeting moiety, small molecule, polypeptide, or polymer via a linker including the structure of Formula I at the 3'-terminus.

In some embodiments, when the polynucleotide of a) is conjugated to the second polynucleotide, e.g., at the 3'-terminus, via a linker including the structure of Formula I, the second polynucleotide is further conjugated to a nucleotide, a third polynucleotide, a targeting moiety, a small molecule, polypeptide, or a polymer, e.g., at the 3'-terminus, via a linker including the structure of Formula I.

In some embodiments, the polynucleotide of a) includes: (a) at least one 5'-cap structure; (b) a 5'-UTR; (c) a coding region; (d) a 3'-UTR; and (e) a poly-A region. In some embodiments, the polynucleotide of a) includes: (a) at least one 5'-cap structure; (b) a 5'-UTR; (c) a coding region; (d) a 3'-UTR; and (e) a poly-A region, and is conjugated at the 5'-terminus via a linker including the structure of Formula I to a small molecule. In some embodiments, the polynucleotide of a) includes: (a) at least one 5'-cap structure; (b) a 5'-UTR; (c) a coding region; (d) a 3'-UTR; and (e) a poly-A region, and is conjugated at the 3'-terminus via a linker including the structure of Formula I to a polynucleotide including a 3'-stabilizing region. In some embodiments, the polynucleotide of a) includes: (a) at least one 5'-cap structure; (b) a 5'-UTR; (c) a coding region; and (d) a 3'-UTR, and is conjugated at the 3'-terminus via a linker including the structure of Formula I to a polynucleotide including a poly-A region. In some embodiments, the polynucleotide of a) includes: (a) at least one 5'-cap structure; (b) a 5'-UTR; and (c) a coding region, and is conjugated at the 3'-terminus via a linker including the structure of Formula I to a polynucleotide including a 3'-UTR. In some embodiments, the polynucleotide of a) includes: (a) at least one 5'-cap structure and (b) a 5'-UTR, and is conjugated at the 3'-terminus via a linker including the structure of Formula I to a polynucleotide including a coding region. In some embodiments, the polynucleotide of a) includes: (a) at least one 5'-cap structure, and is conjugated at the 3'-terminus via a linker including the structure of Formula I to a polynucleotide including a 5'-UTR. In some embodiments of any of the foregoing compounds, the at least one 5'-cap structure is Cap0, Cap1, Cap2, or an ARCA cap.

In some embodiments, the polynucleotide of a) is conjugated to more than one of a nucleotide, a polynucleotide (e.g., including 1 to 500 such as 1 to 200, 1 to 400, 1 to 10, 5 to 15, 10 to 20, 15 to 25, 20 to 30, 25 to 35, 30 to 40, 35 to 45, 40 to 50, 45 to 65, 50 to 70, 65 to 85, 70 to 90, 85 to 105, 90 to 110,105 to 135, 120 to 150, 130 to 170, 150 to 200 or 1, 2, 3, 4, 5, 6, 7, 8, 9, 10, 20, 30, 40, 50, 60, 70, 80, 90, 100, 110, 120, 130, 140, 150, 160, 170, 180, 190, or 200 nucleosides), a targeting moiety, a small molecule, a polypeptide, or a polymer, wherein the polynucleotide of a) is conjugated to each nucleotide, polynucleotide, targeting moiety, small molecule, polypeptide, or polymer via a linker including the structure of Formula 1. For example, in some embodiments, the polynucleotide of a) is conjugated to at least one nucleotide, polynucleotide, targeting moiety, small molecule, polypeptide, or polymer via a linker including the structure of Formula I at the 5'-terminus (e.g., the structure of Formula I is part of a 5'-cap structure) and conjugated to a nucleotide, polynucleotide, targeting moiety, small molecule, polypeptide, or polymer via a linker including the structure of Formula I at the 3'-terminus. In some embodiments, the polynucleotide of a) is conjugated to a small molecule via a linker including the structure of Formula I at the 5'-terminus (e.g., to an inverted 5' cap structure) and to a small molecule via a linker including the structure of Formula I at the 3'-terminus. In some embodiments, when a nucleotide, polynucleotide, targeting moiety, small molecule, polypeptide, or polymer is conjugated to both at the 5'-terminus and 3'-terminus of a polynucleotide, the nucleotide, polynucleotide, targeting moiety, small molecule, polypeptide, or polymer conjugated to the 5'-terminus is different from the nucleotide, polynucleotide, targeting moiety, small molecule, polypeptide, or polymer conjugated to the 3'-terminus. In some embodiments, when a nucleotide, polynucleotide, targeting moiety, small molecule, polypeptide, or polymer is conjugated to both at the 5'-terminus and 3'-terminus of a polynucleotide, the nucleotide, polynucleotide, targeting moiety, small molecule, polypeptide, or polymer conjugated to the 5'-terminus is the same as the nucleotide, polynucleotide, targeting moiety, small molecule, polypeptide, or polymer conjugated to the 3'-terminus.

In some aspects, the compound, or a salt thereof, includes a first polynucleotide conjugated to at least one second polynucleotide (e.g., a polynucleotide including 1 to 500 such as 1 to 200, 1 to 400, 1 to 10, 5 to 15, 10 to 20, 15 to 25, 20 to 30, 25 to 35, 30 to 40, 35 to 45, 40 to 50, 45 to 65, 50 to 70, 65 to 85, 70 to 90, 85 to 105, 90 to 110, 105 to 135, 120 to 150, 130 to 170, 150 to 200 or 1, 2, 3, 4, 5, 6, 7, 8, 9, 10, 20, 30, 40, 50, 60, 70, 80, 90, 100, 110, 120, 130, 140, 150, 160, 170, 180, 190, or 200 nucleosides), targeting moiety, small molecule, or polymer via a linker including the structure of Formula I.

In some embodiments, B is a nucleobase or hydrogen.

In some embodiments, B is a nucleobase.

In some embodiments, the compound includes the structure of Formula II:

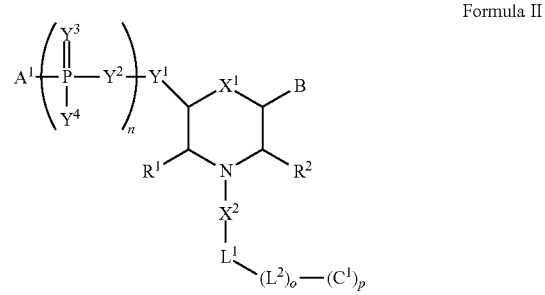

Formula II wherein $A^1$ is the first polynucleotide and includes:
(a) at least one 5'-cap structure;
$C^1$ includes a second polynucleotide, such as a 3'-stabilizing region, an aptamer, an siRNA, or other non-coding RNA, a targeting moiety, a small molecule, polypeptide, or a polymer;
$L^1$ is an unbranched linker;
$L^2$ is a branched linker;
n is 0, 1, 2, or 3;
o is 0 or 1;
p is 1, 2, 3, 4, or 5; and represents the number of $C^1$ moieties bound to $L^1$ or $L^2$, where p is 1, when o is 0.
$X^2$ is —O—, —$NR^{N1}$—, —$NR^{N1}NR^{N1}$—, a bond, optionally substituted $C_1$-$C_{10}$ alkylene, optionally substituted $C_2$-$C_{10}$ alkenylene, optionally substituted $C_2$-$C_{10}$ alkynylene, optionally substituted $C_2$-$C_{10}$ heterocyclylene, optionally substituted $C_6$-$C_{12}$ arylene, optionally substituted $C_2$-$C_{100}$ polyethylene glycolene, or optionally substituted $C_1$-$C_{30}$ heteroalkylene, wherein $R^{N1}$ is H, optionally substituted $C_1$-$C_6$ alkyl, optionally substituted $C_2$-$C_6$ alkenyl, optionally substituted $C_2$-$C_6$ alkynyl, or optionally substituted $C_6$-$C_{10}$ aryl;
$Y^1$ is O, S, Se, optionally substituted $C_1$-$C_6$ alkylene, or optionally substituted $C_1$-$C_6$ heteroalkylene;
each $Y^2$ and $Y^3$ is, independently, O, S, Se, —$NR^{N1}$—, optionally substituted $C_1$-$C_6$ alkylene, or optionally substituted $C_1$-$C_6$ heteroalkylene, wherein $R^{N1}$ is H, optionally substituted $C_1$-$C_6$ alkyl, optionally substituted $C_2$-$C_6$ alkenyl, optionally substituted $C_2$-$C_6$ alkynyl, or optionally substituted $C_6$-$C_{10}$ aryl; and each $Y^4$ is, independently, H, hydroxy, protected hydroxy, halo, thiol, boranyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, or optionally substituted amino, wherein when $Y^2$, $Y^3$, and $X^1$ are each O, $R^1$ and $R^2$ are each hydrogen, $Y^1$ is $CH_2$, $Y^4$ is hydroxy, n is 1, o is 0, p is 1, and $C^1$ is a polynucleotide, $X^2$-$L^1$ is not —P(O)OH— or —P(O)N($R^N$)$_2$—, wherein $R^N$ is optionally substituted $C_1$-$C_6$ alkyl, or a salt thereof.

In some embodimenet, $A^1$ further includes:

(b) a 5'-UTR;

(c) a coding region; and (d) a 3'-UTR.

In some embodiments, $C^1$ includes:

(b) a 5'-UTR;

(c) a coding region; and (d) a 3'-UTR.

In some embodiments, the at least one 5'-cap structure is Cap0, Cap1, Cap2, or an ARCA cap. In some embodiments, $A^1$ includes the structure of Formula XXI:

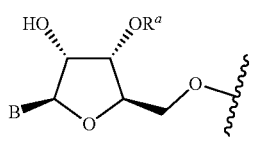

Formula XXI wherein B is a nucleobase; and $R^a$ is hydrogen or methyl.

In some embodiments, when $L^2$ is present, there is at least one $C^1$ at the terminus of each branch of the branched linker.

In some embodiments, $X^1$ is 0. In some embodiments, $R^1$ and $R^2$ are each hydroxy. In some embodiments, $Y^1$ is optionally substituted $C_1$-$C_6$ alkylene (e.g., methylene). In some embodiments, n is 1. In some embodiments, $Y^2$ is O. In some embodiments, $Y^3$ is O. In some embodiments, $Y^4$ is hydroxy. In certain embodiments, $X^2$ is a bond. In certain embodiments, $X^2$ is —O—. In certain embodiments, $X^2$ is —O— alkylene-. In certain embodiments, $X^2$ is —O—$(CH_2)_q$—, wherein q is an integer between 1 and 30, inclusive; preferably, q is 1, 2, 3, 4, 5, 6, 7, 8, 9, 10, 11, or 12. In certain embodiments, $X^2$ is —O-heteroalkylene. In some embodiments, $X^2$ is optionally substituted $C_2$-$C_{100}$ polyethylene glycolene. In some embodiments, $X^2$ is optionally substituted $C_1$-$C_{10}$ heteroalkylene.

In some embodiments, the compound includes the structure of Formula III:

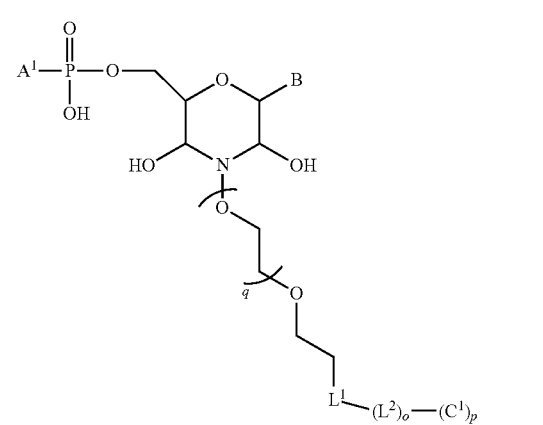

Formula III wherein q is 0, 1, 2, 3, 4, or 5, or a salt thereof.

In some embodiments, the compound includes the structure of Formula IV:

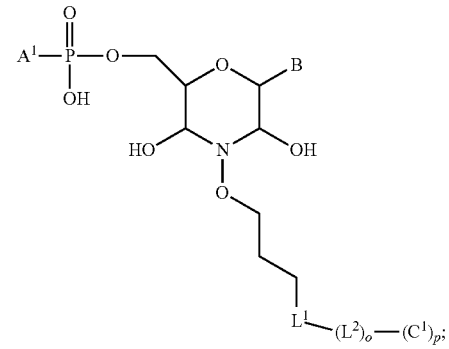

Formula IV or a salt thereof.

In some embodiments, the compound includes the structure of Formula V:

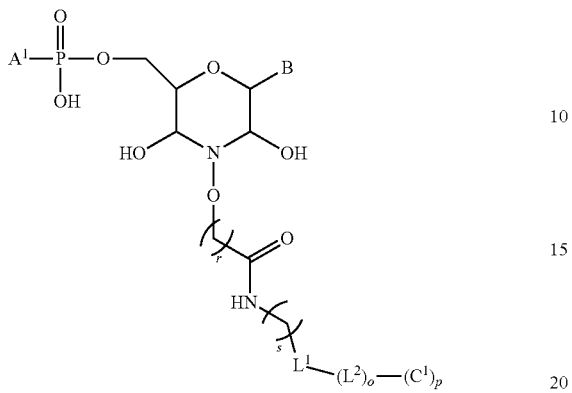

Formula V wherein r and s are each, independently, 1, 2, 3, 4, or 5, or a salt thereof.

In some embodiments, the compound includes the structure of Formula XXII:

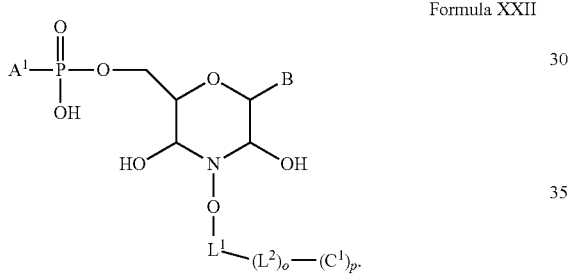

Formula XXII

In some embodiments of any of the foregoing compounds, $L^1$ includes the structure of Formula VI:

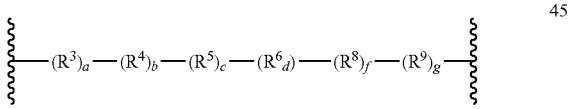

Formula VI wherein a, b, c, e, f, and g are each, independently, 0 or 1;
d is 0, 1, 2, or 3;
each of $R^3$, $R^5$, $R^7$, and $R^9$, is, independently, selected from optionally substituted $C_1$-$C_6$ alkylene, optionally substituted $C_1$-$C_6$ heteroalkylene, optionally substituted $C_2$-$C_{100}$ polyethylene glycolene, O, S, Se, and $NR^{10}$;
$R^4$ and $R^8$ are each, independently, carbonyl, thiocarbonyl, sulfonyl, or phosphoryl;
each $R^6$ is optionally substituted $C_1$-$C_{10}$ alkylene, optionally substituted $C_2$-$C_{10}$ alkenylene, optionally substituted $C_2$-$C_{10}$ alkynylene, optionally substituted $C_2$-$C_{10}$ heterocyclylene, optionally substituted $C_6$-$C_{12}$ arylene, optionally substituted $C_2$-$C_{100}$ polyethylene glycolene, or optionally substituted $C_1$-$C_{10}$ heteroalkylene, or a bond linking $(R^3)_a$—$(R^4)_b$—$(R^5)_c$ to $(R^7)_e$—$(R^8)_f$—$(R^9)_g$; and $R^{10}$ is hydrogen, optionally substituted $C_1$-$C_4$ alkyl, optionally substituted $C_2$-$C_4$ alkenyl, optionally substituted $C_2$-$C_4$ alkynyl, optionally substituted $C_2$-$C_6$ heterocyclyl, optionally substituted $C_6$-$C_{12}$ aryl, or optionally substituted $C_1$-$C_7$ heteroalkyl.

In some embodiments, $L^1$ is a linker that can be formed by a click chemistry reaction between a click chemistry reaction pair, e.g., $L^1$ includes:

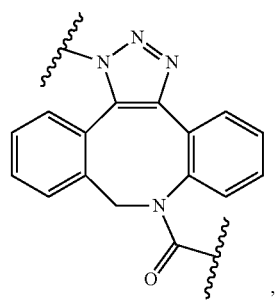

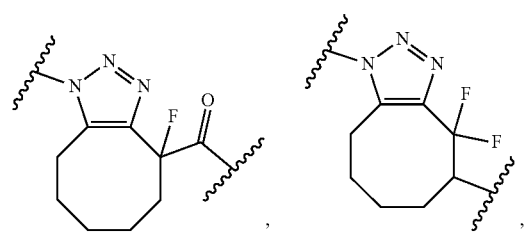

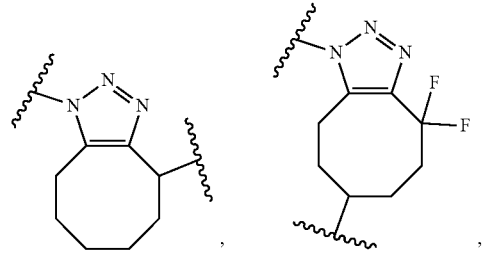

-continued
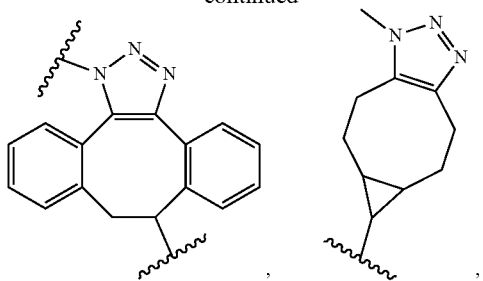
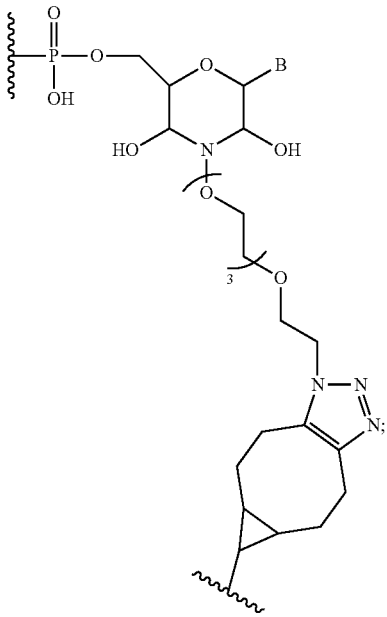
or an amide bond).
In some embodiments, the compound includes the structure of Formula VII:
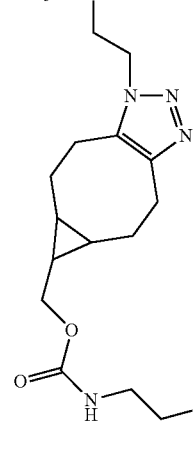
Formula VII
or a salt thereof. In some embodiments of Formula VII, o is 0.
In some embodiments, the compound has the structure of Formula VIII:
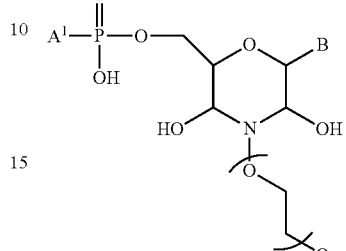
Formula VIII
or a salt thereof.
In some embodiments, p is 1.
In some embodiments, $L^1$ includes:
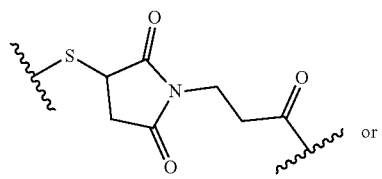 or
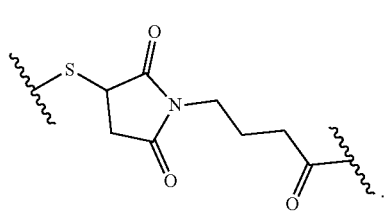

In some embodiments, the compound includes the structure of Formula IX:
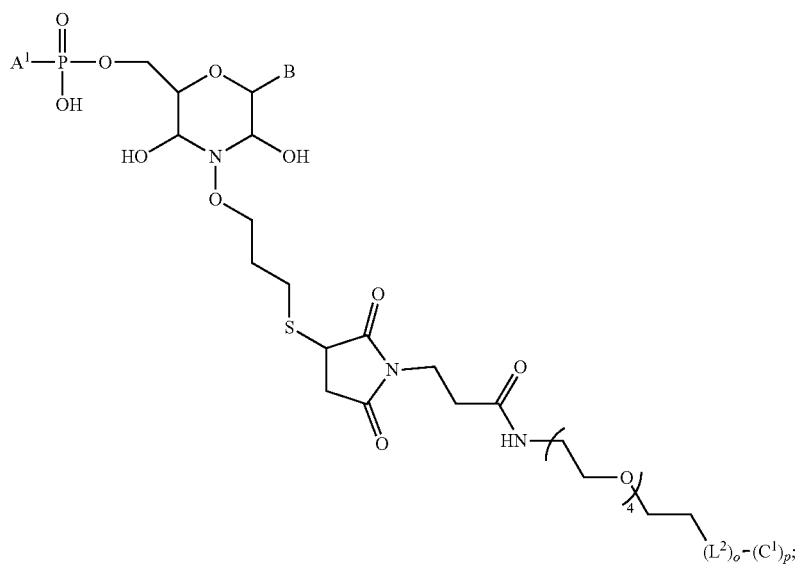
Formula IX
or a salt thereof.
In some embodiments, o is 1.
In some embodiments, p is 3.
In some embodiments, $L^2$ includes:
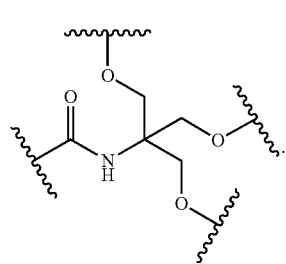 [SMILES: *OCC(CO*)(CO*)NC(*)=O]
In some embodiments, $L^2$ includes:

In some embodiments, the compound includes the structure of Formula X:

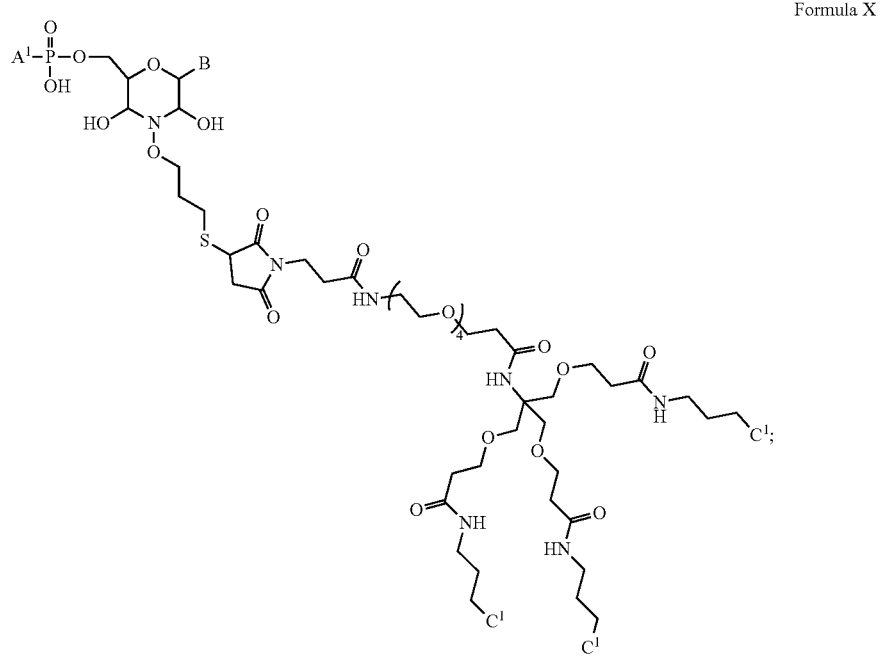

Formula X or a salt thereof.

In some embodiments, the compound includes the structure of Formula XI:

In some embodiments, the compound includes the structure of Formula XII:

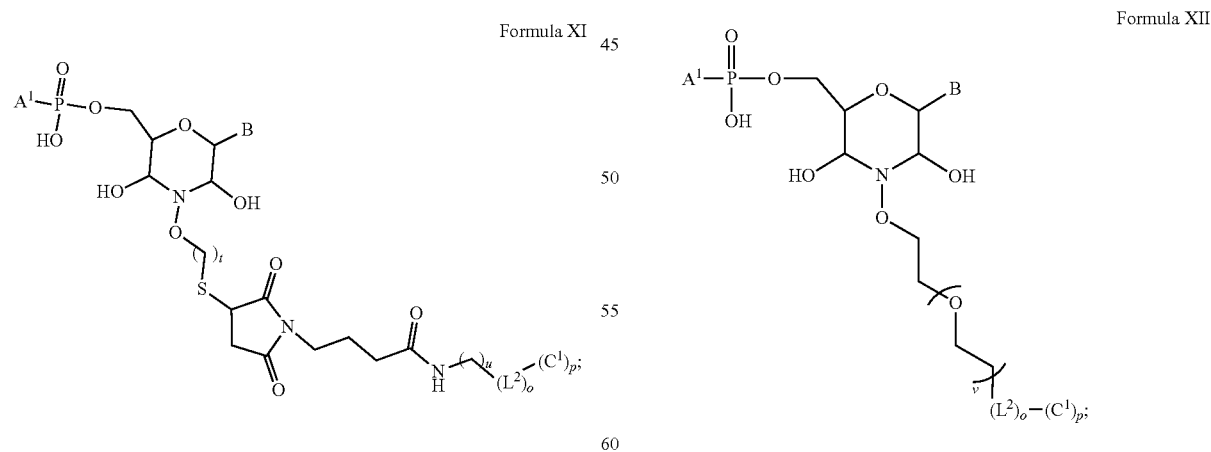

or a salt thereof
wherein t is 1, 2, 3, 4, 5, 6, 7, 8, 9, or 10; and
u is 1, 2, 3, 4, 5, 6, 7, 8, 9, or 10.

In some embodiments, t is 6. In some embodiments, u is 3. In some embodiments, o is 0.

or a salt thereof,
wherein v is 0, 1, 2, 3, 4, 5, 6, 7, 8, 9, or 10.

In some embodiments, v is 4. In some embodiments, o is 0.

In some embodiments, $L^1$ is $C_1$-$C_{10}$ alkylene. In some embodiments, the compound includes the structure of Formula XXIII:

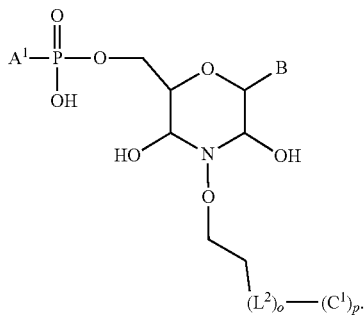

Formula XXIII

In some embodiments, o is 0. In some embodiments, p is 1. In some embodiments of any of the foregoing compounds, $C^1$ includes the second polynucleotide. In some embodiments, the second polynucleotide includes a plurality of adenosines. In some embodiments, all of the nucleosides of the second polynucleotide are adenosines. In some embodiments, the second polynucleotide includes at least one (e.g., 1, 2, 3, 4, 5, 6, 7, 8, 9, or 10) alternative nucleoside (e.g., L-adenosine, 2'-O-methyl-adenosine, alpha-thio-2'-O-methyl-adenosine, 2'-fluoro-adenosine, arabino-adenosine, hexitol-adenosine, LNA-adenosine, PNA-adenosine, or inverted thymidine). In some embodiments, the second polynucleotide includes a plurality of alternative nucleosides. In some embodiments, the second polynucleotide includes at least two different alternative nucleosides (e.g., at least one alternative nucleoside is 2'-O-methyl-adenosine, and at least one alternative nucleoside is inverted thymidine). In some embodiments, the second polynucleotide includes the structure:

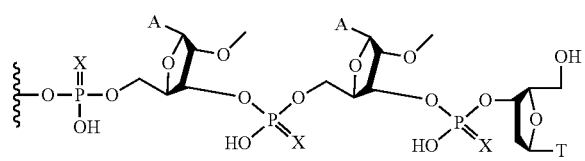

Formula XIII or a salt thereof;
wherein each X is, independently O or S; and
A represents adenine and T represents thymine.

In some embodiments, all of the plurality of alternative nucleosides are the same (e.g., all of the alternative nucleosides are L-adenosine).

In some embodiments, the second polynucleotide includes 10 or 11 nucleosides.

In some embodiments of any of the foregoing compounds, $C^1$ includes a targeting moiety (e.g., a carbohydrate such as N-Acetyl-galactosamine, a lipid, a vitamin, a small receptor ligand, a cell surface carbohydrate binding protein or a ligand thereof, a lectin, an r-type lectin, a galectin, a ligand to a cluster of differentiation (CD) antigen, CD30, CD40, a cytokine such as a type-1 cytokine or a type-2 cytokine, a chemokine, a colony stimulating factor, an interferon, an interleukin, a lymphokine, a monokine, or a mutant, derivative and/or combinations of any thereof).

In some embodiments of any of the foregoing compounds, $C^1$ includes a polypeptide (e.g., a nuclear localizing polypeptide such as a polypeptide having the sequence PKKKRKVEDPY[K(Aoa]G-amide (SEQ ID NO:1), an ER localizing polypeptide such as a polypeptide having the sequence Aoa-KDEL-OH (SEQ ID NO:2), an endosomal escape polypeptide such as a polypeptide having the sequence Aoa-HHHHHHHHHHHHHHHHHHHH-amide (SEQ ID NO:3) or the corresponding all D-amino acid polypeptide, or a polypeptide that can be used in affinity chromatography such as a poly-histidine).

In some embodiments of any of the foregoing compounds, $C^1$ includes a polynucleotide (e.g., an aptamer, a riboswitch, a purification handle, a locked nucleic acid, or a PABP-affinity sequence).

In some embodiments of any of the foregoing compounds, $C^1$ includes a click chemistry handle. In some embodiments, the click chemistry handle is an alkyne. In some embodiments, the click chemistry handle is an azide. In some embodiments, the click chemistry handle is cyclooctyne. In some embodiments, the click chemistry handle is a diene. In some embodiments, the click chemistry handle is a dienophile. In some embodiments, the click chemistry handle is a terminal alkyne. In some embodiments, the click chemistry handle is a strained alkyne. In some embodiments, the click chemistry handle is an activated alkyne. In some embodiments, the click chemistry handle is an electron-deficient alkyne. In some embodiments, the click chemistry handle is an aryne. In some embodiments, the click chemistry handle is a tetrazine. In some embodiments, the click chemistry handle is an alkene. In some embodiments, the click chemistry handle is a phosphine. In some embodiments, the click chemistry handle is a dithioester. In some embodiments, the click chemistry handle is an alkoxyamine. In some embodiments, the click chemistry handle is an alpha, beta-unsaturated carbonyl. In some embodiments, the click chemistry handle is a maleimide. In some embodiments, the click chemistry handle is a thiol. In some embodiments, the click chemistry handle is an enone. In some embodiments, the click chemistry handle is a hydrazide. In some embodiments, the click chemistry handle is an amine. Other suitable click chemistry handles are known to those of skill in the art.

In some embodiments of any of the foregoing compounds, $A^1$ further includes a poly-A region. In some embodiments, the poly-A region, when present, includes at least one alternative nucleoside.

In some embodiments, at least one of the coding region, the 5'-UTR, the 3'-UTR, and/or the 5'-cap structure of $A^1$ includes at least one alternative nucleoside (e.g., a 5-substituted uridine such as 5-methoxy-uridine, a 1-substituted pseudouridine, or a 5-substituted cytidine such as 5-methyl-cytidine).

In some aspects, the disclosure provides a method of modifying a polynucleotide, the method including:
    contacting a polynucleotide including the structure of Formula XIV:

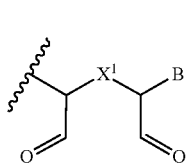

Formula XIV wherein B is a nucleobase, hydrogen, halo, hydroxy, thiol, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, optionally substituted $C_3$-$C_{10}$ cycloalkyl, optionally substituted $C_6$-$C_{10}$ aryl, optionally substituted $C_2$-$C_{12}$ heterocycle; and $X^1$ is O, S, $NR^U$, or $C(R^U)_2$, wherein each $R^U$ is, independently, H, halo, or optionally substituted $C_1$-$C_6$ alkyl;

with a compound, or a salt thereof, having the structure of Formula XV:

    Formula XV wherein $R^{11}$ is optionally substituted $C_1$-$C_{10}$ alkyl, optionally substituted $C_2$-$C_{10}$ alkenyl, optionally substituted $C_2$-$C_{10}$ alkynyl, optionally substituted $C_2$-$C_{10}$ heterocyclyl, optionally substituted $C_6$-$C_{12}$ aryl, optionally substituted $C_2$-$C_{100}$ polyethylene glycol, optionally substituted $C_1$-$C_{10}$ heteroalkyl conjugated to a polynucleotide, or optionally substituted $C_1$-$C_{10}$ heteroalkyl;

under suitable conditions to produce a polynucleotide including the structure of Formula I:

Formula I

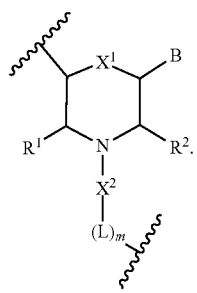

In some embodiments, B is hydrogen or a nucleobase. In some embodiments, B is a nucleobase.

In some embodiments, the method further includes reacting a polynucleotide including the structure of Formula XVI:

Formula XVI

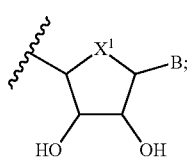

or a salt thereof, under suitable conditions (e.g., conditions including oxidative conditions such as periodate) to produce the polynucleotide including the structure of Formula XIV.

In some embodiments, $R^{11}$ is optionally substituted $C_1$-$C_{10}$ heteroalkyl.

In some embodiments, the compound, or salt thereof, of Formula XIII has the structure of Formula XVII:

    Formula XVII wherein $R^{12}$ is optionally substituted $C_2$-$C_{100}$ polyethylene glycol, optionally substituted $C_1$-$C_{10}$ alkyl, optionally substituted $C_1$-$C_{10}$ heteroalkyl, or optionally substituted $C_1$-$C_{10}$ heteroalkyl conjugated to a polynucleotide, e.g., $C^1$.

In some embodiments, $R^{11}$ includes an azido moiety, a carboxylate moiety, or a thiol.

In some embodiments, the compound of Formula XVII has the structure:

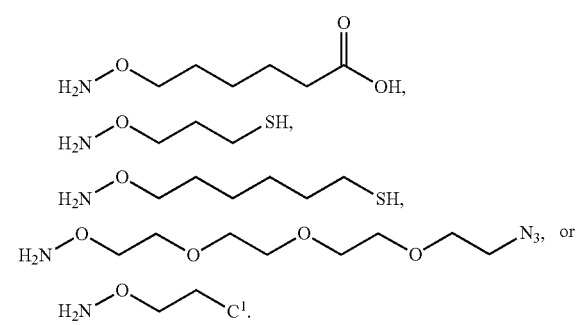

In some embodiments, the method further includes reacting the polynucleotide including the structure of Formula I with a second polynucleotide including an alkyne moiety under suitable conditions to produce a compound including a first polynucleotide and a second polynucleotide conjugated through a linker including a triazole moiety.

In some embodiments, the alkyne moiety includes the structure:

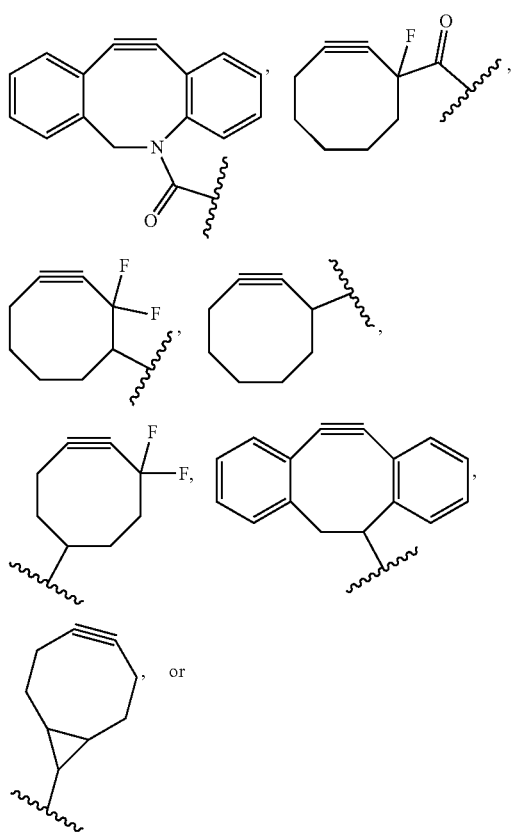

-continued

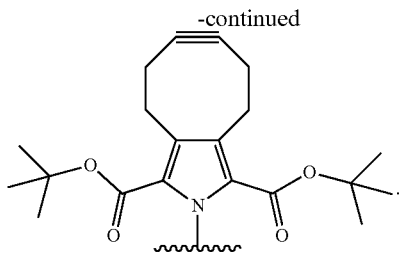

In some embodiments, the method further includes reacting the compound of Formula I with a second polynucleotide including a maleimido moiety under suitable conditions to produce a compound including a first polynucleotide and a second polynucleotide conjugated through a linker including the structure:

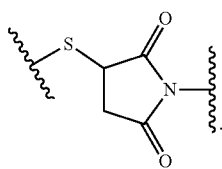 [SMILES: *SC1CC(=O)N(*)C1=O]

In some embodiments, the method further includes reacting the compound of Formula I with a second polynucleotide including an amino moiety under suitable conditions to produce a compound including a first polynucleotide and a second polynucleotide conjugated through a linker including an amide bond.

In some embodiments of any of the foregoing compounds or methods, the targeting moiety, small molecule, polypeptide, or polymer is a therapeutic agent such as a cytotoxin, radioactive ion, chemotherapeutic, or other therapeutic agent. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Radioactive ions include, but are not limited to iodine (e.g., iodine 125 or iodine 131), strontium 89, phosphorous, palladium, cesium, iridium, phosphate, cobalt, yttrium 90, Samarium 153 and praseodymium. Other therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In some embodiments of any of the foregoing compounds or methods, the targeting moiety, small molecule, polypeptide, or polymer is a detectable substance. Examples of detectable substances include various organic small molecules, inorganic compounds, nanoparticles, enzymes or enzyme substrates, fluorescent materials, luminescent materials, bioluminescent materials, chemiluminescent materials, radioactive materials, and contrast agents. Such optically-detectable labels include for example, without limitation, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-I-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5''-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]-naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodarnine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Cyanine-3 (Cy3); Cyanine-5 (Cy5); Cyanine-5.5 (Cy5.5), Cyanine-7 (Cy7); IRD 700; IRD 800; Alexa 647; La Jolta Blue; phthalo cyanine; and naphthalo cyanine. In some embodiments, the detectable label is a fluorescent dye, such as Cy5 and Cy3. In some embodiments, the detectable agent is a non-detectable pre-cursor that becomes detectable upon activation. Examples include fluorogenic tetrazine-fluorophore constructs (e.g., tetrazine-BODIPY FL, tetrazine-Oregon Green 488, ortetrazine-BODIPY TMR-X) or enzyme activatable fluorogenic agents (e.g., PROSENSE (VisEn Medical)).

In some embodiments of any of the foregoing compounds or methods, the targeting moiety, small molecule, polypeptide, or polymer is a luminescent material. Examples luminescent material includes luminol; examples of bioluminescent materials include luciferase, luciferin, and aequorin.

In some embodiments of any of the foregoing compounds or methods, the targeting moiety, small molecule, polypeptide, or polymer includes a radioactive material. Examples of suitable radioactive material include $^{18}F$, $^{67}Ga$, $^{81m}Kr$, $^{82}Rb$, $^{111}In$, $^{123}I$, $^{133}Xe$, $^{201}Tl$, $^{125}I$, $^{35}S$, $^{14}C$, or $^{3}H$, $^{99m}Tc$ (e.g., as pertechnetate (technetate(VII), $TcO_4^-$) either directly or indirectly, or other radioisotope detectable by direct counting of radioemission or by scintillation counting.

In some embodiments of any of the foregoing compounds or methods, the targeting moiety, small molecule, polypeptide, or polymer is a contrast agent. In addition, contrast agents, e.g., contrast agents for MRI or NMR, for X-ray CT, Raman imaging, optical coherence tomography, absorption imaging, ultrasound imaging, or thermal imaging can be used. Exemplary contrast agents include gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons can also be used.

In some embodiments of any of the foregoing compounds or methods, the polymer is a polyethylene glycol (PEG), polypropylene glycol, peptide, a cationic polymer, or any synthetic or naturally occurring macromolecule made up of repeating monomeric units. In some embodiments of any of the foregoing compounds or methods, the polymer is a polyethylene glycol (PEG) or a cationic polymer.

In some embodiments, the polymer is an optionally substituted straight chain polyalkylene, polyalkenylene, or polyoxyalkylene polymer. In some embodiments, the polymer is an optionally substituted branched chain polyalkylene, polyalkenylene, or polyoxyalkylene polymer. In some embodiments, the polymer is an optionally substituted branched polysaccharide. In some embodiments, the polymer is an optionally substituted unbranched polysaccharide. In some embodiments, the polymer is an optionally substituted polyethylene glycol, polypropylene glycol, or polyvinyl alcohol or derivative thereof. In some embodiments, the polymer is a branched chain polyethylene glycol, polypropylene glycol, or polyvinyl alcohol or derivative thereof.

In some embodiments, the polymer is polyethylene glycol (PEG). In some embodiments, the polymer is a derivatized form of PEG (e.g., N-hydroxylsuccinimide (NHS) active esters of PEG such as succinimidyl propionate, benzotriazole active esters, and PEG derivatized with maleimide, vinyl sulfones, or thiol groups). PEG polymers useful in the invention may be linear molecules, or may be branched wherein multiple PEG moieties are present in a single polymer.

In some embodiments of any of the foregoing compounds or methods, the small molecule includes a benzyl group (e.g., the hydroxyl amine used in the reaction to form the morpholino is o-benzylhydroxylamine, O-(2,3,4,5,6-petafluorobenzyl)hydroxylamine, O-tritylhydroxylamine, O-(4-nitro-benzyl) hydroxylamine), In some embodiments of any of the foregoing compounds or methods, the small molecule includes an alkyl group (e.g., the hydroxylamine used in the reaction to form the morpholino is methoxyamine, O-ethylhydroxylamine, O-tert-butylhydroxylamine, O-tert-butyldimethylsilylhydroxylamine, O-(carboxymethyl) hydroxylamine). In some embodiments of any of the foregoing compounds or methods, the small molecule includes a heterocycle (e.g., the hydroxylamine used in the reaction to form the morpholino is O-(tetra-2H-pyran-2-yl) hydroxylamine or 10-[2-(aminooxy)ethyl]-10H-phenothiazine. In some embodiments, the small moledule includes a heteroatom (e.g., the hydroxylamine used in the reaction to form the morpholino is hydroxylamine-O-sulfonic acid or hydroxylamine).

In some embodiments, the compounds can also include a targeting moiety that can be a cell penetrating moiety or agent that enhances intracellular delivery of the compositions. For example, the compositions can include a cell-penetrating peptide sequence that facilitates delivery to the intracellular space, e.g., HIV-derived TAT peptide, penetratins, transportans, or hCT derived cell-penetrating peptides, see, e.g., Caron et al., (2001) Mol Ther. 3(3):310-8; Langel, Cell-Penetrating Peptides: Processes and Applications (CRC Press, Boca Raton FL 2002); El-Andaloussi et al., (2005) Curr Pharm Des. 11(28):3597-611; and Deshayes et al., (2005) Cell Mol Life Sci. 62(16):1839-49. The compositions can also be formulated to include a cell penetrating agent, e.g., liposomes, which enhance delivery of the compositions to the intracellular space.

The compounds described herein can be used to deliver an agent to any biological target for which a specific ligand exists or can be generated. The ligand can bind to the biological target either covalently or non-covalently. Exemplary biological targets include biopolymers, e.g., antibodies, nucleic acids such as RNA and DNA, proteins, enzymes; exemplary proteins include enzymes, receptors, and ion channels. In some embodiments the target is a tissue- or cell-type specific marker, e.g., a protein that is expressed specifically on a selected tissue or cell type. In some embodiments, the target is a receptor, such as, but not limited to, plasma membrane receptors and nuclear receptors; more specific examples include G-protein-coupled receptors, cell pore proteins, transporter proteins, surface-expressed antibodies, HLA proteins, MHC proteins and growth factor receptors.

In some embodiments of any of the foregoing compounds, the poly-A region, if present, includes from about 20 to about 400 nucleosides (e.g., 1 to 10, 5 to 15, 10 to 20, 15 to 25, 20 to 30, 25 to 35, 30 to 40, 35 to 45, 40 to 50, 45 to 65, 50 to 70, 60 to 70, 65 to 85, 70 to 90, 85 to 105, 90 to 110,105 to 135, 120 to 150, 130 to 170, 150 to 200 or 1, 2, 3, 4, 5, 6, 7, 8, 9, 10, 20, 30, 40, 50, 60, 70, 80, 90, 100, 110, 120, 130, 140, 150, 160, 170, 180, 190, or 200). In some embodiments of any of the foregoing compounds, the poly-A region, if present, includes 64 nucleosides. In some embodiments of any of the foregoing compounds, the poly-A region, if present, includes a polyadenylation signal.

In some embodiments of any of the foregoing compounds, the first polynucleotide further includes a poly-C region. In some embodiments of any of the foregoing compounds, the poly-C region, if present, includes 1 to 200 nucleosides (e.g., 1 to 10, 5 to 15, 10 to 20, 15 to 25, 20 to 30, 25 to 35, 30 to 40, 35 to 45, 40 to 50, 45 to 65, 50 to 70, 60 to 70, 65 to 85, 70 to 90, 85 to 105, 90 to 110, 105 to 135, 120 to 150, 130 to 170, 150 to 200 or 1, 2, 3, 4, 5, 6, 7, 8, 9, 10, 20, 30, 40, 50, 60, 70, 80, 90, 100, 110, 120, 130, 140, 150, 160, 170, 180, 190, or 200). In some embodiments of any of the foregoing compounds, the poly-C region, if present, includes 30 nucleosides. In some embodiments of any of the foregoing compounds, the poly-C region, if present, is conjugated to the 3'-terminus of the first polynucleotide. In some embodiments of any of the foregoing compounds, the poly-C region, if present, is conjugated to the 3'-terminus of the poly-A region of the first polynucleotide.

In some aspects, the invention provides a lipid nanoparticle composition including any of the foregoing compounds. The lipid nanoparticle in some embodiments includes a cationic lipid, a PEG-modified lipid, a sterol and a non-cationic lipid. The cationic lipid may be selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy) heptadecanedioate (L319). The lipid nanoparticle in other embodiments has a molar ratio of about 20-60% cationic lipid: about 5-25% non-cationic lipid: about 25-55% sterol; and about 0.5-15% PEG-modified lipid. In some embodiments the lipid nanoparticle comprises a molar ratio of about 50% cationic lipid, about 1.5% PEG-modified lipid, about 38.5% cholesterol and about 10% non-cationic lipid. The lipid nanoparticle has a mean diameter of 50-150 nm, or 80-100 nm in other embodiments.

In some aspects, the invention provides a compound comprising a polynucleotide that has been modified to comprise the structure of Formula I, wherein the modified polynucleotide results in increased polypeptide expression when compared to the unmodified polynucleotide. In some aspects, the invention provides a method of increasing the expression of a recombinant polypeptide of interest in a cell comprising contacting the cell with a polynucleotide encoding the polypeptide, wherein the polynucleotide has been modified to comprise the structure of Formula I, and wherein expression is increased when compared to the unmodified polynucleotide. For example, the modified polynucleotide results in expression levels that are increased by between about 0.1% and about 100% (e.g., about 0.5%, 1%, 2%, 3%, 4%, 5%, 6%, 7%, 8%, 9%, 10%, 15%, 20%, 25%, 30%, 35%, 40%, 45%, 50%, 60%, 70%, 80%, 90%, 95%, 98%, 99%, or about 100%) when compared to the unmodified polynucleotide. In some embodiments, the modified polynucleotide results in expression levels that are increased by about 2-fold to about 100-fold (e.g., about 3-fold, 4-fold, 5-fold, 6-fold, 7-fold, 8-fold, 9-fold, 10-fold, 12-fold, 14-fold, 16-fold, 18-fold, 20-fold, 25-fold, 30-fold, 40-fold, 50-fold, 60-fold, 70-fold, 80-fold, 90-fold, or about 100-fold,) when compared to the unmodified polynucleotide. In some embodiments, the polynucleotide is mRNA. In some embodiments, the polypeptide of interest is a therapeutic polypeptide. In some embodiments, the cell is a mammalian cell. In some embodiments, the mammalian cell is a human cell.

In some aspects, the invention provides a compound comprising a polynucleotide that has been modified to comprise the structure of Formula I, wherein the modified polynucleotide results in increased half-life when compared to the unmodified polynucleotide. In some aspects, the invention provides a method of increasing the half-life of a polynucleotide in a cell comprising contacting the cell with the polynucleotide, wherein the polynucleotide has been modified to comprise the structure of Formula I, and wherein half-life is increased when compared to the unmodified polynucleotide. For example, the modified polynucleotide has a half-life measurement that is increased by between about 0.1% and about 100% (e.g., about 0.5%, 1%, 2%, 3%, 4%, 5%, 6%, 7%, 8%, 9%, 10%, 15%, 20%, 25%, 30%, 35%, 40%, 45%, 50%, 60%, 70%, 80%, 90%, 95%, 98%, 99%, or about 100%) when compared to the unmodified polynucleotide. In some embodiments, the modified polynucleotide has a half-life measurement that is increased by about 2-fold to about 100-fold (e.g., about 3-fold, 4-fold, 5-fold, 6-fold, 7-fold, 8-fold, 9-fold, 10-fold, 12-fold, 14-fold, 16-fold, 18-fold, 20-fold, 25-fold, 30-fold, 40-fold, 50-fold, 60-fold, 70-fold, 80-fold, 90-fold, or about 100-fold,) when compared to the unmodified polynucleotide. In some embodiments, the polynucleotide is mRNA. In some embodiments, the mRNA encodes a therapeutic polypeptide. In some embodiments, the cell is a mammalian cell. In some embodiments, the mammalian cell is a human cell.

DETAILED DESCRIPTION OF THE INVENTION

The present disclosure provides, inter alia, polynucleotides that exhibit improved therapeutic properties including, but not limited to, increased stability, increased expression, and/or a reduced innate immune response when introduced into a population of cells.

In particular, the inventors have identified that mRNA containing a morpholino linker may be particularly effective for use in therapeutic compositions, because they may benefit from increased stability, high expression levels, and limited induction of the innate immune response, as shown in the Examples (in particular, high performance may be observed across the assays in Examples 6-9). Preferably, the compounds are substantially non toxic and non mutagenic. The morpholino linker may be employed in conjunction with connecting various parts of a polynucleotide and/or various other non-nucleotide moieties and the polynucleotide, e.g., at the 5' terminus (e.g., via an inverted structure), 3' terminus, within the polynucleotide sequence, or combinations thereof.

The compositions and methods described herein can be used, in vivo and in vitro, both extracellularly and intracellularly, as well as in assays such as cell free assays.

In another aspect, the present disclosure provides compositions including a compound as described herein. In some embodiments, the composition is a reaction mixture. In some embodiments, the composition is a pharmaceutical composition. In some embodiments, the composition is a cell culture.

It is further appreciated that certain features of the present disclosure, which are, for clarity, described in the context of separate embodiments, can also be provided in combination in a single embodiment. Conversely, various features of the present disclosure which are, for brevity, described in the context of a single embodiment, can also be provided separately or in any suitable subcombination.

Polynucleotides

The polynucleotides of the invention typically include a first region of linked nucleosides encoding a polypeptide of interest (e.g., a coding region), a first flanking region located at the 5'-terminus of the first region (e.g., a 5'-UTR), a second flanking region located at the 3'-terminus of the first region (e.g., a 3'-UTR), at least one 5'-cap region, and a 3'-stabilizing region. In some embodiments, the polynucleotides of the invention further include a poly-A region. In some embodiments, any one of the regions of the polynucleotides of the invention include at least one alternative nucleoside. For example, the 3'-stabilizing region may contain an alternative nucleoside such as an L-nucleoside, an inverted thymidine, or a 2'-O-methyl nucleoside and/or the coding region, 5'-UTR, 3'-UTR, or cap region may include an alternative nucleoside such as a 5-substituted uridine (e.g., 5-methoxyuridine), a 1-substituted pseudouridine (e.g., 1-methyl-pseudouridine), and/or a 5-substituted cytidine (e.g., 5-methyl-cytidine).

Alternative Polynucleotides

The present disclosure provides polynucleotides, including RNAs such as mRNAs that contain one or more alternative nucleosides or nucleotides as described herein (e.g., in a 3'-stabilizing region), which have useful properties including increased stability and/or the lack of a substantial induction of the innate immune response of a cell into which the polynucleotide is introduced. For example, in some embodiments, the alternative polynucleotide exhibits reduced degradation in a cell into which the polynucleotide is introduced, relative to a corresponding unaltered polynucleotide. These alternative polynucleotides may enhance the efficiency of protein production, intracellular retention of the polynucleotides, and/or viability of contacted cells, as well as possess reduced immunogenicity.

The term "polynucleotide," in its broadest sense, includes any compound and/or substance that is or can be incorporated into an oligonucleotide chain. Exemplary polynucleotides for use in accordance with the present disclosure include, but are not limited to, one or more of DNA, RNA including messenger mRNA (mRNA), hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc., described in detail herein.

The polynucleotides of the invention may or may not be uniformly altered along the entire length of the molecule. For example, one or more or all types of nucleotide (e.g., purine or pyrimidine, or any one or more or all of A, G, U, C) may or may not be uniformly altered in a polynucleotide of the invention, or in a given predetermined sequence region thereof. In some embodiments, all nucleotides X in a polynucleotide of the invention (or in a given sequence region thereof) are altered, wherein X may any one of nucleotides A, G, U, C, or any one of the combinations A+G, A+U, A+C, G+U, G+C, U+C, A+G+U, A+G+C, G+U+C or A+G+C.

Different sugar alterations and/or internucleoside linkages (e.g., backbone structures) may exist at various positions in the polynucleotide. One of ordinary skill in the art will appreciate that the nucleotide analogs or other alteration(s) may be located at any position(s) of a polynucleotide such that the function of the polynucleotide is not substantially decreased. An alteration may also be a 5'- or 3'-terminal alteration. In some embodiments, the polynucleotide includes an alteration at the 3'-terminus. The polynucleotide may contain from about 1% to about 100% alternative nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of A, G, U, or C.

The polynucleotides may contain at a minimum one and at maximum 100% alternative nucleotides, or any intervening percentage, such as at least 5% alternative nucleotides, at least 10% alternative nucleotides, at least 25% alternative nucleotides, at least 50% alternative nucleotides, at least 80% alternative nucleotides, or at least 90% alternative nucleotides. For example, the polynucleotides may contain an alternative pyrimidine such as an alternative uracil (e.g., 1-methyl-pseudouridine or other alternative as contemplated herein) or an alternative cytosine (e.g., 5-methyl-cytidine or other alternative as contemplated herein). In some embodiments, at least 5%, at least 10%, at least 25%, at least 50%, at least 80%, at least 90% or 100% of the uracil in the polynucleotide is replaced with an alternative uracil (e.g., a 5-substituted uracil). The alternative uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the polynucleotide is replaced with an alternative cytosine (e.g., a 5-substituted cytosine). The alternative cytosine can be replaced by a compound having a single unique structure, or can be replaced by a plurality of compounds having different structures (e.g., 2, 3, 4 or more unique structures).

Other components of a polynucleotide are optional and are beneficial in some embodiments. For example, a 5'-untranslated region (UTR) and/or a 3'-UTR are provided, wherein either or both may independently contain one or more nucleoside alterations. In some embodiments, nucleoside alterations may also be present in the translatable region. Also provided are polynucleotides containing a Kozak sequence (e.g., in the 5'-UTR). In some embodiments, the polynucleotides of the invention include a poly-A region. In some embodiments, the polynucleotides of the invention include at least one 5'-cap structure.

In certain embodiments, it is desirable to intracellularly degrade an alternative polynucleotide introduced into the cell, for example if precise timing of protein production is desired. Thus, the present disclosure provides an alternative polynucleotide containing a degradation domain, which is capable of being acted on in a directed manner within a cell.

Additionally, provided are polynucleotides containing one or more intronic nucleotide sequences capable of being excised from the polynucleotide.

Further, provided are polynucleotides containing an internal ribosome entry site (IRES). An IRES may act as the sole ribosome binding site, or may serve as one of multiple ribosome binding sites of an mRNA. A polynucleotide containing more than one functional ribosome binding site may encode several peptides or polypeptides that are translated independently by the ribosomes (e.g., multicistronic mRNA). When polynucleotides are provided with an IRES, further optionally provided is a second translatable region. Examples of IRES sequences that can be used according to the present disclosure include without limitation, those from picornaviruses (e.g., FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

Generally, the shortest length of an alternative polynucleotide of the present disclosure can be the length of the polynucleotide sequence that is sufficient to encode for a dipeptide. In another embodiment, the length of the polynucleotide sequence is sufficient to encode for a tripeptide. In another embodiment, the length of the polynucleotide sequence is sufficient to encode for a tetrapeptide. In another embodiment, the length of the polynucleotide sequence is sufficient to encode for a pentapeptide. In another embodiment, the length of the polynucleotide sequence is sufficient to encode for a hexapeptide. In another embodiment, the length of the polynucleotide sequence is sufficient to encode for a heptapeptide. In another embodiment, the length of the polynucleotide sequence is sufficient to encode for an octapeptide. In another embodiment, the length of the polynucleotide sequence is sufficient to encode for a nonapeptide. In another embodiment, the length of the polynucleotide sequence is sufficient to encode for a decapeptide.

Examples of dipeptides that the alternative polynucleotide sequences can encode for include, but are not limited to, carnosine and anserine.

In a further embodiment, the polynucleotide is greater than 30 nucleotides in length. In another embodiment, the polynucleotide molecule is greater than 35 nucleotides in length. In another embodiment, the length is at least 40 nucleotides. In another embodiment, the length is at least 45 nucleotides. In another embodiment, the length is at least 55 nucleotides. In another embodiment, the length is at least 50 nucleotides. In another embodiment, the length is at least 60 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1800 nucleotides. In another embodiment, the length is at least 2000 nucleotides. In another embodiment, the length is at least 2500 nucleotides. In another embodiment, the length is at least 3000 nucleotides. In another embodiment, the length is at least 4000 nucleotides. In another embodiment, the length is at least 5000 nucleotides, or greater than 5000 nucleotides.

5'-Cap Structures

The 5'-cap structure of a polynucleotide is involved in nuclear export and increasing polynucleotide stability and binds the mRNA Cap Binding Protein (CBP), which is responsible for polynucleotide stability in the cell and translation competency through the association of CBP with poly-A binding protein to form the mature cyclic mRNA species. The cap further assists the removal of 5'-proximal introns removal during mRNA splicing.

Endogenous polynucleotide molecules may be 5'-end capped generating a 5'-ppp-5'-triphosphate linkage between a terminal guanosine cap residue and the 5'-terminal transcribed sense nucleotide of the polynucleotide. This 5'-guanylate cap may then be methylated to generate an N7-methyl-guanylate residue. The ribose sugars of the terminal and/or anteterminal transcribed nucleotides of the 5' end of the polynucleotide may optionally also be 2'-O-methylated. 5'-decapping through hydrolysis and cleavage of the guanylate cap structure may target a polynucleotide molecule, such as an mRNA molecule, for degradation.

Alterations to the polynucleotides of the present invention may generate a non-hydrolyzable cap structure preventing decapping and thus increasing polynucleotide half-life. Because cap structure hydrolysis requires cleavage of 5'-ppp-5' phosphorodiester linkages, alternative nucleotides may be used during the capping reaction. For example, a Vaccinia Capping Enzyme from New England Biolabs (Ipswich, MA) may be used with α-thio-guanosine nucleotides according to the manufacturer's instructions to create a phosphorothioate linkage in the 5'-ppp-5' cap. Additional alternative guanosine nucleotides may be used such as α-methyl-phosphonate and seleno-phosphate nucleotides.

Additional alterations include, but are not limited to, 2'-O-methylation of the ribose sugars of 5'-terminal and/or 5'-anteterminal nucleotides of the polynucleotide (as mentioned above) on the 2'-hydroxy group of the sugar. Multiple distinct 5'-cap structures can be used to generate the 5'-cap of a polynucleotide, such as an mRNA molecule.

5'-Cap structures include those described in International Patent Publication Nos. WO2008/127688, WO 2008/016473, and WO 2011/015347, the cap structures of each of which are incorporated herein by reference.

Cap analogs, which herein are also referred to as synthetic cap analogs, chemical caps, chemical cap analogs, or structural or functional cap analogs, differ from natural (i.e., endogenous, wild-type, or physiological) 5'-caps in their chemical structure, while retaining cap function. Cap analogs may be chemically (i.e., non-enzymatically) or enzymatically synthesized and/linked to a polynucleotide.

For example, the Anti-Reverse Cap Analog (ARCA) cap contains two guanosines linked by a 5'-5'-triphosphate group, wherein one guanosine contains an N7-methyl group as well as a 3'-O-methyl group (i.e., N7,3'-O-dimethyl-guanosine-5'-triphosphate-5'-guanosine, $m^7$G-3'mppp-G, which may equivalently be designated 3' O-Me-$m^7$G(5')ppp(5')G). The 3'-O atom of the other, unaltered, guanosine becomes linked to the 5'-terminal nucleotide of the capped polynucleotide (e.g., an mRNA). The N7- and 3'-O-methylated guanosine provides the terminal moiety of the capped polynucleotide (e.g., mRNA).

Another exemplary cap is mCAP, which is similar to ARCA but has a 2'-O-methyl group on guanosine (i.e., N7,2'-O-dimethyl-guanosine-5'-triphosphate-5'-guanosine, $m^7$Gm-ppp-G).

In one embodiment, the cap is a dinucleotide cap analog. As a non-limiting example, the dinucleotide cap analog may be modified at different phosphate positions with a boranophosphate group or a phophoroselenoate group such as the dinucleotide cap analogs described in U.S. Pat. No. 8,519,110, the cap structures of which are herein incorporated by reference.

In another embodiment, the cap analog is a N7-(4-chlorophenoxyethyl) substituted dinucleotide cap analog known in the art and/or described herein. Non-limiting examples of N7-(4-chlorophenoxyethyl) substituted dinucleotide cap analogs include a N7-(4-chlorophenoxyethyl)-G(5')ppp(5')G and a N7-(4-chlorophenoxyethyl)-m3'-OG(5')ppp(5')G cap analog (see, e.g., the various cap analogs and the methods of synthesizing cap analogs described in Kore et al. Bioorganic & Medicinal Chemistry 2013 21:4570-4574; the cap structures of which are herein incorporated by reference). In another embodiment, a cap analog useful in the polynucleotides of the present invention is a 4-chloro/bromophenoxyethyl analog.

While cap analogs allow for the concomitant capping of a polynucleotide in an in vitro transcription reaction, up to 20% of transcripts remain uncapped. This, as well as the structural differences of a cap analog from endogenous 5'-cap structures of polynucleotides produced by the endogenous, cellular transcription machinery, may lead to reduced translational competency and reduced cellular stability.

Alternative polynucleotides of the invention may also be capped post-transcriptionally, using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function, and/or structure as compared to synthetic features or analogs of the prior art, or which outperforms the corresponding endogenous, wild-type, natural, or physiological feature in one or more respects. Non-limiting examples of more authentic 5'-cap structures useful in the polynucleotides of the present invention are those which, among other things, have enhanced binding of cap binding proteins, increased half life, reduced susceptibility to 5'-endonucleases, and/or reduced 5'-decapping, as compared to synthetic 5'-cap structures known in the art (or to a wild-type, natural or physiological 5'-cap structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanosine cap nucleotide wherein the cap guanosine contains an N7-methylation and the 5'-terminal nucleotide of the polynucleotide contains a 2'-O-methyl. Such a structure is termed the Cap1 structure. A Cap2 structure also includes a 2'-O-methyl on the nucleotide adjacent to the 5'-terminal nucleotide. These caps result in a higher translational-competency, cellular stability, and a reduced activation of cellular pro-inflammatory cytokines, as compared, e.g., to other 5'cap analog structures known in the art. Exemplary cap structures include 7mG(5')ppp(5')N,pN2p (Cap 0), 7mG(5')ppp(5')NlmpNp (Cap 1), 7mG(5')-ppp(5')NlmpN2mp (Cap 2), and m(7)Gpppm(3)(6,6,2')Apm(2')Apm(2')Cpm(2)(3,2')Up (Cap 4).

Because the alternative polynucleotides may be capped post-transcriptionally, and because this process is more efficient, nearly 100% of the alternative polynucleotides may be capped. This is in contrast to ~80% when a cap analog is linked to an polynucleotide in the course of an in vitro transcription reaction.

According to the present invention, 5'-terminal caps may include endogenous caps or cap analogs. According to the present invention, a 5'-terminal cap may include a guanosine analog. Useful guanosine analogs include inosine, N1-methyl-guanosine, 2'-fluoro-guanosine, 7-deaza-guanosine, 8-oxo-guanosine, 2-amino-guanosine, LNA-guanosine, and 2-azido-guanosine.

In one embodiment, the polynucleotides described herein may contain a modified 5'-cap. A modification on the 5'-cap may increase the stability of polynucleotide, increase the half-life of the polynucleotide, and could increase the polynucleotide translational efficiency. The modified 5'-cap may include, but is not limited to, one or more of the following modifications: modification at the 2'- and/or 3'-position of a capped guanosine triphosphate (GTP), a replacement of the sugar ring oxygen (that produced the carbocyclic ring) with a methylene moiety ($CH_2$), a modification at the triphosphate bridge moiety of the cap structure, or a modification at the nucleobase (G) moiety.

In some embodiments, the compound includes a morpholino linker having the structure of Formula I, wherein the morpholino group is derived from the sugar moiety at the 5'-terminus of an inverted cap structure. For example, a polynucleotide including an inverted cap structure is treated with an oxidant (e.g., sodium periodate) which results in oxidative ring opening of the sugar to two aldehydes. Condensation with a compound containing an aminooxy group results in condensation to a morpholino structure of Formula I. In some embodiments, oxidation and condensation of an inverted cap structure is carried out simultaneously with the oxidation and condensation of a sugar at the 3'-terminus resulting in addition of a morpholino linker having the structure of Formula I to both the 5'- and 3'-terminus to the polynucleotide. In some embodiments, the compound containing an aminooxy is a small molecule, e.g., an aminooxybenzyl group.

5'-UTRs

A 5'-UTR may be provided as a flanking region to the alternative polynucleotides (e.g., mRNA) of the invention. A 5'-UTR may be homologous or heterologous to the coding region found in the alternative polynucleotides (mRNA) of the invention. Multiple 5'-UTRs may be included in the flanking region and may be the same or of different sequences. Any portion of the flanking regions, including none, may be codon optimized and any may independently contain one or more different structural or chemical alterations, before and/or after codon optimization.

Shown in Table 21 in U.S. Provisional Application No. 61/775,509, and in Table 21 and in Table 22 in U.S. Provisional Application No. 61/829,372, of which are incorporated herein by reference, is a listing of the start and stop site of alternative polynucleotides (e.g., mRNA) of the invention. In Table 21 each 5'-UTR (5'-UTR-005 to 5'-UTR 68511) is identified by its start and stop site relative to its native or wild type (homologous) transcript (ENST; the identifier used in the ENSEMBL database).

To alter one or more properties of the polynucleotides (e.g., mRNA) of the invention, 5'-UTRs which are heterologous to the coding region of the alternative polynucleotides (e.g., mRNA) of the invention may be engineered into compounds of the invention. The alternative polynucleotides (e.g., mRNA) may then be administered to cells, tissue or organisms and outcomes such as protein level, localization, and/or half-life may be measured to evaluate the beneficial effects the heterologous 5'-UTR may have on the alternative polynucleotides (mRNA) of the invention. Variants of the 5'-UTRs may be utilized wherein one or more nucleotides are added or removed to the termini, including A, T, C or G. 5'-UTRs may also be codon-optimized, or altered in any manner described herein.

5'-UTRs, 3'-UTRs, and Translation Enhancer Elements (TEEs)

In one embodiment, the 5'-UTR of the polynucleotides (e.g., mRNA) may include at least one translation enhancer element. The term "translational enhancer element" refers to sequences that increase the amount of polypeptide or protein produced from a polynucleotide. As a non-limiting example, the TEE may be located between the transcription promoter and the start codon. The polynucleotides (e.g., mRNA) with at least one TEE in the 5'-UTR may include a cap at the 5'-UTR. Further, at least one TEE may be located in the 5'-UTR of polynucleotides (e.g., mRNA) undergoing cap-dependent or cap-independent translation.

In one aspect, TEEs are conserved elements in the UTR which can promote translational activity of a polynucleotide such as, but not limited to, cap-dependent or cap-independent translation. The conservation of these sequences has been previously shown by Panek et al. (Nucleic Acids Research, 2013, 1-10) across 14 species including humans.

In one non-limiting example, the TEEs known may be in the 5'-leader of the Gtx homeodomain protein (Chappell et al., Proc. Natl. Acad. Sci. USA 101:9590-9594, 2004, the TEEs of which are incorporated herein by reference).

In another non-limiting example, TEEs are disclosed as SEQ ID NOs: 1-35 in US Patent Publication No. 2009/0226470, SEQ ID NOs: 1-35 in US Patent Publication No. 2013/0177581, SEQ ID NOs: 1-35 in International Patent Publication No. WO2009/075886, SEQ ID NOs: 1-5, and 7-645 in International Patent Publication No. WO2012/009644, SEQ ID NO: 1 in International Patent Publication No. WO1999/024595, SEQ ID NO: 1 in U.S. Pat. No. 6,310,197, and SEQ ID NO: 1 in U.S. Pat. No. 6,849,405, the TEE sequences of each of which are incorporated herein by reference.

In yet another non-limiting example, the TEE may be an internal ribosome entry site (IRES), HCV-IRES or an IRES element such as, but not limited to, those described in U.S. Pat. No. 7,468,275, US Patent Publication Nos. 2007/0048776 and 2011/0124100 and International Patent Publication Nos. WO2007/025008 and WO2001/055369, the IRES sequences of each of which are incorporated herein by reference. The IRES elements may include, but are not limited to, the Gtx sequences (e.g., Gtx9-nt, Gtx8-nt, Gtx7-nt) described by Chappell et al. (Proc. Natl. Acad. Sci. USA 101:9590-9594, 2004) and Zhou et al. (Proc. Natl. Acad. Sci. USA 102:6273-6278, 2005) and in US Patent Publication Nos. 2007/0048776 and 2011/0124100 and International Patent Publication No. WO2007/025008, the IRES sequences of each of which are incorporated herein by reference.

"Translational enhancer polynucleotides" are polynucleotides which include one or more of the specific TEE exemplified herein and/or disclosed in the art (see e.g., U.S. Pat. Nos. 6,310,197, 6,849,405, 7,456,273, 7,183,395, U.S. Patent Publication Nos. 20090/226470, 2007/0048776, 2011/0124100, 2009/0093049, 2013/0177581, International Patent Publication Nos. WO2009/075886, WO2007/025008, WO2012/009644, WO2001/055371 WO1999/024595, and European Patent Nos. 2610341 and 2610340; the TEE sequences of each of which are incorporated herein by reference) or their variants, homologs or functional derivatives. One or multiple copies of a specific TEE can be present in the polynucleotides (e.g., mRNA). The TEEs in the translational enhancer polynucleotides can be organized in one or more sequence segments. A sequence segment can harbor one or more of the specific TEEs exemplified herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the specific TEEs exemplified herein, identical or different number of copies of each of the specific TEEs, and/or identical or different organization of the TEEs within each sequence segment.

In one embodiment, the polynucleotides, (e.g., mRNA) may include at least one TEE that is described in International Patent Publication Nos. WO1999/024595, WO2012/009644, WO2009/075886, WO2007/025008, WO1999/024595, European Patent Publication Nos. 2610341 and 2610340, U.S. Pat. Nos. 6,310,197, 6,849,405, 7,456,273, 7,183,395, and US Patent Publication Nos. 2009/0226470, 2011/0124100, 2007/0048776, 2009/0093049, and 2013/0177581 the TEE sequences of each of which are incorporated herein by reference. The TEE may be located in the 5'-UTR of the polynucleotides (e.g., mRNA).

In another embodiment, the polynucleotides (e.g., mRNA) may include at least one TEE that has at least 50%, at least 55%, at least 60%, at least 65%, at least 70%, at least 75%, at least 80%, at least 85%, at least 90%, at least 95% or at least 99% identity with the TEEs described in US Patent Publication Nos. 2009/0226470, 2007/0048776, 2013/0177581 and 2011/0124100, International Patent Publication Nos. WO1999/024595, WO2012/009644, WO2009/075886 and WO2007/025008, European Patent Publication Nos. 2610341 and 2610340, U.S. Pat. Nos. 6,310,197, 6,849,405, 7,456,273, 7,183,395, the TEE sequences of each of which are incorporated herein by reference.

In one embodiment, the 5'-UTR of the polynucleotides (e.g., mRNA) may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 5'-UTR of the polynucleotides (e.g., mRNA) of the present invention may be the same or different TEE sequences. The TEE sequences may be in a pattern such as ABABAB, AABBAABBAABB, or ABCABCABC, or variants thereof, repeated once, twice, or more than three times. In these patterns, each letter, A, B, or C represent a different TEE sequence at the nucleotide level.

In one embodiment, the 5'-UTR may include a spacer to separate two TEE sequences. As a non-limiting example, the spacer may be a 15 nucleotide spacer and/or other spacers known in the art. As another non-limiting example, the 5'-UTR may include a TEE sequence-spacer module repeated at least once, at least twice, at least 3 times, at least 4 times, at least 5 times, at least 6 times, at least 7 times, at least 8 times, at least 9 times, or more than 9 times in the 5'-UTR.

In another embodiment, the spacer separating two TEE sequences may include other sequences known in the art which may regulate the translation of the polynucleotides (e.g., mRNA) of the present invention such as, but not limited to, miR sequences (e.g., miR binding sites and miR seeds). As a non-limiting example, each spacer used to separate two TEE sequences may include a different miR sequence or component of a miR sequence (e.g., miR seed sequence).

In one embodiment, the TEE in the 5'-UTR of the polynucleotides (e.g., mRNA) of the present invention may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in US Patent Publication Nos. 2009/0226470, 2007/0048776, 2013/0177581 and 2011/0124100, International Patent Publication Nos. WO1999/024595, WO2012/009644, WO2009/075886 and WO2007/025008, European Patent Publication Nos. 2610341 and 2610340, and U.S. Pat. Nos. 6,310,197, 6,849,405, 7,456, 273, and 7,183,395 the TEE sequences of each of which are incorporated herein by reference. In another embodiment, the TEE in the 5'-UTR of the polynucleotides (e.g., mRNA) of the present invention may include a 5-30 nucleotide fragment, a 5-25 nucleotide fragment, a 5-20 nucleotide fragment, a 5-15 nucleotide fragment, a 5-10 nucleotide fragment of the TEE sequences disclosed in US Patent Publication Nos. 2009/0226470, 2007/0048776, 2013/0177581 and 2011/0124100, International Patent Publication Nos. WO1999/024595, WO2012/009644, WO2009/075886 and WO2007/025008, European Patent Publication Nos. 2610341 and 2610340, and U.S. Pat. Nos. 6,310,197, 6,849,405, 7,456,273, and 7,183,395; the TEE sequences of each of which are incorporated herein by reference.

In one embodiment, the TEE in the 5'-UTR of the polynucleotides (e.g., mRNA) of the present invention may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in Chappell et al. (Proc. Natl. Acad. Sci. USA 101:9590-9594, 2004) and Zhou et al. (Proc. Natl. Acad. Sci. USA 102:6273-6278, 2005), in Supplemental Table 1 and in Supplemental Table 2 disclosed by Wellensiek et al (Genome-wide profiling of human cap-independent translation-enhancing elements, Nature Methods, 2013; DOI:10.1038/NMETH.2522); the TEE sequences of each of which are herein incorporated by reference. In another embodiment, the TEE in the 5'-UTR of the polynucleotides (e.g., mRNA) of the present invention may include a 5-30 nucleotide fragment, a 5-25 nucleotide fragment, a 5-20 nucleotide fragment, a 5-15 nucleotide fragment, a 5-10 nucleotide fragment of the TEE sequences disclosed in Chappell et al. (Proc. Natl. Acad. Sci. USA 101:9590-9594, 2004) and Zhou et al. (Proc. Natl. Acad. Sci. USA 102:6273-6278, 2005), in Supplemental Table 1 and in Supplemental Table 2 disclosed by Wellensiek et al (Genome-wide profiling of human cap-independent translation-enhancing elements, Nature Methods, 2013; DOI:10.1038/NMETH.2522); the TEE sequences of each of which is incorporated herein by reference.

In one embodiment, the TEE used in the 5'-UTR of the polynucleotides (e.g., mRNA) of the present invention is an IRES sequence such as, but not limited to, those described in U.S. Pat. No. 7,468,275 and International Patent Publication No. WO2001/055369, the TEE sequences of each of which are incorporated herein by reference.

In one embodiment, the TEEs used in the 5'-UTR of the polynucleotides (e.g., mRNA) of the present invention may be identified by the methods described in US Patent Publication Nos. 2007/0048776 and 2011/0124100 and International Patent Publication Nos. WO2007/025008 and WO2012/009644, the methods of each of which are incorporated herein by reference.

In another embodiment, the TEEs used in the 5'-UTR of the polynucleotides (e.g., mRNA) of the present invention may be a transcription regulatory element described in U.S. Pat. Nos. 7,456,273 and 7,183,395, US Patent Publication No. 2009/0093049, and International Publication No. WO2001/055371, the TEE sequences of each of which is incorporated herein by reference. The transcription regulatory elements may be identified by methods known in the art, such as, but not limited to, the methods described in U.S. Pat. Nos. 7,456,273 and 7,183,395, US Patent Publication No. 2009/0093049, and International Publication No. WO2001/055371, the methods of each of which is incorporated herein by reference.

In yet another embodiment, the TEE used in the 5'-UTR of the polynucleotides (e.g., mRNA) of the present invention is a polynucleotide or portion thereof as described in U.S. Pat. Nos. 7,456,273 and 7,183,395, US Patent Publication No. 2009/0093049, and International Publication No. WO2001/055371, the TEE sequences of each of which are incorporated herein by reference.

The 5'-UTR including at least one TEE described herein may be incorporated in a monocistronic sequence such as, but not limited to, a vector system or a polynucleotide vector. As a non-limiting example, the vector systems and polynucleotide vectors may include those described in U.S. Pat. Nos. 7,456,273 and 7,183,395, US Patent Publication Nos. 2007/0048776, 2009/0093049 and 2011/0124100, and International Patent Publication Nos. WO2007/025008 and WO2001/055371, the TEE sequences of each of which are incorporated herein by reference.

In one embodiment, the TEEs described herein may be located in the 5'-UTR and/or the 3'-UTR of the polynucleotides (e.g., mRNA). The TEEs located in the 3'-UTR may be the same and/or different than the TEEs located in and/or described for incorporation in the 5'-UTR.

In one embodiment, the 3'-UTR of the polynucleotides (e.g., mRNA) may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 3'-UTR of the polynucleotides (e.g., mRNA) of the present invention may be the same or different TEE sequences. The TEE sequences may be in a pattern such as ABABAB, AABBAABBAABB, or ABCABCABC, or variants thereof, repeated once, twice, or more than three times. In these patterns, each letter, A, B, or C represent a different TEE sequence at the nucleotide level.

In one embodiment, the 3'-UTR may include a spacer to separate two TEE sequences. As a non-limiting example, the spacer may be a 15 nucleotide spacer and/or other spacers known in the art. As another non-limiting example, the 3'-UTR may include a TEE sequence-spacer module repeated at least once, at least twice, at least 3 times, at least 4 times, at least 5 times, at least 6 times, at least 7 times, at least 8 times, at least 9 times, or more than 9 times in the 3'-UTR.

In another embodiment, the spacer separating two TEE sequences may include other sequences known in the art which may regulate the translation of the polynucleotides (e.g., mRNA) of the present invention such as, but not limited to, miR sequences described herein (e.g., miR binding sites and miR seeds). As a non-limiting example, each spacer used to separate two TEE sequences may include a different miR sequence or component of a miR sequence (e.g., miR seed sequence).

In one embodiment, the incorporation of a miR sequence and/or a TEE sequence changes the shape of the stem loop region which may increase and/or decrease translation. (see e.g, Kedde et al. A *Pumilio*-induced RNA structure switch in p27-3'UTR controls miR-221 and miR-22 accessibility. Nature Cell Biology. 2010).

Sensor Sequences

In one embodiment, alternative polynucleotides (e.g., mRNA) of the invention would not only encode a polypeptide but also a sensor sequence. Sensor sequences include, for example, miRNA binding sites, transcription factor binding sites, structured mRNA sequences, and/or motifs, or artificial binding sites engineered to act as pseudo-receptors for endogenous polynucleotide binding molecules. Non-limiting examples, of polynucleotides including at least one sensor sequence are described in U.S. Provisional Patent Application Nos. 61/753,661, 61/754,159, 61/781,097, 61/829,334, 61/839,893, 61/842,733, and 61/857,304, the sensor sequences of each of which are incorporated herein by reference.

In one embodiment, microRNA ("miRNA") profiling of the target cells or tissues is conducted to determine the presence or absence of miRNA in the cells or tissues.

miRNAs (or miRNA) are 19-25 nucleotide long noncoding RNAs that bind to the 3'-UTR of polynucleotides and down-regulate gene expression either by reducing polynucleotide stability or by inhibiting translation. The alternative polynucleotides (e.g., mRNA) of the invention may include one or more miRNA target sequences, miRNA sequences, or miRNA seeds. Such sequences may correspond to any known miRNA such as those taught in US Publication Nos. 2005/0261218 and 2005/0059005, the miRNA sequences of which are incorporated herein by reference.

A miRNA sequence includes a "seed" region, i.e., a sequence in the region of positions 2-8 of the mature miRNA, which sequence has perfect Watson-Crick complementarity to the miRNA target sequence. A miRNA seed may include positions 2-8 or 2-7 of the mature miRNA. In some embodiments, a miRNA seed may include 7 nucleotides (e.g., nucleotides 2-8 of the mature miRNA), wherein the seed-complementary site in the corresponding miRNA target is flanked by an adenosine (A) opposed to miRNA position 1. In some embodiments, a miRNA seed may include 6 nucleotides (e.g., nucleotides 2-7 of the mature miRNA), wherein the seed-complementary site in the corresponding miRNA target is flanked by an adenosine (A) opposed to miRNA position 1. See for example, Grimson A, Farh K K, Johnston W K, Garrett-Engele P, Lim L P, Bartel D P; Mol Cell. 2007 Jul. 6; 27(1):91-105. The bases of the miRNA seed have complete complementarity with the target sequence. By engineering miRNA target sequences into the 3'-UTR of polynucleotides (e.g., mRNA) of the invention one can target the molecule for degradation or reduced translation, provided the miRNA in question is available. This process will reduce the hazard of off target effects upon polynucleotide molecule delivery. Identification of miRNA, miRNA target regions, their expression patterns, and their role in biology have been reported (e.g., see Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403; and all references therein).

For example, if the polynucleotide is not intended to be delivered to the liver but ends up there, then miR-122, a miRNA abundant in liver, can inhibit the expression of the polypeptide of interest if one or multiple target sites of miR-122 are engineered into the 3'-UTR of the alternative polynucleotides. Introduction of one or multiple binding sites for different miRNA can be engineered to further decrease the longevity, stability, and protein translation of an alternative polynucleotides. As used herein, the term "miRNA site" refers to a miRNA target site or a miRNA recognition site, or any nucleotide sequence to which a miRNA binds or associates. It should be understood that "binding" may follow traditional Watson-Crick hybridization rules or may reflect any stable association of the miRNA with the target sequence at or adjacent to the miRNA site.

Conversely, for the purposes of the alternative polynucleotides of the present invention, miRNA binding sites can be engineered out of (i.e., removed from) sequences in which they naturally occur in order to increase protein expression in specific tissues. For example, miR-122 binding sites may be removed to improve protein expression in the liver.

In one embodiment, the alternative polynucleotides of the present invention may include at least one miRNA-binding site in the 3'-UTR in order to direct cytotoxic or cytoprotective polynucleotide therapeutics to specific cells such as, but not limited to, normal and/or cancerous cells (e.g., HEP3B or SNU449).

In another embodiment, the alternative polynucleotides of the present invention may include three miRNA-binding sites in the 3'-UTR in order to direct cytotoxic or cytoprotective polynucleotide therapeutics to specific cells such as, but not limited to, normal, and/or cancerous cells (e.g., HEP3B or SNU449).

Regulation of expression in multiple tissues can be accomplished through introduction and/or removal of one or several polynucleotide binding sites. The decision of removal and/or insertion of miRNA binding sites, or any combination, is dependent on miRNA expression patterns and their profilings in diseases.

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126).

Specifically, miRNAs are known to be differentially expressed in immune cells, such as antigen presenting cells (APCs) (e.g., dendritic cells and macrophages), macrophages, monocytes, B lymphocytes, T lymphocytes, granuocytes, and natural killer cells. Immune cell specific miRNAs are involved in immunogenicity, autoimmunity, the immune-response to infection, inflammation, as well as unwanted immune response after gene therapy and tissue/organ transplantation. Immune cells specific miRNAs also regulate many aspects of development, proliferation, differentiation and apoptosis of immune cells. For example, miR-142 and miR-146 are exclusively expressed in the immune cells, particularly abundant in myeloid dendritic cells. It was demonstrated in the art that the immune response to exogenous polynucleotides was shut-off by adding miR-142 binding sites to the 3'-UTR of the delivered gene construct, enabling more stable gene transfer in tissues and cells. miR-142 efficiently degrades the exogenous polynucleotide in antigen presenting cells and suppresses cytotoxic elimination of transduced cells (e.g., see Annoni A et al., Blood, 2009, 114, 5152-5161; Brown B D, et al., Nat Med. 2006, 12(5), 585-591; and Brown B D, et al., Blood, 2007, 110(13): 4144-4152).

An antigen-mediated immune response can refer to an immune response triggered by foreign antigens, which, when entering an organism, are processed by the antigen presenting cells and displayed on the surface of the antigen presenting cells. T-cells can recognize the presented antigen and induce a cytotoxic elimination of cells that express the antigen.

Introducing the miR-142 binding site into the 3'-UTR of a polynucleotide of the present invention can selectively repress the gene expression in the antigen presenting cells through miR-142 mediated polynucleotide degradation, limiting antigen presentation in APCs (e.g., dendritic cells), and thereby preventing antigen-mediated immune response after the delivery of the polynucleotides. The polynucleotides are therefore stably expressed in target tissues or cells without triggering cytotoxic elimination.

In one embodiment, miRNAs binding sites that are known to be expressed in immune cells, in particular, the antigen presenting cells, can be engineered into the polynucleotide to suppress the expression of the sensor-signal polynucleotide in APCs through miRNA mediated polynucleotide degradation, subduing the antigen-mediated immune response, while the expression of the polynucleotide is maintained in non-immune cells where the immune cell specific miRNAs are not expressed. For example, to prevent the immunogenic reaction caused by a liver specific protein expression, the miR-122 binding site can be removed and the miR-142 (and/or miR-146) binding sites can be engineered into the 3'-UTR of the polynucleotide.

To further drive the selective degradation and suppression of polynucleotides in APCs and macrophage, the polynucleotide may include another negative regulatory element in the 3'-UTR, either alone or in combination with mir-142 and/or mir-146 binding sites. As a non-limiting example, one regulatory element is the Constitutive Decay Elements (CDEs).

In one embodiment, the binding sites of embryonic stem cell specific miRNAs can be included in or removed from the 3'-UTR of the polynucleotide to modulate the development and/or differentiation of embryonic stem cells, to inhibit the senescence of stem cells in a degenerative condition (e.g., degenerative diseases), or to stimulate the senescence and apoptosis of stem cells in a disease condition (e.g., cancer stem cells).

As a non-limiting example, miRNA sites that are over-expressed in certain cancer and/or tumor cells can be removed from the 3'-UTR of the polynucleotide encoding the polypeptide of interest, restoring the expression suppressed by the over-expressed miRNAs in cancer cells, thus ameliorating the co-responsive biological function, for instance, transcription stimulation and/or repression, cell cycle arrest, apoptosis, and cell death. Normal cells and tissues, wherein miRNAs expression is not up-regulated, will remain unaffected.

MiRNA can also regulate complex biological processes such as angiogenesis (miR-132) (Anand and Cheresh Curr Opin Hematol 2011 18:171-176). In the alternative polynucleotides of the invention, binding sites for miRNAs that are involved in such processes may be removed or introduced, in order to tailor the expression of the alternative polynucleotides expression to biologically relevant cell types or to the context of relevant biological processes. In this context, the polynucleotides are defined as auxotrophic polynucleotides.

MiRNA gene regulation may be influenced by the sequence surrounding the miRNA such as, but not limited to, the species of the surrounding sequence, the type of sequence (e.g., heterologous, homologous, or artificial), regulatory elements in the surrounding sequence and/or structural elements in the surrounding sequence. The miRNA may be influenced by the 5'-UTR and/or the 3'-UTR. As a non-limiting example, a non-human 3'-UTR may increase the regulatory effect of the miRNA sequence on the expression of a polypeptide of interest compared to a human 3'-UTR of the same sequence type.

In one embodiment, other regulatory elements and/or structural elements of the 5'-UTR can influence miRNA mediated gene regulation. One example of a regulatory element and/or structural element is a structured IRES (Internal Ribosome Entry Site) in the 5'UTR, which is necessary for the binding of translational elongation factors to initiate protein translation. EIF4A2 binding to this secondarily structured element in the 5'-UTR is necessary for miRNA mediated gene expression (e.g., see Meijer H A et al., Science, 2013, 340, 82-85). The alternative polynucleotides of the invention can further be alternative to include this structured 5'-UTR in order to enhance miRNA mediated gene regulation.

At least one miRNA site can be engineered into the 3'-UTR of the alternative polynucleotides of the present invention. In this context, at least two, at least three, at least four, at least five, at least six, at least seven, at least eight, at least nine, at least ten, or more miRNA sites may be engineered into the 3'-UTR of the polynucleotides of the present invention. In one embodiment, the miRNA sites incorporated into the alternative polynucleotides may be the same or may be different miRNA sites. In another embodiment, the miRNA sites incorporated into the alternative polynucleotides may target the same or different tissues in the body. As a non-limiting example, through the introduction of tissue-, cell-type-, or disease-specific miRNA binding sites in the 3'-UTR of an alternative polynucleotide (e.g., mRNA), the degree of expression in specific cell types (e.g., hepatocytes, myeloid cells, endothelial cells, cancer cells) can be reduced.

In one embodiment, a miRNA site can be engineered near the 5'-terminus of the 3'-UTR, about halfway between the 5'-terminus and 3'-terminus of the 3'-UTR, and/or near the 3'-terminus of the 3'-UTR. As a non-limiting example, a miRNA site may be engineered near the 5'-terminus of the 3'-UTR and about halfway between the 5'-terminus and 3'-terminus of the 3'-UTR. As another non-limiting example, a miRNA site may be engineered near the 3'-terminus of the 3'-UTR and about halfway between the 5'-terminus and 3'-terminus of the 3'-UTR. As yet another non-limiting example, a miRNA site may be engineered near the 5'-terminus of the 3'-UTR and near the 3'-terminus of the 3'-UTR.

In another embodiment, a 3'-UTR can include four miRNA sites. The miRNA sites may be complete miRNA binding sites, miRNA seed sequences, and/or miRNA binding site sequences without the seed sequence.

In one embodiment, a polynucleotide of the invention may be engineered to include at least one miRNA in order to dampen the antigen presentation by antigen presenting cells. The miRNA may be the complete miRNA sequence, the miRNA seed sequence, the miRNA sequence without the seed or a combination thereof. As a non-limiting example, the miRNA incorporated into the polynucleotide may be specific to the hematopoietic system. As another non-limiting example, the miRNA incorporated into the polynucleotide of the invention to dampen antigen presentation is miR-142-3p.

In one embodiment, a polynucleotide may be engineered to include miRNA sites which are expressed in different tissues of a subject. As a non-limiting example, an alternative polynucleotide of the present invention may be engineered to include miR-192 and miR-122 to regulate expression of the alternative polynucleotide in the liver and kidneys of a subject. In another embodiment, an alternative polynucleotide may be engineered to include more than one miRNA sites for the same tissue. For example, an alternative polynucleotide of the present invention may be engineered to include miR-17-92 and miR-126 to regulate expression of the alternative polynucleotide in endothelial cells of a subject.

In one embodiment, the therapeutic window and or differential expression associated with the target polypeptide encoded by the alternative polynucleotide encoding a signal (also referred to herein as a polynucleotide) of the invention may be altered. For example, polynucleotides may be designed whereby a death signal is more highly expressed in cancer cells (or a survival signal in a normal cell) by virtue of the miRNA signature of those cells. Where a cancer cell expresses a lower level of a particular miRNA, the polynucleotide encoding the binding site for that miRNA (or miRNAs) would be more highly expressed. Hence, the target polypeptide encoded by the polynucleotide is selected as a protein which triggers or induces cell death. Neighboring non-cancer cells, harboring a higher expression of the same miRNA would be less affected by the encoded death signal as the polynucleotide would be expressed at a lower level due to the effects of the miRNA binding to the binding site or "sensor" encoded in the 3'-UTR. Conversely, cell survival or cytoprotective signals may be delivered to tissues containing cancer and non-cancerous cells where a miRNA has a higher expression in the cancer cells—the result being a lower survival signal to the cancer cell and a larger survival signature to the normal cell. Multiple polynucleotides may be designed and administered having different signals according to the previous paradigm.

In one embodiment, the expression of a polynucleotide may be controlled by incorporating at least one sensor sequence in the polynucleotide and formulating the polynucleotide. As a non-limiting example, a polynucleotide may be targeted to an orthotopic tumor by having a polynucleotide incorporating a miR-122 binding site and formulated in a lipid nanoparticle including the cationic lipid DLin-KC2-DMA.

According to the present invention, the polynucleotides may be altered as to avoid the deficiencies of other polypeptide-encoding molecules of the art. Hence, in this embodiment the polynucleotides are referred to as alternative polynucleotides.

Through an understanding of the expression patterns of miRNA in different cell types, alternative polynucleotides can be engineered for more targeted expression in specific cell types or only under specific biological conditions. Through introduction of tissue-specific miRNA binding sites, alternative polynucleotides could be designed that would be optimal for protein expression in a tissue or in the context of a biological condition.

Transfection experiments can be conducted in relevant cell lines, using engineered alternative polynucleotides and protein production can be assayed at various time points post-transfection. For example, cells can be transfected with different miRNA binding site-engineering polynucleotides (e.g., mRNA) and by using an ELISA kit to the relevant protein and assaying protein produced at 6 hours, 12 hours, 24 hours, 48 hours, 72 hours, and 7 days post-transfection. In vivo experiments can also be conducted using miRNA-binding site-engineered molecules to examine changes in tissue-specific expression of formulated alternative polynucleotides.

In some embodiments, alternative polynucleotides can be designed to incorporate miRNA binding region sites that either have 100% identity to known seed sequences or have less than 100% identity to seed sequences. The seed sequence can be partially mutated to decrease miRNA binding affinity and as such result in reduced downmodulation of that polynucleotide transcript. In essence, the degree of match or mis-match between the target polynucleotide and the miRNA seed can act as a rheostat to more finely tune the ability of the miRNA to modulate protein expression. In addition, mutation in the non-seed region of a miRNA binding site may also impact the ability of a miRNA to modulate protein expression.

In one embodiment, a miR sequence may be incorporated into the loop of a stem loop.

In another embodiment, a miR seed sequence may be incorporated in the loop of a stem loop and a miR binding site may be incorporated into the 5'- or 3'-stem of the stem loop.

In one embodiment, a TEE may be incorporated on the 5'-end of the stem of a stem loop and a miR seed may be incorporated into the stem of the stem loop. In another embodiment, a TEE may be incorporated on the 5'-end of the stem of a stem loop, a miR seed may be incorporated into the stem of the stem loop, and/or a miR binding site may be incorporated into the 3'-end of the stem or the sequence after the stem loop. The miR seed and the miR binding site may be for the same and/or different miR sequences.

In one embodiment, the incorporation of a miR sequence and/or a TEE sequence changes the shape of the stem loop region which may increase and/or decrease translation. (see e.g, Kedde et al. Nature Cell Biology. 2010).

In one embodiment, the incorporation of a miR sequence and/or a TEE sequence changes the shape of the stem loop region which may increase and/or decrease translation. (see e.g, Kedde et al. Nature Cell Biology. 2010).

In one embodiment, the 5'-UTR may include at least one miRNA sequence. The miRNA sequence may be, but is not limited to, a 19 or 22 nucleotide sequence and/or a miRNA sequence without the seed.

In one embodiment the miRNA sequence in the 5'-UTR may be used to stabilize the polynucleotide (e.g., mRNA) described herein.

In another embodiment, a miRNA sequence in the 5'-UTR may be used to decrease the accessibility of the site of translation initiation such as, but not limited to a start codon. Matsuda et al (PLoS One. 2010 11 (5):e15057) used antisense locked nucleic acid (LNA) oligonucleotides and exon-junction complexes (EJCs) around a start codon (−4 to +37 where the A of the AUG codons is +1) in order to decrease the accessibility to the first start codon (AUG). Matsuda showed that by altering the sequence around the start codon with an LNA or EJC the efficiency, length, and structural stability of the polynucleotide (e.g., mRNA) is affected. The polynucleotides (e.g., mRNA) of the present invention may include a miRNA sequence, instead of the LNA or EJC sequence described by Matsuda et al, near the site of translation initiation in order to decrease the accessibility to the site of translation initiation. The site of translation initiation may be prior to, after or within the miRNA sequence. As a non-limiting example, the site of translation initiation may be located within a miRNA sequence such as a seed sequence or binding site. As another non-limiting example, the site of translation initiation may be located within a miR-122 sequence such as the seed sequence or the mir-122 binding site.

In one embodiment, the polynucleotides (e.g., mRNA) of the present invention may include at least one miRNA in order to dampen the antigen presentation by antigen presenting cells. The miRNA may be the complete miRNA sequence, the miRNA seed sequence, the miRNA sequence without the seed or a combination thereof. As a non-limiting example, the miRNA incorporated into the polynucleotides (e.g., mRNA) of the present invention may be specific to the hematopoietic system. As another non-limiting example, the miRNA incorporated into the polynucleotides (e.g., mRNA) of the present invention to dampen antigen presentation is miR-142-3p.

In one embodiment, the polynucleotides (e.g., mRNA) of the present invention may include at least one miRNA in order to dampen expression of the encoded polypeptide in a cell of interest. As a non-limiting example, the polynucleotides (e.g., mRNA) of the present invention may include at least one miR-122 binding site in order to dampen expression of an encoded polypeptide of interest in the liver. As another non-limiting example, the polynucleotides (e.g., mRNA) of the present invention may include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence.

In one embodiment, the polynucleotides (e.g., mRNA) of the present invention may include at least one miRNA binding site in the 3'-UTR in order to selectively degrade polynucleotide therapeutics in the immune cells to subdue unwanted immunogenic reactions caused by therapeutic delivery. As a non-limiting example, the miRNA binding site may be the alternative polynucleotides more unstable in antigen presenting cells. Non-limiting examples of these miRNA include mir-142-5p, mir-142-3p, mir-146a-5p and mir-146-3p.

In one embodiment, the polynucleotides (e.g., mRNA) of the present invention includes at least one miRNA sequence in a region of the polynucleotide (e.g., mRNA) which may interact with a RNA binding protein.

RNA Motifs for RNA Binding Proteins (RBPs)

RNA binding proteins (RBPs) can regulate numerous aspects of co- and post-transcription gene expression such as, but not limited to, RNA splicing, localization, translation, turnover, polyadenylation, capping, alteration, export and localization. RNA-binding domains (RBDs), such as, but not limited to, RNA recognition motifs (RR) and hnRNP K-homology (KH) domains, typically regulate the sequence association between RBPs and their RNA targets (Ray et al. Nature 2013. 499:172-177). In one embodiment, the canonical RBDs can bind short RNA sequences. In another embodiment, the canonical RBDs can recognize structure RNAs.

In one embodiment, to increase the stability of the polynucleotide of interest, an polynucleotide encoding HuR can be co-transfected or co-injected along with the polynucleotide of interest into the cells or into the tissue. These proteins can also be tethered to the polynucleotide of interest in vitro and then administered to the cells together. Poly A binding protein, PABP interacts with eukaryotic translation initiation factor eIF4G to stimulate translational initiation. Co-administration of polynucleotides encoding these RBPs along with the polynucleotide drug and/or tethering these proteins to the polynucleotide drug in vitro and administering the protein-bound polynucleotide into the cells can increase the translational efficiency of the polynucleotide. The same concept can be extended to co-administration of polynucleotide along with polynucleotides encoding various translation factors and facilitators as well as with the proteins themselves to influence polynucleotide stability and/or translational efficiency.

In one embodiment, the polynucleotides (e.g., mRNA) may include at least one RNA-binding motif such as, but not limited to a RNA-binding domain (RBD).

In one embodiment, the RBD may be any of the RBDs, fragments, or variants thereof described by Ray et al. (Nature 2013. 499:172-177; the RBD sequences of which are incorporated herein by reference).

In one embodiment, the polynucleotides (e.g., mRNA) of the present invention may include a sequence for at least one RNA-binding domain (RBDs). When the polynucleotides (e.g., mRNA) of the present invention include more than one RBD, the RBDs do not need to be from the same species or even the same structural class.

In one embodiment, at least one flanking region (e.g., the 5'-UTR and/or the 3'-UTR) may include at least one RBD.

In another embodiment, the first flanking region and the second flanking region may both include at least one RBD. The RBD may be the same or each of the RBDs may have at least 60% sequence identity to the other RBD. As a non-limiting example, at least one RBD may be located before, after, and/or within the 3'-UTR of the polynucleotides (e.g., mRNA) of the present invention. As another non-limiting example, at least one RBD may be located before or within the first 300 nucleosides of the 3'-UTR.

In another embodiment, the polynucleotides (e.g., mRNA) of the present invention may include at least one RBD in the first region of linked nucleosides. The RBD may be located before, after, or within a coding region (e.g., the ORF).

In yet another embodiment, the first region of linked nucleosides and/or at least one flanking region may include at least one RBD. As a non-limiting example, the first region of linked nucleosides may include a RBD related to splicing factors and at least one flanking region may include a RBD for stability and/or translation factors.

In one embodiment, the polynucleotides (e.g., mRNA) of the present invention may include at least one RBD located in a coding and/or non-coding region of the polynucleotides (e.g., mRNA).

In one embodiment, at least one RBD may be incorporated into at least one flanking region to increase the stability of the polynucleotides (e.g., mRNA) of the present invention.

In one embodiment, a miRNA sequence in a RNA binding protein motif may be used to decrease the accessibility of the site of translation initiation such as, but not limited to a start codon. The polynucleotides (e.g., mRNA) of the present invention may include a miRNA sequence, instead of the LNA or EJC sequence described by Matsuda et al, near the site of translation initiation in order to decrease the accessibility to the site of translation initiation. The site of translation initiation may be prior to, after, or within the miRNA sequence. As a non-limiting example, the site of translation initiation may be located within a miRNA sequence such as a seed sequence or binding site. As another non-limiting example, the site of translation initiation may be located within a miR-122 sequence such as the seed sequence or the mir-122 binding site.

In another embodiment, an antisense locked nucleic acid (LNA) oligonucleotides and exon-junction complexes (EJCs) may be used in the RNA binding protein motif. The LNA and EJCs may be used around a start codon (−4 to +37 where the A of the AUG codons is +1) in order to decrease the accessibility to the first start codon (AUG).

3'-UTRs and Triple Helices

In one embodiment, polynucleotides of the present invention may include a triple helix on the 3'-end of the alternative polynucleotide. The 3'-end of the polynucleotides of the present invention may include a triple helix alone or in combination with a poly-A region.

In one embodiment, the polynucleotide of the present invention may include at least a first and a second U-rich region, a conserved stem loop region between the first and second region, and/or an A-rich region. The first and second U-rich region and the A-rich region may associate to form a triple helix on the 3'-end of the polynucleotide. This triple helix may stabilize the polynucleotide, enhance the translational efficiency of the polynucleotide and/or protect the 3'-end from degradation. Exemplary triple helices include, but are not limited to, the triple helix sequence of metastasis-associated lung adenocarcinoma transcript 1 (MALAT1), MEN-β and polyadenylated nuclear (PAN) RNA (See Wilusz et al., Genes & Development 2012 26:2392-2407; the triple helix sequence of which are herein incorporated by reference). In one embodiment, the 3'-end of the alternative polynucleotides of the present invention includes a first U-rich region including TTTTTCTTTT (SEQ ID NO: 4), a second U-rich region including TTTTGCTTTTT (SEQ ID NO: 5) or TTTTGCTTTT (SEQ ID NO: 6), and/or an A-rich region including AAAAAGCAAAA (SEQ ID NO: 7). In another embodiment, the 3'-end of the polynucleotides of the present invention includes a triple helix formation structure including a first U-rich region, a conserved region, a second U-rich region, and an A-rich region.

In one embodiment, the triple helix may be formed from the cleavage of a MALAT1 sequence prior to the cloverleaf structure. While not meaning to be bound by theory, MALAT1 is a long non-coding RNA which, when cleaved, forms a triple helix and a tRNA-like cloverleaf structure. The MALAT1 transcript then localizes to nuclear speckles and the tRNA-like cloverleaf localizes to the cytoplasm (e.g., see Wilusz et al. Cell 2008 135(5): 919-932).

As a non-limiting example, the terminal end of the polynucleotide of the present invention including the MALAT1 sequence can then form a triple helix structure, after RNaseP cleavage from the cloverleaf structure, which stabilizes the polynucleotide (e.g., see Peart et al. Non-mRNA 3'-end formation: how the other half lives; WIREs RNA 2013).

In one embodiment, the polynucleotides (e.g., mRNA) described herein include a MALAT1 sequence. In another embodiment, the polynucleotides (e.g., mRNA) may be polyadenylated. In yet another embodiment, the polynucleotides (e.g., mRNA) is not polyadenylated but has an increased resistance to degradation compared to unaltered polynucleotides (e.g., mRNA).

In one embodiment, the polynucleotides of the present invention may include a MALAT1 sequence in the second flanking region (e.g., the 3'-UTR). As a non-limiting example, the MALAT1 sequence may be human or mouse.

In another embodiment, the cloverleaf structure of the MALAT1 sequence may also undergo processing by RNaseZ and CCA adding enzyme to form a tRNA-like structure called mascRNA (MALAT1-associated small cytoplasmic RNA). As a non-limiting example, the mascRNA may encode a protein or a fragment thereof and/or may include a miRNA sequence. The mascRNA may include at least one chemical alteration described herein.

Stem Loops

In one embodiment, the polynucleotides of the present invention may include a stem loop such as, but not limited to, a histone stem loop. The stem loop may be a nucleotide sequence that is about 25 or about 26 nucleotides in length such as, but not limited to, SEQ ID NOs: 7-17 as described in International Patent Publication No. WO2013/103659, of which SEQ ID NOs: 7-17 are incorporated herein by reference. The histone stem loop may be located 3'-relative to the coding region (e.g., at the 3'-terminus of the coding region). As a non-limiting example, the stem loop may be located at the 3'-end of a polynucleotide described herein. In some embodiments, the polynucleotide includes more than one stem loop (e.g., two stem loops). In some embodiments, the polynucleotides include any of the stem loop sequences described in International Patent Publication Nos. WO2012/019780 and WO201502667, the stem loop sequences of which are herein incorporated by reference. In some embodiments, the polynucleotide includes the stem loop sequence CAAAGGCTCTTTTCAGAGCCACCA (SEQ ID NO: 8). In some embodiments, the polynucleotide includes the stem loop sequence CAAAGGCUCUUUUCAGAGC-CACCA (SEQ ID NO: 9).

In one embodiment, the stem loop may be located in a second terminal region. As a non-limiting example, the stem loop may be located within an untranslated region (e.g., 3'-UTR) in a second terminal region.

In one embodiment, the polynucleotide such as, but not limited to mRNA, which includes the histone stem loop may be stabilized by the addition of a 3'-stabilizing region (e.g., a 3'-stabilizing region including at least one chain terminating nucleoside). Not wishing to be bound by theory, the addition of at least one chain terminating nucleoside may slow the degradation of a polynucleotide and thus can increase the half-life of the polynucleotide.

In another embodiment, the polynucleotide such as, but not limited to mRNA, which includes the histone stem loop may be stabilized by an alteration to the 3'-region of the polynucleotide that can prevent and/or inhibit the addition of oligio(U) (see e.g., International Patent Publication No. WO2013/103659,).

In yet another embodiment, the polynucleotide such as, but not limited to mRNA, which includes the histone stem loop may be stabilized by the addition of an oligonucleotide that terminates in a 3'-deoxynucleoside, 2',3'-dideoxy-nucleoside 3'-O— methylnucleosides, 3'-O-ethylnucleosides, 3'-arabinosides, and other alternative nucleosides known in the art and/or described herein.

In one embodiment, the polynucleotides of the present invention may include a histone stem loop, a poly-A region, and/or a 5'-cap structure. The histone stem loop may be before and/or after the poly-A region. The polynucleotides including the histone stem loop and a poly-A region sequence may include a chain terminating nucleoside described herein.

In another embodiment, the polynucleotides of the present invention may include a histone stem loop and a 5'-cap structure. The 5'-cap structure may include, but is not limited to, those described herein and/or known in the art.

In one embodiment, the conserved stem loop region may include a miR sequence described herein. As a non-limiting example, the stem loop region may include the seed sequence of a miR sequence described herein. In another non-limiting example, the stem loop region may include a miR-122 seed sequence.

In another embodiment, the conserved stem loop region may include a miR sequence described herein and may also include a TEE sequence.

In one embodiment, the incorporation of a miR sequence and/or a TEE sequence changes the shape of the stem loop region which may increase and/or decrease translation. (see e.g, Kedde et al. A Pumilio-induced RNA structure switch in p27-3'UTR controls miR-221 and miR-22 accessibility. Nature Cell Biology. 2010, herein incorporated by reference in its entirety).

In one embodiment, the alternative polynucleotides described herein may include at least one histone stem-loop and a poly-A region or polyadenylation signal. Non-limiting examples of polynucleotide sequences encoding for at least one histone stem-loop and a poly-A region or a polyadenylation signal are described in International Patent Publication No. WO2013/120497, WO2013/120629, WO2013/120500, WO2013/120627, WO2013/120498, WO2013/120626, WO2013/120499 and WO2013/120628, the sequences of each of which are incorporated herein by reference. In one embodiment, the polynucleotide encoding for a histone stem loop and a poly-A region or a polyadenylation signal may code for a pathogen antigen or fragment thereof such as the polynucleotide sequences described in International Patent Publication No WO2013/120499 and WO2013/120628, the sequences of both of which are incorporated herein by reference. In another embodiment, the polynucleotide encoding for a histone stem loop and a poly-A region or a polyadenylation signal may code for a therapeutic protein such as the polynucleotide sequences described in International Patent Publication No WO2013/120497 and WO2013/120629, the sequences of both of which are incorporated herein by reference. In one embodiment, the polynucleotide encoding for a histone stem loop and a poly-A region or a polyadenylation signal may code for a tumor antigen or fragment thereof such as the polynucleotide sequences described in International Patent Publication No WO2013/120500 and WO2013/120627, the sequences of both of which are incorporated herein by reference. In another embodiment, the polynucleotide encoding for a histone stem loop and a poly-A region or a polyadenylation signal may code for a allergenic antigen or an autoimmune self-antigen such as the polynucleotide sequences described in International Patent Publication No WO2013/120498 and WO2013/120626, the sequences of both of which are incorporated herein by reference.

Poly-A Regions

During RNA processing, a long chain of adenosine nucleotides (poly-A region) is normally added to messenger RNA (mRNA) molecules to increase the stability of the molecule. Immediately after transcription, the 3'-end of the transcript is cleaved to free a 3'-hydroxy. Then poly-A polymerase adds a chain of adenosine nucleotides to the RNA. The process, called polyadenylation, adds a poly-A region that is between 100 and 250 residues long (SEQ ID NO: 31).

Unique poly-A region lengths may provide certain advantages to the alternative polynucleotides of the present invention.

Generally, the length of a poly-A region of the present invention is at least 30 nucleotides in length. In another embodiment, the poly-A region is at least 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 70 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1700 nucleotides. In another embodiment, the length is at least 1800 nucleotides. In another embodiment, the length is at least 1900 nucleotides. In another embodiment, the length is at least 2000 nucleotides. In another embodiment, the length is at least 2500 nucleotides. In another embodiment, the length is at least 3000 nucleotides.

In one embodiment, the poly-A region may be 80 nucleotides, 120 nucleotides, 160 nucleotides in length on an alternative polynucleotide molecule described herein.

In another embodiment, the poly-A region may be 20, 40, 80, 100, 120, 140 or 160 nucleotides in length on an alternative polynucleotide molecule described herein.

In one embodiment, the poly-A region is designed relative to the length of the overall alternative polynucleotide. This design may be based on the length of the coding region of the alternative polynucleotide, the length of a particular feature or region of the alternative polynucleotide (such as mRNA), or based on the length of the ultimate product expressed from the alternative polynucleotide. When relative to any feature of the alternative polynucleotide (e.g., other than the mRNA portion which includes the poly-A region) the poly-A region may be 10, 20, 30, 40, 50, 60, 70, 80, 90 or 100% greater in length than the additional feature. The poly-A region may also be designed as a fraction of the alternative polynucleotide to which it belongs. In this context, the poly-A region may be 10, 20, 30, 40, 50, 60, 70, 80, or 90% or more of the total length of the construct or the total length of the construct minus the poly-A region.

In one embodiment, engineered binding sites and/or the conjugation of polynucleotides (e.g., mRNA) for poly-A binding protein may be used to enhance expression. The engineered binding sites may be sensor sequences which can operate as binding sites for ligands of the local microenvironment of the polynucleotides (e.g., mRNA). As a non-limiting example, the polynucleotides (e.g., mRNA) may include at least one engineered binding site to alter the binding affinity of poly-A binding protein (PABP) and analogs thereof. The incorporation of at least one engineered binding site may increase the binding affinity of the PABP and analogs thereof.

Additionally, multiple distinct polynucleotides (e.g., mRNA) may be linked together to the PABP (poly-A binding protein) through the 3'-end using alternative nucleotides at the 3'-terminus of the poly-A region. Transfection experiments can be conducted in relevant cell lines at and protein production can be assayed by ELISA at 12 hours, 24 hours, 48 hours, 72 hours, and day 7 post-transfection. As a non-limiting example, the transfection experiments may be used to evaluate the effect on PABP or analogs thereof binding affinity as a result of the addition of at least one engineered binding site.

In one embodiment, a poly-A region may be used to modulate translation initiation. While not wishing to be bound by theory, the poly-A region recruits PABP which in turn can interact with translation initiation complex and thus may be essential for protein synthesis.

In another embodiment, a poly-A region may also be used in the present invention to protect against 3'-5'-exonuclease digestion.

In one embodiment, the polynucleotides (e.g., mRNA) of the present invention are designed to include a polyA-G Quartet. The G-quartet is a cyclic hydrogen bonded array of four guanosine nucleotides that can be formed by G-rich sequences in both DNA and RNA. In this embodiment, the G-quartet is incorporated at the end of the poly-A region. The resultant polynucleotides (e.g., mRNA) may be assayed for stability, protein production and other parameters including half-life at various time points. It has been discovered that the polyA-G quartet results in protein production equivalent to at least 75% of that seen using a poly-A region of 120 nucleotides alone (SEQ ID NO: 30).

In one embodiment, the polynucleotides (e.g., mRNA) of the present invention may include a poly-A region and may be stabilized by the addition of a 3'-stabilizing region. The polynucleotides (e.g., mRNA) with a poly-A region may further include a 5'-cap structure.

In another embodiment, the polynucleotides (e.g., mRNA) of the present invention may include a poly-A-G Quartet. The polynucleotides (e.g., mRNA) with a poly-A-G Quartet may further include a 5'-cap structure.

In one embodiment, the 3'-stabilizing region which may be used to stabilize the polynucleotides (e.g., mRNA) including a poly-A region or poly-A-G Quartet may be, but is not limited to, those described in International Patent Publication No. WO2013/103659, the poly-A regions and poly-A-G Quartets of which are incorporated herein by reference. In another embodiment, the 3'-stabilizing region which may be used with the present invention include a chain termination nucleoside such as 3'-deoxyadenosine (cordycepin), 3'-deoxyuridine, 3'-deoxycytosine, 3'-deoxyguanosine, 3'-deoxythymine, 2',3'-dideoxynucleosides, such as 2',3'-dideoxyadenosine, 2',3'-dideoxyuridine, 2',3'-dideoxycytosine, 2',3'-dideoxyguanosine, 2',3'-dideoxythymine, a 2'-deoxynucleoside, or an O-methylnucleoside.

In another embodiment, the polynucleotide such as, but not limited to mRNA, which include a polyA region or a poly-A-G Quartet may be stabilized by an alteration to the 3'-region of the polynucleotide that can prevent and/or inhibit the addition of oligio(U) (see e.g., International Patent Publication No. WO2013/103659).

In yet another embodiment, the polynucleotide such as, but not limited to mRNA, which include a poly-A region or a poly-A-G Quartet may be stabilized by the addition of an oligonucleotide that terminates in a 3'-deoxynucleoside, 2',3'-dideoxynucleoside 3'-O— methylnucleosides, 3'-O-ethylnucleosides, 3'-arabinosides, and other alternative nucleosides known in the art and/or described herein.

Poly-C Regions

In some embodiments, the polynucleotides of the invention include a poly-C region.

Unique poly-C region lengths may provide certain advantages to the alternative polynucleotides of the present invention.

Generally, the length of a poly-C region of the present invention is at least 10 nucleotides in length. In another embodiment, the poly-C region is at least 15 nucleotides in length. In another embodiment, the poly-C region is at least 20 nucleotides in length. In another embodiment, the poly-C region is at least 25 nucleotides in length. In another embodiment, the poly-C region is at least 30 nucleotides in length. In another embodiment, the poly-C region is at least 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 70 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1700 nucleotides. In another embodiment, the length is at least 1800 nucleotides. In another embodiment, the length is at least 1900 nucleotides. In another embodiment, the length is at least 2000 nucleotides. In another embodiment, the length is at least 2500 nucleotides. In another embodiment, the length is at least 3000 nucleotides.

In one embodiment, the poly-C region may be 80 nucleotides, 120 nucleotides, or 160 nucleotides in length in an alternative polynucleotide molecule described herein.

In another embodiment, the poly-C region may be 20, 40, 80, 100, 120, 140 or 160 nucleotides in length in an alternative polynucleotide molecule described herein.

In one embodiment, the length of the poly-C region is designed relative to the length of the overall alternative polynucleotide. This design may be based on the length of the coding region of the alternative polynucleotide, the length of a particular feature or region of the alternative polynucleotide (such as mRNA), or based on the length of the ultimate product expressed from the alternative polynucleotide. When relative to any feature of the alternative polynucleotide (e.g., other than the mRNA portion which includes the poly-C region) the poly-C region may be 10, 20, 30, 40, 50, 60, 70, 80, 90 or 100% greater in length than the additional feature. The poly-C region may also be designed as a fraction of the alternative polynucleotide to which it belongs. In this context, the poly-C region may be 10, 20, 30, 40, 50, 60, 70, 80, or 90% or more of the total length of the construct or the total length of the construct minus the poly-C region.

Complimentary Stabilizing Polynucleotides

In some embodiments, the polynucleotides of the invention further include one or more complimentary stabilizing polynucleotides. A complimentary stabilizing polynucleotide is a polynucleotide including 5 to 20 nucleotides which is complementary to at or near one of both termini of a polynucleotide (e.g., mRNA). In some embodiments, a complimentary stabilizing polynucleotide increases the stability (e.g., plasma stability) and/or expression levels of a polynucleotide of the invention. In some embodiments, a complimentary stabilizing polynucleotide is complementary at or near the 5'-terminus of a polynucleotide of the invention. In some embodiments, a complimentary stabilizing polynucleotide is complementary at or near the 3'-terminus of a polynucleotide of the invention. In some embodiments, one or more complimentary stabilizing polynucleotides are complementary to both a 5'-region and a 3'-region of a polynucleotide of the invention and when bound to the polynucleotide of the invention form a circulized construct with the polynucleotide of the invention. In some aspects, the invention provides a composition including a polynucleotide of the invention and one or more complementary stabilizing polynucleotides that form a circularized construct when bound to the polynucleotide of the invention.

3'-Stabilizing Regions

In eukaryotes, the 3'-ends of most polynucleotides are polyadenylated. The poly-A tail is added to the 3'-end to promote translation and inhibit degradation of the polynucleotide by the exosome and exonucleases. Polyadenylation also plays a role in transcription termination, export of polynucleotide from the nucleus to the cytosol, and translation. Polyadenylation regulates intracellular molecular activities, including RNA stability and translational efficiency.

Stabilization of a specific polynucleotide in eukaryotic cells is of interest because the protein encoded by the polynucleotide may be produced in larger quantities because of a longer exposure of the polynucleotide to translational machinery.

In some embodiments, the present invention features compounds including a second polynucleotide conjugated to a first polynucleotide through a morpholino linker. In some embodiments, the second polynucleotide is a 3'-stabilizing region which results in increased stability of the compound as compared to the corresponding compound without the 3'-stabilizing region. In some embodiments, the 3'-stabilizing region includes an alternative nucleoside. In some embodiments, the 3'-stabilizing region is conjugated to the remainder of the polynucleotide through a linker described herein. In some embodiments, the 3'-stabilizing region includes the 3'-terminus of the compound. In some embodiments, the 3'-stabilizing region is conjugated to the 3'-UTR of the first polynucleotide. In some embodiments, the 3'-stabilizing region is conjugated to the poly-A region of the first polynucleotide.

In some embodiments, the first polynucleotide includes i) a coding region; ii) a 5'-UTR optionally including a Kozak sequence; iii) a 3'-UTR; iv) at least one 5'-cap structure; v) a poly-A region; and vi) a 3'-stabilizing region, wherein the 3'-stabilizing region is conjugated to the poly-A region through a morpholino linker described herein. In some embodiments, the 3'-stabilizing region includes L-nucleosides (e.g., L-adenosine). In some embodiments, all of the nucleosides in the 3'-stabilizing region are L-nucleosides (e.g., L-adenosine). In some embodiments, the 3'-stabilizing region includes at least two different alternative nucleosides (e.g., 2'-O-methyl adenosine and an inverted thymidine or α-thio-2'-O-methyl adenosine and an inverted thymidine). In some embodiments, the 3'-stabilizing region has at least 5 nucleosides (e.g., at least 10 nucleosides, at least 20 nucleosides, at least 30 nucleosides, at least 40 nucleosides, at least 50 nucleosides).

In some embodiments, the first polynucleotide comprises i) a coding region which encodes a polypeptide; ii) a 5'-UTR including a Kozak sequence; iii) a 3'-UTR; iv) at least one 5'-cap structure such as Cap0, Cap1, Cap2, or an ARCA cap; v) a poly-A region (e.g., a poly-A region including 100 adenosine); and vi) a 3'-stabilizing region (e.g., a 3'-stabilizing region including ten nucleosides such as ten L-adenosine or seven adenosines, two 2'-O-methyl adenosines, and an inverted thymidine, wherein the 3'-stabilizing region in conjugated to the poly-A region through a morpholino linker described herein.

Polypeptides Conjugated to the Polynucleotide

In some embodiments, a polypeptide is conjugated to a polynucleotide via a linker having the structure of Formula I. For example, a polynucleotide is reacted with an oxidant (e.g., sodium periodate) resulting in oxidative ring opening of the sugar at the 3'-terminus into a dialdehyde, followed by condensation with a polypeptide including an aminooxy group, e.g., at the N-terminus, at the C-terminus, or at an internal position such as a modified lysine. Polypeptides which may be conjugated to the polynucleotides of the invention include nuclear localization peptides, ER localization peptides, endosomal escape peptides, immune stimulation peptides, golgi apparatus localization peptides, lysosomal localization peptides, mitochondrial localization peptides, and/or peptide which may be used in affinity chromatography. The polypeptides conjugated to the polynucleotides of the invention may add in localization of the polynucleotide to a desired location in the cell and/or aid in purification of the polynucleotide. In some embodiments, the polypeptide conjugated to the polynucleotides of the invention is any of the polypeptides listed in Table 1:

TABLE 1

| Selected Polypeptides | |
|---|---|
| Aoa-HHHHHHHHHHHHHHHHHHHH-amide | (SEQ ID NO: 10) |
| Aoa-HHHHHHHHHHHHHHHHHHHH-amide (all D-amino acids) | (SEQ ID NO: 11) |
| Aoa-HHHHH-OH | (SEQ ID NO: 12) |
| Aoa-HHHHHHHHHH-OH | (SEQ ID NO: 13) |
| Aoa-HHHHHHHHHHHHHHH-OH | (SEQ ID NO: 14) |
| Aoa-HHHHHHHHHHHHHHHHHHHH-OH | (SEQ ID NO: 15) |
| Ac-PKKKRKVEDPY[K(Aoa]G-amide | (SEQ ID NO: 16) |
| Aoa-KDEL-OH | (SEQ ID NO: 17) |
| Aoa-FFRKSIINFEKL-OH | (SEQ ID NO: 18) |
| Aoa-KTKKL-OH | (SEQ ID NO: 19) |
| Aoa-KKSL-OH | (SEQ ID NO: 20) |
| Aoa-KPRRE-OH | (SEQ ID NO: 21) |
| Aoa-KFERQ-OH | (SEQ ID NO: 22) |
| H2N-MSSESGKPIAKPIRKPGYTNPALKALG(KAoa)-amide | (SEQ ID NO: 23) |
| H2N-MLSLRQSIRFFKPATRTLCSSRYLL(KAoa)-amide | (SEQ ID NO: 24) |
| H2N-MLSLRQSIRFFK(KAoa)-amide | (SEQ ID NO: 25) |
| Aoa-WEAKLAKALAKALAKHLAKALAKALKACEA-amide | (SEQ ID NO: 26) |
| Aoa-WEAALAEALAEALAEHLAEALAEALEALAA-amide | (SEQ ID NO: 27) |

Linkers

The compounds of the invention may include a branched and/or unbranched linker. The term "linker," as used herein, refers to a chemical group or molecule linking two adjacent molecules or moieties, e.g., a morpholino group to a polynucleotide. Typically, an unbranched linker is positioned between, or flanked by, two groups, molecules, or other moieties and connected to each one via a covalent bond, thus connecting the two. Alternatively, a branched linker connects three or more groups, molecules, or other moieties and typically functions as the structural point of convergence for the three or more groups, molecules, or other moieties. In some embodiments of any of the compounds herein, the linker is not a natural phosphate linker or a phosphoramidite linker. In some embodiments, the linker is an organic molecule, group, polymer, or chemical moiety.

In certain embodiments, the linker group comprises a combination of one or more groups of the formula:

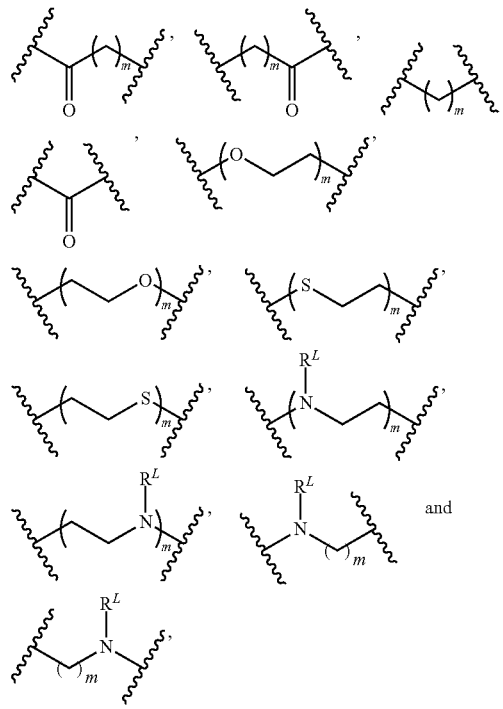

wherein $R^L$ is hydrogen or substituted or unsubstituted alkyl, m is 0 or an integer between 1 to 10, inclusive, e.g., 1, 2, 3, 4, 5, 6, 7, 8, 9, or 10. In certain embodiments, m is 3 or 4.

The linkers may be conjugated through reactions of sulfhydryl groups (—SH), amino groups (amines), and/or hydroxyls or any appropriate reactive group. Homobifunctional and heterobifunctional cross-linkers (conjugation agents) are available from many commercial sources. The cross-linker may include a flexible arm, e.g., of 2, 3, 4, 5, 6, 7, 8, 9, 10, 11, 12, 13, 14, or 15 carbon atoms. Exemplary cross-linkers include BS3 ([Bis(sulfosuccinimidyl)suberate]; BS3 is a homobifunctional N-hydroxysuccinimide ester that targets accessible primary amines), NHS/EDC (N-hydroxysuccinimide and N-ethyl-N'-(dimethylaminopropyl)carbodimide; NHS/EDC allows for the conjugation of primary amine groups with carboxyl groups), sulfo-EMCS ([N-e-Maleimidocaproic acid]hydrazide; sulfo-EMCS are heterobifunctional reactive groups (maleimide and NHS-ester) that are reactive toward sulfhydryl and amino groups), hydrazide, and SATA (N-succinimidyl-S-acetylthioacetate; SATA is reactive towards amines and adds protected sulfhydryls groups).

To form covalent bonds, one can use as a chemically reactive group a wide variety of active carboxyl groups (e.g., esters) capable of reaction with a nucleoside. Particular agents include N-hydroxysuccinimide (NHS), N-hydroxysulfosuccinimide (sulfo-NHS), maleimide-benzoyl-succinimide (MBS), gamma-maleimido-butyryloxy succinimide ester (GMBS), maleimido propionic acid (MPA) maleimido hexanoic acid (MHA), and maleimido undecanoic acid (MUA).

Primary amines are the principal targets for NHS esters. Accessible α-amine groups present on the N-termini of a polynucleotide or 3'-stabilizing region may react with NHS esters. An amide bond is formed when the NHS ester reacts with primary amines releasing N-hydroxysuccinimide. In certain embodiments of the invention, the functional group on the polynucleotide or 3'-stabilizing region will be a thiol group, and the chemically reactive group will be a maleimido-containing group such as gamma-maleimide-butyrylamide (GMBA or MPA).

The maleimido group is most selective for sulfhydryl groups when the pH of the reaction mixture is 6.5-7.4. At pH 7.0, the rate of reaction of maleimido groups with sulfhydryls is 1000-fold faster than with amines. Thus, a stable thioether linkage between the maleimido group and the sulfhydryl can be formed.

In some embodiments, the unbranched linker has the structure:

Formula VI

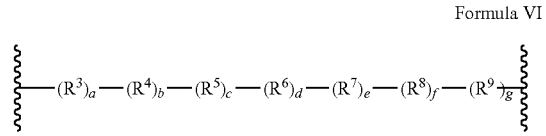

wherein a, b, c, e, f, and g are each, independently, 0 or 1;

d is 0, 1, 2, or 3;

each of $R^3$, $R^5$, $R^7$, and $R^9$, is, independently, selected from optionally substituted $C_1$-$C_6$ alkylene, optionally substituted $C_1$-$C_6$ heteroalkylene, optionally substituted $C_2$-$C_{100}$ polyethylene glycolene, O, S, Se, and $NR^{10}$;

$R^4$ and $R^8$ are each, independently, carbonyl, thiocarbonyl, sulfonyl, or phosphoryl;

each $R^6$ is optionally substituted $C_1$-$C_{10}$ alkylene, optionally substituted $C_2$-$C_{10}$ alkenylene, optionally substituted $C_2$-$C_{10}$ alkynylene, optionally substituted $C_2$-$C_{10}$ heterocyclylene, optionally substituted $C_6$-$C_{12}$ arylene, optionally substituted $C_2$-$C_{100}$ polyethylene glycolene, or optionally substituted $C_1$-$C_{10}$ heteroalkylene, or a bond linking $(R^3)_a$—$(R^4)_b$—$(R^5)_c$ to $(R^7)_e$—$(R^8)_f$—$(R^9)g$; and $R^{10}$ is hydrogen, optionally substituted $C_1$-$C_4$ alkyl, optionally substituted $C_2$-$C_4$ alkenyl, optionally substituted $C_2$-$C_4$ alkynyl, optionally substituted $C_2$-$C_6$ heterocyclyl, optionally substituted $C_6$-$C_{12}$ aryl, or optionally substituted $C_1$-$C_7$ heteroalkyl.

In some embodiments, the branched linker has the structure:

Formula XVI

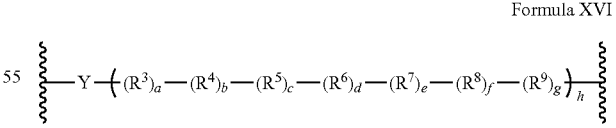

wherein a, b, c, e, f, and g are each, independently, 0 or 1;

d is 0, 1, 2, or 3;

h is 2, 3, 4, or 5;

Y is a optionally substituted branched $C_1$-$C_6$ alkylene, optionally substituted $C_2$-$C_{10}$ branched alkenylene, optionally substituted $C_2$-$C_{10}$ branched alkynylene, optionally substituted $C_2$-$C_{10}$ branched heterocyclylene, optionally substituted $C_6$-$C_{12}$ branched arylene, optionally substituted $C_2$-$C_{10}$ branched polyethylene glycolene, or optionally substituted $C_1$-$C_{10}$ branched heteroalkylene;

each of $R^3$, $R^5$, $R^7$, and $R^9$, is, independently, selected from optionally substituted $C_1$-$C_6$ alkylene, optionally substituted $C_1$-$C_6$ heteroalkylene, optionally substituted $C_2$-$C_{100}$ polyethylene glycolene, O, S, Se, and $NR^{10}$;

$R^4$ and $R^8$ are each, independently, carbonyl, thiocarbonyl, sulfonyl, or phosphoryl;

each $R^6$ is optionally substituted $C_1$-$C_{10}$ alkylene, optionally substituted $C_2$-$C_{10}$ alkenylene, optionally substituted $C_2$-$C_{10}$ alkynylene, optionally substituted $C_2$-$C_{10}$ heterocyclene, optionally substituted $C_6$-$C_{12}$ arylene, optionally substituted $C_2$-$C_{100}$ polyethylene glycolene, or optionally substituted $C_1$-$C_{10}$ heteroalkylene, or a bond linking $(R^3)_a$—$(R^4)_b$—$(R^5)_c$ to $(R^7)_e$—$(R^8)_f$—$(R^9)g$; and $R^{10}$ is hydrogen, optionally substituted $C_1$-$C_4$ alkyl, optionally substituted $C_2$-$C_4$ alkenyl, optionally substituted $C_2$-$C_4$ alkynyl, optionally substituted $C_2$-$C_6$ heterocyclyl, optionally substituted $C_6$-$C_{12}$ aryl, or optionally substituted $C_1$-$C_7$ heteroalkyl.

Click-Chemistry Linkers

In particular embodiments, the linker is formed by the reaction between a click-chemistry reaction pair. By "click-chemistry reaction pair" is meant a pair of reactive groups that participates in a modular reaction with high yield and a high thermodynamic gain, thus producing a click-chemistry linker. In this embodiment, one of the reactive groups is attached to the 3'-stabilizing region, and the other reactive group is attached to the remainder of the polynucleotide. Exemplary reactions and click-chemistry pairs include a Huisgen 1,3-dipolar cycloaddition reaction between an alkynyl group and an azido group to form a triazole-containing linker; a Diels-Alder reaction between a diene having a 4π electron system (e.g., an optionally substituted 1,3-unsaturated compound, such as optionally substituted 1,3-butadiene, 1-methoxy-3-trimethylsilyloxy-1,3-butadiene, cyclopentadiene, cyclohexadiene, or furan) and a dienophile or heterodienophile having a 2π electron system (e.g., an optionally substituted alkenyl group or an optionally substituted alkynyl group); a ring opening reaction with a nucleophile and a strained heterocyclyl electrophile; a splint ligation reaction with a phosphorothioate group and an iodo group; and a reductive amination reaction with an aldehyde group and an amino group (Kolb et al., *Angew. Chem. Int. Ed.*, 40:2004-2021 (2001); Van der Eycken et al., *QSAR Comb. Sci.*, 26:1115-1326 (2007)).

In particular embodiments of the invention, the 3'-stabilizing region is linked to the remainder of the polynucleotide by means of a triazole-containing linker formed by the reaction between an alkynyl group and an azido group click-chemistry pair. In such cases, the azido group may be attached to the 3'-terminus of the polynucleotide and the alkynyl group may be attached to the 5'-terminus of the 3'-stabilizing region. Alternatively, the azido group may be attached to the 5'-terminus of the 3'-stabilizing region and the alkynyl group may be attached to the 3'-terminus of the polynucleotide. In certain embodiments, the reaction between an azido group and the alkynyl group is uncatalyzed, and in other embodiments the reaction is catalyzed by a copper(I) catalyst (e.g., copper(I) iodide), a copper(II) catalyst in the presence of a reducing agent (e.g., copper(II) sulfate or copper(II) acetate with sodium ascorbate), or a ruthenium-containing catalyst (e.g., Cp*RuCl(PPh$_3$)$_2$ or Cp*RuCl(COD)).

Exemplary linkers include linkers containing monofluorocyclooctyne (MFCO), difluorocyclooctyne (DFCO), cyclooctyne (OCT), dibenzocyclooctyne (DIBO), biarylazacyclooctyne (BARAC), difluorobenzocyclooctyne (DIFBO), and bicyclo[6.1.0]nonyne (BCN).

The linkers may be conjugated through reacting click chemistry handle pairs. The term "click chemistry handle," as used herein, refers to a reactant, or a reactive group, that can partake in a click chemistry reaction. For example, a strained alkyne, e.g., a cyclooctyne, is a click chemistry handle, since it can partake in a strain-promoted cycloaddition. In general, click chemistry reactions require at least two molecules comprising click chemistry handles that can react with each other. For example, an azide is a partner click chemistry handle to a cyclooctyne or any other alkyne. Additional examples of partner click chemistry handle pairs include a diene and a dienophile, an azide and a terminal alkyne, an azide and a strained alkyne, an azide and an activated alkyne, an azide and an electron-deficient alkyne, an azide and an aryne, a tetrazine and an alkene, a tetrazole and an alkene, a dithioester and a diene, an anthracene and a maleimide, a thiol and an alkene, a thiol and an enone, a thiol and a maleimide, a thiol and para-fluoro, and an amine and para-fluoro. Other suitable click chemistry handles are known to those of skill in the art.

Additional click chemistry handles suitable for use in the methods described herein are well known to those of skill in the art, and such click chemistry handles include, but are not limited to, the click chemistry reaction partners, groups, and handles described in [1] H. C. Kolb, M. G. Finn, K. B. Sharpless, Angew. Chem. 2001, 113, 2056-2075; Angew. Chem. Int. Ed. 2001, 40, 2004-2021. [2] a) C. J. Hawker, K. L. Wooley, Science 2005, 309, 1200-1205; b) D. Fournier, R. Hoogenboom, U. S. Schubert, Chem. Soc. Rev. 2007, 36, 1369-1380; c) W. H. Binder, R. Sachsenhofer, Macromol. Rapid Commun. 2007, 28, 15-54; d) H. C. Kolb, K. B. Sharpless, Drug Discovery Today 2003, 8, 1128-1137; e) V. D. Bock, H. Hiemstra, J. H. van Maarseveen, Eur. J. Org. Chem. 2006, 51-68. [3] a) V. O. Rodionov, V. V. Fokin, M. G. Finn, Angew. Chem. 2005, 117, 2250-2255; Angew. Chem. Int. Ed. 2005, 44, 2210-2215; b) P. L. Golas, N. V. Tsarevsky, B. S. Sumerlin, K. Matyjaszewski, Macromolecules 2006, 39, 6451-6457; c) C. N. Urbani, C. A. Bell, M. R. Whittaker, M. J. Monteiro, Macromolecules 2008, 41, 1057-1060; d) S. Chassaing, A. S. S. Sido, A. Alix, M. Kumarraja, P. Pale, J. Sommer, Chem. Eur. J. 2008, 14, 6713-6721; e) B. C. Boren, S. Narayan, L. K. Rasmussen, L. Zhang, H. Zhao, Z. Lin, G. Jia, V. V. Fokin, J. Am. Chem. Soc. 2008, 130, 8923-8930; f) B. Saba, S. Sharma, D. Sawant, B. Kundu, Synlett 2007, 1591-1594. [4] J. F. Lutz, Angew. Chem. 2008, 120, 2212-2214; Angew. Chem. Int. Ed. 2008, 47, 2182-2184. [5] a) Q. Wang, T. R. Chan, R. Hilgraf, V. V. Fokin, K. B. Sharpless, M. G. Finn, J. Am. Chem. Soc. 2003, 125, 3192-3193; b) J. Gierlich, G. A. Burley, P. M. E. Gramlich, D. M. Hammond, T. Carell, Org. Lett. 2006, 8, 3639-3642. [6] a) J. M. Baskin, J. A. Prescher, S. T. Laughlin, N. J. Agard, P. V. Chang, I. A. Miller, A. Lo, J. A. Codelli, C. R. Bertozzi, Proc. Natl. Acad. Sci. USA 2007, 104, 16793-16797; b) S. T. Laughlin, J. M. Baskin, S. L. Amacher, C. R. Bertozzi, Science 2008, 320, 664-667; c) J. A. Johnson, J. M. Baskin, C. R. Bertozzi, J. F. Koberstein, N. J. Turro, Chem. Commun. 2008, 3064-3066; d) J. A. Codelli, J. M. Baskin, N. J. Agard, C. R. Bertozzi, J. Am. Chem. Soc. 2008, 130, 11486-11493; e) E. M. Sletten, C. R. Bertozzi, Org. Lett. 2008, 10, 3097-3099; f) J. M. Baskin, C. R. Bertozzi, QSAR Comb. Sci. 2007, 26, 1211-1219. [7] a) G. Wittig, A. Krebs, Chem. Ber. Recl. 1961, 94, 3260-3275;

b) A. T. Blomquist, L. H. Liu, J. Am. Chem. Soc. 1953, 75, 2153-2154. [8] D. H. Ess, G. O. Jones, K. N. Houk, Org. Lett. 2008, 10, 1633-1636. [9] W. D. Sharpless, P. Wu, T. V. Hansen, J. G. Lindberg, J. Chem. Educ. 2005, 82, 1833-1836. [10] Y. Zou, J. Yin, Bioorg. Med. Chem. Lett. 2008, 18, 5664-5667. [11] X. Ning, J. Guo, M. A. Wolfert, G. J. Boons, Angew. Chem. 2008, 120, 2285-2287; Angew. Chem. Int. Ed. 2008, 47, 2253-2255. [12] S. Sawoo, P. Dutta, A. Chakraborty, R. Mukhopadhyay, O. Bouloussa, A. Sarkar, Chem. Commun. 2008, 5957-5959. [13] a) Z. Li, T. S. Seo, J. Ju, Tetrahedron Lett. 2004, 45, 3143-3146; b) S. S. van Berkel, A. J. Dirkes, M. F. Debets, F. L. van Delft, J. J. L. Cornelissen, R. J. M. Nolte, F. P. J. Rutjes, ChemBioChem 2007, 8, 1504-1508; c) S. S. van Berkel, A. J. Dirks, S. A. Meeuwissen, D. L. L. Pingen, O. C. Boerman, P. Laverman, F. L. van Delft, J. J. L. Cornelissen, F. P. J. Rutjes, ChemBio—Chem 2008, 9, 1805-1815. [14] F. Shi, J. P. Waldo, Y. Chen, R. C. Larock, Org. Lett. 2008, 10, 2409-2412. [15] L. Campbell-Verduyn, P. H. Elsinga, L. Mirfeizi, R. A. Dierckx, B. L. Feringa, Org. Biomol. Chem. 2008, 6, 3461-3463. [16] a) The Chemistry of the Thiol Group (Ed.: S. Patai), Wiley, New York, 1974; b) A. F. Jacobine, In Radiation Curing in Polymer Science and Technology III (Eds.: J. D. Fouassier, J. F. Rabek), Elsevier, London, 1993, Chap. 7, pp. 219-268. [17] C. E. Hoyle, T. Y. Lee, T. Roper, J. Polym. Sci. Part A 2008, 42, 5301-5338. [18] L. M. Campos, K. L. Killops, R. Sakai, J. M. J. Paulusse, D. Damiron, E. Drockenmuller, B. W. Messmore, C. J. Hawker, Macromolecules 2008, 41, 7063-7070. [19] a) R. L. A. David, J. A. Kornfield, Macromolecules 2008, 41, 1151-1161; b) C. Nilsson, N. Simpson, M. Malkoch, M. Johansson, E. Malmstrom, J. Polym. Sci. Part A 2008, 46, 1339-1348; c) A. Dondoni, Angew. Chem. 2008, 120, 9133-9135; Angew. Chem. Int. Ed. 2008, 47, 8995-8997; d) J. F. Lutz, H. Schlaad, Polymer 2008, 49, 817-824. [20] A. Gress, A. Voelkel, H. Schlaad, Macromolecules 2007, 40, 7928-7933. [21] N. ten Brummelhuis, C. Diehl, H. Schlaad, Macromolecules 2008, 41, 9946-9947. [22] K. L. Killops, L. M. Campos, C. J. Hawker, J. Am. Chem. Soc. 2008, 130, 5062-5064. [23] J. W. Chan, B. Yu, C. E. Hoyle, A. B. Lowe, Chem. Commun. 2008, 4959-4961. [24] a) G. Moad, E. Rizzardo, S. H. Thang, Acc. Chem. Res. 2008, 41, 1133-1142; b) C. Barner-Kowollik, M. Buback, B. Charleux, M. L. Coote, M. Drache, T. Fukuda, A. Goto, B. Klumperman, A. B. Lowe, J. B. McLeary, G. Moad, M. J. Monterio, R. D. Sanderson, M. P. Tonge, P. Vana, J. Polym. Sci. Part A 2006, 44, 5809-5831. [25] a) R. J. Pounder, M. J. Stanford, P. Brooks, S. P. Richards, A. P. Dove, Chem. Commun. 2008, 5158-5160; b) M. J. Stanford, A. P. Dove, Macromolecules 2009, 42, 141-147. [26] M. Li, P. De, S. R. Gondi, B. S. Sumerlin, J. Polym. Sci. Part A 2008, 46, 5093-5100. [27] Z. J. Witczak, D. Lorchak, N. Nguyen, Carbohydr. Res. 2007, 342, 1929-1933. [28] a) D. Samaroo, M. Vinodu, X. Chen, C. M. Drain, J. Comb. Chem. 2007, 9, 998-1011; b) X. Chen, D. A. Foster, C. M. Drain, Biochemistry 2004, 43, 10918-10929; c) D. Samaroo, C. E. Soll, L. J. Todaro, C. M. Drain, Org. Lett. 2006, 8, 4985-4988. [29] P. Battioni, O. Brigaud, H. Desvaux, D. Mansuy, T. G. Traylor, Tetrahedron Lett. 1991, 32, 2893-2896. [30] C. Ott, R. Hoogenboom, U. S. Schubert, Chem. Commun. 2008, 3516-3518. [31] a) V. Ladmiral, G. Mantovani, G. J. Clarkson, S. Cauet, J. L. Irwin, D. M. Haddleton, J. Am. Chem. Soc. 2006, 128, 4823-4830; b) S. G. Spain, M. I. Gibson, N. R. Cameron, J. Polym. Sci. Part A 2007, 45, 2059-2072. [32] C. R. Becer, K. Babiuch, K. Pilz, S. Hornig, T. Heinze, M. Gottschaldt, U. S. Schubert, Macromolecules 2009, 42, 2387-2394. [33] Otto Paul Hermann Diels and Kurt Alder first documented the reaction in 1928. They received the Nobel Prize in Chemistry in 1950 for their work on the eponymous reaction. [34] a) H. L. Holmes, R. M. Husband, C. C. Lee, P. Kawulka, J. Am. Chem. Soc. 1948, 70, 141-142; b) M. Lautens, W. Klute, W. Tam, Chem. Rev. 1996, 96, 49-92; c) K. C. Nicolaou, S. A. Snyder, T. Montagnon, G. Vassilikogiannakis, Angew. Chem. 2002, 114, 1742-1773; Angew. Chem. Int. Ed. 2002, 41, 1668-1698; d) E. J. Corey, Angew. Chem. 2002, 114, 1724-1741; Angew. Chem. Int. Ed. 2002, 41, 1650-1667. [35] a) H. Durmaz, A. Dag, O. Altintas, T. Erdogan, G. Hizal, U. Tunca, Macromolecules 2007, 40, 191-198; b) H. Durmaz, A. Dag, A. Hizal, G. Hizal, U. Tunca, J. Polym. Sci. Part A 2008, 46, 7091-7100; c) A. Dag, H. Durmaz, E. Demir, G. Hizal, U. Tunca, J. Polym. Sci. Part A 2008, 46, 6969-6977; d) B. Gacal, H. Akat, D. K. Balta, N. Arsu, Y. Yagci, Macromolecules 2008, 41, 2401-2405; e) A. Dag, H. Durmaz, U. Tunca, G. Hizal, J. Polym. Sci. Part A 2009, 47, 178-187. [36] M. L. Blackman, M. Royzen, J. M. Fox, J. Am. Chem. Soc. 2008, 130, 13518-13519. [38] N. K. Devaraj, R. Weissleder, S. A. Hilderbrand, Bioconjugate Chem. 2008, 19, 2297-2299. [39] W. Song, Y. Wang, J. Qu, Q. Lin, J. Am. Chem. Soc. 2008, 130, 9654-9655. [40] W. Song, Y. Wang, J. Qu, M. M. Madden, Q. Lin, Angew. Chem. 2008, 120, 2874-2877; Angew. Chem. Int. Ed. 2008, 47, 2832-2835. [41] A. Dag, H. Durmaz, G. Hizal, U. Tunca, J. Polym. Sci. Part A 2008, 46, 302-313. [42] a) A. J. Inglis, S. Sinnwell, T. P. Davis, C. Barner-Kowollik, M. H. Stenzel, Macromolecules 2008, 41, 4120-4126; b) S. Sinnwell, A. J. Inglis, T. P. Davis, M. H. Stenzel, C. Barner-Kowollik, Chem. Commun. 2008, 2052-2054. [43] A. J. Inglis, S. Sinwell, M. H. Stenzel, C. Barner-Kowollik, Angew. Chem. 2009, 121, 2447-2450; Angew. Chem. Int. Ed. 2009, 48, 2411-2414. All references cited above are incorporated herein by reference for disclosure of click chemistry handles suitable for installation according to inventive concepts and methods provided herein.

Morpholino Linkers

The compounds of the invention include a morpholino moiety. The morpholino linker may be formed by oxidation (e.g., by treatment with sodium periodate) of a cis-diol of the sugar of a nucleoside such as the 3'-terminal nucleoside on the polynucleotide followed by condensation of the resulting di-aldehyde with a reactive amino moiety such as an alkoxyamino moiety as shown below.

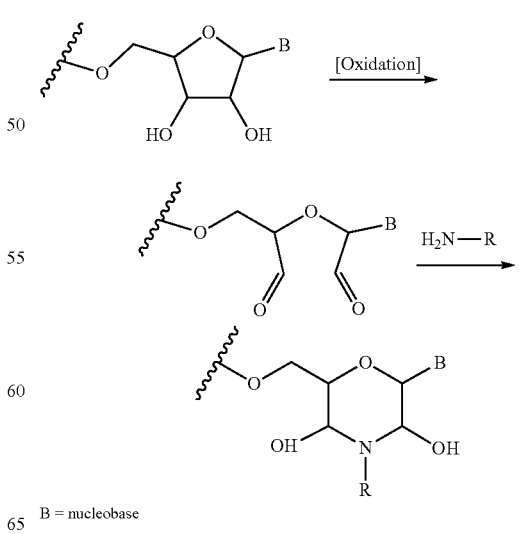

B = nucleobase

In some embodiments, the reaction is carried out in the presence of a inverted 5'-cap structure resulting in a nucleotide, polynucleotide, targeting moiety, small molecule, polypeptide, or polymer conjugated at the 5'-terminus through a morpholino linker as shown below:

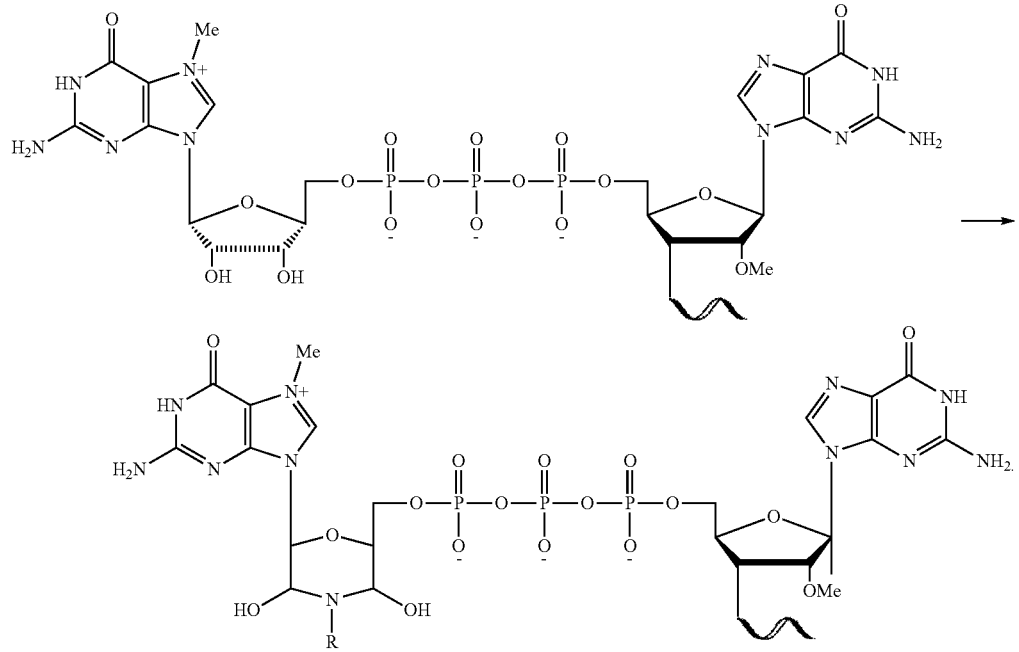

In some embodiments, the linker includes the structure:

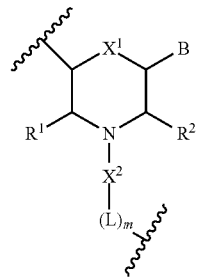

Formula I wherein B is a nucleobase; and
R¹ and R2 are each, independently, hydrogen or hydroxy.
In some embodiments, the linker includes the structure:

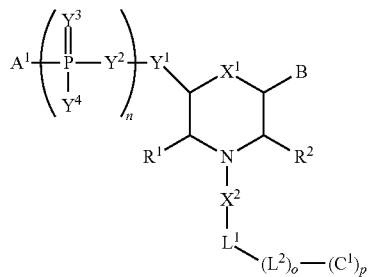

Formula II or a salt thereof;
wherein A¹ is a first polynucleotide and includes:
(a) at least one 5'-cap structure;
(b) a 5'-UTR;
(c) a coding region; and
(d) a 3'-UTR;
C¹ includes a second polynucleotide, a targeting moiety, a small molecule, a polypeptide, or a polymer;
L¹ is an unbranched linker;
L² is a branched linker;
m is 0, 1, 2, or 3;
n is 0 or 1;
o is 1, 2, 3, 4, or 5;
X² is —O—, —NR$^{N1}$—, —NR$^{N1}$NR$^{N1}$—, a bond, optionally substituted $C_1$-$C_{10}$ alkylene, optionally substituted $C_2$-$C_{10}$ alkenylene, optionally substituted $C_2$-$C_{10}$ alkynylene, optionally substituted $C_2$-$C_{10}$ heterocyclylene, optionally substituted $C_6$-$C_{12}$ arylene, optionally substituted $C_2$-$C_{100}$ polyethylene glycolene, or optionally substituted $C_1$-$C_{30}$ heteroalkylene, wherein R$^{N1}$ is H, optionally substituted $C_1$-$C_6$ alkyl, optionally substituted $C_2$-$C_6$ alkenyl, optionally substituted $C_2$-$C_6$ alkynyl, or optionally substituted $C_6$-$C_{10}$ aryl;
Y¹ is O, S, Se, optionally substituted $C_1$-$C_6$ alkylene, or optionally substituted $C_1$-$C_6$ heteroalkylene;
each Y² and Y³ is, independently, O, S, Se, —NR$^{N1}$—, optionally substituted $C_1$-$C_6$ alkylene, or optionally substituted $C_1$-$C_6$ heteroalkylene, wherein R$^{N1}$ is H, optionally substituted $C_1$-$C_6$ alkyl, optionally substituted $C_2$-$C_6$ alkenyl, optionally substituted $C_2$-$C_6$ alkynyl, or optionally substituted $C_6$-$C_{10}$ aryl; and
each Y⁴ is, independently, H, hydroxy, protected hydroxy, halo, thiol, boranyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, or optionally substituted amino, wherein when $Y^2$, $Y^3$, and $X^1$ are each O, $R^1$ and $R^2$ are each hydrogen, $Y^1$ is $CH_2$, $Y^4$ is hydroxy, n is 0, o is 1, and $C_1$ is a polynucleotide, $X^2$-$L^1$ is not —P(O)OH— or —P(O)N($R^N$)$_2$—, wherein $R^N$ is optionally substituted $C_1$-$C_6$ alkyl.

As will be appreciated by one of skill in the art, the structure:

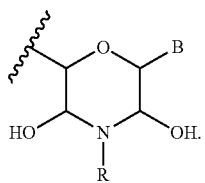

may exist in equilibrium with other structures as shown below.

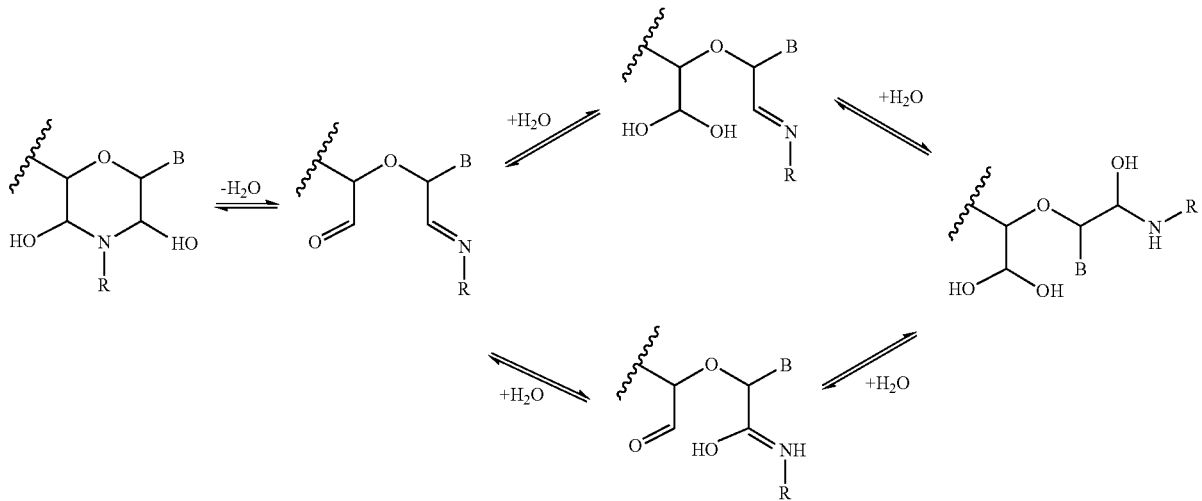

wherein R includes an optionally substituted $C_1$-$C_{10}$ alkylene, an optionally substituted $C_2$-$C_{10}$ alkenylene, an optionally substituted $C_2$-$C_{10}$ alkynylene, an optionally substituted $C_2$-$C_{10}$ heterocyclylene, an optionally substituted $C_6$-$C_{12}$ arylene, an optionally substituted $C_2$-$C_{100}$ polyethylene glycolene, and/or an optionally substituted $C_1$-$C_{10}$ heteroalkylene.

The present invention is intended to encompass all of the potential structures in equilibrium with the morpholino structure.

Codon Optimization

The polynucleotides of the invention, their regions, parts, or subregions may be codon optimized. Codon optimization methods are known in the art and may be useful in efforts to achieve one or more of several goals. These goals include to match codon frequencies in target and host organisms to ensure proper folding, bias GC content to increase mRNA stability or reduce secondary structures, minimize tandem repeat codons or base runs that may impair gene construction or expression, customize transcriptional and translational control regions, insert or remove protein trafficking sequences, remove/add post translation modification sites in encoded protein (e.g., glycosylation sites), add, remove or shuffle protein domains, insert or delete restriction sites, modify ribosome binding sites and mRNA degradation sites, to adjust translational rates to allow the various domains of the protein to fold properly, or to reduce or eliminate problem secondary structures within the polynucleotide. Codon optimization tools, algorithms and services are known in the art, non-limiting examples include services from GeneArt (Life Technologies), DNA2.0 (Menlo Park CA) and/or proprietary methods. In one embodiment, the ORF sequence is optimized using optimization algorithms. Codon options for each amino acid are given in Table 2.

TABLE 2

Codon Options.

| Amino Acid | Single Letter Code | Codon Options |
|---|---|---|
| Isoleucine | I | ATT, ATC, ATA |
| Leucine | L | CTT, CTC, CTA, CTG, TTA, TTG |
| Valine | V | GTT, GTC, GTA, GTG |

TABLE 2-continued

Codon Options.

| Amino Acid | Single Letter Code | Codon Options |
|---|---|---|
| Phenylalanine | F | TTT, TTC |
| Methionine | M | ATG |
| Cysteine | C | TGT, TGC |
| Alanine | A | GCT, GCC, GCA, GCG |
| Glycine | G | GGT, GGC, GGA, GGG |
| Proline | P | CCT, CCC, CCA, CCG |
| Threonine | T | ACT, ACC, ACA, ACG |
| Serine | S | TCT, TCC, TCA, TCG, AGT, AGC |
| Tyrosine | Y | TAT, TAC |
| Tryptophan | W | TGG |
| Glutamine | Q | CAA, CAG |
| Asparagine | N | AAT, AAC |
| Histidine | H | CAT, CAC |
| Glutamic acid | E | GAA, GAG |
| Aspartic acid | D | GAT, GAC |
| Lysine | K | AAA, AAG |

TABLE 2-continued

Codon Options.

| Amino Acid | Single Letter Code | Codon Options |
|---|---|---|
| Arginine | R | CGT, CGC, CGA, CGG, AGA, AGG |
| Selenocysteine | Sec | UGA in mRNA in presence of Selenocystein insertion element (SECIS) |
| Stop codons | Stop | TAA, TAG, TGA |

"Codon optimized" refers to the modification of a starting nucleotide sequence by replacing at least one codon of the starting nucleotide sequence with another codon encoding the same amino acid (e.g., to increase in vivo expression). Table 3 contains the codon usage frequency for humans (Codon usage database: [[www.]]kazusa.or.jp/codon/cgi-bin/showcodon.cgi?species=9606&aa=1 &style=N).

TABLE 3

Codon usage frequency table for humans.

| Codon | Amino Acid | % | Codon | Amino Acid | % | Codon | Amino Acid | % | Codon | Amino Acid | % |
|---|---|---|---|---|---|---|---|---|---|---|---|
| UUU | F (2) | 46 | UCU | S (3) | 19 | UAU | Y (2) | 44 | UGU | C (2) | 46 |
| UUC | F (1) | 54 | UCC | S (2) | 22 | UAC | Y (1) | 56 | UGC | C (1) | 54 |
| UUA | L (5) | 8 | UCA | S (4) | 15 | UAA | * | 30 | UGA | * | 47 |
| UUG | L (4) | 13 | UCG | S (6) | 5 | UAG | * | 24 | UGG | W (1) | 100 |
| CUU | L (3) | 13 | CCU | P (2) | 29 | CAU | H (2) | 42 | CGU | R (6) | 8 |
| CUC | L (2) | 20 | CCC | P (1) | 32 | CAC | H (1) | 58 | CGC | R (4) | 18 |
| CUA | L (6) | 7 | CCA | P (3) | 28 | CAA | Q (2) | 27 | CGA | R (5) | 11 |
| CUG | L (1) | 40 | CCG | P (4) | 11 | CAG | Q (1) | 73 | CGG | R (3) | 20 |
| AUU | I (2) | 36 | ACU | T (3) | 25 | AAU | N (2) | 47 | AGU | S (5) | 15 |
| AUC | I (1) | 47 | ACC | T (1) | 36 | AAC | N (1) | 53 | AGC | S (1) | 24 |
| AUA | I (3) | 17 | ACA | T (2) | 28 | AAA | K (2) | 43 | AGA | R (2) | 21 |
| AUG | M (1) | 100 | ACG | T (4) | 11 | AAG | K (1) | 57 | AGG | R (1) | 21 |
| GUU | V (3) | 18 | GCU | A (2) | 27 | GAU | D (2) | 46 | GGU | G (4) | 16 |
| GUC | V (2) | 24 | GCC | A (1) | 40 | GAC | D (1) | 54 | GGC | G (1) | 34 |
| GUA | V (4) | 12 | GCA | A (3) | 23 | GAA | E (2) | 42 | GGA | G (2) | 25 |
| GUG | V (1) | 46 | GCG | A (4) | 11 | GAG | E (1) | 58 | GGG | G (3) | 25 |

In Table 3, the number in parentheses after the one letter amino acid code indicates the frequency of that codon relative to other codons encoding the same amino acid, where "1" is the highest frequency and higher integers indicate less frequent codons.

A guanine maximized codon is a codon having the highest number of guanines possible for a specified amino acid. A cytosine maximized codon is a codon having the highest number of cytosines possivle for a specified amino acid. A guanine maximized codon and/or cytosine maximized codon refers to a codon having the highest number of guanines, cytosines, or combination of guanines and cytosines for a specified amino acid. When two or more codons have the same number of guanines, cytosines, or combination thereo for a specified amino acid, a low frequency maximized codon is a codon having a higher integer value than another maximized codon in Table 3.

In one embodiment, after a nucleotide sequence has been codon optimized it may be further evaluated for regions containing restriction sites. At least one nucleotide within the restriction site regions may be replaced with another nucleotide in order to remove the restriction site from the sequence but the replacement of nucleotides does alter the amino acid sequence which is encoded by the codon optimized nucleotide sequence.

Features, which may be considered beneficial in some embodiments of the present invention, may be encoded by regions of the polynucleotide and such regions may be upstream (5') or downstream (3') to a region which encodes a polypeptide. These regions may be incorporated into the polynucleotide before and/or after codon optimization of the protein encoding region or open reading frame (ORF). It is not required that a polynucleotide contain both a 5'- and 3'-flanking region. Examples of such features include, but are not limited to, untranslated regions (UTRs), Kozak sequences, an oligo(dT) sequence, and detectable tags and may include multiple cloning sites which may have XbaI recognition.

In some embodiments, a 5'-UTR and/or a 3'-UTR region may be provided as flanking regions. Multiple 5'- or 3'-UTRs may be included in the flanking regions and may be the same or of different sequences. Any portion of the flanking regions, including none, may be codon optimized and any may independently contain one or more different structural or chemical alterations, before and/or after codon optimization.

After optimization (if desired), the polynucleotides components are reconstituted and transformed into a vector such as, but not limited to, plasmids, viruses, cosmids, and artificial chromosomes. For example, the optimized polynucleotide may be reconstituted and transformed into chemically competent E. coli, yeast, neurospora, maize, drosophila, etc. where high copy plasmid-like or chromosome structures occur by methods described herein.

Alternative Nucleotides, Nucleosides and Polynucleotides of the Invention

Herein, in a nucleotide, nucleoside, or polynucleotide (such as the polynucleotides of the invention, e.g., mRNA molecule), the terms "alteration" or, as appropriate, "alternative" refer to alteration with respect to A, G, U or C ribonucleotides. Generally, herein, these terms are not intended to refer to the ribonucleotide alterations in naturally occurring 5'-terminal mRNA cap moieties.

The alterations may be various distinct alterations. In some embodiments, where the polynucleotide is an mRNA, the coding region, the flanking regions and/or the terminal regions (e.g., a 3'-stabilizing region) may contain one, two, or more (optionally different) nucleoside or nucleotide alterations. In some embodiments, an alternative polynucleotide introduced to a cell may exhibit reduced degradation in the cell, as compared to an unaltered polynucleotide.

The polynucleotides of the invention can include any useful alteration, such as to the nucleobase, the sugar, or the internucleoside linkage (e.g., to a linking phosphate/to a phosphodiester linkage/to the phosphodiester backbone). In certain embodiments, alterations (e.g., one or more alterations) are present in each of the nucleobase, the sugar, and the internucleoside linkage. Alterations according to the present invention may be alterations of ribonucleic acids (RNAs) to deoxyribonucleic acids (DNAs), e.g., the substitution of the 2'-OH of the ribofuranosyl ring to 2'-H, threose nucleic acids (TNAs), glycol nucleic acids (GNAs), peptide nucleic acids (PNAs), locked nucleic acids (LNAs), or hybrids thereof. Additional alterations are described herein.

As described herein, in some embodiments, the polynucleotides of the invention do not substantially induce an innate immune response of a cell into which the polynucleotide (e.g., mRNA) is introduced. Features of an induced innate immune response include 1) increased expression of pro-inflammatory cytokines, 2) activation of intracellular PRRs (RIG-I, MDA5, etc, and/or 3) termination or reduction in protein translation.

The polynucleotides can optionally include other agents (e.g., RNAi-inducing agents, RNAi agents, siRNAs, shRNAs, miRNAs, antisense RNAs, ribozymes, catalytic DNA, tRNA, RNAs that induce triple helix formation, aptamers, vectors). In some embodiments, the polynucleotides may include one or more messenger RNAs (mRNAs) having one or more alternative nucleoside or nucleotides (i.e., alternative mRNA molecules). Details for these polynucleotides follow.

Nucleobase Alternatives

The alternative nucleosides and nucleotides can include an alternative nucleobase. Examples of nucleobases found in RNA include, but are not limited to, adenine, guanine, cytosine, and uracil. Examples of nucleobases found in DNA include, but are not limited to, adenine, guanine, cytosine, and thymine. These nucleobases can be altered or wholly replaced to provide polynucleotide molecules having enhanced properties, e.g., increased stability such as resistance to nucleases.

Alternative nucleotide base pairing encompasses not only the standard adenine-thymine, adenine-uracil, or guanine-cytosine base pairs, but also base pairs formed between nucleotides and/or alternative nucleotides including non-standard or alternative bases, wherein the arrangement of hydrogen bond donors and hydrogen bond acceptors permits hydrogen bonding between a non-standard base and a standard base or between two complementary non-standard base structures. One example of such non-standard base pairing is the base pairing between the alternative nucleotide inosine and adenine, cytosine, or uracil.

In some embodiments, the nucleobase is an alternative uracil. Exemplary nucleobases and nucleosides having an alternative uracil include pseudouridine ($\psi$), pyridin-4-one ribonucleoside, 5-aza-uracil, 6-aza-uracil, 2-thio-5-aza-uracil, 2-thio-uracil ($s^2U$), 4-thio-uracil ($s^4U$), 4-thio-pseudouridine, 2-thio-pseudouridine, 5-hydroxy-uracil ($ho^5U$), 5-aminoallyl-uracil, 5-halo-uracil (e.g., 5-iodo-uracil or 5-bromo-uracil), 3-methyl-uracil ($m^3U$), 5-methoxy-uracil ($mo^5U$), uracil 5-oxyacetic acid ($cmo^5U$), uracil 5-oxyacetic acid methyl ester ($mcmo^5U$), 5-carboxymethyl-uracil ($cm^5U$), 1-carboxymethyl-pseudouridine, 5-carboxyhydroxymethyl-uracil ($chm^5U$), 5-carboxyhydroxymethyl-uracil methyl ester ($mchm^5U$), 5-methoxycarbonylmethyl-uracil ($mcm^5U$), 5-methoxycarbonylmethyl-2-thio-uracil ($mcm^5s^2U$), 5-aminomethyl-2-thio-uracil ($nm^5s^2U$), 5-methylaminomethyl-uracil ($mnm^5U$), 5-methylaminomethyl-2-thio-uracil ($mnm^5s^2U$), 5-methylaminomethyl-2-seleno-uracil ($mnm^5se^2U$), 5-carbamoylmethyl-uracil ($ncm^5U$), 5-carboxymethylaminomethyl-uracil ($cmnm^5U$), 5-carboxymethylaminomethyl-2-thio-uracil ($cmnm^5s^2U$), 5-propynyl-uracil, 1-propynyl-pseudouracil, 5-taurinomethyl-uracil ($\tau m^5U$), 1-taurinomethyl-pseudouridine, 5-taurinomethyl-2-thio-uracil($\tau m^5s^2U$), 1-taurinomethyl-4-thio-pseudouridine, 5-methyl-uracil ($m^5U$, i.e., having the nucleobase deoxythymine), 1-methyl-pseudouridine ($m^1\psi$), 5-methyl-2-thio-uracil ($m^5s^2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouracil (D), dihydropseudouridine, 5,6-dihydrouracil, 5-methyl-dihydrouracil ($m^5D$), 2-thio-dihydrouracil, 2-thio-dihydropseudouridine, 2-methoxy-uracil, 2-methoxy-4-thio-uracil, 4-methoxy-pseudouridine, 4-methoxy-2-thio-pseudouridine, N1-methyl-pseudouridine, 3-(3-amino-3-carboxypropyl)uracil ($acp^3U$), 1-methyl-3-(3-amino-3-carboxypropyl)pseudouridine ($acp^3\psi$), 5-(isopentenylaminomethyl)uracil ($inm^5U$), 5-(isopentenylaminomethyl)-2-thio-uracil ($inm^5s^2U$), 5,2'-O-dimethyl-uridine ($m^5Um$), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uracil, deoxythymidine, 5-(2-carbomethoxyvinyl)-uracil, 5-(carbamoylhydroxymethyl)-uracil, 5-carbamoylmethyl-2-thio-uracil, 5-carboxymethyl-2-thio-uracil, 5-cyanomethyl-uracil, 5-methoxy-2-thio-uracil, and 5-[3-(1-E-propenylamino)]uracil.

In some embodiments, the nucleobase is an alternative cytosine. Exemplary nucleobases and nucleosides having an alternative cytosine include 5-aza-cytosine, 6-aza-cytosine, pseudoisocytidine, 3-methyl-cytosine (m3C), N4-acetyl-cytosine (ac4C), 5-formyl-cytosine (f5C), N4-methyl-cytosine (m4C), 5-methyl-cytosine (m5C), 5-halo-cytosine (e.g., 5-iodo-cytosine), 5-hydroxymethyl-cytosine (hm5C), 1-methyl-pseudoisocytidine, pyrrolo-cytosine, pyrrolo-pseudoisocytidine, 2-thio-cytosine (s2C), 2-thio-5-methyl-cytosine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytosine, 2-methoxy-5-methyl-cytosine, 4-methoxy-pseudoisocytidine, 4-methoxy-1-methyl-pseudoisocytidine, lysidine (k2C), 5,2'-O-dimethyl-cytidine (m5Cm), N4-acetyl-2'-O-methyl-cytidine (ac4Cm), N4,2'-O-dimethyl-cytidine (m4Cm), 5-formyl-2'-O-methyl-cytidine (f5Cm), N4,N4,2'-O-trimethyl-cytidine (m42Cm), 1-thio-cytosine, 5-hydroxy-cytosine, 5-(3-azidopropyl)-cytosine, and 5-(2-azidoethyl)-cytosine.

In some embodiments, the nucleobase is an alternative adenine. Exemplary nucleobases and nucleosides having an alternative adenine include 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenine (m1A), 2-methyl-adenine (m2A), N6-methyl-adenine (m6A), 2-methylthio-N6-methyl-adenine (ms2m6A), N6-isopentenyl-adenine (i6A), 2-methylthio-N6-isopentenyl-adenine (ms2i6A), N6-(cis-hydroxyisopentenyl)adenine (io6A), 2-methylthio-N6-(cis-hydroxyisopentenyl)adenine (ms2io6A), N6-glycinylcarbamoyl-adenine (g6A), N6-threonylcarbamoyl-adenine (t6A), N6-methyl-N6-threonylcarbamoyl-adenine (m6t6A), 2-methylthio-N6-threonylcarbamoyl-adenine (ms2g6A), N6,N6-dimethyl-adenine (m62A), N6-hydroxynorvalylcarbamoyl-adenine (hn6A), 2-methylthio-N6-hydroxynorvalylcarbamoyl-adenine (ms2hn6A), N6-acetyl-adenine (ac6A), 7-methyl-adenine, 2-methylthio-adenine, 2-methoxy-adenine, N6,2'-O-dimethyl-adenosine (m6Am), N6,N6,2'-O-trimethyl-adenosine (m62Am), 1,2'-O-dimethyl-adenosine (m1Am), 2-amino-N6-methyl-purine, 1-thio-adenine, 8-azido-adenine, N6-(19-amino-pentaoxanonadecyl)-adenine, 2,8-dimethyl-adenine, N6-formyl-adenine, and N6-hydroxymethyl-adenine.

In some embodiments, the nucleobase is an alternative guanine. Exemplary nucleobases and nucleosides having an alternative guanine include inosine (I), 1-methyl-inosine (m1I), wyosine (imG), methylwyosine (mimG), 4-demethyl-wyosine (imG-14), isowyosine (imG2), wybutosine (yW), peroxywybutosine (o2yW), hydroxywybutosine (OHyW), undermodified hydroxywybutosine (OHyW*), 7-deaza-guanine, queuosine (Q), epoxyqueuosine (oQ), galactosyl-queuosine (galQ), mannosyl-queuosine (manQ), 7-cyano-7-deaza-guanine (preQ0), 7-aminomethyl-7-deaza-guanine (preQ1), archaeosine (G+), 7-deaza-8-aza-guanine, 6-thio-guanine, 6-thio-7-deaza-guanine, 6-thio-7-deaza-8-aza-guanine, 7-methyl-guanine (m7G), 6-thio-7-methyl-guanine, 7-methyl-inosine, 6-methoxy-guanine, 1-methyl-guanine (m1G), N2-methyl-guanine (m2G), N2,N2-dimethyl-guanine (m22G), N2,7-dimethyl-guanine (m2,7G), N2, N2,7-dimethyl-guanine (m2,2,7G), 8-oxo-guanine, 7-methyl-8-oxo-guanine, 1-methyl-6-thio-guanine, N2-methyl-6-thio-guanine, N2,N2-dimethyl-6-thio-guanine, N2-methyl-2'-O-methyl-guanosine (m2Gm), N2,N2-dimethyl-2'-O-methyl-guanosine (m22Gm), 1-methyl-2'-O-methyl-guanosine (m1Gm), N2,7-dimethyl-2'-O-methyl-guanosine (m2,7Gm), 2'-O-methyl-inosine (Im), 1,2'-O-dimethyl-inosine (m1Im), 1-thio-guanine, and O-6-methyl-guanine.

The alternative nucleobase of a nucleotide can be independently a purine, a pyrimidine, a purine or pyrimidine analog. For example, the nucleobase can be an alternative to adenine, cytosine, guanine, uracil, or hypoxanthine. In another embodiment, the nucleobase can also include, for example, naturally-occurring and synthetic derivatives of a base, including pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxy and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; or 1,3,5 triazine. When the nucleotides are depicted using the shorthand A, G, C, T or U, each letter refers to the representative base and/or derivatives thereof, e.g., A includes adenine or adenine analogs, e.g., 7-deaza adenine).

Alterations on the Sugar

The alternative nucleosides and nucleotides, which may be incorporated into a polynucleotide of the invention (e.g., RNA or mRNA, as described herein), can be altered on the sugar of the nucleoside or nucleotide. In some embodiments, the alternative nucleosides or nucleotides include the structure:

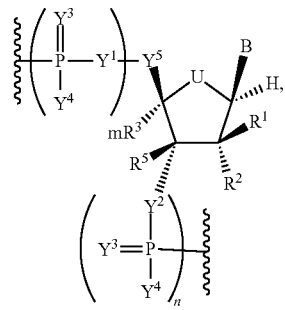

Formula XVII

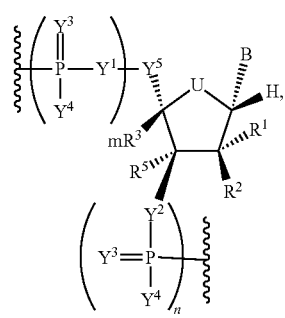

Formula XVIII

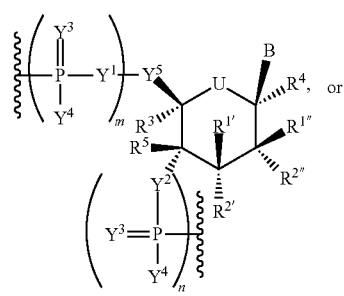

Formula XIX

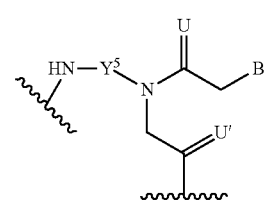

Formula XX wherein B is a nucleobase;
each U and U' is, independently, O, S, N($R^U$)$_{nu}$, or C($R^U$)$_{nu}$, wherein nu is 1 or 2 (e.g., 1 for N($R^U$)$_{nu}$ and 2 for C($R^U$)$_{nu}$) and each $R^U$ is, independently, H, halo, or optionally substituted $C_1$-$C_6$ alkyl;
each of $R^1$, $R^{1'}$, $R^{1''}$, $R^2$, $R^{2'}$, $R^{2''}$, $R^3$, $R^4$, and $R^5$ is, independently, H, halo, hydroxy, thiol, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, optionally substituted $C_6$-$C_{10}$ aryl; or $R^3$ and/or $R^5$ can join together with one of $R^1$, $R^{1'}$, $R^{1''}$, $R^2$, $R^{2'}$, or $R^{2''}$ to form together with the carbons to which they are attached an optionally substituted $C_3$-$C_{10}$ carbocycle or an optionally substituted $C_3$—C heterocyclyl;

each of m and n is independently, 0, 1, 2, 3, 4, or 5;

each of $Y^1$, $Y^2$, and $Y^3$, is, independently, O, S, Se, —$NR^{N1}$—, optionally substituted $C_1$-$C_6$ alkylene, or optionally substituted $C_1$-$C_6$ heteroalkylene, wherein $R^{N1}$ is H, optionally substituted $C_1$-$C_6$ alkyl, optionally substituted $C_2$-$C_6$ alkenyl, optionally substituted $C_2$-$C_6$ alkynyl, or optionally substituted $C_6$-$C_{10}$ aryl; and each $Y^4$ is, independently, H, hydroxy, protected hydroxy, halo, thiol, boranyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, or optionally substituted amino; and $Y^5$ is O, S, Se, optionally substituted $C_1$-$C_6$ alkylene, or optionally substituted $C_1$-$C_6$ heteroalkylene;

or a salt thereof.

In some embodiments, the 2'-hydroxy group (OH) can be modified or replaced with a number of different substituents. Exemplary substitutions at the 2'-position include, but are not limited to, H, azido, halo (e.g., fluoro), optionally substituted $C_{1-6}$ alkyl (e.g., methyl); optionally substituted $C_{1-6}$ alkoxy (e.g., methoxy or ethoxy); optionally substituted $C_{6-10}$ aryloxy; optionally substituted $C_{3-8}$ cycloalkyl; optionally substituted $C_{6-10}$ aryl-$C_{1-6}$ alkoxy, optionally substituted $C_{1-12}$ (heterocyclyl)oxy; a sugar (e.g., ribose, pentose, or any described herein); a polyethyleneglycol (PEG), —O(CH$_2$CH$_2$O)$_n$CH$_2$CH$_2$OR, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxy is connected by a $C_{1-6}$ alkylene or $C_{1-6}$ heteroalkylene bridge to the 4'-carbon of the same ribose sugar, where exemplary bridges included methylene, propylene, ether, or amino bridges; aminoalkyl, as defined herein; aminoalkoxy, as defined herein; amino as defined herein; and amino acid, as defined herein.

Generally, RNA includes the sugar group ribose, which is a 5-membered ring having an oxygen. Exemplary, non-limiting alternative nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino (that also has a phosphoramidate backbone)); multicyclic forms (e.g., tricyclo and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone).

In some embodiments, the sugar group contains one or more carbons that possess the opposite stereochemical configuration of the corresponding carbon in ribose. Thus, a polynucleotide molecule can include nucleotides containing, e.g., arabinose or L-ribose, as the sugar.

In some embodiments, the polynucleotide of the invention includes at least one nucleoside wherein the sugar is L-ribose, 2'-O-methyl-ribose, 2'-fluoro-ribose, arabinose, hexitol, an LNA, or a PNA.

Alterations on the Internucleoside Linkage

The alternative nucleotides, which may be incorporated into a polynucleotide of the invention, can be altered on the internucleoside linkage (e.g., phosphate backbone). Herein, in the context of the polynucleotide backbone, the phrases "phosphate" and "phosphodiester" are used interchangeably. Backbone phosphate groups can be altered by replacing one or more of the oxygen atoms with a different substituent.

The alternative nucleotides can include the wholesale replacement of an unaltered phosphate moiety with another internucleoside linkage as described herein. Examples of alternative phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be altered by the replacement of a linking oxygen with nitrogen (bridged phosphoramidates), sulfur (bridged phosphorothioates), and carbon (bridged methylene-phosphonates).

The alternative nucleosides and nucleotides can include the replacement of one or more of the non-bridging oxygens with a borane moiety (BH$_3$), sulfur (thio), methyl, ethyl, and/or methoxy. As a non-limiting example, two non-bridging oxygens at the same position (e.g., the alpha (α), beta (ρ) or gamma (γ) position) can be replaced with a sulfur (thio) and a methoxy.

The replacement of one or more of the oxygen atoms at the α position of the phosphate moiety (e.g., α-thio phosphate) is provided to confer stability (such as against exonucleases and endonucleases) to RNA and DNA through the unnatural phosphorothioate backbone linkages. Phosphorothioate DNA and RNA have increased nuclease resistance and subsequently a longer half-life in a cellular environment.

Other internucleoside linkages that may be employed according to the present invention, including internucleoside linkages which do not contain a phosphorous atom, are described herein.

Synthesis of Polynucleotide Molecules

The polynucleotide molecules for use in accordance with the invention may be prepared according to any useful technique known in the art. The alternative nucleosides and nucleotides used in the synthesis of polynucleotide molecules disclosed herein can be prepared from readily available starting materials using the following general methods and procedures. Where typical or preferred process conditions (e.g., reaction temperatures, times, mole ratios of reactants, solvents, pressures, etc.) are provided, a skilled artisan would be able to optimize and develop additional process conditions. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Preparation of polynucleotide molecules of the present invention can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 2d. Ed., Wiley & Sons, 1991.

The reactions of the processes described herein can be carried out in suitable solvents, which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of alternative polynucleotides (e.g., alternative mRNA molecules) can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

Synthesis of Alternative Polynucleotides

Polynucleotides for use in accordance with the present disclosure may be prepared according to any available technique including, but not limited to chemical synthesis, enzymatic synthesis, which is generally termed in vitro transcription, enzymatic or chemical cleavage of a longer precursor. Alternative nucleosides and nucleotides can be prepared by methods known in the art, e.g., according to the synthetic methods described in Ogata et al., J. Org. Chem. 74:2585-2588 (2009); Purmal et al., Nucl. Acids Res. 22(1): 72-78, (1994); Fukuhara et al., Biochemistry, 1(4): 563-568 (1962); and Xu et al., Tetrahedron, 48(9): 1729-1740 (1992). Further methods of synthesizing RNAs are known in the art (see, e.g., Gait, M. J. (ed.) Oligonucleotide synthesis: a practical approach, Oxford [Oxfordshire], Washington, DC: IRL Press, 1984; and Herdewijn, P. (ed.) Oligonucleotide synthesis: methods and applications, Methods in Molecular Biology, v. 288 (Clifton, N.J.) Totowa, N.J.: Humana Press, 2005).

In certain embodiments, a method for producing a polynucleotide encoding a polypeptide of interest includes contacting a cDNA that encodes the protein of interest with an RNA polymerase in the presence of a nucleotide triphosphate mix, e.g., wherein at least 90% (e.g., at least 95% or 100%) of the uracils are 5-methoxyuracil. The invention also provides polynucleotides produced by such methods. The methods may include additional steps, such as capping (e.g., the addition of a 5' cap structure), addition of a poly-A region, and/or formulation into a pharmaceutical composition. The RNA polymerase may be T7 RNA polymerase. The in vitro transcription reaction mixture may include a transcription buffer (such as 400 mM Tris-HCl pH 8.0, or an equivalent) and may include $MgCl_2$, DTT, and/or spermidine or equivalents. An RNase inhibitor may be included. The remaining reaction volume is generally made up with $dH_2O$. The reaction may be incubated at approximately 37° C. (such as between 30 and 40° C.) and may be incubated for 3 hours-5 hours (such as 3½ hours-4½ hours, or about 4 hr). The polynucleotide may then be purified using DNase and a purification kit.

For example, the alternative polynucleotides described herein can be prepared using methods that are known to those skilled in the art of polynucleotide synthesis.

In some embodiments, the present disclosure provides for methods of synthesizing a pharmaceutical polynucleotide, including the steps of:
 a) providing a complementary deoxyribonucleic acid (cDNA) that encodes a pharmaceutical protein of interest;
 b) selecting a nucleotide and
 c) contacting the provided cDNA and the selected nucleotide with an RNA polymerase, under conditions such that the pharmaceutical polynucleotide is synthesized.

In further embodiments, the pharmaceutical polynucleotide is a ribonucleic acid (RNA).

In still a further aspect of the present disclosure, the alternative polynucleotides can be prepared using solid phase synthesis methods.

In some embodiments, the polynucleotides of the invention are produced by a) synthesizing a polynucleotide including i) a coding region; ii) a 5'-UTR optionally including a Kozak sequence; iii) a 3'-UTR; iv) at least one 5'-cap structure; and v) a poly-A region; b) incorporation of a 3'-azido-containing nucleoside; and c) conjugation of a 3'-stabilizing region containing an alkyne functional group (e.g., a cyclooctyne-containing functional group) at the 5'-terminus.

Prevention or Reduction of Innate Cellular Immune Response

The term "innate immune response" includes a cellular response to exogenous single stranded polynucleotides, generally of viral or bacterial origin, which involves the induction of cytokine expression and release, particularly the interferons, and cell death. Protein synthesis is also reduced during the innate cellular immune response. While it is advantageous to eliminate the innate immune response in a cell which is triggered by introduction of exogenous polynucleotides, the present disclosure provides alternative polynucleotides such as mRNAs that substantially reduce the immune response, including interferon signaling, without entirely eliminating such a response. In some embodiments, the immune response is reduced by 10%, 20%, 30%, 40%, 50%, 60%, 70%, 80%, 90%, 95%, 99%, 99.9%, or greater than 99.9% as compared to the immune response induced by a corresponding unaltered polynucleotide. Such a reduction can be measured by expression or activity level of Type 1 interferons or the expression of interferon-regulated genes such as the toll-like receptors (e.g., TLR7 and TLR8). Reduction or lack of induction of innate immune response can also be measured by decreased cell death following one or more administrations of alternative RNAs to a cell population; e.g., cell death is 10%, 25%, 50%, 75%, 85%, 90%, 95%, or over 95% less than the cell death frequency observed with a corresponding unaltered polynucleotide. Moreover, cell death may affect fewer than 50%, 40%, 30%, 20%, 10%, 5%, 1%, 0.1%, 0.01% or fewer than 0.01% of cells contacted with the alternative polynucleotides.

In some embodiments, the alternative polynucleotides, including mRNA molecules are alternative in such a way as to not induce, or induce only minimally, an immune response by the recipient cell or organism. Such evasion or avoidance of an immune response trigger or activation is a novel feature of the alternative polynucleotides of the present invention.

The present disclosure provides for the repeated introduction (e.g., transfection) of alternative polynucleotides into a target cell population, e.g., in vitro, ex vivo, or in vivo. The step of contacting the cell population may be repeated one or more times (such as two, three, four, five or more than five times). In some embodiments, the step of contacting the cell population with the alternative polynucleotides is repeated a number of times sufficient such that a predetermined efficiency of protein translation in the cell population is achieved. Given the reduced cytotoxicity of the target cell population provided by the nucleotide alterations, such repeated transfections are achievable in a diverse array of cell types in vitro and/or in vivo.

Methods of determining the effectiveness of an alternative polynucleotide as compared to wild-type may involve the measure and analysis of one or more cytokine the expression of which is triggered by the administration of the exogenous polynucleotide of the invention. These values are compared to administration of an unaltered polynucleotide or to a standard metric such as cytokine response, or PolyIC, R-848. One example of a standard metric is the measure of the ratio of the level or amount of encoded polypeptide (protein) produced in the cell, tissue or organism to the level or amount of one or more (or a panel) of cytokines whose expression is triggered in the cell, tissue or organism as a result of administration or contact with the alternative polynucleotide. Such ratios are referred to herein as the Protein:Cytokine Ratio or "PC" Ratio. The higher the PC ratio, the more efficacious the alternative polynucleotide (polynucleotide encoding the protein measured). Preferred PC Ratios, by cytokine, of the present invention may be greater than 1, greater than 10, greater than 100, greater than 1000, greater than 10,000 or more. Alternative polynucleotides having higher PC Ratios than an alternative polynucleotide of a different or unaltered construct are preferred. The PC ratio may be further qualified by the percent alteration present in the polynucleotide. For example, normalized to a 100% alternative polynucleotide, the protein production as a function of cytokine (or risk) or cytokine profile can be determined.

Polypeptides

Polypeptides of interest expressed by the polynucleotides of the invention, may be selected from any polypeptide known in the art, e.g., those disclosed in US Patent Publication Nos. 2013/0259924 and 2013/0259923, International Publication Nos. WO 2013/151663, WO 2013/151669, WO 2013/151670, WO 2013/151664, WO 2013/151665, WO 2013/151736, U.S. Provisional Patent Application Nos. 61/618,862, 61/681,645, 61/618,873, 61/681,650, 61/618,878, 61/681,654, 61/618,885, 61/681,658, 61/618,911, 61/681,667, 61/618,922, 61/681,675, 61/618,935, 61/681,687, 61/618,945, 61/681,696, 61/618,953, and 61/681,704, the polypeptides of each of which are incorporated herein by reference.

Erythropoietin (EPO) and granulocyte colony-stimulating factor (GCSF) are exemplary polypeptides.

Polypeptide Variants

Also provided are polynucleotides that encode variant polypeptides, which have a certain identity with a reference polypeptide sequence. The term "identity" as known in the art, refers to a relationship between the sequences of two or more peptides, as determined by comparing the sequences. In the art, "identity" also means the degree of sequence relatedness between peptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

In some embodiments, the polypeptide variant has the same or a similar activity as the reference polypeptide. Alternatively, the variant has an altered activity (e.g., increased or decreased) relative to a reference polypeptide. Generally, variants of a particular polynucleotide or polypeptide of the present disclosure will have at least about 40%, 45%, 50%, 55%, 60%, 65%, 70%, 75%, 80%, 85%, 90%, 91%, 92%, 93%, 94%, 95%, 96%, 97%, 98%, 99%, or more sequence identity to that particular reference polynucleotide or polypeptide as determined by sequence alignment programs and parameters described herein and known to those skilled in the art.

As recognized by those skilled in the art, protein fragments, functional protein domains, and homologous proteins are also considered to be within the scope of this present disclosure. For example, provided herein is any protein fragment of a reference protein (meaning a polypeptide sequence at least one amino acid residue shorter than a reference polypeptide sequence but otherwise identical) 10, 20, 30, 40, 50, 60, 70, 80, 90, 100, or greater than 100 amino acids in length. In another example, any protein that includes a stretch of about 20, about 30, about 40, about 50, or about 100 amino acids which are about 40%, about 50%, about 60%, about 70%, about 80%, about 90%, about 95%, or about 100% identical to any of the sequences described herein can be utilized in accordance with the present disclosure. In certain embodiments, a protein sequence to be utilized in accordance with the present disclosure includes 2, 3, 4, 5, 6, 7, 8, 9, 10, or more mutations as shown in any of the sequences provided or referenced herein.

Polynucleotide Libraries

Also provided are polynucleotide libraries containing nucleoside alterations, wherein the polynucleotides individually contain a first polynucleotide sequence encoding a polypeptide, such as an antibody, protein binding partner, scaffold protein, and other polypeptides known in the art. Preferably, the polynucleotides are mRNA in a form suitable for direct introduction into a target cell host, which in turn synthesizes the encoded polypeptide.

In certain embodiments, multiple variants of a protein, each with different amino acid alteration(s), are produced and tested to determine the best variant in terms of pharmacokinetics, stability, biocompatibility, and/or biological activity, or a biophysical property such as expression level. Such a library may contain 10, $10^2$, $10^3$, $10^4$, $10^5$, $10^6$, $10^7$, $10^8$, $10^9$, or over $10^9$ possible variants (including substitutions, deletions of one or more residues, and insertion of one or more residues).

Polypeptide-Polynucleotide Complexes

Proper protein translation involves the physical aggregation of a number of polypeptides and polynucleotides associated with the mRNA. Provided by the present disclosure are protein-polynucleotide complexes, containing a translatable mRNA having one or more nucleoside alterations (e.g., at least two different nucleoside alterations) and one or more polypeptides bound to the mRNA. Generally, the proteins are provided in an amount effective to prevent or reduce an innate immune response of a cell into which the complex is introduced.

Uses of Compounds of the Invention

Therapeutic Agents

The compounds described herein can be used as therapeutic agents. For example, a compound described herein can be administered to an animal or subject, wherein the first polynucleotide is translated in vivo to produce a therapeutic peptide in the animal or subject. Accordingly, provided herein are compounds, compositions (such as pharmaceutical compositions), methods, kits, and reagents for treatment or prevention of disease or conditions in humans and other mammals. The active therapeutic agents of the present disclosure include compounds, cells containing compounds or polypeptides translated from the compounds, cells contacted with cells containing compounds or polypeptides translated from the compounds, tissues containing cells containing compounds and organs containing tissues containing cells containing compounds.

Provided are methods of inducing translation of a synthetic or recombinant polynucleotide to produce a polypeptide in a cell population using the compounds described herein. Such translation can be in vivo, ex vivo, in culture, or in vitro. The cell population is contacted with an effective amount of a composition containing a polynucleotide that has at least one nucleoside alteration, and a translatable region encoding the polypeptide. The population is contacted under conditions such that the polynucleotide is localized into one or more cells of the cell population and the recombinant polypeptide is translated in the cell from the polynucleotide.

An effective amount of the composition is provided based, at least in part, on the target tissue, target cell type, means of administration, physical characteristics of the polynucleotide (e.g., size, and extent of alternative nucleosides), and other determinants. In general, an effective amount of the composition provides efficient protein production in the cell, preferably more efficient than a composition containing a corresponding unaltered polynucleotide. Increased efficiency may be demonstrated by increased cell transfection (i.e., the percentage of cells transfected with the polynucleotide), increased protein translation from the polynucleotide, decreased polynucleotide degradation (as demonstrated, e.g., by increased duration of protein translation from a modified polynucleotide), or reduced innate immune response of the host cell or improve therapeutic utility.

Aspects of the present disclosure are directed to methods of inducing in vivo translation of a recombinant polypeptide in a mammalian subject in need thereof. Therein, an effective amount of a composition containing a polynucleotide including a translatable region encoding the polypeptide is administered to the subject using the delivery methods described herein. The polynucleotide is provided in an amount and under other conditions such that the polynucleotide is localized into a cell or cells of the subject and the recombinant polypeptide is translated in the cell from the polynucleotide. The cell in which the polynucleotide is localized, or the tissue in which the cell is present, may be targeted with one or more than one rounds of polynucleotide administration.

Other aspects of the present disclosure relate to transplantation of cells containing compounds to a mammalian subject. Administration of cells to mammalian subjects is known to those of ordinary skill in the art, such as local implantation (e.g., topical or subcutaneous administration), organ delivery or systemic injection (e.g., intravenous injection or inhalation), as is the formulation of cells in pharmaceutically acceptable carrier. Compositions containing alternative polynucleotides are formulated for administration intramuscularly, transarterially, intraperitoneally, intravenously, intranasally, subcutaneously, endoscopically, transdermally, or intrathecally. In some embodiments, the composition is formulated for extended release.

In some embodiments, the subject to whom the therapeutic agent is administered suffers from or is at risk of developing a disease, disorder, or deleterious condition. Provided are methods of identifying, diagnosing, and classifying subjects, which may include clinical diagnosis, biomarker levels, genome-wide association studies (GWAS), and other methods known in the art.

In certain embodiments, the administered compound directs production of one or more recombinant polypeptides that provide a functional activity which is substantially absent in the cell in which the recombinant polypeptide is translated. For example, the missing functional activity may be enzymatic, structural, or gene regulatory in nature.

In other embodiments, the administered compound directs production of one or more recombinant polypeptides that replace a polypeptide (or multiple polypeptides) that is substantially absent in the cell in which the recombinant polypeptide is translated. Such absence may be due to genetic mutation of the encoding gene or regulatory pathway thereof. In other embodiments, the administered compound directs production of one or more recombinant polypeptides to supplement the amount of polypeptide (or multiple polypeptides) that is present in the cell in which the recombinant polypeptide is translated. Alternatively, the recombinant polypeptide functions to antagonize the activity of an endogenous protein present in, on the surface of, or secreted from the cell. Usually, the activity of the endogenous protein is deleterious to the subject, for example, due to mutation of the endogenous protein resulting in altered activity or localization. Additionally, the recombinant polypeptide antagonizes, directly or indirectly, the activity of a biological moiety present in, on the surface of, or secreted from the cell. Examples of antagonized biological moieties include lipids (e.g., cholesterol), a lipoprotein (e.g., low density lipoprotein), a polynucleotide, a carbohydrate, or a small molecule toxin.

The recombinant proteins described herein are engineered for localization within the cell, potentially within a specific compartment such as the nucleus, or are engineered for secretion from the cell or translocation to the plasma membrane of the cell.

As described herein, a useful feature of the compounds of the present disclosure is the capacity to reduce, evade, avoid or eliminate the innate immune response of a cell to an exogenous polynucleotide. Provided are methods for performing the titration, reduction or elimination of the immune response in a cell or a population of cells. In some embodiments, the cell is contacted with a first composition that contains a first dose of a first exogenous polynucleotide including a translatable region, and the level of the innate immune response of the cell to the first exogenous polynucleotide is determined. Subsequently, the cell is contacted with a second composition, which includes a second dose of the first exogenous polynucleotide, the second dose containing a lesser amount of the first exogenous polynucleotide as compared to the first dose. Alternatively, the cell is contacted with a first dose of a second exogenous polynucleotide. The second exogenous polynucleotide may contain one or more alternative nucleosides, which may be the same or different from the first exogenous polynucleotide or, alternatively, the second exogenous polynucleotide may not contain alternative nucleosides. The steps of contacting the cell with the first composition and/or the second composition may be repeated one or more times. Additionally, efficiency of protein production (e.g., protein translation) in the cell is optionally determined, and the cell may be re-transfected with the first and/or second composition repeatedly until a target protein production efficiency is achieved.

Therapeutics for Diseases and Conditions

Provided are methods for treating or preventing a symptom of diseases characterized by missing or aberrant protein activity, by replacing the missing protein activity or overcoming the aberrant protein activity. Because of the rapid initiation of protein production following introduction of alternative mRNAs, as compared to viral DNA vectors, the compounds of the present disclosure are particularly advantageous in treating acute diseases such as sepsis, stroke, and myocardial infarction. Moreover, the lack of transcriptional regulation of the alternative mRNAs of the present disclosure is advantageous in that accurate titration of protein production is achievable. Multiple diseases are characterized by missing (or substantially diminished such that proper protein function does not occur) protein activity. Such proteins may not be present, are present in very low quantities or are essentially non-functional. The present disclosure provides a method for treating such conditions or diseases in a subject by introducing polynucleotide or cell-based therapeutics containing the compounds provided herein, wherein the compounds encode for a protein that replaces the protein activity missing from the target cells of the subject.

Diseases characterized by dysfunctional or aberrant protein activity include, but are not limited to, cancer and other proliferative diseases, genetic diseases (e.g., cystic fibrosis), autoimmune diseases, diabetes, neurodegenerative diseases, cardiovascular diseases, and metabolic diseases. The present disclosure provides a method for treating such conditions or diseases in a subject by introducing polynucleotide or cell-based therapeutics containing the compounds provided herein, wherein the compounds encode for a protein that antagonizes or otherwise overcomes the aberrant protein activity present in the cell of the subject.

Specific examples of a dysfunctional protein are the missense or nonsense mutation variants of the cystic fibrosis transmembrane conductance regulator (CFTR) gene, which produce a dysfunctional or nonfunctional, respectively, protein variant of CFTR protein, which causes cystic fibrosis.

Thus, provided are methods of treating cystic fibrosis in a mammalian subject by contacting a cell of the subject with a compound having a translatable region that encodes a functional CFTR polypeptide, under conditions such that an effective amount of the CTFR polypeptide is present in the cell. Preferred target cells are epithelial cells, such as the lung, and methods of administration are determined in view of the target tissue; i.e., for lung delivery, the compounds are formulated for administration by inhalation. Therefore, in certain embodiments, the polypeptide of interest encoded by the compound of the invention is the CTFR polypeptide and the compound or pharmaceutical composition of the invention is for use in treating cystic fibrosis.

In another embodiment, the present disclosure provides a method for treating hyperlipidemia in a subject, by introducing into a cell population of the subject with a compound encoding Sortilin, a protein recently characterized by genomic studies, thereby ameliorating the hyperlipidemia in a subject. The SORT1 gene encodes a trans-Golgi network (TGN) transmembrane protein called Sortilin. Genetic studies have shown that one of five individuals has a single nucleotide polymorphism, rs12740374, in the 1p13 locus of the SORT1 gene that predisposes them to having low levels of low-density lipoprotein (LDL) and very-low-density lipoprotein (VLDL). Each copy of the minor allele, present in about 30% of people, alters LDL cholesterol by 8 mg/dL, while two copies of the minor allele, present in about 5% of the population, lowers LDL cholesterol 16 mg/dL. Carriers of the minor allele have also been shown to have a 40% decreased risk of myocardial infarction. Functional in vivo studies in mice describes that overexpression of SORT1 in mouse liver tissue led to significantly lower LDL-cholesterol levels, as much as 80% lower, and that silencing SORT1 increased LDL cholesterol approximately 200% (Musunuru K et al. From noncoding variant to phenotype via SORT1 at the 1p13 cholesterol locus. Nature 2010; 466: 714-721). Therefore, in certain embodiments, the polypeptide of interest encoded by the compound of the invention is Sortilin and the compound or pharmaceutical composition of the invention is for use in treating hyperlipidemia.

In certain embodiments, the polypeptide of interest encoded by the compound of the invention is granulocyte colony-stimulating factor (GCSF), and the compound or pharmaceutical composition of the invention is for use in treating a neurological disease such as cerebral ischemia, or treating neutropenia, or for use in increasing the number of hematopoietic stem cells in the blood (e.g., before collection by leukapheresis for use in hematopoietic stem cell transplantation).

In certain embodiments, the polypeptide of interest encoded by the compound of the invention is erythropoietin (EPO), and the compound or pharmaceutical composition of the invention is for use in treating anemia, inflammatory bowel disease (such as Crohn's disease and/or ulcer colitis), or myelodysplasia.

Methods of Cellular Polynucleotide Delivery

Methods of the present disclosure enhance polynucleotide delivery into a cell population, in vivo, ex vivo, or in culture. For example, a cell culture containing a plurality of host cells (e.g., eukaryotic cells such as yeast or mammalian cells) is contacted with a composition that contains a compound having a translatable region. The composition also generally contains a transfection reagent or other compound that increases the efficiency of compound uptake into the host cells. The compound exhibits enhanced retention in the cell population, relative to a corresponding unaltered polynucleotide. The retention of the compound is greater than the retention of the unaltered polynucleotide. In some embodiments, it is at least about 50%, 75%, 90%, 95%, 100%, 150%, 200%, or more than 200% greater than the retention of the unaltered polynucleotide. Such retention advantage may be achieved by one round of transfection with the compound, or may be obtained following repeated rounds of transfection.

In some embodiments, the compound is delivered to a target cell population with one or more additional compounds or polynucleotides. Such delivery may be at the same time, or the alternative polynucleotide is delivered prior to delivery of the one or more additional compounds or polynucleotides. The additional one or more polynucleotides may be alternative polynucleotides or unaltered polynucleotides. It is understood that the initial presence of the alternative polynucleotides does not substantially induce an innate immune response of the cell population and, moreover, that the innate immune response will not be activated by the later presence of the unaltered polynucleotides. In this regard, the alternative polynucleotide may not itself contain a translatable region, if the protein desired to be present in the target cell population is translated from the unaltered polynucleotides.

Targeting Moieties

In embodiments of the present disclosure, compounds are provided to express a protein-binding partner or a receptor on the surface of the cell, which functions to target the cell to a specific tissue space or to interact with a specific moiety, either in vivo or in vitro. Suitable protein-binding partners include antibodies and functional fragments thereof, scaffold proteins, or peptides. Additionally, compounds can be employed to direct the synthesis and extracellular localization of lipids, carbohydrates, or other biological moieties.

Permanent Gene Expression Silencing

A method for epigenetically silencing gene expression in a mammalian subject, including a polynucleotide where the translatable region encodes a polypeptide or polypeptides capable of directing sequence-specific histone H3 methylation to initiate heterochromatin formation and reduce gene transcription around specific genes for the purpose of silencing the gene. For example, a gain-of-function mutation in the Janus Kinase 2 gene is responsible for the family of Myeloproliferative Diseases.

Lipid Nanoparticles

In some embodiments, the compounds of the invention are encapsulated in lipid nanoparticles. Accordingly, in some aspects the invention provides nanoparticle compositions including a polynucleotide of the invention encapsulated in a lipid nanoparticle. Nanoparticle compositions include, for example, lipid nanoparticles (LNPs), liposomes, lipid vesicles, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers may be functionalized and/or crosslinked to one another. Lipid bilayers may include one or more ligands, proteins, or channels.

Cationic/Ionizable Lipids

Nanoparticle compositions of the invention comprise a lipid component in addition to a polynucleotide of the invention. The lipid component of a nanoparticle composition may include one or more lipids. For example, a nanoparticle composition may include one or more cationic and/or ionizable lipids. Cationic and/or ionizable lipids may be selected from the non-limiting group consisting of 3-(didodecylamino)-N1,N1,4-tridodecyl-1-piperazineethanamine (KL10), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA),1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy] octyl}oxy)-N,N-dimethyl-3-[(9Z,12Z)-octadeca-9,12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)). In addition to these, a cationic lipid may also be a lipid including a cyclic amine.

PEG Lipids

The lipid component of a nanoparticle composition of the invention may include one or more PEG or PEG-modified lipids. Such species may be alternately referred to as PEGylated lipids. A PEG lipid is a lipid modified with polyethylene glycol.

The lipid component may include one or more PEG lipids. A PEG lipid may be selected from the non-limiting group consisting of PEG-modified phosphatidylethanolamines, PEG-modified phosphatidic acids, PEG-modified ceramides, PEG-modified dialkylamines, PEG-modified diacylglycerols, and PEG-modified dialkylglycerols. For example, a PEG lipid may be PEG-c-DOMG, PEG-DMG, PEG-DLPE, PEG-DMPE, PEG-DPPC, or a PEG-DSPE lipid.

Structural Lipids

The lipid component of a nanoparticle composition may include one or more structural lipids (e.g., cholesterol fecosterol, sitosterol, campesterol, stigmasterol, brassicasterol, ergosterol, tomatidine, tomatine, ursolic acid, or alpha-tocopherol).

Phospholipids

The lipid component of a nanoparticle composition may include one or more phospholipids, such as one or more (poly)unsaturated lipids. In general, such lipids may include a phospholipid moiety and one or more fatty acid moieties. For example, a phospholipid may be a lipid according to the formula:

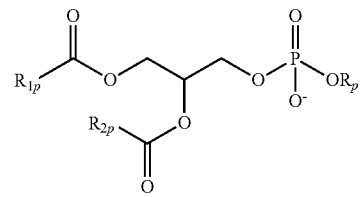

in which $R_p$ represents a phospholipid moiety and $R_{1p}$ and $R_{2p}$ represent fatty acid moieties with or without saturation that may be the same or different. A phospholipid moiety may be selected from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin. A fatty acid moiety may be selected from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid. Non-natural species including natural species with modifications and substitutions including branching, oxidation, cyclization, and alkynes are also contemplated.

In some embodiments a nanoparticle composition may include 1,2-distearoyl-sn-glycero-3-phosphocholine (DSPC), 1,2-dioleoyl-sn-glycero-3-phosphoethanolamine (DOPE), or both DSPC and DOPE. Phospholipids useful in the compositions and methods of the invention may be selected from the non-limiting group consisting of DSPC, DOPE, 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin.

Other Components

A nanoparticle composition may include one or more components in addition to those described in the preceding sections. For example, a nanoparticle composition may include one or more small hydrophobic molecules such as a vitamin (e.g., vitamin A or vitamin E) or a sterol.

Nanoparticle compositions may also include one or more permeability enhancer molecules, carbohydrates, polymers, therapeutic agents, surface altering agents, or other components. A permeability enhancer molecule may be a molecule described by U.S. patent application publication No. 2005/0222064, for example. Carbohydrates may include simple sugars (e.g., glucose) and polysaccharides (e.g., glycogen and derivatives and analogs thereof).

A polymer may be included in and/or used to encapsulate or partially encapsulate a nanoparticle composition. A polymer may be biodegradable and/or biocompatible. A polymer may be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates. For example, a polymer may include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, polyoxamines, poly(ortho) esters, poly(butyric acid), poly(valeric acid), poly(lactide-co-caprolactone), and trimethylene carbonate.

Therapeutic agents may include, but are not limited to, cytotoxic, chemotherapeutic, and other therapeutic agents. Cytotoxic agents may include, for example, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, rachelmycin, and analogs thereof. Radioactive ions may also be used as therapeutic agents and may include, for example, radioactive iodine, strontium, phosphorous, palladium, cesium, iridium, cobalt, yttrium, samarium, and praseodymium. Other therapeutic agents may include, for example, antimetabolites (e.g., methotrexate, 6-mercaptopurine, 6-thioguanine, cytarabine, and 5-fluorouracil, and decarbazine), alkylating agents (e.g., mechlorethamine, thiotepa, chlorambucil, rachelmycin, melphalan, carmustine, lomustine, cyclophosphamide, busulfan, dibromomannitol, streptozotocin, mitomycin C, and cis-dichlorodiamine platinum (II) (DDP), and cisplatin), anthracyclines (e.g., daunorubicin and doxorubicin), antibiotics (e.g., dactinomycin, bleomycin, mithramycin, and anthramycin), and anti-mitotic agents (e.g., vincristine, vinblastine, taxol, and maytansinoids).

Surface altering agents may include, but are not limited to, anionic proteins (e.g., bovine serum albumin), surfactants (e.g., cationic surfactants such as dimethyldioctadecyl-ammonium bromide), sugars or sugar derivatives (e.g., cyclodextrin), nucleic acids, polymers (e.g., heparin, polyethylene glycol, and poloxamer), mucolytic agents (e.g., acetylcysteine, mugwort, bromelain, papain, clerodendrum, bromhexine, carbocisteine, eprazinone, mesna, ambroxol, sobrerol, domiodol, letosteine, stepronin, tiopronin, gelsolin, thymosin β4, dornase alfa, neltenexine, and erdosteine), and DNases (e.g., rhDNase). A surface altering agent may be disposed within a nanoparticle and/or on the surface of a nanoparticle composition (e.g., by coating, adsorption, covalent linkage, or other process).

In addition to these components, nanoparticle compositions of the invention may include any substance useful in pharmaceutical compositions. For example, the nanoparticle composition may include one or more pharmaceutically acceptable excipients or accessory ingredients such as, but not limited to, one or more solvents, dispersion media, diluents, dispersion aids, suspension aids, granulating aids, disintegrants, fillers, glidants, liquid vehicles, binders, surface active agents, isotonic agents, thickening or emulsifying agents, buffering agents, lubricating agents, oils, preservatives, and other species. Excipients such as waxes, butters, coloring agents, coating agents, flavorings, and perfuming agents may also be included. Pharmaceutically acceptable excipients are well known in the art (see for example Remington's The Science and Practice of Pharmacy, 21$^{st}$ Edition, A. R. Gennaro; Lippincott, Williams & Wilkins, Baltimore, M D, 2006).

Examples of diluents may include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and/or combinations thereof. Granulating and dispersing agents may be selected from the non-limiting list consisting of potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, and/or combinations thereof.

Surface active agents and/or emulsifiers may include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN®20], polyoxyethylene sorbitan [TWEEN® 60], polyoxyethylene sorbitan monooleate [TWEEN®80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g. polyoxyethylene monostearate [MYRJ® 45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLURONIC® F 68, POLOXAMER® 188, cetrimonium bromide, cetylpyridinium chloride, benzalkonium chloride, docusate sodium, and/or combinations thereof.

A binding agent may be starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan); alginates; polyethylene oxide; polyethylene glycol; inorganic calcium salts; silicic acid; polymethacrylates; waxes; water; alcohol; and combinations thereof, or any other suitable binding agent.

Preservatives include, but are not limited to, antioxidants, chelating agents, antimicrobial preservatives, antifungal preservatives, alcohol preservatives, acidic preservatives, and/or other preservatives. Antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Examples of alcohol preservatives include, but are not limited to, ethanol, polyethylene glycol, phenol, benzyl alcohol, phenolic compounds, bisphenol, chlorobutanol, hydroxybenzoate, and/or phenylethyl alcohol. Examples of acidic preservatives include, but are not limited to, vitamin A, vitamin C, vitamin E, beta-carotene, citric acid, acetic acid, dehydroascorbic acid, ascorbic acid, sorbic acid, and/or phytic acid. Other preservatives include, but are not limited to, tocopherol, tocopherol acetate, deteroxime mesylate, cetrimide, butylated hydroxyanisole (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN® II, NEOLONE™, KATHON™, and/or EUXYL®.

Examples of buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, calcium lactobionate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, amino-sulfonate buffers (e.g. HEPES), magnesium hydroxide, aluminum hydroxide, alginic acid, pyrogen-free water, isotonic saline, Ringer's solution, ethyl alcohol, and/or combinations thereof. Lubricating agents may selected from the non-limiting group consisting of magnesium stearate, calcium stearate, stearic acid, silica, talc, malt, glyceryl behenate, hydrogenated vegetable oils, polyethylene glycol, sodium benzoate, sodium acetate, sodium chloride, leucine, magnesium lauryl sulfate, sodium lauryl sulfate, and combinations thereof.

Examples of oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils as well as butyl stearate, caprylic triglyceride, capric triglyceride, cyclomethicone, diethyl sebacate, dimethicone 360, simethicone, isopropyl myristate, mineral oil, octyldodecanol, oleyl alcohol, silicone oil, and/or combinations thereof.

Compositions

A nanoparticle composition may include a compound of the invention, a cationic/ionizable lipid, a phospholipid (such as an unsaturated lipid, e.g., DOPE), a PEG lipid, and a structural lipid, as follows.

In some embodiments, the lipid component includes a cationic/ionizable lipid, a phospholipid, a PEG lipid, and a structural lipid. The lipid component may include about 35 mol % to about 45 mol % a cationic/ionizable lipid, about 10 mol % to about 20 mol % phospholipid, about 38.5 mol % to about 48.5 mol % structural lipid, and about 1.5 mol % PEG lipid, provided that the total mol % does not exceed 100%. For example, the lipid component may include about 40 mol % a cationic/ionizable lipid, about 20 mol % phospholipid, about 38.5 mol % structural lipid, and about 1.5 mol % PEG lipid. In some embodiments, the phospholipid may be DOPE and/or the structural lipid may be cholesterol.

In some embodiments, the lipid component may include about 40 mol % a cationic/ionizable lipid, about 15 mol % phospholipid, about 43.5 mol % structural lipid, and about 1.5 mol % PEG lipid. In some instances, the phospholipid may be DOPE. In other embodiments, the lipid may be DSPC. In certain embodiments, the structural lipid may be cholesterol.

In other embodiments, the lipid component may include about 45 mol % to about 55 mol % a cationic/ionizable lipid, about 15 mol % to about 25 mol % phospholipid, about 23.5 mol % to about 33.5 mol % structural lipid, and about 1.5 mol % PEG lipid, provided that the total mol % does not exceed 100%. For example, the lipid component may include about 50 mol % a cationic/ionizable lipid, about 20 mol % phospholipid, about 28.5 mol % structural lipid, and about 1.5 mol % PEG lipid. In some embodiments, the phospholipid may be DOPE. In other instances, the phospholipid may be DSPC. In certain embodiments, the structural lipid may be cholesterol.

A nanoparticle composition may be designed for one or more specific applications or targets. For example, a nanoparticle composition may be designed to deliver a polynucleotide of the invention to a particular cell, tissue, organ, or system or group thereof in a mammal's body, such as the renal system. Physiochemical properties of nanoparticle compositions may be altered in order to increase selectivity for particular bodily targets. For instance, particle sizes may be adjusted based on the fenestration sizes of different organs. The polynucleotide of the invention included in a nanoparticle composition may also depend on the desired delivery target or targets. For example, a polynucleotide of the invention may be selected for a particular indication, condition, disease, or disorder and/or for delivery to a particular cell, tissue, organ, or system or group thereof (e.g., localized or specific delivery). A nanoparticle composition may include one or more polynucleotides of the invention encoding one or more polypeptides of interest.

The amount of polynucleotide of the invention in a nanoparticle composition may depend on the size, sequence, and other characteristics of the polynucleotide of the invention. The amount of polynucleotide of the invention in a nanoparticle composition may also depend on the size, composition, desired target, and other characteristics of the nanoparticle composition. The relative amounts of polynucleotide of the invention and other elements (e.g., lipids) may also vary. In some embodiments, the wt/wt ratio of the lipid component to a polynucleotide of the invention in a nanoparticle composition may be from about 5:1 to about 50:1, such as 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, and 50:1. For example, the wt/wt ratio of the lipid component to a polynucleotide of the invention may be from about 10:1 to about 40:1. The amount of a polynucleotide of the invention in a nanoparticle composition may, for example, be measured using absorption spectroscopy (e.g., ultraviolet-visible spectroscopy).

In some embodiments, the one or more polynucleotides of the invention, lipids, and amounts thereof may be selected to provide a specific N:P ratio. The N:P ratio of the composition refers to the molar ratio of nitrogen atoms in one or more lipids to the number of phosphate groups in a polynucleotide of the invention. In general, a lower N:P ratio is preferred. The one or more polynucleotides of the invention, lipids, and amounts thereof may be selected to provide an N:P ratio from about 2:1 to about 8:1, such as 2:1, 3:1, 4:1, 5:1, 6:1, 7:1, and 8:1. In certain embodiments, the N:P ratio may be from about 2:1 to about 5:1. In preferred embodiments, the N:P ratio may be about 4:1. In other embodiments, the N:P ratio is from about 5:1 to about 8:1. For example, the N:P ratio may be about 5.0:1, about 5.5:1, about 5.67:1, about 6.0:1, about 6.5:1, or about 7.0:1.

Physical Properties

The characteristics of a nanoparticle composition will depend on the components thereof. Characteristics may also vary depending on the method and conditions of preparation of the nanoparticle composition.

The mean size of a nanoparticle composition of the invention may be between 10s of nm and 100s of nm. For example, the mean size may be from about 40 nm to about 150 nm, such as about 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm. In some embodiments, the mean size of a nanoparticle composition may be from about 80 nm to about 120 nm, from about 80 nm to about 110 nm, from about 80 nm to about 100 nm, from about 80 nm to about 90 nm, from about 90 nm to about 120 nm, from about 90 nm to about 110 nm, from about 90 nm to about 100 nm, from about 100 nm to about 120 nm, or from about 110 nm to about 120 nm. In a particular embodiment, the mean size may be about 90 nm. In another particular embodiment, the mean size may be about 100 nm.

A nanoparticle composition of the invention may be relatively homogenous. A polydispersity index may be used to indicate the homogeneity of a nanoparticle composition, e.g., the particle size distribution of the nanoparticle compositions. A small (e.g., less than 0.3) polydispersity index generally indicates a narrow particle size distribution. A nanoparticle composition of the invention may have a polydispersity index from about 0 to about 0.18, such as 0.01, 0.02, 0.03, 0.04, 0.05, 0.06, 0.07, 0.08, 0.09, 0.10, 0.11, 0.12, 0.13, 0.14, 0.15, 0.16, 0.17, or 0.18. In some embodiments, the polydispersity index of a nanoparticle composition may be from about 0.13 to about 0.17.

The zeta potential of a nanoparticle composition may be used to indicate the electrokinetic potential of the composition. Nanoparticle compositions with relatively low charges, positive or negative, are generally desirable, as more highly charged species may interact undesirably with cells, tissues, and other elements in the body. In some embodiments, the zeta potential of a nanoparticle composition of the invention may be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

The efficiency of encapsulation of a polynucleotide of the invention describes the amount of polynucleotide of the invention that is encapsulated or otherwise associated with a nanoparticle composition after preparation, relative to the initial amount provided. The encapsulation efficiency is desirably high (e.g., close to 100%). For the nanoparticle compositions of the invention, the encapsulation efficiency of an polynucleotide of the invention may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%.

A nanoparticle composition of the invention may optionally comprise one or more coatings. For example, a nanoparticle composition may be formulated in a capsule, film, or tablet having a coating. A capsule, film, or tablet including a composition of the invention may have any useful size, tensile strength, hardness, or density.

Pharmaceutical Compositions

The present disclosure provides compounds capable of expressing proteins. Pharmaceutical compositions may optionally include one or more additional therapeutically active substances. In accordance with some embodiments, a method of administering pharmaceutical compositions including a compound encoding one or more proteins to be delivered to a subject in need thereof is provided. In some embodiments, compositions are administered to humans. For the purposes of the present disclosure, the phrase "active ingredient" generally refers to a protein, protein encoding or protein-containing complex as described herein. Nanoparticle compositions of the invention may also be formulated in whole or in part as pharmaceutical compositions. Pharmaceutical compositions of the invention may include one or more nanoparticle compositions. For example, a pharmaceutical composition may include one or more nanoparticle compositions including one or more different compounds.

Although the descriptions of pharmaceutical compositions provided herein are principally directed to pharmaceutical compositions which are suitable for administration to humans, it will be understood by the skilled artisan that such compositions are generally suitable for administration to animals of all sorts.

Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition including a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure will vary, depending upon the identity, size, and/or condition of the subject treated and further depending upon the route by which the composition is to be administered. By way of example, the composition may include between 0.1% and 100% (w/w) active ingredient.

Pharmaceutical formulations may additionally include a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, and lubricants, as suited to the particular dosage form desired. Remington's *The Science and Practice of Pharmacy*, 21$^{st}$ Edition, A. R. Gennaro (Lippincott, Williams & Wilkins, Baltimore, M D, 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this present disclosure.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and/or combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite [aluminum silicate] and Veegum® [magnesium aluminum silicate]), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate [Tween®20], polyoxyethylene sorbitan [Tween®60], polyoxyethylene sorbitan monooleate [Tween®80], sorbitan monopalmitate [Span®40], sorbitan monostearate [Span®60], sorbitan tristearate [Span®65], glyceryl monooleate, sorbitan monooleate [Span®80]), polyoxyethylene esters (e.g., polyoxyethylene monostearate [Myrj®45], polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether [Brij®30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F 68, Poloxamer®188, cetrimonium bromide, cetylpyridinium chloride, benzalkonium chloride, docusate sodium, and/or combinations thereof.

Exemplary binding agents include, but are not limited to, starch (e.g., cornstarch and starch paste); gelatin; sugars (e.g., sucrose, glucose, dextrose, dextrin, molasses, lactose, lactitol, mannitol,); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus®, Phenonip®, methylparaben, Germall®115, Germaben® II, Neolone™, Kathon™, and/or Euxyl®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may include inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as Cremophor®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, an active ingredient is mixed with at least one inert, pharmaceutically acceptable excipient such as sodium citrate or dicalcium phosphate and/or fillers or extenders (e.g., starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato or tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), and mixtures thereof. In the case of capsules, tablets and pills, the dosage form may include buffering agents.

Solid compositions of a similar type may be employed as fillers in soft and hard-filled gelatin capsules using such excipients as lactose or milk sugar as well as high molecular weight polyethylene glycols. Solid dosage forms of tablets, dragees, capsules, pills, and granules can be prepared with coatings and shells such as enteric coatings and other coatings well known in the pharmaceutical formulating art. They may optionally include opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required. Additionally, the present disclosure contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publication Nos. WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, include from about 1% to about 10% (w/w) active ingredient, although the concentration of active ingredient may be as high as the solubility limit of the active ingredient in the solvent. Formulations for topical administration may further include one or more of the additional ingredients described herein.

A pharmaceutical composition may be prepared, packaged, and/or sold in a formulation suitable for pulmonary administration via the buccal cavity. Such a formulation may include dry particles which include the active ingredient and which have a diameter in the range from about 0.5 nm to about 7 nm or from about 1 nm to about 6 nm. Such compositions are conveniently in the form of dry powders for administration using a device including a dry powder reservoir to which a stream of propellant may be directed to disperse the powder and/or using a self propelling solvent/powder dispensing container such as a device including the active ingredient dissolved and/or suspended in a low-boiling propellant in a sealed container. Such powders include particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and active ingredient may constitute 0.1% to 20% (w/w) of the composition. A propellant may further include additional ingredients such as a liquid non-ionic and/or solid anionic surfactant and/or a solid diluent (which may have a particle size of the same order as particles including the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, including active ingredient, and may conveniently be administered using any nebulization and/or atomization device. Such formulations may further include one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm.

Formulations described herein as being useful for pulmonary delivery are useful for intranasal delivery of a pharmaceutical composition. Another formulation suitable for intranasal administration is a coarse powder including the active ingredient and having an average particle from about 0.2 m to 500 m. Such a formulation is administered in the manner in which snuff is taken, i.e., by rapid inhalation through the nasal passage from a container of the powder held close to the nose.

Formulations suitable for nasal administration may, for example, include from about as little as 0.1% (w/w) and as much as 100% (w/w) of active ingredient, and may include one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance including an orally dissolvable and/or degradable composition and, optionally, one or more of the additional ingredients described herein. Alternately, formulations suitable for buccal administration may include a powder and/or an aerosolized and/or atomized solution and/or suspension including active ingredient. Such powdered, aerosolized, and/or aerosolized formulations, when dispersed, may have an average particle and/or droplet size in the range from about 0.1 nm to about 200 nm, and may further include one or more of any additional ingredients described herein.

A pharmaceutical composition may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further include buffering agents, salts, and/or one or more of any additional ingredients described herein. Other opthalmically-administrable formulations which are useful include those which include the active ingredient in microcrystalline form and/or in a liposomal preparation. Ear drops and/or eye drops are contemplated as being within the scope of this present disclosure.

General considerations in the formulation and/or manufacture of pharmaceutical agents may be found, for example, in Remington's *The Science and Practice of Pharmacy*, 21$^{st}$ Edition, A. R. Gennaro (Lippincott, Williams & Wilkins, Baltimore, M D, 2006.

Administration

The present disclosure provides methods including administering compounds in accordance with the present disclosure to a subject in need thereof. Compounds, or pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, and its mode of activity. Compositions in accordance with the present disclosure are typically formulated in dosage unit form for ease of administration and uniformity of dosage. It will be understood, however, that the total daily usage of the compositions of the present disclosure will be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Compounds to be delivered and/or pharmaceutical, prophylactic, diagnostic, or imaging compositions thereof may be administered to animals, such as mammals (e.g., humans, domesticated animals, cats, dogs, mice, rats, etc.). In some embodiments, pharmaceutical, prophylactic, diagnostic, or imaging compositions thereof are administered to humans.

Compounds to be delivered and/or pharmaceutical, prophylactic, diagnostic, or imaging compositions thereof in accordance with the present disclosure may be administered by any route. In some embodiments, polynucleotides and/or pharmaceutical, prophylactic, diagnostic, or imaging compositions thereof, are administered by one or more of a variety of routes, including oral, intravenous, intramuscular, intra-arterial, intramedullary, intrathecal, subcutaneous, intraventricular, transdermal, interdermal, rectal, intravaginal, intraperitoneal, topical (e.g., by powders, ointments, creams, gels, lotions, and/or drops), mucosal, nasal, buccal, enteral, vitreal, intratumoral, sublingual; by intratracheal instillation, bronchial instillation, and/or inhalation; as an oral spray, nasal spray, and/or aerosol, and/or through a portal vein catheter. In some embodiments, polynucleotides, and/or pharmaceutical, prophylactic, diagnostic, or imaging compositions thereof, are administered by systemic intravenous injection. In specific embodiments, polynucleotides and/or pharmaceutical, prophylactic, diagnostic, or imaging compositions thereof may be administered intravenously and/or orally. In specific embodiments, polynucleotides, and/or pharmaceutical, prophylactic, diagnostic, or imaging compositions thereof, may be administered in a way which allows the polynucleotide to cross the blood-brain barrier, vascular barrier, or other epithelial barrier.

However, the present disclosure encompasses the delivery of compounds, and/or pharmaceutical, prophylactic, diagnostic, or imaging compositions thereof, by any appropriate route taking into consideration likely advances in the sciences of drug delivery.

In general the most appropriate route of administration will depend upon a variety of factors including the nature of the polynucleotide including polynucleotides associated with at least one agent to be delivered (e.g., its stability in the environment of the gastrointestinal tract, bloodstream, etc.), the condition of the patient (e.g., whether the patient is able to tolerate particular routes of administration), etc. The present disclosure encompasses the delivery of the pharmaceutical, prophylactic, diagnostic, or imaging compositions by any appropriate route taking into consideration likely advances in the sciences of drug delivery.

In certain embodiments, compositions in accordance with the present disclosure may be administered at dosage levels sufficient to deliver from about 0.0001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Compounds may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that improve their bioavailability, reduce and/or modify their metabolism, inhibit their excretion, and/or modify their distribution within the body.

It will further be appreciated that therapeutically, prophylactically, diagnostically, or imaging active agents utilized in combination may be administered together in a single composition or administered separately in different compositions. In general, it is expected that agents utilized in combination with be utilized at levels that do not exceed the levels at which they are utilized individually. In some embodiments, the levels utilized in combination will be lower than those utilized individually.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer in accordance with the present disclosure may be administered concurrently with a chemotherapeutic agent), or they may achieve different effects (e.g., control of any adverse effects).

Kits

The present disclosure provides a variety of kits for conveniently and/or effectively carrying out methods of the present disclosure. Typically kits will include sufficient amounts and/or numbers of components to allow a user to perform multiple treatments of a subject(s) and/or to perform multiple experiments.

In one aspect, the disclosure provides kits for protein production, including a first polynucleotide including a translatable region and a nucleotide alteration, wherein the polynucleotide is capable of evading or avoiding induction of an innate immune response of a cell into which the first isolated polynucleotide is introduced, and packaging and instructions.

In one aspect, the disclosure provides kits for protein production, including: a first polynucleotide including a translatable region, provided in an amount effective to produce a desired amount of a protein encoded by the translatable region when introduced into a target cell; a second polynucleotide including an inhibitory polynucleotide, provided in an amount effective to substantially inhibit the innate immune response of the cell; and packaging and instructions.

In one aspect, the disclosure provides kits for protein production, including a first polynucleotide including a translatable region and a nucleoside alteration, wherein the polynucleotide exhibits reduced degradation by a cellular nuclease, and packaging and instructions.

In one aspect, the disclosure provides kits for protein production, including a first polynucleotide including a translatable region and at least two different nucleoside alterations, wherein the polynucleotide exhibits reduced degradation by a cellular nuclease, and packaging and instructions.

In one aspect, the disclosure provides kits for protein production, including a first polynucleotide including a translatable region and at least one nucleoside alteration, wherein the polynucleotide exhibits reduced degradation by a cellular nuclease; a second polynucleotide including an inhibitory polynucleotide; and packaging and instructions.

In another aspect, the disclosure provides compositions for protein production, including a first polynucleotide including a translatable region and a nucleoside alteration, wherein the polynucleotide exhibits reduced degradation by a cellular nuclease, and a mammalian cell suitable for translation of the translatable region of the first polynucleotide.

Definitions

Chemical Terms:

The term "acyl," as used herein, represents a hydrogen or an alkyl group (e.g., a haloalkyl group), as defined herein, that is attached to the parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 7, from 1 to 11, or from 1 to 21 carbons. In some embodiments, the alkyl group is further substituted with 1, 2, 3, or 4 substituents as described herein.

The term "acylamino," as used herein, represents an acyl group, as defined herein, attached to the parent molecular group though an amino group, as defined herein (i.e., —N($R^{N1}$)—C(O)—R, where R is H or an optionally substituted $C_{1-6}$, $C_{1-10}$, or $C_{1-20}$ alkyl group (e.g., haloalkyl) and $R^{N1}$ is as defined herein). Exemplary unsubstituted acylamino groups include from 1 to 41 carbons (e.g., from 1 to 7, from 1 to 13, from 1 to 21, from 2 to 7, from 2 to 13, from 2 to 21, or from 2 to 41 carbons). In some embodiments, the alkyl group is further substituted with 1, 2, 3, or 4 substituents as described herein, and/or the amino group is —$NH_2$ or —$NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, aryl, acyl (e.g., acetyl, trifluoroacetyl, or others described herein), or alkoxycarbonylalkyl, and each $R^{N2}$ can be H, alkyl, or aryl.

The term "acylaminoalkyl," as used herein, represents an acyl group, as defined herein, attached to an amino group that is in turn attached to the parent molecular group though an alkyl group, as defined herein (i.e., -alkyl-N($R^{N1}$)—C(O)—R, where R is H or an optionally substituted $C_{1-6}$, $C_{1-10}$, or $C_{1-20}$ alkyl group (e.g., haloalkyl) and $R^{N1}$ is as defined herein). Exemplary unsubstituted acylamino groups include from 1 to 41 carbons (e.g., from 1 to 7, from 1 to 13, from 1 to 21, from 2 to 7, from 2 to 13, from 2 to 21, or from 2 to 41 carbons). In some embodiments, the alkyl group is further substituted with 1, 2, 3, or 4 substituents as described herein, and/or the amino group is —$NH_2$ or —$NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, aryl, acyl (e.g., acetyl, trifluoroacetyl, or others described herein), or alkoxycarbonylalkyl, and each $R^{N2}$ can be H, alkyl, or aryl.

The term "acyloxy," as used herein, represents an acyl group, as defined herein, attached to the parent molecular group though an oxygen atom (i.e., —O—C(O)—R, where R is H or an optionally substituted $C_{1-6}$, $C_{1-10}$, or $C_{1-20}$ alkyl group). Exemplary unsubstituted acyloxy groups include from 1 to 21 carbons (e.g., from 1 to 7 or from 1 to 11 carbons). In some embodiments, the alkyl group is further substituted with 1, 2, 3, or 4 substituents as described herein.

The term "acyloxyalkyl," as used herein, represents an acyl group, as defined herein, attached to an oxygen atom that in turn is attached to the parent molecular group though an alkyl group (i.e., -alkyl-O—C(O)—R, where R is H or an optionally substituted $C_{1-6}$, $C_{1-10}$, or $C_{1-20}$ alkyl group). Exemplary unsubstituted acyloxyalkyl groups include from 1 to 21 carbons (e.g., from 1 to 7 or from 1 to 11 carbons). In some embodiments, the alkyl group is, independently, further substituted with 1, 2, 3, or 4 substituents as described herein.

The term "alkaryl," as used herein, represents an aryl group, as defined herein, attached to the parent molecular group through an alkylene group, as defined herein. Exemplary unsubstituted alkaryl groups are from 7 to 30 carbons (e.g., from 7 to 16 or from 7 to 20 carbons, such as $C_{6-10}$ aryl $C_{1-6}$ alkyl, $C_{6-10}$ aryl $C_{1-10}$ alkyl, or $C_{6-10}$ aryl $C_{1-20}$ alkyl). In some embodiments, the alkylene and the aryl each can be further substituted with 1, 2, 3, or 4 substituent groups as defined herein for the respective groups.

The term "alkcycloalkyl" represents a cycloalkyl group, as defined herein, attached to the parent molecular group through an alkylene group, as defined herein (e.g., an alkylene group of from 1 to 4, from 1 to 6, from 1 to 10, or form 1 to 20 carbons). In some embodiments, the alkylene and the cycloalkyl each can be further substituted with 1, 2, 3, or 4 substituent groups as defined herein for the respective group.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, and 2-butenyl. Alkenyls include both cis and trans isomers. Alkenyl groups may be optionally substituted with 1, 2, 3, or 4 substituent groups that are selected, independently, from amino, aryl, cycloalkyl, or heterocyclyl (e.g., heteroaryl), as defined herein, or any of the exemplary alkyl substituent groups described herein.

The term "alkenylene" as used herein, represent a divalent alkenyl group derived by the removal of two hydrogen atoms, and is exemplified by ethenylene, and isopropenylene. The term "Cx-y alkenylene" represent alkenylene groups having between x and y carbons. Exemplary values for x are 2, 3, 4, 5, and 6, and exemplary values for y are 2, 3, 4, 5, 6, 7, 8, 9, 10, 12, 14, 16, 18, or 20 (e.g., $C_{2-6}$, $C_{2-10}$, or $C_{2-20}$ alkenylene). In some embodiments, the alkenylene can be further substituted with 1, 2, 3, or 4 substituent groups as defined herein for an alkenyl group. The term "branched alkenylene" as used herein, refers to a multivalent alkenyl group derived by the removal of more than two hydrogen atoms.

The term "alkenyloxy" represents a chemical substituent of formula —OR, where R is a $C_{2-20}$ alkenyl group (e.g., $C_{2-6}$ or $C_{2-10}$ alkenyl), unless otherwise specified. Exemplary alkenyloxy groups include ethenyloxy, and propenyloxy. In some embodiments, the alkenyl group can be further substituted with 1, 2, 3, or 4 substituent groups as defined herein (e.g., a hydroxy group).

The term "alkheteroaryl" refers to a heteroaryl group, as defined herein, attached to the parent molecular group through an alkylene group, as defined herein. Exemplary unsubstituted alkheteroaryl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-12}$ heteroaryl $C_{1-6}$ alkyl, $C_{1-12}$ heteroaryl $C_{1-10}$ alkyl, or $C_{1-12}$ heteroaryl $C_{1-20}$ alkyl). In some embodiments, the alkylene and the heteroaryl each can be further substituted with 1, 2, 3, or 4 substituent groups as defined herein for the respective group. Alkheteroaryl groups are a subset of alkheterocyclyl groups.

The term "alkheterocyclyl" represents a heterocyclyl group, as defined herein, attached to the parent molecular group through an alkylene group, as defined herein. Exemplary unsubstituted alkheterocyclyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-12}$ heterocyclyl $C_{1-6}$ alkyl, $C_{1-12}$ heterocyclyl $C_{1-10}$ alkyl, or $C_{1-12}$ heterocyclyl $C_{1-20}$ alkyl). In some embodiments, the alkylene and the heterocyclyl each can be further substituted with 1, 2, 3, or 4 substituent groups as defined herein for the respective group.

The term "alkoxy" represents a chemical substituent of formula —OR, where R is a $C_{1-20}$ alkyl group (e.g., $C_{1-6}$ or $C_{1-10}$ alkyl), unless otherwise specified. Exemplary alkoxy groups include methoxy, ethoxy, propoxy (e.g., n-propoxy and isopropoxy), and t-butoxy. In some embodiments, the alkyl group can be further substituted with 1, 2, 3, or 4 substituent groups as defined herein (e.g., hydroxy or alkoxy).

The term "alkoxyalkoxy" represents an alkoxy group that is substituted with an alkoxy group. Exemplary unsubstituted alkoxyalkoxy groups include between 2 to 40 carbons (e.g., from 2 to 12 or from 2 to 20 carbons, such as $C_{1-6}$ alkoxy-$C_{1-6}$ alkoxy, $C_{1-10}$ alkoxy-$C_{1-10}$ alkoxy, or $C_{1-20}$ alkoxy-$C_{1-20}$ alkoxy). In some embodiments, the each alkoxy group can be further substituted with 1, 2, 3, or 4 substituent groups as defined herein.

The term "alkoxyalkyl" represents an alkyl group that is substituted with an alkoxy group. Exemplary unsubstituted alkoxyalkyl groups include between 2 to 40 carbons (e.g., from 2 to 12 or from 2 to 20 carbons, such as $C_{1-6}$ alkoxy-$C_{1-6}$ alkyl, $C_{1-10}$ alkoxy-$C_{1-10}$ alkyl, or $C_{1-20}$ alkoxy-$C_{1-20}$ alkyl). In some embodiments, the alkyl and the alkoxy each can be further substituted with 1, 2, 3, or 4 substituent groups as defined herein for the respective group.

The term "alkoxycarbonyl," as used herein, represents an alkoxy, as defined herein, attached to the parent molecular group through a carbonyl atom (e.g., —C(O)—OR, where R is H or an optionally substituted $C_{1-6}$, $C_{1-10}$, or $C_{1-20}$ alkyl group). Exemplary unsubstituted alkoxycarbonyl include from 1 to 21 carbons (e.g., from 1 to 11 or from 1 to 7 carbons). In some embodiments, the alkoxy group is further substituted with 1, 2, 3, or 4 substituents as described herein.

The term "alkoxycarbonylacyl," as used herein, represents an acyl group, as defined herein, that is substituted with an alkoxycarbonyl group, as defined herein (e.g., —C(O)-alkyl-C(O)—OR, where R is an optionally substituted $C_{1-6}$, $C_{1-10}$, or $C_{1-20}$ alkyl group). Exemplary unsubstituted alkoxycarbonylacyl include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ acyl, $C_{1-10}$ alkoxycarbonyl-$C_{1-10}$ acyl, or $C_{1-20}$ alkoxycarbonyl-$C_{1-20}$ acyl). In some embodiments, each alkoxy and alkyl group is further independently substituted with 1, 2, 3, or 4 substituents, as described herein (e.g., a hydroxy group) for each group.

The term "alkoxycarbonylalkoxy," as used herein, represents an alkoxy group, as defined herein, that is substituted with an alkoxycarbonyl group, as defined herein (e.g., —O-alkyl-C(O)—OR, where R is an optionally substituted $C_{1-6}$, $C_{1-10}$, or $C_{1-20}$ alkyl group). Exemplary unsubstituted alkoxycarbonylalkoxy include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkoxy, $C_{1-10}$ alkoxycarbonyl-$C_{1-10}$ alkoxy, or $C_{1-20}$ alkoxycarbonyl-$C_{1-20}$ alkoxy). In some embodiments, each alkoxy group is further independently substituted with 1, 2, 3, or 4 substituents, as described herein (e.g., a hydroxy group).

The term "alkoxycarbonylalkyl," as used herein, represents an alkyl group, as defined herein, that is substituted with an alkoxycarbonyl group, as defined herein (e.g., -alkyl-C(O)—OR, where R is an optionally substituted $C_{1-20}$, $C_{1-10}$, or $C_{1-6}$ alkyl group). Exemplary unsubstituted alkoxycarbonylalkyl include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkyl, $C_{1-10}$ alkoxycarbonyl-$C_{1-10}$ alkyl, or $C_{1-20}$ alkoxycarbonyl-$C_{1-20}$ alkyl). In some embodiments, each alkyl and alkoxy group is further independently substituted with 1, 2, 3, or 4 substituents as described herein (e.g., a hydroxy group).

The term "alkoxycarbonylalkenyl," as used herein, represents an alkenyl group, as defined herein, that is substituted with an alkoxycarbonyl group, as defined herein (e.g., -alkenyl-C(O)—OR, where R is an optionally substituted $C_{1-20}$, $C_{1-10}$, or $C_{1-6}$ alkyl group). Exemplary unsubstituted alkoxycarbonylalkenyl include from 4 to 41 carbons (e.g., from 4 to 10, from 4 to 13, from 4 to 17, from 4 to 21, or from 4 to 31 carbons, such as $C_{1-6}$ alkoxycarbonyl-$C_{2-6}$ alkenyl, $C_{1-10}$ alkoxycarbonyl-$C_{2-10}$ alkenyl, or $C_{1-20}$ alkoxycarbonyl-$C_{2-20}$ alkenyl). In some embodiments, each alkyl, alkenyl, and alkoxy group is further independently substituted with 1, 2, 3, or 4 substituents as described herein (e.g., a hydroxy group).

The term "alkoxycarbonylalkynyl," as used herein, represents an alkynyl group, as defined herein, that is substituted with an alkoxycarbonyl group, as defined herein (e.g., -alkynyl-C(O)—OR, where R is an optionally substituted $C_{1-20}$, $C_{1-10}$, or $C_{1-6}$ alkyl group). Exemplary unsubstituted alkoxycarbonylalkynyl include from 4 to 41 carbons (e.g., from 4 to 10, from 4 to 13, from 4 to 17, from 4 to 21, or from 4 to 31 carbons, such as $C_{1-6}$ alkoxycarbonyl-$C_{2-6}$ alkynyl, $C_{1-10}$ alkoxycarbonyl-$C_{2-10}$ alkynyl, or $C_{1-20}$ alkoxycarbonyl-$C_{2-20}$ alkynyl). In some embodiments, each alkyl, alkynyl, and alkoxy group is further independently substituted with 1, 2, 3, or 4 substituents as described herein (e.g., a hydroxy group).

The term "alkyl," as used herein, is inclusive of both straight chain and branched chain saturated groups from 1 to 20 carbons (e.g., from 1 to 10 or from 1 to 6), unless otherwise specified. Alkyl groups are exemplified by methyl, ethyl, n- and iso-propyl, n-, sec-, iso- and tert-butyl, and neopentyl, and may be optionally substituted with one, two, three, or, in the case of alkyl groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —NH$_2$) or a substituted amino (i.e., —N($R^{N1}$)$_2$, where $R^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy, optionally substituted with an O-protecting group; (9) nitro; (10) oxo (e.g., carboxyaldehyde or acyl); (11) $C_{1-7}$ spirocyclyl; (12) thioalkoxy; (13) thiol; (14) —CO$_2$$R^{A'}$, optionally substituted with an O-protecting group and where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c)$C_{6-10}$ aryl, (d) hydrogen, (e)$C_{6-10}$ aryl $C_{1-6}$ alkyl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (15) —C(O)NR$^{B'}$R$^{C'}$, where each of R$^{B'}$ and R$^{C'}$ is, independently, selected from the group consisting of (a) hydrogen, (b) $C_{1-6}$ alkyl, (c) $C_{6-10}$ aryl, and (d) $C_{6-10}$ aryl $C_{1-6}$ alkyl; (16) —SO$_2$R$^{D'}$ where R$^{D'}$ is selected from the group consisting of (a) $C_{1-6}$ alkyl, (b) $C_{6-10}$ aryl, (c) $C_{6-10}$ aryl $C_{1-6}$ alkyl, and (d) hydroxy; (17) —SO$_2$NR$^{E'}$R$^{F'}$, where each of R$^{E'}$ and R$^{F'}$ is, independently, selected from the group consisting of (a) hydrogen, (b) $C_{1-6}$ alkyl, (c) $C_{6-10}$ aryl and (d) $C_{6-10}$ aryl $C_{1-6}$ alkyl; (18) —C(O)R$^{G'}$, where R$^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{6-10}$ aryl $C_{1-6}$ alkyl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) —NR$^{H'}$C(O)R$^{I'}$, wherein R$^{H'}$ is selected from the group consisting of (a1) hydrogen and (b1) $C_{1-6}$ alkyl, and R$^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{6-10}$ aryl $C_{1-6}$ alkyl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) —NR$^{J'}$C(O)OR$^{K'}$, wherein R$^{J'}$ is selected from the group consisting of (a1) hydrogen and (b1) $C_{1-6}$ alkyl, and R$^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{6-10}$ aryl $C_{1-6}$ alkyl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from to 4), each of $s^2$ and $s^3$, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein. For example, the alkylene group of a $C_1$-alkaryl can be further substituted with an oxo group to afford the respective aryloyl substituent.

The term "alkylene" as used herein, represent a saturated divalent hydrocarbon group derived from a straight or branched chain saturated hydrocarbon by the removal of two hydrogen atoms, and is exemplified by methylene, ethylene, and isopropylene. The term "$C_{x-y}$ alkylene" represent alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., $C_{1-6}$, $C_{1-10}$, $C_{2-20}$, $C_{2-6}$, $C_{2-10}$, or $C_{2-20}$ alkylene). In some embodiments, the alkylene can be further substituted with 1, 2, 3, or 4 substituent groups as defined herein for an alkyl group. The term "branched "alkylene" as used herein, refers to a multivalent alkyl group derived by the removal of more than two hydrogen atoms.

The term "alkylsulfinyl," as used herein, represents an alkyl group attached to the parent molecular group through an —S(O)— group. Exemplary unsubstituted alkylsulfinyl groups are from 1 to 6, from 1 to 10, or from 1 to 20 carbons. In some embodiments, the alkyl group can be further substituted with 1, 2, 3, or 4 substituent groups as defined herein.

The term "alkylsulfinylalkyl," as used herein, represents an alkyl group, as defined herein, substituted by an alkylsulfinyl group. Exemplary unsubstituted alkylsulfinyl-alkyl groups are from 2 to 12, from 2 to 20, or from 2 to 40 carbons. In some embodiments, each alkyl group can be further substituted with 1, 2, 3, or 4 substituent groups as defined herein.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl and 1-propynyl. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

The term "alkynylene" as used herein, represents a divalent alkynyl group derived by the removal of two hydrogen atoms. The term "$C_{x-y}$ alkynylene" represent alkynylene groups having between x and y carbons. Exemplary values for x are 2, 3, 4, 5, and 6, and exemplary values for y are 2, 3, 4, 5, 6, 7, 8, 9, 10, 12, 14, 16, 18, or 20 (e.g., $C_{2-6}$, $C_{2-10}$, or $C_{2-20}$ alkynylene). In some embodiments, the alkynylene can be further substituted with 1, 2, 3, or 4 substituent groups as defined herein for an alkynyl group. The term "branched alkynylene" as used herein, refers to a multivalent alkynyl group derived by the removal of more than two hydrogen atoms.

The term "alkynyloxy" represents a chemical substituent of formula —OR, where R is a $C_{2-20}$ alkynyl group (e.g., $C_{2-6}$ or $C_{2-10}$ alkynyl), unless otherwise specified. Exemplary alkynyloxy groups include ethynyloxy and propynyloxy. In some embodiments, the alkynyl group can be further substituted with 1, 2, 3, or 4 substituent groups as defined herein (e.g., a hydroxy group).

The term "amidine," as used herein, represents a —C(=NH)NH$_2$ group.

The term "amino," as used herein, represents —N(R$^{N1}$)$_2$, wherein each R$^{N1}$ is, independently, H, OH, NO$_2$, N(R$^{N2}$)$_2$, SO$_2$OR$^{N2}$, SO$_2$R$^{N2}$, SOR$^{N2}$, an N-protecting group, alkyl, alkenyl, alkynyl, alkoxy, aryl, alkaryl, cycloalkyl, alkcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl (e.g., heteroaryl), or alkheterocyclyl (e.g., alkheteroaryl), wherein each of these recited R$^{N1}$ groups can be optionally substituted, as defined herein for each group; or two R$^{N1}$ combine to form a heterocyclyl or an N-protecting group, and wherein each R$^{N2}$ is, independently, H, alkyl, or aryl. The amino groups of the invention can be an unsubstituted amino (i.e., —NH$_2$) or a substituted amino (i.e., —N(R$^{N1}$)$_2$). In a preferred embodiment, amino is —NH$_2$ or —NHR$^{N1}$, wherein R$^{N1}$ is, independently, OH, NO$_2$, NH$_2$, NR$^{N2}$$_2$, SO$_2$OR$^{N2}$, SO$_2$R$^{N2}$, SOR$^{N2}$, alkyl, carboxyalkyl, sulfoalkyl, acyl (e.g., acetyl, trifluoroacetyl, or others described herein), alkoxycarbonylalkyl (e.g., t-butoxycarbonylalkyl) or aryl, and each R$^{N2}$ can be H, $C_{1-20}$ alkyl (e.g., $C_{1-6}$ alkyl), or $C_{6-10}$ aryl.

The term "amino acid," as described herein, refers to a molecule having a side chain, an amino group, and an acid group (e.g., a carboxy group of —CO$_2$H or a sulfo group of —SO$_3$H), wherein the amino acid is attached to the parent molecular group by the side chain, amino group, or acid group (e.g., the side chain). In some embodiments, the amino acid is attached to the parent molecular group by a carbonyl group, where the side chain or amino group is attached to the carbonyl group. Exemplary side chains include an optionally substituted alkyl, aryl, heterocyclyl, alkaryl, alkheterocyclyl, aminoalkyl, carbamoylalkyl, and carboxyalkyl. Exemplary amino acids include alanine, arginine, asparagine, aspartic acid, cysteine, glutamic acid, glutamine, glycine, histidine, hydroxynorvaline, isoleucine, leucine, lysine, methionine, norvaline, ornithine, phenylalanine, proline, pyrrolysine, selenocysteine, serine, taurine, threonine, tryptophan, tyrosine, and valine. Amino acid groups may be optionally substituted with one, two, three, or, in the case of amino acid groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —NH$_2$) or a substituted amino (i.e., —N(R$^{N1}$)$_2$, where R$^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy; (9) nitro; (10) oxo (e.g., carboxyaldehyde or acyl); (11) $C_{1-7}$ spirocyclyl; (12) thioalkoxy; (13) thiol; (14) —CO$_2$R$^{A'}$, where R$^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{6-10}$ aryl $C_{1-6}$ alkyl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (15) —C(O)NR$^{B'}$R$^{C'}$, where each of R$^{B'}$ and R$^{C'}$ is, independently, selected from the group consisting of (a) hydrogen, (b) $C_{1-6}$ alkyl, (c) $C_{6-10}$ aryl, and (d) $C_{6-10}$ aryl $C_{1-6}$ alkyl; (16) —SO$_2$R$^{D40}$, where R$^{D'}$ is selected from the group consisting of (a) $C_{1-6}$ alkyl, (b) $C_{6-10}$ aryl, (c) $C_{6-10}$ aryl $C_{1-6}$ alkyl, and (d) hydroxy; (17) —SO$_2$NR$^{E'}$R$^{F'}$, where each of R$^{E'}$ and R$^{F'}$ is, independently, selected from the group consisting of (a) hydrogen, (b) $C_{1-6}$ alkyl, (c) $C_{6-10}$ aryl and (d) $C_{6-10}$ aryl $C_{1-6}$ alkyl; (18) —C(O)R$^{G'}$, where R$^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{6-10}$ aryl $C_{1-6}$ alkyl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (19) —NR$^{H'}$C(O)R', wherein R$^{H'}$ is selected from the group consisting of (a1) hydrogen and (b1) $C_{1-6}$ alkyl, and R'' is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{6-10}$ aryl $C_{1-6}$ alkyl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted C$_{1-6}$ alkyl; (20) —NR$^{J'}$C(O)OR$^{K'}$, wherein R$^{J'}$ is selected from the group consisting of (a1) hydrogen and (b1) C$_{1-6}$ alkyl, and R$^{K'}$ is selected from the group consisting of (a2) C$_{1-20}$ alkyl (e.g., C$_{1-6}$ alkyl), (b2) C$_{2-20}$ alkenyl (e.g., C$_{2-6}$ alkenyl), (c2) C$_{6-10}$ aryl, (d2) hydrogen, (e2) C$_{6-10}$ aryl C$_{1-6}$ alkyl, (f2) amino-C$_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C$_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted C$_{1-6}$ alkyl; and (21) amidine. In some embodiments, each of these groups can be further substituted as described herein.

The term "aminoalkoxy," as used herein, represents an alkoxy group, as defined herein, substituted by an amino group, as defined herein. The alkyl and amino each can be further substituted with 1, 2, 3, or 4 substituent groups as described herein for the respective group (e.g., CO$_2$R$^{A'}$, where R$^{A'}$ is selected from the group consisting of (a) C$_{1-6}$ alkyl, (b) C$_{6-10}$ aryl, (c) hydrogen, and (d) C$_{6-10}$ aryl C$_{1-6}$ alkyl, e.g., carboxy).

The term "aminoalkyl," as used herein, represents an alkyl group, as defined herein, substituted by an amino group, as defined herein. The alkyl and amino each can be further substituted with 1, 2, 3, or 4 substituent groups as described herein for the respective group (e.g., CO$_2$R$^{A'}$ where R$^{A'}$ is selected from the group consisting of (a) C$_{1-6}$ alkyl, (b) C$_{6-10}$ aryl, (c) hydrogen, and (d) C$_{6-10}$ aryl C$_{1-6}$ alkyl, e.g., carboxy, and/or an N-protecting group).

The term "aminoalkenyl," as used herein, represents an alkenyl group, as defined herein, substituted by an amino group, as defined herein. The alkenyl and amino each can be further substituted with 1, 2, 3, or 4 substituent groups as described herein for the respective group (e.g., CO$_2$R$^{A'}$, where R$^{A'}$ is selected from the group consisting of (a) C$_{1-6}$ alkyl, (b) C$_{6-10}$ aryl, (c) hydrogen, and (d) C$_{6-10}$ aryl C$_{1-6}$ alkyl, e.g., carboxy, and/or an N-protecting group).

The term "aminoalkynyl," as used herein, represents an alkynyl group, as defined herein, substituted by an amino group, as defined herein. The alkynyl and amino each can be further substituted with 1, 2, 3, or 4 substituent groups as described herein for the respective group (e.g., CO$_2$R$^{A'}$ where R$^{A'}$ is selected from the group consisting of (a) C$_{1-6}$ alkyl, (b) C$_{6-10}$ aryl, (c) hydrogen, and (d) C$_{6-10}$ aryl C$_{1-6}$ alkyl, e.g., carboxy, and/or an N-protecting group).

The term "aryl," as used herein, represents a mono-, bicyclic, or multicyclic carbocyclic ring system having one or more aromatic rings and is exemplified by phenyl, naphthyl, 1,2-dihydronaphthyl, 1,2,3,4-tetrahydronaphthyl, anthracenyl, phenanthrenyl, fluorenyl, indanyl, and indenyl, and may be optionally substituted with 1, 2, 3, 4, or 5 substituents independently selected from the group consisting of: (1) C$_{1-7}$ acyl (e.g., carboxyaldehyde); (2) C$_{1-20}$ alkyl (e.g., C$_{1-6}$ alkyl, C$_{1-6}$ alkoxy-C$_{1-6}$ alkyl, C$_{1-6}$ alkylsulfinyl-C$_{1-6}$ alkyl, amino-C$_{1-6}$ alkyl, azido-C$_{1-6}$ alkyl, (carboxyaldehyde)-C$_{1-6}$ alkyl, halo-C$_{1-6}$ alkyl (e.g., perfluoroalkyl), hydroxy-C$_{1-6}$ alkyl, nitro-C$_{1-6}$ alkyl, or C$_{1-6}$ thioalkoxy-C$_{1-6}$ alkyl); (3) C$_{1-20}$ alkoxy (e.g., C$_{1-6}$ alkoxy, such as perfluoroalkoxy); (4) C$_{1-6}$ alkylsulfinyl; (5) C$_{6-10}$ aryl; (6) amino; (7) C$_{6-10}$ aryl C$_{1-6}$ alkyl; (8) azido; (9) C$_{3-8}$ cycloalkyl; (10) C$_{3-8}$ cycloalkyl C$_{1-6}$ alkyl; (11) halo; (12) C$_{1-12}$ heterocyclyl (e.g., C$_{1-12}$ heteroaryl); (13) (C$_{1-12}$ heterocyclyl)oxy; (14) hydroxy; (15) nitro; (16) C$_{1-20}$ thioalkoxy (e.g., C$_{1-6}$ thioalkoxy); (17) —(CH$_2$)$_q$CO$_2$R$^{A'}$ where q is an integer from zero to four, and R$^{A'}$ is selected from the group consisting of (a) C$_{1-6}$ alkyl, (b) C$_{6-10}$ aryl, (c) hydrogen, and (d) C$_{6-10}$ aryl C$_{1-6}$ alkyl; (18) —(CH$_2$)$_q$CONR$^{B'}$R$^{C'}$, where q is an integer from zero to four and where R$^{B'}$ and R$^{C'}$ are independently selected from the group consisting of (a) hydrogen, (b) C$_{1-6}$ alkyl, (c) C$_{6-10}$ aryl, and (d) C$_{6-10}$ aryl C$_{1-6}$ alkyl; (19) —(CH$_2$)$_q$SO$_2$R$^{D'}$, where q is an integer from zero to four and where R$^{D'}$ is selected from the group consisting of (a) alkyl, (b) C$_{6-10}$ aryl, and (c) C$_{6-10}$ aryl alkyl; (20) —(CH$_2$)$_q$SO$_2$NR$^{E'}$R$^{F'}$, where q is an integer from zero to four and where each of R$^{E'}$ and R$^{F'}$ is, independently, selected from the group consisting of (a) hydrogen, (b) C$_{1-6}$ alkyl, (c) C$_{6-10}$ aryl, and (d) C$_{6-10}$ aryl C$_{1-6}$ alkyl; (21) thiol; (22) C$_{6-10}$ aryloxy; (23) C$_{3-8}$ cycloalkoxy; (24) C$_{6-10}$ aryl-C$_{1-6}$ alkoxy; (25) C$_{1-12}$ heterocyclyl C$_{1-6}$ alkyl (e.g., C$_{1-12}$ heteroaryl C$_{1-6}$ alkyl); (26) C$_{2-20}$ alkenyl; and (27) C$_{2-20}$ alkynyl. In some embodiments, each of these groups can be further substituted as described herein. For example, the alkylene group of a C$_1$-alkaryl or a C$_1$-alkheterocyclyl can be further substituted with an oxo group to afford the respective aryloyl and (heterocyclyl)oyl substituent group.

The term "arylene" as used herein, represent a divalent aryl group derived by the removal of two hydrogen atoms. The term "C$_{x-y}$ arylene" represent arylene groups having between x and y carbons. Exemplary values for x are 6 and 10, and exemplary values for y are 10, 12, 14, 16, 18, or 20 (e.g., C$_{6-10}$ or C$_{6-20}$ arylene). In some embodiments, the arylene can be further substituted with 1, 2, 3, or 4 substituent groups as defined herein for an aryl group. The term "branched arylene" as used herein, refers to a multivalent aryl group derived by the removal of more than two hydrogen atoms.

The term "arylalkoxy," as used herein, represents an alkaryl group, as defined herein, attached to the parent molecular group through an oxygen atom. Exemplary unsubstituted arylalkoxy groups include from 7 to 30 carbons (e.g., from 7 to 16 or from 7 to 20 carbons, such as C$_{6-10}$ aryl-C$_{1-6}$ alkoxy, C$_{6-10}$ aryl-C$_{1-10}$ alkoxy, or C$_{6-10}$ aryl-C$_{1-20}$ alkoxy). In some embodiments, the arylalkoxy group can be substituted with 1, 2, 3, or 4 substituents as defined herein The term "arylalkoxycarbonyl," as used herein, represents an arylalkoxy group, as defined herein, attached to the parent molecular group through a carbonyl (e.g., —C(O)—O-alkyl-aryl). Exemplary unsubstituted arylalkoxy groups include from 8 to 31 carbons (e.g., from 8 to 17 or from 8 to 21 carbons, such as C$_{6-10}$ aryl-C$_{1-6}$ alkoxy-carbonyl, C$_{6-10}$ aryl-C$_{1-10}$ alkoxy-carbonyl, or C$_{6-10}$ aryl-C$_{1-20}$ alkoxy-carbonyl). In some embodiments, the arylalkoxycarbonyl group can be substituted with 1, 2, 3, or 4 substituents as defined herein.

The term "aryloxy" represents a chemical substituent of formula —OR', where R' is an aryl group of 6 to 18 carbons, unless otherwise specified. In some embodiments, the aryl group can be substituted with 1, 2, 3, or 4 substituents as defined herein.

The term "aryloyl," as used herein, represents an aryl group, as defined herein, that is attached to the parent molecular group through a carbonyl group. Exemplary unsubstituted aryloyl groups are of 7 to 11 carbons. In some embodiments, the aryl group can be substituted with 1, 2, 3, or 4 substituents as defined herein.

The term "azido" represents an —N3 group, which can also be represented as —N=N=N.

The term "bicyclic," as used herein, refer to a structure having two rings, which may be aromatic or non-aromatic. Bicyclic structures include spirocyclyl groups, as defined herein, and two rings that share one or more bridges, where such bridges can include one atom or a chain including two, three, or more atoms. Exemplary bicyclic groups include a bicyclic carbocyclyl group, where the first and second rings are carbocyclyl groups, as defined herein; a bicyclic aryl groups, where the first and second rings are aryl groups, as defined herein; bicyclic heterocyclyl groups, where the first ring is a heterocyclyl group and the second ring is a carbocyclyl (e.g., aryl) or heterocyclyl (e.g., heteroaryl) group; and bicyclic heteroaryl groups, where the first ring is a heteroaryl group and the second ring is a carbocyclyl (e.g., aryl) or heterocyclyl (e.g., heteroaryl) group. In some embodiments, the bicyclic group can be substituted with 1, 2, 3, or 4 substituents as defined herein for cycloalkyl, heterocyclyl, and aryl groups.

The term "boranyl," as used herein, represents —B($R^{B1}$)$_3$, where each $R^{B1}$ is, independently, selected from the group consisting of H and optionally substituted alkyl. In some embodiments, the boranyl group can be substituted with 1, 2, 3, or 4 substituents as defined herein for alkyl.

The terms "carbocyclic" and "carbocyclyl," as used herein, refer to an optionally substituted $C_{3-12}$ monocyclic, bicyclic, or tricyclic structure in which the rings, which may be aromatic or non-aromatic, are formed by carbon atoms. Carbocyclic structures include cycloalkyl, cycloalkenyl, and aryl groups.

The term "carbamoyl," as used herein, represents —C(O)—N($R^{N1}$)$_2$, where the meaning of each $R^{N1}$ is found in the definition of "amino" provided herein.

The term "carbamoylalkyl," as used herein, represents an alkyl group, as defined herein, substituted by a carbamoyl group, as defined herein. The alkyl group can be further substituted with 1, 2, 3, or 4 substituent groups as described herein.

The term "carbamyl," as used herein, refers to a carbamate group having the structure —$NR^{N1}$C(=O)OR or —OC(=O)N($R^{N1}$)$_2$, where the meaning of each $R^{N1}$ is found in the definition of "amino" provided herein, and R is alkyl, cycloalkyl, alkcycloalkyl, aryl, alkaryl, heterocyclyl (e.g., heteroaryl), or alkheterocyclyl (e.g., alkheteroaryl), as defined herein.

The term "carbonyl," as used herein, represents a C(O) group, which can also be represented as C=O.

The term "carboxyaldehyde" represents an acyl group having the structure —CHO.

The term "carboxy," as used herein, means —$CO_2$H.

The term "carboxyalkoxy," as used herein, represents an alkoxy group, as defined herein, substituted by a carboxy group, as defined herein. The alkoxy group can be further substituted with 1, 2, 3, or 4 substituent groups as described herein for the alkyl group, and the carboxy group can be optionally substituted with one or more O-protecting groups.

The term "carboxyalkyl," as used herein, represents an alkyl group, as defined herein, substituted by a carboxy group, as defined herein. The alkyl group can be further substituted with 1, 2, 3, or 4 substituent groups as described herein, and the carboxy group can be optionally substituted with one or more O-protecting groups.

The term "carboxyaminoalkyl," as used herein, represents an aminoalkyl group, as defined herein, substituted by a carboxy, as defined herein. The carboxy, alkyl, and amino each can be further substituted with 1, 2, 3, or 4 substituent groups as described herein for the respective group (e.g., $CO_2R^{A'}$ where $R^{A'}$ is selected from the group consisting of (a) $C_{1-6}$ alkyl, (b) $C_{6-10}$ aryl, (c) hydrogen, and (d) $C_{6-10}$ aryl $C_{1-6}$ alkyl, e.g., carboxy, and/or an N-protecting group, and/or an O-protecting group).

The term "cyano," as used herein, represents an —CN group.

The term "cycloalkoxy" represents a chemical substituent of formula —OR, where R is a $C_{3-8}$ cycloalkyl group, as defined herein, unless otherwise specified. The cycloalkyl group can be further substituted with 1, 2, 3, or 4 substituent groups as described herein. Exemplary unsubstituted cycloalkoxy groups are from 3 to 8 carbons. In some embodiment, the cycloalkyl group can be further substituted with 1, 2, 3, or 4 substituent groups as described herein.

The term "cycloalkyl," as used herein represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, and bicycle heptyl. When the cycloalkyl group includes one carbon-carbon double bond, the cycloalkyl group can be referred to as a "cycloalkenyl" group. Exemplary cycloalkenyl groups include cyclopentenyl and cyclohexenyl. The cycloalkyl groups of this invention can be optionally substituted with: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{6-10}$ aryl $C_{1-6}$ alkyl; (8) azido; (9) $C_{3-8}$ cycloalkyl; (10) $C_{3-8}$ cycloalkyl $C_{1-6}$ alkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{6-10}$ aryl $C_{1-6}$ alkyl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{8-10}$ alkyl, (c) $C_{6-10}$ aryl, and (d) $C_{6-10}$ aryl $C_{1-6}$ alkyl; (19) —$(CH_2)_qSO_2R^{D'}$, where q is an integer from zero to four and where $R^{D'}$ is selected from the group consisting of (a) $C_{8-10}$ alkyl, (b) $C_{6-10}$ aryl, and (c) $C_{6-10}$ aryl $C_{1-6}$ alkyl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{6-10}$ alkyl, (c) $C_{6-10}$ aryl, and (d) $C_{6-10}$ aryl $C_{1-6}$ alkyl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-12}$ heterocyclyl $C_{1-6}$ alkyl (e.g., $C_{1-12}$ heteroaryl $C_{1-6}$ alkyl); (26) oxo; (27) $C_{2-20}$ alkenyl; and (28) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "diastereomer," as used herein means stereoisomers that are not mirror images of one another and are non-superimposable on one another.

The term "effective amount" of an agent, as used herein, is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "halo," as used herein, represents a halogen selected from bromine, chlorine, iodine, or fluorine.

The term "haloalkoxy," as used herein, represents an alkoxy group, as defined herein, substituted by a halogen group (i.e., F, Cl, Br, or I). A haloalkoxy may be substituted with one, two, three, or, in the case of alkyl groups of two carbons or more, four halogens. Haloalkoxy groups include perfluoroalkoxys (e.g., —$OCF_3$), —$OCHF_2$, —$OCH_2F$, —$OCCl_3$, —$OCH_2CH_2Br$, —$OCH_2CH(CH_2CH_2Br)CH_3$, and —$OCHICH_3$. In some embodiments, the haloalkoxy group can be further substituted with 1, 2, 3, or 4 substituent groups as described herein for alkyl groups.

The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens. Haloalkyl groups include perfluoroalkyls (e.g., —$CF_3$), —$CHF_2$, —$CH_2F$, —$CCl_3$, —$CH_2CH_2Br$, —$CH_2CH(CH_2CH_2Br)CH_3$, and —$CHICH_3$. In some embodiments, the haloalkyl group can be further substituted with 1, 2, 3, or 4 substituent groups as described herein for alkyl groups.

The term "heteroalkylene," as used herein, refers to an alkylene group, as defined herein, in which one or two of the constituent carbon atoms have each been replaced by nitrogen, oxygen, or sulfur. In some embodiments, the heteroalkylene group can be further substituted with 1, 2, 3, or 4 substituent groups as described herein for alkylene groups. The term "branched "heteroalkylene" as used herein, refers to a multivalent heteroalkylene group derived by the removal of more than two hydrogen atoms.

The term "heteroaryl," as used herein, represents that subset of heterocyclyls, as defined herein, which are aromatic: i.e., they contain 4n+2 pi electrons within the mono- or multicyclic ring system. Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiment, the heteroaryl is substituted with 1, 2, 3, or 4 substituents groups as defined for a heterocyclyl group.

The term "heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, and benzothienyl. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, and benzothienyl, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo, 4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3,7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl. Heterocyclic groups also include groups of the formula

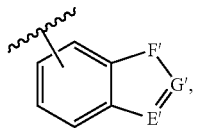

where

E' is selected from the group consisting of —N— and —CH—; F' is selected from the group consisting of —N=CH—, —NH—CH$_2$—, —NH—C(O)—, —NH—, —CH=N—, —CH$_2$—NH—, —C(O)—NH—, —CH=CH—, —CH$_2$—, —CH$_2$CH$_2$—, —CH$_2$O—, —OCH$_2$—, —O—, and —S—; and G' is selected from the group consisting of —CH— and —N—. Any of the heterocyclyl groups mentioned herein may be optionally substituted with one, two, three, four or five substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-C-6 alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{6-10}$ aryl $C_{1-6}$ alkyl; (8) azido; (9) $C_{3-8}$ cycloalkyl; (10) $C_{3-8}$ cycloalkyl $C_{1-6}$ alkyl; (11) halo; (12) $C_{1-12}$ heterocyclyl (e.g., $C_{2-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —(CH$_2$)$_q$CO$_2$R$^{A'}$, where q is an integer from zero to four, and R$^{A'}$ is selected from the group consisting of (a) $C_{1-6}$ alkyl, (b) $C_{6-10}$ aryl, (c) hydrogen, and (d) $C_{6-10}$ aryl $C_{1-6}$ alkyl; (18) —(CH$_2$)$_q$CONR$^{B'}$R$^{C'}$, where q is an integer from zero to four and where R$^{B'}$ and R$^{C'}$ are independently selected from the group consisting of (a) hydrogen, (b) $C_{1-6}$ alkyl, (c) $C_{6-10}$ aryl, and (d) $C_{6-10}$ aryl $C_{1-6}$ alkyl; (19) —(CH$_2$)$_q$SO$_2$R$^{D'}$, where q is an integer from zero to four and where R$^{D'}$ is selected from the group consisting of (a) $C_{1-6}$ alkyl, (b) $C_{6-10}$ aryl, and (c) $C_{6-10}$ aryl $C_{1-6}$ alkyl; (20) —(CH$_2$)$_q$SO$_2$NR$^{E'}$R$^{F'}$, where q is an integer from zero to four and where each of R$^{E'}$ and R$^{F'}$ is, independently, selected from the group consisting of (a) hydrogen, (b) $C_{1-6}$ alkyl, (c) $C_{6-10}$ aryl, and (d) $C_{6-10}$ aryl $C_{1-6}$ alkyl; (21) thiol; (22) $C_{6-10}$ aryloxy; (23) $C_{3-8}$ cycloalkoxy; (24) arylalkoxy; (25) $C_{1-12}$ heterocyclyl $C_{1-6}$ alkyl (e.g., $C_{1-12}$ heteroaryl $C_{1-6}$ alkyl); (26) oxo; (27) ($C_{1-12}$ heterocyclyl)imino; (28) $C_{2-20}$ alkenyl; and (29) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "heterocyclylene" as used herein, represent a divalent heterocyclyl group derived by the removal of two hydrogen atoms. The term "$C_{x-y}$ heterocyclylene" represent heterocyclylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., $C_{1-6}$, $C_{1-10}$, $C_{2-20}$, $C_{2-6}$, $C_{2-10}$, or $C_{2-20}$ alkylene). In some embodiments, the heterocyclylene can be further substituted with 1, 2, 3, or 4 substituent groups as defined herein for an alkyl group. The term "branched heterocyclylene" as used herein, refers to a multivalent heterocyclylene group derived by the removal of more than two hydrogen atoms.

The term "(heterocyclyl) imino," as used herein, represents a heterocyclyl group, as defined herein, attached to the parent molecular group through an imino group. In some embodiments, the heterocyclyl group can be substituted with 1, 2, 3, or 4 substituent groups as defined herein.

The term "(heterocyclyl)oxy," as used herein, represents a heterocyclyl group, as defined herein, attached to the parent molecular group through an oxygen atom. In some embodiments, the heterocyclyl group can be substituted with 1, 2, 3, or 4 substituent groups as defined herein.

The term "(heterocyclyl)oyl," as used herein, represents a heterocyclyl group, as defined herein, attached to the parent molecular group through a carbonyl group. In some embodiments, the heterocyclyl group can be substituted with 1, 2, 3, or 4 substituent groups as defined herein.

The term "hydrocarbon," as used herein, represents a group consisting only of carbon and hydrogen atoms.

The term "hydroxy," as used herein, represents an —OH group. In some embodiments, the hydroxy group can be substituted with 1, 2, 3, or 4 substituent groups (e.g., O-protecting groups) as defined herein for an alkyl.

The term "hydroxyalkenyl," as used herein, represents an alkenyl group, as defined herein, substituted by one to three hydroxy groups, with the proviso that no more than one hydroxy group may be attached to a single carbon atom of the alkyl group, and is exemplified by dihydroxypropenyl and hydroxyisopentenyl. In some embodiments, the hydroxyalkenyl group can be substituted with 1, 2, 3, or 4 substituent groups (e.g., O-protecting groups) as defined herein for an alkyl.

The term "hydroxyalkyl," as used herein, represents an alkyl group, as defined herein, substituted by one to three hydroxy groups, with the proviso that no more than one hydroxy group may be attached to a single carbon atom of the alkyl group, and is exemplified by hydroxymethyl and dihydroxypropyl. In some embodiments, the hydroxyalkyl group can be substituted with 1, 2, 3, or 4 substituent groups (e.g., O-protecting groups) as defined herein for an alkyl.

The term "hydroxyalkynyl," as used herein, represents an alkynyl group, as defined herein, substituted by one to three hydroxy groups, with the proviso that no more than one hydroxy group may be attached to a single carbon atom of the alkyl group. In some embodiments, the hydroxyalkynyl group can be substituted with 1, 2, 3, or 4 substituent groups (e.g., O-protecting groups) as defined herein for an alkyl.

The term "isomer," as used herein, means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "N-protected amino," as used herein, refers to an amino group, as defined herein, to which is attached one or two N-protecting groups, as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, and phenylalanine; sulfonyl-containing groups such as benzenesulfonyl and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, and cyclohexyloxycarbonyl, phenylthiocarbonyl, alkaryl groups such as benzyl, triphenylmethyl, and benzyloxymethyl and silyl groups, such as trimethylsilyl. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —NO$_2$ group.

The term "O-protecting group," as used herein, represents those groups intended to protect an oxygen containing (e.g., phenol, hydroxy, or carbonyl) group against undesirable reactions during synthetic procedures. Commonly used O-protecting groups are disclosed in Greene, "Protective Groups in Organic Synthesis," 3$^{rd}$ Edition (John Wiley & Sons, New York, 1999), which is incorporated herein by reference. Exemplary O-protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl; alkylcarbonyl groups, such as acyl, acetyl, propionyl, and pivaloyl; optionally substituted arylcarbonyl groups, such as benzoyl; silyl groups, such as trimethylsilyl (TMS), tert-butyldimethylsilyl (TBDMS), tri-iso-propylsilyloxymethyl (TOM), and triisopropylsilyl (TIPS); ether-forming groups with the hydroxy, such methyl, methoxymethyl, tetrahydropyranyl, benzyl, p-methoxybenzyl, and trityl; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, and methyloxycarbonyl; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, and 3-methyl-2-butenoxycarbonyl; haloalkoxycarbonyls, such as 2-chloroethoxycarbonyl, 2-chloroethoxycarbonyl, and 2,2,2-trichloroethoxycarbonyl; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxy-carbonyl, and fluorenylmethyloxycarbonyl; and optionally substituted aryloxycarbonyl groups, such as phenoxycarbonyl, p-nitrophenoxycarbonyl, o-nitrophenoxycarbonyl, 2,4-dinitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, and 2-chloro-4-nitrophenoxycarbonyl); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal and 1,3-dioxolane; acylal groups; and dithiane groups, such as 1,3-dithianes and 1,3-dithiolane); carboxylic acid-protecting groups (e.g., ester groups, such as methyl ester, benzyl ester, t-butyl ester, and orthoesters; and oxazoline groups.

The term "oxo" as used herein, represents =O.

The term "perfluoroalkyl," as used herein, represents an alkyl group, as defined herein, where each hydrogen radical bound to the alkyl group has been replaced by a fluoride radical. Perfluoroalkyl groups are exemplified by trifluoromethyl and pentafluoroethyl.

The term "perfluoroalkoxy," as used herein, represents an alkoxy group, as defined herein, where each hydrogen radical bound to the alkoxy group has been replaced by a fluoride radical. Perfluoroalkoxy groups are exemplified by trifluoromethoxy and pentafluoroethoxy.

The term "phosphoryl," as used herein refers to a divalent group:

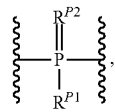

wherein R$^{P1}$ is any suitable substituent, e.g., H, hydroxy, protected hydroxy, halo, thiol, boranyl, optionally substituted alkyl, optionally substituted alkenyl, optionally substituted alkynyl, optionally substituted hetereoalkyl, optionally substituted heteroalkenyl, optionally substituted heteroalkynyl, or optionally substituted amino, or a salt thereof; and $R^{P2}$ is O, S, Se, —$NR^{N1}$—, optionally substituted alkynlene, or optionally substituted hetereoalkylene, wherein $R^{N1}$ is H, optionally substituted alkyl, optionally substituted alkenyl, optionally substituted alkynylene, or optionally substituted arylene.

The term "polyethylene glycolene" as used herein, represents a divalent polyethylene glycol group derived by the removal of two hydrogen atoms. The term "$C_2$-$C_{100}$ polyethylene glycolene" represent polyethylene glycolene groups having between x and y carbons. Exemplary values for x are 2, 4, 6, 8, 10, and 20, and exemplary values for y are 10, 20, 40, 60, or 80 (e.g., $C_{2-10}$ or $C_{6-20}$ polyethylene glycolene). In some embodiments, a monomeric unit of the polyethylene glycolene can be further substituted with 1, 2, 3, or 4 substituent groups as defined herein for a heteroalkylene group. The term "branched polyethylene glycolene" as used herein, refers to a multivalent polyethylene glycol group derived by the removal of more than two hydrogen atoms.

The term "spirocyclyl," as used herein, represents a $C_{2-7}$ alkylene diradical, both ends of which are bonded to the same carbon atom of the parent group to form a spirocyclic group, and also a $C_1$-s heteroalkylene diradical, both ends of which are bonded to the same atom. The heteroalkylene radical forming the spirocyclyl group can containing one, two, three, or four heteroatoms independently selected from the group consisting of nitrogen, oxygen, and sulfur. In some embodiments, the spirocyclyl group includes one to seven carbons, excluding the carbon atom to which the diradical is attached. The spirocyclyl groups of the invention may be optionally substituted with 1, 2, 3, or 4 substituents provided herein as optional substituents for cycloalkyl and/or heterocyclyl groups.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

The term "sulfoalkyl," as used herein, represents an alkyl group, as defined herein, substituted by a sulfo group of —$SO_3H$. In some embodiments, the alkyl group can be further substituted with 1, 2, 3, or 4 substituent groups as described herein, and the sulfo group can be further substituted with one or more O-protecting groups (e.g., as described herein).

The term "sulfonyl," as used herein, represents an —$S(O)_2$— group.

The term "thioalkaryl," as used herein, represents a chemical substituent of formula —SR, where R is an alkaryl group. In some embodiments, the alkaryl group can be further substituted with 1, 2, 3, or 4 substituent groups as described herein.

The term "thioalkheterocyclyl," as used herein, represents a chemical substituent of formula —SR, where R is an alkheterocyclyl group. In some embodiments, the alkheterocyclyl group can be further substituted with 1, 2, 3, or 4 substituent groups as described herein.

The term "thioalkoxy," as used herein, represents a chemical substituent of formula —SR, where R is an alkyl group, as defined herein. In some embodiments, the alkyl group can be further substituted with 1, 2, 3, or 4 substituent groups as described herein.

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$alkyl.

About: As used herein, the term "about" when used in the context of the amount of an alternative nucleobase or nucleoside in a polynucleotide means +/−10% of the recited value. For example, a polynucleotide containing about 25% of an alternative uracil includes between 22.5-27.5% of the alternative uracil.

Administered in combination: As used herein, the term "administered in combination" or "combined administration" means that two or more agents are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Altered: As used herein "altered" refers to a changed state or structure of a molecule of the invention. Molecules may be altered in many ways including chemically, structurally, and functionally. In one embodiment, the mRNA molecules of the present invention are altered by the introduction of non-natural nucleosides and/or nucleotides, e.g., as it relates to the natural ribonucleotides A, U, G, and C. Noncanonical nucleotides such as the cap structures are not considered "altered" although they differ from the chemical structure of the A, C, G, U ribonucleotides.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Antigens of interest or desired antigens: As used herein, the terms "antigens of interest" or "desired antigens" include those proteins and other biomolecules provided herein that are immunospecifically bound by the antibodies and fragments, mutants, variants, and alterations thereof described herein. Examples of antigens of interest include, but are not limited to, insulin, insulin-like growth factor, hGH, tPA, cytokines, such as interleukins (IL), e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosis factor (TNF), such as TNF alpha and TNF beta, TNF gamma, TRAIL; G-CSF, GM-CSF, M-CSF, MCP-1 and VEGF.

Approximately: As used herein, the term "approximately" or "about," as applied to one or more values of interest other than the amount of an alternative nucleobase or nucleoside in a polynucleotide, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a polynucleotide of the present invention may be considered biologically active if even a portion of the polynucleotide is biologically active or mimics an activity considered biologically relevant.

Compound: As used herein, the term "compound," is meant to include all stereoisomers, geometric isomers, tautomers, and isotopes of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins and C=N double bonds can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are the to be "highly conserved" if they are about 70% identical, about 80% identical, about 90% identical, about 95%, about 98%, or about 99% identical to one another. In some embodiments, two or more sequences are the to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are the to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an oligonucleotide or polypeptide or may apply to a portion, region or feature thereof.

Cyclic or Cyclized: As used herein, the term "cyclic" refers to the presence of a continuous loop. Cyclic molecules need not be circular, only joined to form an unbroken chain of subunits. Cyclic molecules such as the mRNA of the present invention may be single units or multimers or include one or more components of a complex or higher order structure.

Cytostatic: As used herein, "cytostatic" refers to inhibiting, reducing, suppressing the growth, division, or multiplication of a cell (e.g., a mammalian cell (e.g., a human cell)), bacterium, virus, fungus, protozoan, parasite, prion, or a combination thereof.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivery: As used herein, "delivery" refers to the act or manner of delivering a compound, substance, entity, moiety, cargo or payload.

Delivery Agent: As used herein, "delivery agent" refers to any substance which facilitates, at least in part, the in vivo delivery of a polynucleotide to targeted cells.

Destabilized: As used herein, the term "destable," "destabilize," or "destabilizing region" means a region or molecule that is less stable than a starting, wild-type or native form of the same region or molecule.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, and absorbance. Detectable labels include radioisotopes, fluorophores, chromophores, enzymes, dyes, metal ions, ligands such as biotin, avidin, streptavidin and haptens, and quantum dots. Detectable labels may be located at any position in the peptides or proteins disclosed herein. They may be within the amino acids, the peptides, or proteins, or located at the N- or C— termini.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Encoded protein cleavage signal: As used herein, "encoded protein cleavage signal" refers to the nucleotide sequence which encodes a protein cleavage signal.

Engineered: As used herein, embodiments of the invention are "engineered" when they are designed to have a feature or property, whether structural or chemical, that varies from a starting point, wild type or native molecule.

Expression: As used herein, "expression" of a polynucleotide sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Feature: As used herein, a "feature" refers to a characteristic, a property, or a distinctive element.

Formulation: As used herein, a "formulation" includes at least a polynucleotide and a delivery agent.

Fragment: A "fragment," as used herein, refers to a portion. For example, fragments of proteins may include polypeptides obtained by digesting full-length protein isolated from cultured cells.

Functional: As used herein, a "functional" biological molecule is a biological molecule in a form in which it exhibits a property and/or activity by which it is characterized.

Homology: As used herein, the term "homology" refers to the overall relatedness between polymeric molecules, e.g., between polynucleotide molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the invention, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the invention, two protein sequences are considered to be homologous if the proteins are at least about 50%, 60%, 70%, 80%, or 90% identical for at least one stretch of at least about 20 amino acids.

Identity: As used herein, the term "identity" refers to the overall relatedness between polymeric molecules, e.g., between oligonucleotide molecules (e.g., DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second polynucleotide sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTAn altschul, S. F. et al., *J. Molec. Biol.,* 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

L-nucleoside: As used herein, an L-nucleoside refers to a nucleoside including L-ribose.

Maximized codons: As used herein the term "maximized codon" refers to a codon with the highest number of a nucleotide. For example, a "guanine maximized codon" is the codon for a particular amino acid that has the highest number of guanines.

Naturally occurring: As used herein, "naturally occurring" means existing in nature without artificial aid.

Non-human vertebrate: As used herein, a "non human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Paratope: As used herein, a "paratope" refers to the antigen-binding site of an antibody.

Patient: As used herein, "patient" refers to a subject who may seek or be in need of treatment, requires treatment, is receiving treatment, will receive treatment, or a subject who is under care by a trained professional for a particular disease or condition.

Optionally substituted: Herein a phrase of the form "optionally substituted X" (e.g., optionally substituted alkyl) is intended to be equivalent to "X, wherein X is optionally substituted" (e.g., "alkyl, wherein the alkyl is optionally substituted"). It is not intended to mean that the feature "X" (e.g., alkyl) per se is optional.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is altered by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's *The Science and Practice of Pharmacy*, 21$^{st}$ Edition, A. R. Gennaro (Lippincott, Williams & Wilkins, Baltimore, M D, 2006, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, and benzyl benzoate. When water is the solvent, the solvate is referred to as a "hydrate."

Physicochemical: As used herein, "physicochemical" means of or relating to a physical and/or chemical property.

Polymer: As used herein, a "polymer" is a molecule or compound having two or more different monomeric units, and includes copolymers having two monomeric units, terpolymers having three monomeric units, tetrapolymers having four monomeric units, pentapolymers having five monomeric units, etc. It will also be appreciated that copolymers may be random copolymers, block copolymers, alternating copolymers, or a combination including two or more of these motifs. The polymer may also have a compositional gradient.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxy, amino, sulfhydryl, or carboxyl groups are bonded to any group that, when administered to a mammalian subject, cleaves to form a free hydroxy, amino, sulfhydryl, or carboxyl group respectively. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Purified: As used herein, "purify," "purified," "purification" means to make substantially pure or clear from unwanted components, material defilement, admixture or imperfection.

Sample: As used herein, the term "sample" or "biological sample" refers to a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or polynucleotide.

Signal Sequences: As used herein, the phrase "signal sequences" refers to a sequence which can direct the transport or localization of a protein.

Significant or Significantly: As used herein, the terms "significant" or "significantly" are used synonymously with the term "substantially."

Single unit dose: As used herein, a "single unit dose" is a dose of any therapeutic administed in one dose/at one time/single route/single point of contact, i.e., single administration event.

Similarity: As used herein, the term "similarity" refers to the overall relatedness between polymeric molecules, e.g., between polynucleotide molecules (e.g., DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Small Molecule: As used herein, "small molecule" refers to a non-peptidic, non-oligomeric organic compound either synthesized in the laboratory or found in nature. Small molecules, as used herein, can refer to compounds that are "natural product-like," however, the term "small molecule" is not limited to "natural product-like" compounds. Rather, a small molecule is typically characterized in that it possesses one or more of the following characteristics including having several carbon-carbon bonds, having multiple stereocenters, having multiple functional groups, having at least two different types of functional groups, and having a molecular weight of less than 1500 Da, although this characterization is not intended to be limiting for the purposes of the disclosure.

Split dose: As used herein, a "split dose" is the division of single unit dose or total daily dose into two or more doses.

Stable: As used herein "stable" refers to a compound that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term means within 2 seconds.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or polynucleotide associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Synthetic: The term "synthetic" means produced, prepared, and/or manufactured by the hand of man. Synthesis of polynucleotides or polypeptides or other molecules of the present invention may be chemical or enzymatic.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Theoretical Minimum: The term "theoretical minimum" refers to a nucleotide sequence with all of the codons in the open reading frame replaced to minimize the number of uracils in the sequence.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., polynucleotide, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hours period. It may be administered as a single unit dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unaltered: As used herein, "unaltered" refers to any substance, compound or molecule prior to being changed in any way. Unaltered may, but does not always, refer to the wild type or native form of a biomolecule. Molecules may undergo a series of alterations whereby each alternative molecule may serve as the "unaltered" starting molecule for a subsequent alteration.

Wild-type Sequence: As used herein, a "wild-type sequence" is the sequence of the naturally occurring mRNA that encodes the polypeptide of interest.

EXAMPLES

The present disclosure is further described in the following examples, which do not limit the scope of the disclosure described in the claims.

Example 1: PCR for cDNA Production

PCR procedures for the preparation of cDNA were performed using 2× KAPA HIFI™ HotStart ReadyMix by Kapa Biosystems (Woburn, MA). This system includes 2× KAPA ReadyMix 12.5 µl; Forward Primer (10 µM) 0.75 µl; Reverse Primer (10 µM) 0.75 µl; Template cDNA 100 ng; and dH$_2$O diluted to 25.0 µl. The reaction conditions were at 95° C. for 5 minutes and 25 cycles of 98° C. for 20 sec, then 58° C. for 15 sec, then 72° C. for 45 sec, then 72° C. for 5 minutes then 4° C. to termination.

The reverse primer of the instant invention incorporated a poly-T$_{120}$ (SEQ ID NO: 32) for a poly-A$_{120}$ (SEQ ID NO: 30) in the mRNA. Other reverse primers with longer or shorter poly-T tracts can be used to adjust the length of the poly-A tail in the mRNA.

The reaction was purified using Invitrogen's PURELINK™ PCR Micro Kit (Carlsbad, CA) per manufacturer's instructions (up to 5 µg). Following the purification, the cDNA was quantified using the NanoDrop and analyzed by agarose gel electrophoresis to confirm the cDNA is the expected size. The cDNA was then submitted for sequencing analysis before proceeding to the in vitro transcription reaction.

Example 2. In Vitro Transcription (IVT)

A. Materials and Methods

Alternative mRNAs according to the invention are made using standard laboratory methods and materials for in vitro transcription with the exception that the nucleotide mix contains alternative nucleotides. The open reading frame (ORF) of the gene of interest may be flanked by a 5'-untranslated region (UTR) containing a strong Kozak translational initiation signal and an alpha-globin 3'-UTR terminating with an oligo(dT) sequence for templated addition of a polyA tail for mRNAs not incorporating adenosine analogs. Adenosine-containing mRNAs are synthesized without an oligo (dT) sequence to allow for post-transcription poly (A) polymerase poly-(A) tailing.

The ORF may also include various upstream or downstream additions (such as, but not limited to, β-globin, tags, etc.) may be ordered from an optimization service such as, but limited to, DNA2.0 (Menlo Park, CA) and may contain multiple cloning sites which may have XbaI recognition. Upon receipt of the construct, it may be reconstituted and transformed into chemically competent *E. coli*.

For the present invention, NEB DH5-alpha Competent *E. coli* may be used. Transformations are performed according to NEB instructions using 100 ng of plasmid. The protocol is as follows:

Thaw a tube of NEB 5-alpha Competent *E. coli* cells on ice for 10 minutes.
Add 1-5 µl containing 1 µg-100 ng of plasmid DNA to the cell mixture. Carefully flick the tube 4-5 times to mix cells and DNA. Do not vortex.
Place the mixture on ice for 30 minutes. Do not mix.
Heat shock at 42° C. for exactly 30 seconds. Do not mix.
Place on ice for 5 minutes. Do not mix.
Pipette 950 µl of room temperature SOC into the mixture.
Place at 37° C. for 60 minutes. Shake vigorously (250 rpm) or rotate.
Warm selection plates to 37° C.
Mix the cells thoroughly by flicking the tube and inverting.
Spread 50-100 µl of each dilution onto a selection plate and incubate overnight at 37° C. Alternatively, incubate at 30° C. for 24-36 hours or 25° C. for 48 hours.

A single colony is then used to inoculate 5 ml of LB growth media using the appropriate antibiotic and then allowed to grow (250 RPM, 37° C.) for 5 hours. This is then used to inoculate a 200 ml culture medium and allowed to grow overnight under the same conditions.

To isolate the plasmid (up to 850 µg), a maxi prep is performed using the Invitrogen PURELINK™ HiPure Maxiprep Kit (Carlsbad, CA), following the manufacturer's instructions.

In order to generate cDNA for In Vitro Transcription (IVT), the plasmid is first linearized using a restriction enzyme such as XbaI. A typical restriction digest with XbaI will include the following: Plasmid 1.0 µg; 10× Buffer 1.0 µl; XbaI 1.5 µl; dH$_2$O up to 10 µl; incubated at 37° C. for 1 hour. If performing at lab scale (<5 µg), the reaction is cleaned up using Invitrogen's PURELINK™ PCR Micro Kit (Carlsbad, CA) per manufacturer's instructions. Larger scale purifications may need to be done with a product that has a larger load capacity such as Invitrogen's standard PURELINK™ PCR Kit (Carlsbad, CA). Following the cleanup, the linearized vector is quantified using the Nano-Drop and analyzed to confirm linearization using agarose gel electrophoresis.

IVT Reaction

The in vitro transcription reaction generates mRNA containing alternative nucleotides or alternative RNA. The input nucleotide triphosphate (NTP) mix is made in-house using natural and un-natural NTPs.

| A typical in vitro transcription reaction includes the following: | |
|---|---|
| Template cDNA | 1.0 µg |
| 10x transcription buffer (400 mM Tris-HCl pH 8.0, 190 mM MgCl2, 50 mM DTT, 10 mM Spermidine) | 2.0 µl |
| Custom NTPs (25 mM each) | 7.2 µl |
| RNase Inhibitor | 20 U |
| T7 RNA polymerase | 3000 U |
| dH$_2$O | up to 20.0 µl |

Incubation at 37° C. for 3 hours-5 hours.

The crude IVT mix may be stored at 4° C. overnight for cleanup the next day. 1 U of RNase-free DNase is then used to digest the original template. After 15 minutes of incubation at 37° C., the mRNA is purified using Ambion's MEGACLEAR™ Kit (Austin, TX) following the manufacturer's instructions. This kit can purify up to 500 µg of RNA. Following the cleanup, the RNA is quantified using the NanoDrop and analyzed by agarose gel electrophoresis to confirm the RNA is the proper size and that no degradation of the RNA has occurred.

The T7 RNA polymerase may be selected from, T7 RNA polymerase, T3 RNA polymerase and mutant polymerases such as, but not limited to, the novel polymerases able to incorporate alternative NTPs as well as those polymerases described by Liu (Esvelt et al. (Nature (2011) 472(7344): 499-503 and U.S. Publication No. 20110177495) which recognize alternate promoters, Ellington (Chelliserrykattil and Ellington, Nature Biotechnology (2004) 22(9):1155-1160) describing a T7 RNA polymerase variant to transcribe 2'-O-methyl RNA and Sousa (Padilla and Sousa, Nucleic Acids Research (2002) 30(24): e128) describing a T7 RNA polymerase double mutant; herein incorporated by reference in their entireties.

B. Agarose Gel Electrophoresis of Alternative mRNA

Individual alternative mRNAs (200-400 ng in a 20 µl volume) are loaded into a well on a non-denaturing 1.2% Agarose E-Gel (Invitrogen, Carlsbad, CA) and run for 12-15 minutes according to the manufacturer protocol.

C. Agarose Gel Electrophoresis of RT-PCR Products

Individual reverse transcribed-PCR products (200-400 ng) are loaded into a well of a non-denaturing 1.2% Agarose E-Gel (Invitrogen, Carlsbad, CA) and run for 12-15 minutes according to the manufacturer protocol.

D. Nanodrop Alternative mRNA Quantification and UV Spectral Data

Alternative mRNAs in TE buffer (1 µl) are used for Nanodrop UV absorbance readings to quantitate the yield of each alternative mRNA from an in vitro transcription reaction (UV absorbance traces are not shown).

Example 3. Enzymatic Capping of mRNA

Capping of the mRNA is performed as follows where the mixture includes: IVT RNA 60 µg-180 µg and dH$_2$O up to 72 µl. The mixture is incubated at 65° C. for 5 minutes to denature RNA, and then is transferred immediately to ice.

The protocol then involves the mixing of 10× Capping Buffer (0.5 M Tris-HCl (pH 8.0), 60 mM KCl, 12.5 mM MgCl$_2$) (10.0 µl); 20 mM GTP (5.0 µl); 20 mM S-Adenosyl Methionine (2.5 µl); RNase Inhibitor (100 U); 2'-O-Methyltransferase (400U); Vaccinia capping enzyme (Guanylyl transferase) (40 U); dH$_2$O (Up to 28 µl); and incubation at 37° C. for 30 minutes for 60 µg RNA or up to 2 hours for 180 µg of RNA.

The mRNA is then purified using Ambion's MEGACLEAR™ Kit (Austin, TX) following the manufacturer's instructions. Following the cleanup, the RNA is quantified using the NANODROP™ (ThermoFisher, Waltham, MA) and analyzed by agarose gel electrophoresis to confirm the RNA is the proper size and that no degradation of the RNA has occurred. The RNA product may also be sequenced by running a reverse-transcription-PCR to generate the cDNA for sequencing.

Example 4. 5'-Guanosine Capping

A. Materials and Methods

The cloning, gene synthesis and vector sequencing may be performed by DNA2.0 Inc. (Menlo Park, CA). The ORF is restriction digested using XbaI and used for cDNA synthesis using tailed- or tail-less-PCR. The tailed-PCR cDNA product is used as the template for the alternative mRNA synthesis reaction using 25 mM each alternative nucleotide mix (all alternative nucleotides may be custom synthesized or purchased from TriLink Biotech, San Diego, CA except pyrrolo-C triphosphate which may be purchased from Glen Research, Sterling VA; unmodifed nucleotides are purchased from Epicenter Biotechnologies, Madison, WI) and CellScript MEGASCRIPT™ (Epicenter Biotechnologies, Madison, WI) complete mRNA synthesis kit.

The in vitro transcription reaction is run for 4 hours at 37° C. Alternative mRNAs incorporating adenosine analogs are poly (A) tailed using yeast Poly (A) Polymerase (Affymetrix, Santa Clara, CA). The PCR reaction uses HiFi PCR 2× MASTER MIX™ (Kapa Biosystems, Woburn, MA). Alternative mRNAs are post-transcriptionally capped using recombinant Vaccinia Virus Capping Enzyme (New England BioLabs, Ipswich, MA) and a recombinant 2'-O-methyl-transferase (Epicenter Biotechnologies, Madison, WI) to generate the 5'-guanosine Cap1 structure. Cap 2 structure and Cap 2 structures may be generated using additional 2'-O-methyltransferases. The In vitro transcribed mRNA product is run on an agarose gel and visualized. Alternative mRNA may be purified with Ambion/Applied Biosystems (Austin, TX) MEGAClear RNA™ purification kit. The PCR uses PURELINK™ PCR purification kit (Invitrogen, Carlsbad, CA). The product is quantified on NANODROP™ UV Absorbance (ThermoFisher, Waltham, MA). Quality, UV absorbance quality and visualization of the product was performed on an 1.2% agarose gel. The product is resuspended in TE buffer.

B. 5' Capping Alternative Polynucleotide (mRNA) Structure

5'-capping of alternative mRNA may be completed concomitantly during the in vitro-transcription reaction using the following chemical RNA cap analogs to generate the 5'-guanosine cap structure according to manufacturer protocols: 3'-O-Me-m$^7$G(5)ppp(5')G (the ARCA cap); G(5')ppp (5')A; G(5)ppp(5')G; m$^7$G(5')ppp(5')A; m$^7$G(5')ppp(5')G (New England BioLabs, Ipswich, MA). 5'-capping of alternative mRNA may be completed post-transcriptionally using a Vaccinia Virus Capping Enzyme to generate the "Cap 0" structure: m$^7$G(5')ppp(5')G (New England BioLabs, Ipswich, MA). Cap 1 structure may be generated using both Vaccinia Virus Capping Enzyme and a 2'-O methyl-transferase to generate: m$^7$G(5)ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes are preferably derived from a recombinant source.

When transfected into mammalian cells, the alternative mRNAs have a stability of 12-18 hours or more than 18 hours, e.g., 24, 36, 48, 60, 72, or greater than 72 hours.

Example 5. Poly-A Region Addition Reaction

Without a poly-T in the cDNA, a poly-A region addition reaction must be performed before cleaning the final product. This is done by mixing Capped IVT RNA (100 µl); RNase Inhibitor (20 U); 10× Tailing Buffer (0.5 M Tris-HCl (pH 8.0), 2.5 M NaCl, 100 mM MgCl$_2$)(12.0 µl); 20 mM ATP (6.0 µl); Poly-A Polymerase (20 U); dH$_2$O up to 123.5 µl and incubation at 37° C. for 30 minutes If the poly-A tail is already in the transcript, then the tailing reaction may be skipped and proceed directly to cleanup with Ambion's MEGACLEAR™ kit (Austin, TX) (up to 500 µg). Poly-A Polymerase is preferably a recombinant enzyme expressed in yeast.

For studies performed and described herein, the poly-A region is encoded in the IVT template to include 160 nucleotides in length. However, it should be understood that the processivity or integrity of the poly-A tailing reaction may not always result in exactly 160 nucleotides. Hence poly-A regions of approximately 160 nucleotides, acid about 150-165, 155, 156, 157, 158, 159, 160, 161, 162, 163, 164 or 165 are within the scope of the invention.

Example 6. Method of Screening for Protein Expression

A. Electrospray Ionization

A biological sample which may contain proteins encoded by alternative RNA administered to the subject is prepared and analyzed according to the manufacturer protocol for electrospray ionization (ESI) using 1, 2, 3 or 4 mass analyzers. A biologic sample may also be analyzed using a tandem ESI mass spectrometry system.

Patterns of protein fragments, or whole proteins, are compared to known controls for a given protein and identity is determined by comparison.

B. Matrix-Assisted Laser Desorption/Ionization

A biological sample which may contain proteins encoded by alternative RNA administered to the subject is prepared and analyzed according to the manufacturer protocol for matrix-assisted laser desorption/ionization (MALDI).

Patterns of protein fragments, or whole proteins, are compared to known controls for a given protein and identity is determined by comparison.

C. Liquid Chromatography-Mass Spectrometry-Mass Spectrometry

A biological sample, which may contain proteins encoded by alternative RNA, may be treated with a trypsin enzyme to digest the proteins contained within. The resulting peptides are analyzed by liquid chromatography-mass spectrometry-mass spectrometry (LC/MS/MS). The peptides are fragmented in the mass spectrometer to yield diagnostic patterns that can be matched to protein sequence databases via computer algorithms. The digested sample may be diluted to achieve 1 ng or less starting material for a given protein. Biological samples containing a simple buffer background (e.g., water or volatile salts) are amenable to direct in-solution digest; more complex backgrounds (e.g., detergent, non-volatile salts, glycerol) require an additional clean-up step to facilitate the sample analysis.

Patterns of protein fragments, or whole proteins, are compared to known controls for a given protein and identity is determined by comparison.

Example 7. Transfection

A. Reverse Transfection

For experiments performed in a 24-well collagen-coated tissue culture plate, Keratinocytes or other cells are seeded at a cell density of 1×10$^5$. For experiments performed in a 96-well collagen-coated tissue culture plate, Keratinocytes are seeded at a cell density of 0.5×10$^5$. For each alternative mRNA to be transfected, alternative mRNA: RNAIMAX™ are prepared as described and mixed with the cells in the multi-well plate within 6 hours of cell seeding before cells had adhered to the tissue culture plate.

B. Forward Transfection

In a 24-well collagen-coated tissue culture plate, Cells are seeded at a cell density of 0.7×10$^5$. For experiments performed in a 96-well collagen-coated tissue culture plate, Keratinocytes, if used, are seeded at a cell density of 0.3×10$^5$. Cells are then grown to a confluency of >70% for over 24 hours. For each alternative mRNA to be transfected, alternative mRNA: RNAIMAX™ are prepared as described and transfected onto the cells in the multi-well plate over 24 hours after cell seeding and adherence to the tissue culture plate.

C. Translation Screen: ELISA

Cells are grown in EpiLife medium with Supplement S7 from Invitrogen at a confluence of >70%. Cells are reverse transfected with 300 ng of the indicated chemically alternative mRNA complexed with RNAIMAX™ from Invitrogen. Alternatively, cells are forward transfected with 300 ng alternative mRNA complexed with RNAIMAX™ from Invitrogen. The RNA: RNAIMAX™ complex is formed by first incubating the RNA with Supplement-free EPILIFE® media in a 5× volumetric dilution for 10 minutes at room temperature.

In a second vial, RNAIMAX™ reagent is incubated with Supplement-free EPILIFE® Media in a 10× volumetric dilution for 10 minutes at room temperature. The RNA vial is then mixed with the RNAIMAX™ vial and incubated for 20-30 minutes at room temperature before being added to the cells in a drop-wise fashion. Secreted polypeptide concentration in the culture medium is measured at 18 hours post-transfection for each of the chemically alternative mRNAs in triplicate. Secretion of the polypeptide of interest from transfected human cells is quantified using an ELISA kit from Invitrogen or R&D Systems (Minneapolis, MN) following the manufacturers recommended instructions.

D. Dose and Duration: ELISA

Cells are grown in EPILIFE® medium with Supplement S7 from Invitrogen at a confluence of >70%. Cells are reverse transfected with 0 ng, 46.875ng, 93.75ng, 187.5ng, 375ng, 750ng, or 1500ng alternative mRNA complexed with RNAIMAX™ from Invitrogen. The alternative mRNA: RNAIMAX™ complex is formed as described. Secreted polypeptide concentration in the culture medium is measured at 0, 6, 12, 24, and 48 hours post-transfection for each concentration of each alternative mRNA in triplicate. Secretion of the polypeptide of interest from transfected human cells is quantified using an ELISA kit from Invitrogen or R&D Systems following the manufacturers recommended instructions.

Example 8. Cellular Innate Immune Response: IFN-Beta ELISA and TNF-Alpha ELISA

An enzyme-linked immunosorbent assay (ELISA) for Human Tumor Necrosis Factor-α (TNF-α), Human Interferon-β (IFN-β) and Human Granulocyte-Colony Stimulating Factor (G-CSF) secreted from in vitro-transfected Human Keratinocyte cells is tested for the detection of a cellular innate immune response.

Cells are grown in EPILIFE® medium with Human Growth Supplement in the absence of hydrocortisone from Invitrogen at a confluence of >70%. Cells are reverse transfected with 0 ng, 93.75ng, 187.5ng, 375ng, 750ng, 1500ng or 3000ng of the indicated chemically alternative mRNA complexed with RNAIMAX™ from Invitrogen as described in triplicate. Secreted TNF-α in the culture medium is measured 24 hours post-transfection for each of the chemically alternative mRNAs using an ELISA kit from Invitrogen according to the manufacturer protocols.

Secreted IFN-β is measured 24 hours post-transfection for each of the alternative mRNAs using an ELISA kit from Invitrogen according to the manufacturer protocols. Secreted hu-G-CSF concentration is measured at 24 hours post-transfection for each of the alternative mRNAs. Secretion of the polypeptide of interest from transfected human cells is quantified using an ELISA kit from Invitrogen or R&D Systems (Minneapolis, MN) following the manufacturers recommended instructions. These data indicate which alternative mRNA are capable eliciting a reduced cellular innate immune response in comparison to natural and other alternative polynucleotides or reference compounds by measuring exemplary type 1 cytokines such as TNF-alpha and IFN-beta.

Example 9. Cytotoxicity and Apoptosis

This experiment demonstrates cellular viability, cytotoxicity and apoptosis for distinct alternative mRNA-in vitro transfected Human Keratinocyte cells. Keratinocytes are grown in EPILIFE® medium with Human Keratinocyte Growth Supplement in the absence of hydrocortisone from Invitrogen at a confluence of >70%. Keratinocytes are reverse transfected with 0 ng, 46.875ng, 93.75ng, 187.5ng, 375ng, 750ng, 1500ng, 3000ng, or 6000ng of alternative mRNA complexed with RNAIMAX™ from Invitrogen. The alternative mRNA: RNAIMAX™ complex is formed. Secreted huG-CSF concentration in the culture medium is measured at 0, 6, 12, 24, and 48 hours post-transfection for each concentration of each alternative mRNA in triplicate. Secretion of the polypeptide of interest from transfected human keratinocytes is quantified using an ELISA kit from Invitrogen or R&D Systems following the manufacturers recommended instructions. Cellular viability, cytotoxicity and apoptosis is measured at 0, 12, 48, 96, and 192 hours post-transfection using the APOTOX-GLO™ kit from Promega (Madison, WI) according to manufacturer instructions.

Example 10. In Vivo Assays with Human EPO Containing Alternative Nucleotides

Formulation

Alternative hEPO mRNAs were formulated in lipid nanoparticles (LNPs) comprising DLin-KC2-DMA, DSPC, Cholesterol, and PEG-DMG at 50:10:38.5:1.5 mol % respectively (Table 4). The LNPs were made by direct injection utilizing nanoprecipitation of ethanol solubilized lipids into a pH 4.0 50 mM citrate mRNA solution. The EPO LNP particle size distributions were characterized by DLS. Encapsulation efficiency (EE) was determined using a Ribogreen™ fluorescence-based assay for detection and quantification of nucleic acids.

TABLE 4

| Formulation Conditions | | | |
|---|---|---|---|
| Ionizable Lipid | Phospholipid | Cholesterol | PEG Lipid |
| 2-(2,2-di((9Z,12Z)-octadeca-9,12-dien-1yl)-1,3-diocolan-4-yl)-N,N-dimethyletanamine (Lipid/Mol %) | 1,2-distearoyl-sn-glycero-3-phosphocholine (Lipid/Mol %) | cholest-5-en-3ß-ol (Lipid/Mol %) | 1,2-Dimyristoyl-sn-glycerol, methoxypolyethylene Glycol (Lipid/Mol %) |
| DLin-KC2-DMA | DSPC | Cholesterol | PEG-DMG |
| 50 | 10 | 38.5 | 1.5 |

Methods and Data

Female Balb/c mice (n=5) were administered 0.05 mg/kg IM (50 µl in the quadriceps) or IV (100 ul in the tail vein) of human EPO mRNA. At time 8 hours after the injection mice were euthanized and blood was collected in serum separator tubes. The samples were spun and serum samples were then run on an EPO ELISA following the kit protocol (Stem Cell Technologies Catalog #01630).

Example 11. Synthesis of Alternative mRNA with 3'-Stabilized Tail Attached Via Morpholino Linker An mRNA with an A100 tail was dissolved in 50 mM HEPES-Na, pH 8, containing 33% DMSO, and incubated with 1000-fold molar excess of NaIO$_4$ in the presence of 1000-fold molar excess of an aldehyde-reactive molecule. In this case the reactive group was an aminooxy, but hydrazides, thiosemicarbazides, and amines followed by reduction with sodium cyanoborohydride can also be used to covalently link a group to the 3' end of an mRNA.

The reaction is performed in the dark for 30 minutes on ice. After the reaction is done, glycerol is added as a quench in 100-fold molar excess to NaIO$_4$ and mixed well. Purification of the modified mRNA away from the reaction by products can be achieved by any of a number of methods including size exclusion, anion exchange, reverse phase, hydrophobic interaction, and ligand capture.

For attachment of the BCN-LA10 tail, aminooxy-TEG-azide was first attached to the mRNA as shown in Scheme 6, and unreacted mRNA was purified away from reacted mRNA by reverse phase HPLC to high purity.

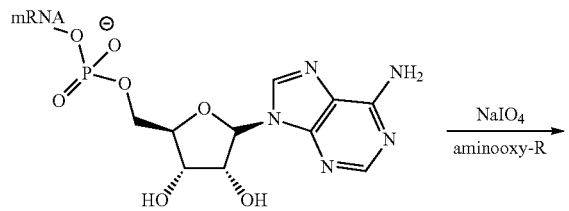

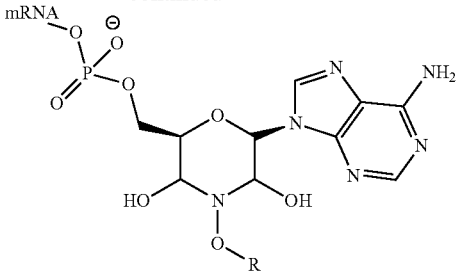

Scheme 6. Formation of Morpholino Linker

After periodate treatment, a capping reaction was performed on the mRNA using vaccinia, 2'-O-methyl tranferase, GTP, and SAM to cap the mRNA with Cap1.

Next, 10-fold molar excess of BCN-LA10 was added to the mRNA and the reaction was taken to dryness in vacuo under mild heating. Excess BCN-LA10 was removed from the modified mRNA by size exclusion chromatography providing an mRNA containing a 10 L-ribose adenosines (SEQ ID NO: 29) attached to its 3' end (3'-ATA-BCNLA10) as shown in Scheme 7 below.

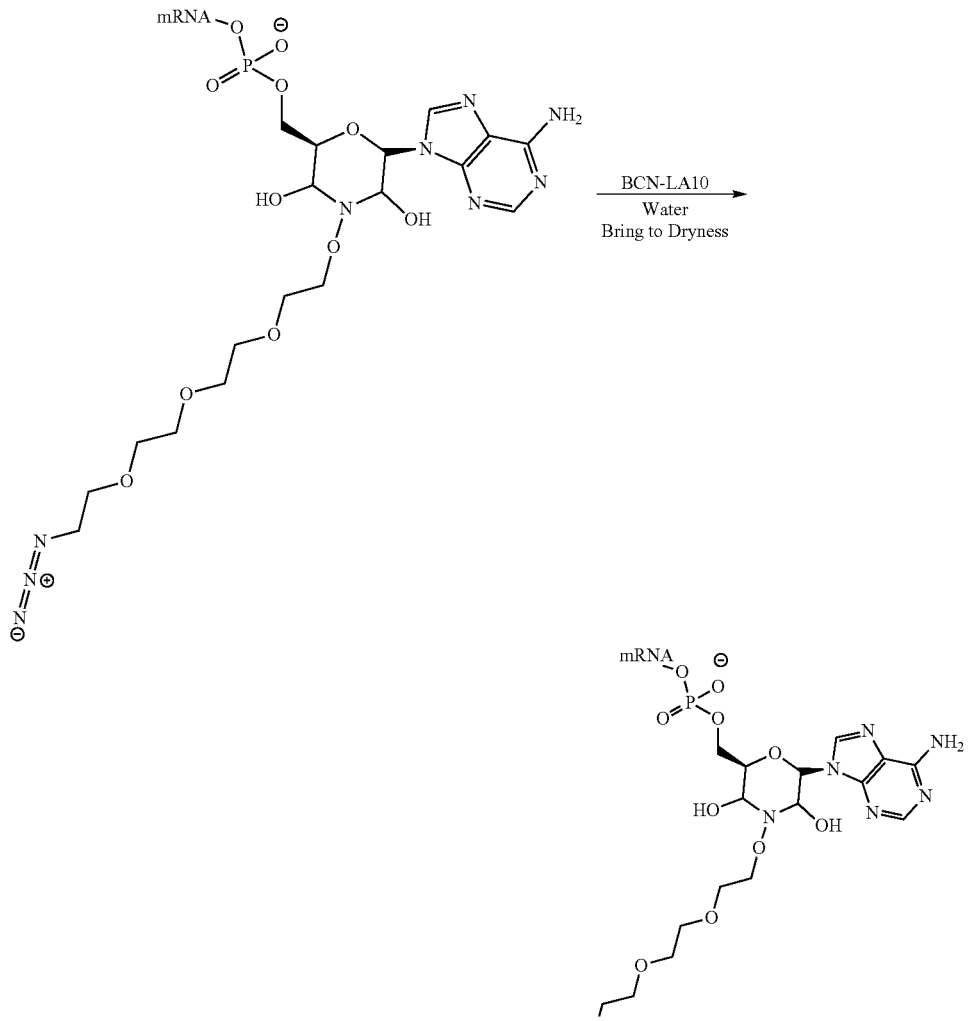

-continued

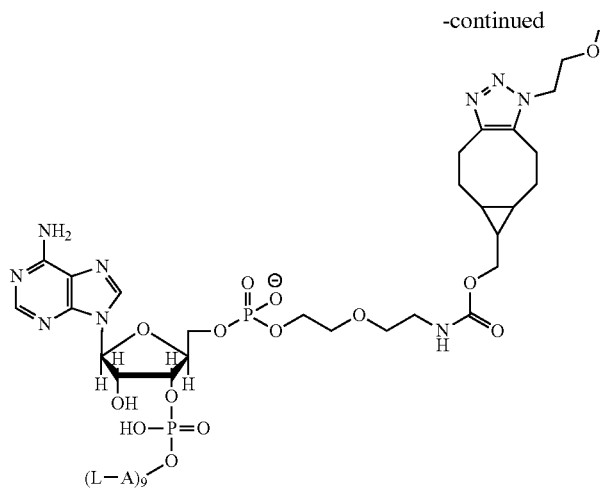

Scheme 7. Synthesis of 3'-Stabilized Tail Containing mRNA

The starting mRNA sequence for hEPO expression experiments was (SEQ ID NO: 28):

N7mGpppmGGGAAAUAAGAGAGAAAAGAAGAGUAAGAAGAAAUAUAAGA

GCCACCAUGGGAGUGCACGAGUGUCCCGCGUGGUUGUGGUUGCUGCUGU

CGCUCUUGAGCCUCCCACUGGGACUGCCUGUGCUGGGGGCACCACCCAG

AUUGAUCUGCGACUCACGGGUACUUGAGAGGUACCUUCUUGAAGCCAAA

GAAGCCGAAAACAUCACAACCGGAUGCGCCGAGCACUGCUCCCUCAAUG

AGAACAUUACUGUACCGGAUACAAAGGUCAAUUUCUAUGCAUGGAAGAG

AAUGGAAGUAGGACAGCAGGCCGUCGAAGUGUGGCAGGGGCUCGCGCUU

UUGUCGGAGGCGGUGUUGCGGGGUCAGGCCCUCCUCGUCAACUCAUCAC

AGCCGUGGGAGCCCCUCCAACUUCAUGUCGAUAAAGCGGUGUCGGGGCU

CCGCAGCUUGACGACGUUGCUUCGGGCUCUGGGCGCACAAAAGGAGGCU

AUUUCGCCGCCUGACGCGGCCUCCGCGGCACCCCUCCGAACGAUCACCG

CGGACACGUUUAGGAAGCUUUUUAGAGUGUACAGCAAUUUCCUCCGCGG

AAAGCUGAAAUUGUAUACUGGUGAAGCGUGUAGGACAGGGGAUCGCUGA

UAAUAGGCUGGAGCCUCGGUGGCCAUGCUUCUUGCCCCUUGGGCCUCCC

CCCAGCCCCUCCUCCCCUUCCUGCACCCGUACCCCCGUGGUCUUUGAAU

AAAGUCUGAGUGGGCGGCAAAAAAAAAAAAAAAAAAAAAAAAAAAAAAA

AAAAAAAAAAAAAAAAAAAAAAAAAAAAAAAAAAAAAAAAAAAAAAAA

AAAAAAAAAAAAAAAAAAAA, wherein each U is 5-methoxy-uridine.

Example 12. In Vitro Expression of hEPO in BJ Fibroblasts with Alternative mRNA with 3'-Stabilized Tail Attached Via Morpholino Linker Using the method described in Example 6, expression of the alternative mRNA of Example 24 was compared with a control mRNA lacking a 3'-stabilized tail. As shown in Table 5 below, at 48 hours, the mRNA containing the 3'-stabilized tail has greater expression than the control mRNA.

TABLE 5

In vitro expression of hEPO in BJ Fibroblasts at 48 hours

| mRNA | ng/mL hEPO expressed | Standard Deviation |
|---|---|---|
| Control | 5936 | 163 |
| 3'-ATA-BCNLA10 | 11360 | 875 |

Example 13. In Vitro INFβ Induction in BJ Fibroblasts

Indicated mRNA was transfected in triplicate using Lipofectamine2000™ into BJ fibroblasts. After incubation for 48 hrs, the supernatant was collected and used to measure the levels of human Interferon-β (R&D Systems). Table 6 gives the amount of detected IFNβ for conjugates and appropriate controls.

TABLE 6

INFβ induction in BJ Fibroblasts from mRNA with 3'-stabilized tails

| mRNA | INFβ induction (pg/mL) | Standard Deviation |
|---|---|---|
| Control | 203 | 84 |
| 3'-ATA-BCNLA10 | not detected | n/a |

Example 14. Synthesis of Alternative mRNA with 3'-Stabilized Tail Attached Via Morpholino Linker An mRNA with an A100 tail was dissolved in 50 mM HEPES-Na, pH 8, containing 33% DMSO, and incubated with 1000-fold molar excess of $NaIO_4$ in the presence of 500-fold molar excess of an aldehyde-reactive molecule containing a disulfide bond. In this case the reactive group was an aminooxy, but hydrazides, thiosemicarbazides, and amines followed by reduction with sodium cyanoborohydride can also be used to covalently link a group to the 3' end of an mRNA.

The reaction is performed in the dark for one hour on ice. After the reaction is done, glycerol is added as a quench in 100-fold molar excess to $NaIO_4$ and mixed well. Purification of the modified mRNA away from the reaction by products can be achieved by any of a number of methods including size exclusion, anion exchange, reverse phase, hydrophobic interaction, ligand capture, etc.

For attachment of the LA10 tail, aminooxy-PEG-S—S-PEG-biotin (APSSPB) was attached to the mRNA, and oligo affinity capture purification was performed to remove excess APSSPB from mRNA. The reactive oligo was prepared by reacting 5' amino-terminated LA10 with N-γ-maleimidobutyryl-oxysulfosuccinimide ester (sulfo-GMBS) in PBS on the bench for 30 minutes before ultrafiltration was used to remove excess sulfo-GMBS. The APSSPB-terminated mRNA was activated by cleaving the disulfide bond by reacting with 5000-fold molar excess of tris(2-carboxyethyl) phosphine (TCEP) in 50 mM HEPES-Na, pH 6.5 on the bench for 1 hour. Free thio-containing PEG biotin was removed from the mRNA through ultrafiltration.

mRNA containing the free 3' thiol was mixed with 12-fold molar excess of the LA10 oligo containing a 5' maleimide and taken to dryness in vacuo under mild heating. Excess maleimide-LA10 was removed from the modified mRNA by oligo affinity capture purification.

The structure of Mal-thio-LA10 is:

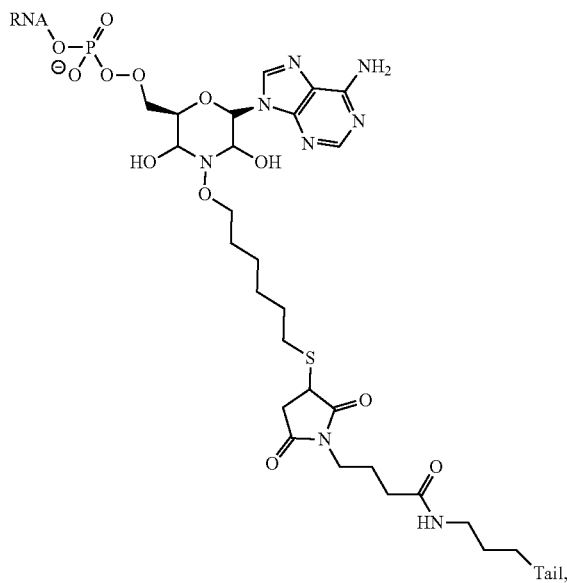

wherein "Tail" is 10 consecutive L-adenosines (SEQ ID NO: 29).

Example 15. In Vivo Expression of hEPO by mRNA with and without 3'-Stabilized Tails Using the method described in Example 6, expression of selected alternative mRNA was compared with a control mRNA lacking a 3'-stabilized tail. Five female CD-1 mice were administered the mRNAs intravenously at 0.05 mg/kg. As shown in Table 7 below the mRNA containing the 3'-stabilized tails had greater expression than the control mRNA.

TABLE 7

In vivo expression of hEPO

| mRNA | Sample | hEPO expression at 6 hrs (pg/mL) | hEPO expression at 24 hrs (pg/mL) | hEPO expression at 48 hrs (pg/mL) |
|---|---|---|---|---|
| T7 T100 hEPO | 1 | 300032 | 218596 | 8702 |
| | 2 | 209480 | 69300 | 1352 |
| | 3 | 186276 | 47656 | 1006 |
| | Average | 231929 | 111851 | 3687 |
| Process Control | 1 | 77772 | 14788 | 1482 |
| | 2 | 90436 | 17016 | 898 |
| | 3 | 58004 | 8096 | 624 |
| | Average | 75404 | 13300 | 1001 |
| 3'-ATA-BCNLA-10 | 1 | 136684 | 97240 | 50872 |
| | 2 | 108544 | 55084 | 26614 |
| | 3 | 130532 | 79608 | 31468 |
| | Average | 125253 | 77311 | 36318 |
| Thio-PEG-Biotin int. | 1 | 67144 | 25648 | 3171 |
| | 2 | 59588 | 23016 | 2076 |
| | 3 | 93540 | 47416 | 8187 |
| | Average | 73424 | 32027 | 4478 |
| Mal-thio LA10 | 1 | 120672 | 86396 | 36488 |
| | 2 | 77864 | 46984 | 16728 |
| | 3 | 57324 | 31972 | 12279 |
| | Average | 85287 | 55117 | 21832 |

T7 T100 hEPO has the sequence of SEQ ID NO:4.

Thio-PEG-Biotin int. was prepared using the procedure used to prepare 3'-ATA-BCNLA-10 described in Example 11, wherein alkoxyamine-PEG4-SS-PEG$_4$-Biotin was used in place of aminooxy-TEG-azide.

Example 16. Synthesis of Alternative mRNA with Small Molecule Conjugated at the 5'- and 3'-Terminus Via Morpholino Linker An mRNA containing a 5' inverted N$^7$m-guanosine cap was dissolved in 50 mM HEPES-Na, pH 8, containing 33% DMSO, and incubated with 1000-fold molar excess of an aminooxy-containing molecule (e.g., O-(2,3,4,5,6-petafluorobenzyl) hydroxylamine) and 1000-fold molar excess of sodium metaperiodate. After 1 hour at 4° C. in the dark, the reaction was quenched by the addition of 10-fold molar excess of glycerol to sodium metaperiodate. The reaction is then purified by a method such as ultrafiltration, oligo affinity chromatography, size exclusion chromatography, ion-exchange chromatography, hydrophobic interaction chromatography, and/or reverse phase chromatography.

Example 17. Synthesis of Alternative mRNA with a Polypeptide Attached at the 3'-Terminus Via Morpholino Linker An mRNA was dissolved in 50 mM sodium citrate buffer, pH 6, with 10 mM EDTA to a final concentration of 0.5 mg/mL. A stock of peptide containing an aminooxy reactive group was dissolved and added to the mRNA in a 100-fold molar excess. To initiate the conjugation, sodium metaperiodate was added to a final concentration of 1000-fold molar excess of the mRNA. After incubation at 25° C. for 1 hour, the reaction was quenched through the addition of 10-fold molar excess of glycerol to sodium metaperiodate. The reaction is then purified by a method such as oligo affinity, size exclusion, and/or reverse phase chromatography.

Example 18. Synthesis of Alternative mRNA with a 5'-Cap Attached Via Morpholino Linker An in vitro transcription was performed with 10-fold excess of 5'-aminooxy-ethyl-guanosine-5'-monophosphate to GTP. The resulting green fluorescent protein transcript contained a mixture where </=92% of the final RNA contains a 5'-aminooxy. After oligo dT affinity purification, the aminooxy-containing transcript was incubated with 1000-fold molar excess of sodium periodate to RNA in the presence of 1000-fold molar excess of a cap dinucleotide (3'-O-methyl-methyl-7-guanosine-(5')ppp(5')-guanosine (i.e., ARCA)) to RNA, 50 mM HEPES-KOH, pH 8.0, 10 mM EDTA, and 5% methanol at 37 deg C. The reaction was quenched after 30 min by addition of 100-molar excess of glycerol to periodate and the mixture was purified by oligo dT affinity purification, buffer-exchanged by ultrafiltration, and transfected into BJ fibroblasts using lipoplex and the manufacturer protocol. Protein expression was detected by fluorescence microscopy (Incucyte). The resulting mRNA had the structure shown below:

tions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

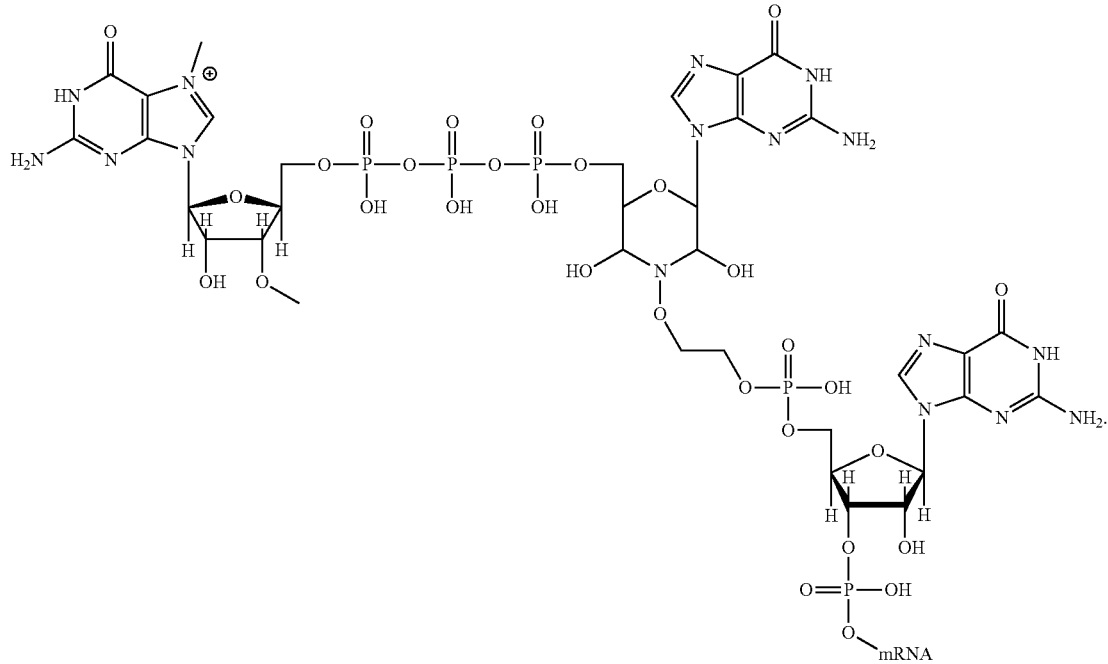

Other Embodiments

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any polynucleotide or protein encoded thereby; any method of production; any method of use) can be excluded from any one or more claims, for any reason, whether or not related to the existence of prior art.

What is claimed is:

1. A compound, or a salt thereof, including:

a) a polynucleotide; and b) at least one of a nucleotide, a second polynucleotide, targeting moiety, small molecule, polypeptide, or polymer, wherein the polynucleotide of a) is conjugated to the nucleotide, second polynucleotide, targeting moiety, small molecule, polypeptide, or polymer via a linker including the structure of Formula I:

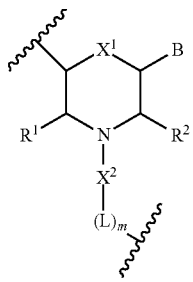

Formula I wherein B is a nucleobase, hydrogen, halo, hydroxy, thiol, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, optionally substituted $C_3$-$C_{10}$ cycloalkyl, optionally substituted $C_6$-$C_{10}$ aryl, or optionally substituted $C_2$-$C_{12}$ heterocycle;

$X^1$ is O, S, $NR^U$, or $C(R^U)_2$, wherein each $R^U$ is, independently, H, halo, or optionally substituted $C_1$-$C_6$ alkyl;

$X^2$ is —O—, —$NR^{N1}$—, —$NR^{N1}NR^{N1}$—, a bond, optionally substituted $C_1$-$C_{10}$ alkylene, optionally substituted $C_2$-$C_{10}$ alkenylene, optionally substituted $C_2$-$C_{10}$ alkynylene, optionally substituted $C_2$-$C_{10}$ heterocyclylene, optionally substituted $C_6$-$C_{12}$ arylene, optionally substituted $C_2$-$C_{100}$ polyethylene glycolene, or optionally substituted $C_1$-$C_{30}$ heteroalkylene, wherein $R^{N1}$ is H, optionally substituted $C_1$-$C_6$ alkyl, optionally substituted $C_2$-$C_6$ alkenyl, optionally substituted $C_2$-$C_6$ alkynyl, or optionally substituted $C_6$-$C_{10}$ aryl;

m is 1, 2, 3, 4, or 5;

each L is, independently, an unbranched or branched linker;

$R^1$ and $R^2$ are each, independently, hydrogen, hydroxyl, or $C_1$-$C_6$ alkoxy, and wherein if B is nucleobase, $R^1$ and $R^2$ are hydrogen and the linker conjugates the polynucleotide of a) to the second polynucleotide then $X^2$-$(L)_m$ is not a furanylmethyl moiety, a pyranylmethyl moiety, —P(O)OH—, or —P(O)N($R^N$)$_2$—, wherein $R^N$ is optionally substituted $C_1$-$C_6$ alkyl.

2. The compound of claim 1, wherein said compound comprises the structure of Formula II:

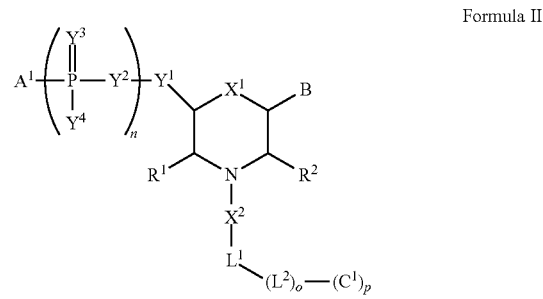

Formula II wherein $A^1$ is said first polynucleotide and comprises:

(a) at least one 5'-cap structure;

each $C^1$ independently comprises said second polynucleotide, a targeting moiety, a small molecule, a polypeptide, or a polymer;

$L^1$ is an unbranched linker;

$L^2$ is a branched linker;

n is 0, 1, 2, or 3;

o is 0 or 1;

p is 1, 2, 3, 4, or 5;

$X^2$—O—, —$NR^{N1}$—, —$NR^{N1}NR^{N1}$—, a bond, optionally substituted $C_1$-$C_{10}$ alkylene, optionally substituted $C_2$-$C_{10}$ alkenylene, optionally substituted $C_2$-$C_{10}$ alkynylene, optionally substituted $C_2$-$C_{10}$ heterocyclylene, optionally substituted $C_6$-$C_{12}$ arylene, optionally substituted $C_2$-$C_{100}$ polyethylene glycolene, or optionally substituted $C_1$-$C_{30}$ heteroalkylene, wherein $R^{N1}$ is H, optionally substituted $C_1$-$C_6$ alkyl, optionally substituted $C_2$-$C_6$ alkenyl, optionally substituted $C_2$-$C_6$ alkynyl, or optionally substituted $C_6$-$C_{10}$ aryl;

$Y^1$ is O, S, Se, optionally substituted $C_1$-$C_6$ alkylene, or optionally substituted $C_1$-$C_6$ heteroalkylene;

each $Y^2$ and $Y^3$ is, independently, O, S, Se, —$NR^{N1}$—, optionally substituted $C_1$-$C_6$ alkylene, or optionally substituted $C_1$-$C_6$ heteroalkylene, wherein $R^{N1}$ is H, optionally substituted $C_1$-$C_6$ alkyl, optionally substituted $C_2$-$C_6$ alkenyl, optionally substituted $C_2$-$C_6$ alkynyl, or optionally substituted $C_6$-$C_{10}$ aryl; and each $Y^4$ is, independently, H, hydroxy, protected hydroxy, halo, thiol, boranyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, or optionally substituted amino, wherein when $Y^2$, $Y^3$, and $X^1$ are each O, $R^1$ and $R^2$ are each hydrogen, $Y^1$ is $CH_2$, $Y^4$ is hydroxy, n is 1, o is 0, p is 1, and $C^1$ is a polynucleotide, $X^2$-$L^1$ is not —P(O)OH— or —P(O)N($R^N$)$_2$—, wherein $R^N$ is optionally substituted $C_1$-$C_6$ alkyl.

3. The compound of claim 2, wherein $A^1$ further comprises:

(b) a 5'-UTR;

(c) a coding region; and (d) a 3'-UTR.

4. The compound of claim 2, wherein said compound comprises the structure of Formula III:

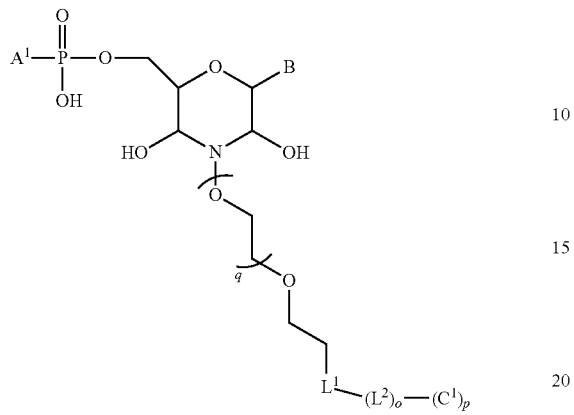

Formula III wherein q is 0, 1, 2, 3, 4, or 5.

5. The compound of claim 2, wherein said compound comprises the structure of Formula IV:

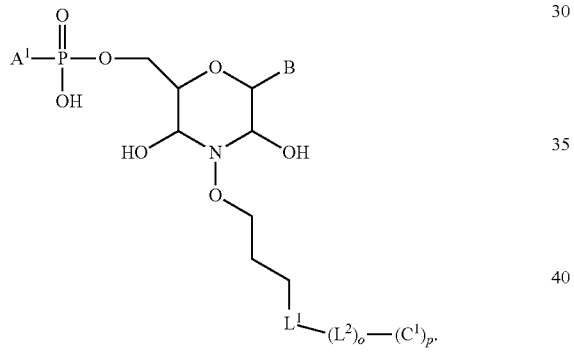

Formula IV or wherein said compound comprises the structure of Formula V:

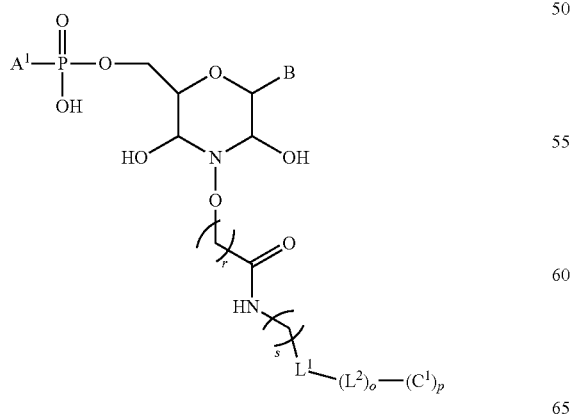

Formula V wherein r and s are each, independently, 1, 2, 3, 4, or 5.

6. The compound of claim 2, wherein the compound includes the structure of Formula XXII:

Formula XXII

7. The compound of claim 2, wherein $L^1$ comprises the structure of Formula VI:

Formula VI wherein a, b, c, e, f, and g are each, independently, 0 or 1;

d is 0, 1, 2, or 3;

each of $R^3$, $R^5$, $R^7$, and $R^9$, is, independently, selected from optionally substituted $C_1$-$C_6$ alkylene, optionally substituted $C_1$-$C_6$ heteroalkylene, optionally substituted $C_2$-$C_{100}$ polyethylene glycolene, O, S, Se, and $NR^{10}$;

$R^4$ and $R^8$ are each, independently, carbonyl, thiocarbonyl, sulfonyl, or phosphoryl;

each $R^6$ is optionally substituted $C_1$-$C_{10}$ alkylene, optionally substituted $C_2$-$C_{10}$ alkenylene, optionally substituted $C_2$-$C_{10}$ alkynylene, optionally substituted $C_2$-$C_{10}$ heterocyclylene, optionally substituted $C_6$-$C_{12}$ arylene, optionally substituted $C_2$-$C_{100}$ polyethylene glycolene, or optionally substituted $C_1$-$C_{10}$ heteroalkylene, or a bond linking $(R^3)_a$—$(R^4)_b$—$(R^5)_c$ to $(R^7)_e$—$(R^8)_f$—$(R^9)g$; and $R^{10}$ is hydrogen, optionally substituted $C_1$-$C_4$ alkyl, optionally substituted $C_2$-$C_4$ alkenyl, optionally substituted $C_2$-$C_4$ alkynyl, optionally substituted $C_2$-$C_6$ heterocyclyl, optionally substituted $C_6$-$C_{12}$ aryl, or optionally substituted $C_1$-$C_7$ heteroalkyl.

8. The compound of claim 2, wherein said compound comprises the structure of Formula VII:
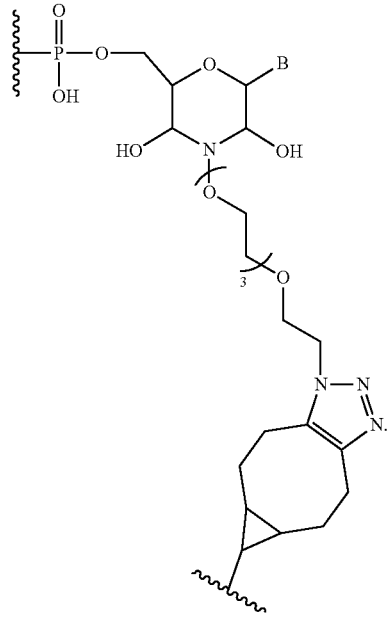
Formula VII
9. The compound of claim 2, wherein said compound has the structure of Formula VIII:
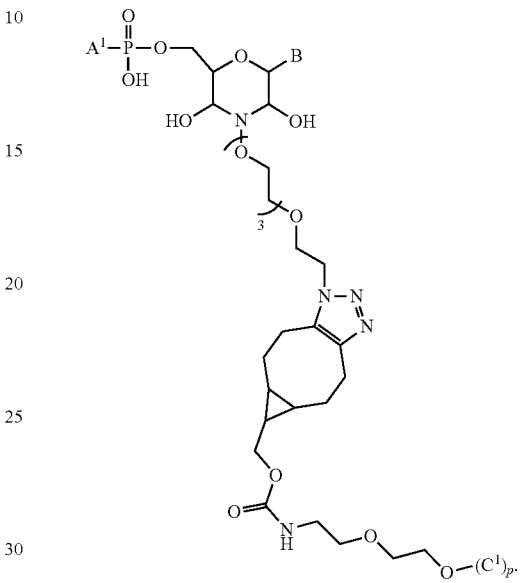
Formula VIII
10. The compound of claim 2, wherein said compound comprises the structure of Formula IX:
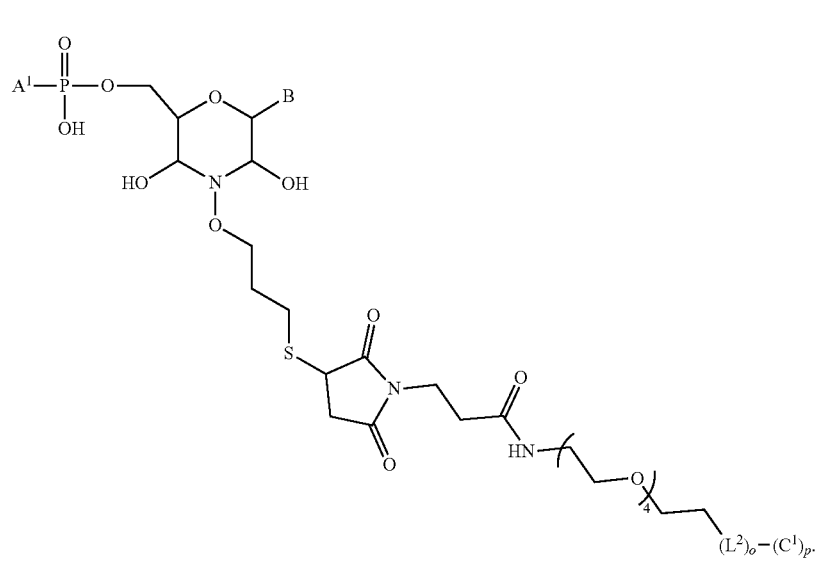
Formula IX

11. The compound of claim 2, wherein said compound comprises the structure of Formula X:
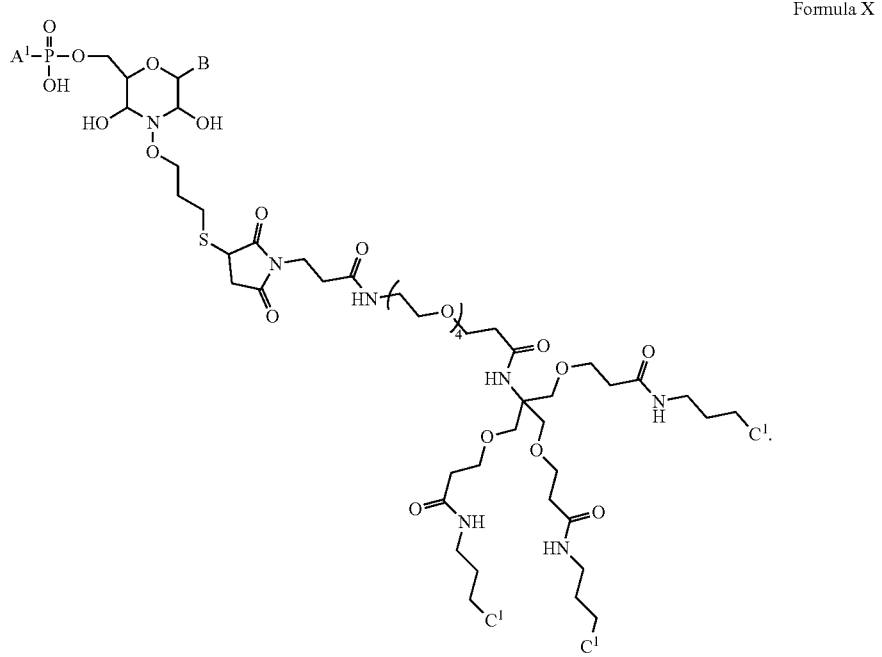
Formula X
12. The compound of claim 2, wherein the compound comprises the structure of Formula XI:
13. The compound of claim 2, wherein the compound comprises the structure of Formula XII:
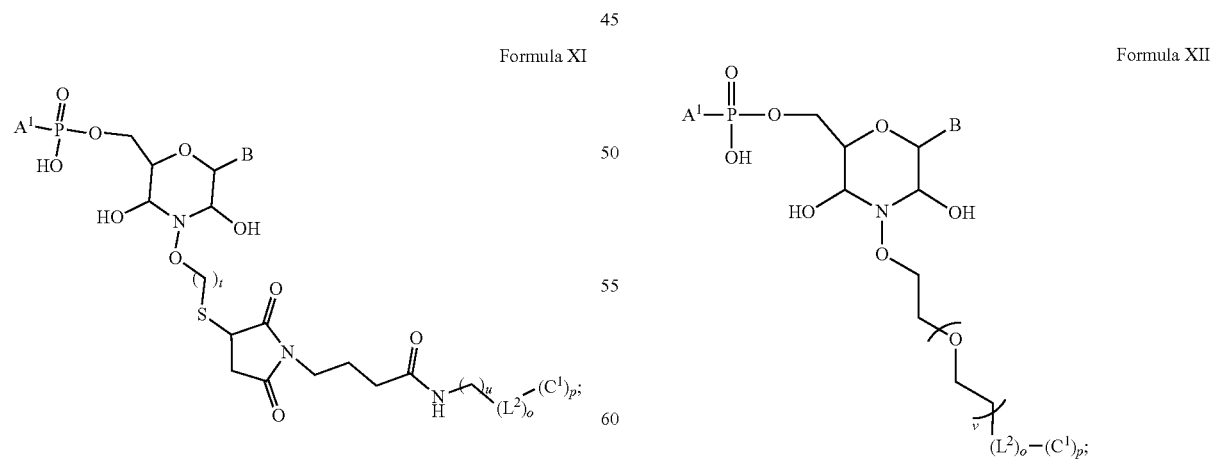
or a salt thereof
wherein t is 1, 2, 3, 4, 5, 6, 7, 8, 9, or 10; and
u is 1, 2, 3, 4, 5, 6, 7, 8, 9, or 10.
or a salt thereof,
wherein v is 0, 1, 2, 3, 4, 5, 6, 7, 8, 9, or 10.

14. The compound of claim 2, wherein the compound comprises the structure of Formula XXIII:

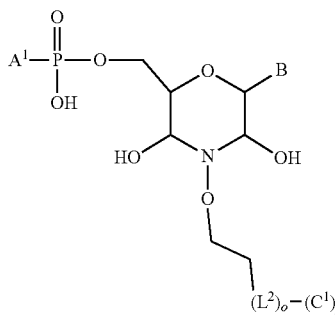

Formula XXIII

15. The compound of claim 2, wherein said second polynucleotide comprises the structure:

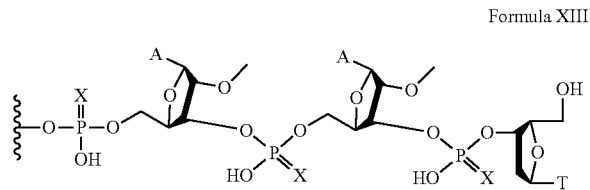

Formula XIII or a salt thereof;
wherein each X is, independently O or S; and
A represents adenine and T represents thymine.

16. A method of modifying a polynucleotide, said method comprising:
contacting a polynucleotide comprising the structure of Formula XIV:

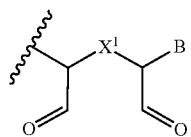

Formula XIV wherein B is a nucleobase; and
$X^1$ is O, S, $NR^U$, or $C(R^U)_2$, wherein each $R^U$ is, independently, H, halo, or optionally substituted $C_1$-$C_6$ alkyl;
with a compound having the structure of Formula XV:

$H_2N—R^{11}$     Formula XV wherein $R^{11}$ is optionally substituted $C_1$-$C_{10}$ alkyl, optionally substituted $C_2$-$C_{10}$ alkenyl, optionally substituted $C_2$-$C_{10}$ alkynyl, optionally substituted $C_2$-$C_{10}$ heterocyclyl, optionally substituted $C_6$-$C_{12}$ aryl, optionally substituted $C_2$-$C_{100}$ polyethylene glycol, optionally substituted $C_1$-$C_{10}$ alkyl conjugated to a polynucleotide, or optionally substituted $C_1$-$C_{10}$ heteroalkyl;
under suitable conditions to produce a polynucleotide comprising the structure of Formula I:

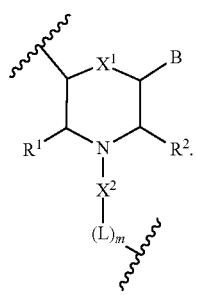

Formula I

17. A method of increasing the expression of a recombinant polypeptide of interest in a cell comprising contacting the cell with a polynucleotide encoding said polypeptide, wherein said polynucleotide is a compound of claim 1, and wherein expression is increased when compared to the unmodified polynucleotide.

18. A method of increasing the half-life of a polynucleotide in a cell comprising contacting the cell with said polynucleotide, wherein the polynucleotide is a compound of claim 1, and wherein half-life is increased when compared to the unmodified polynucleotide.

19. The compound of claim 2, wherein $A^1$ comprises the structure of Formula XXI:

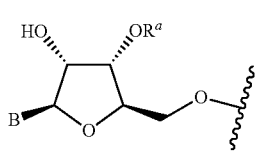

Formula XXI wherein B is a nucleobase; and
$R^a$ is hydrogen or methyl.

20. The compound of claim 1, wherein the compound has the structure of:
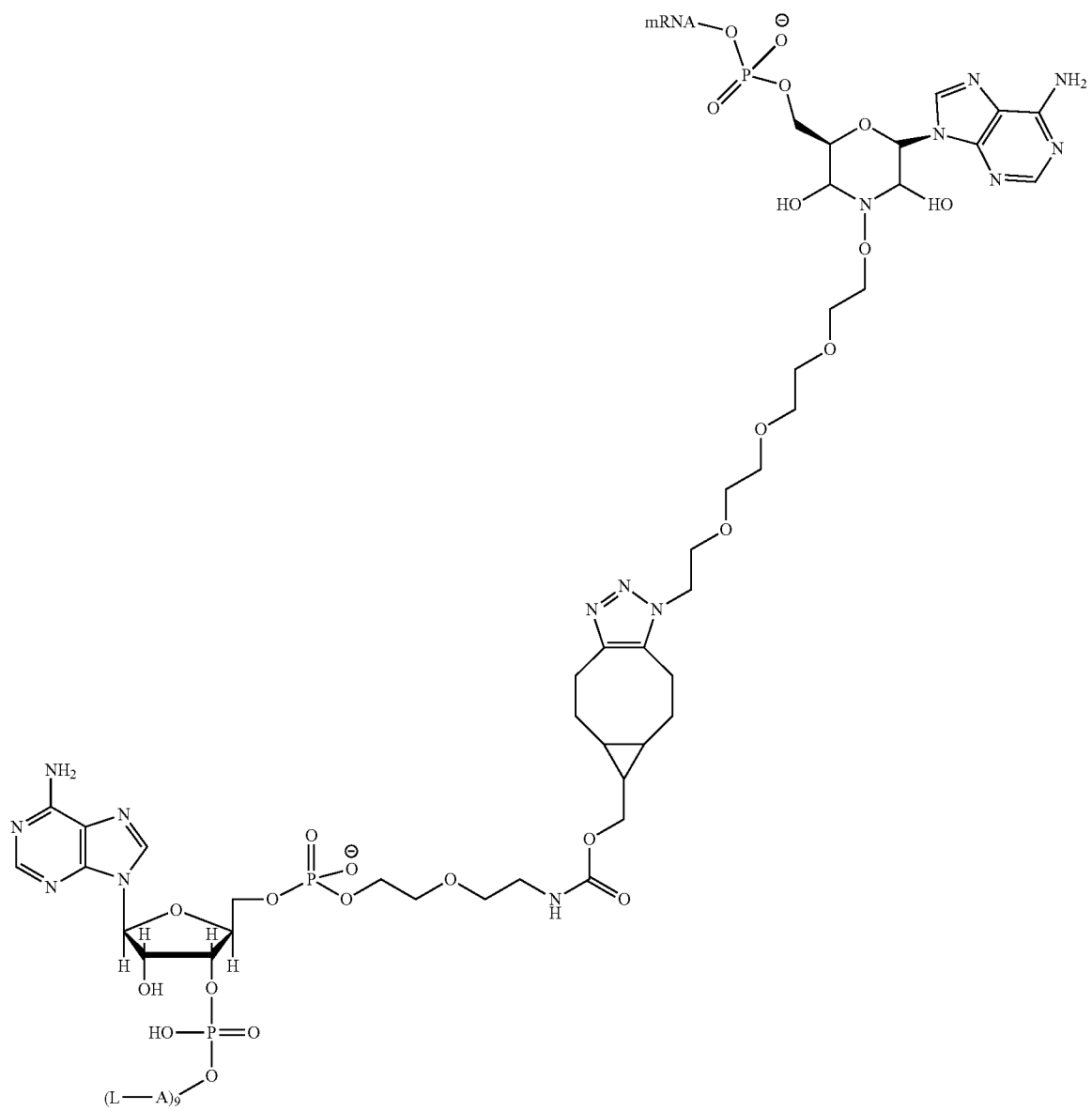

wherein mRNA is an mRNA molecule and L-A is L-adenosine;
or
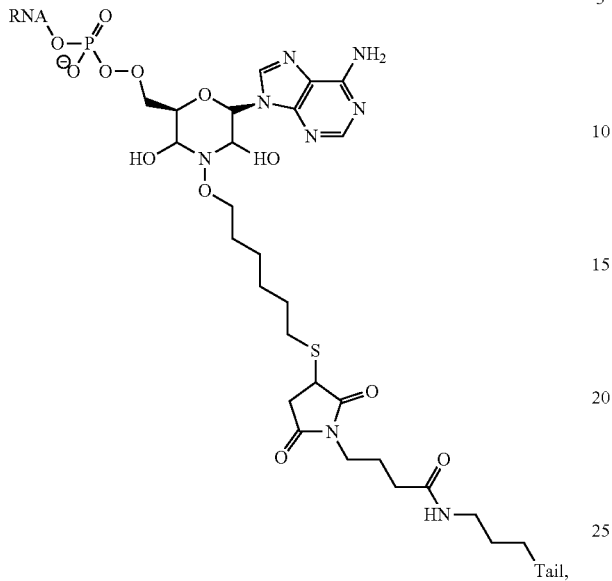
wherein RNA is an mRNA molecule and tail is 10 consecutive L-adenosines;
or
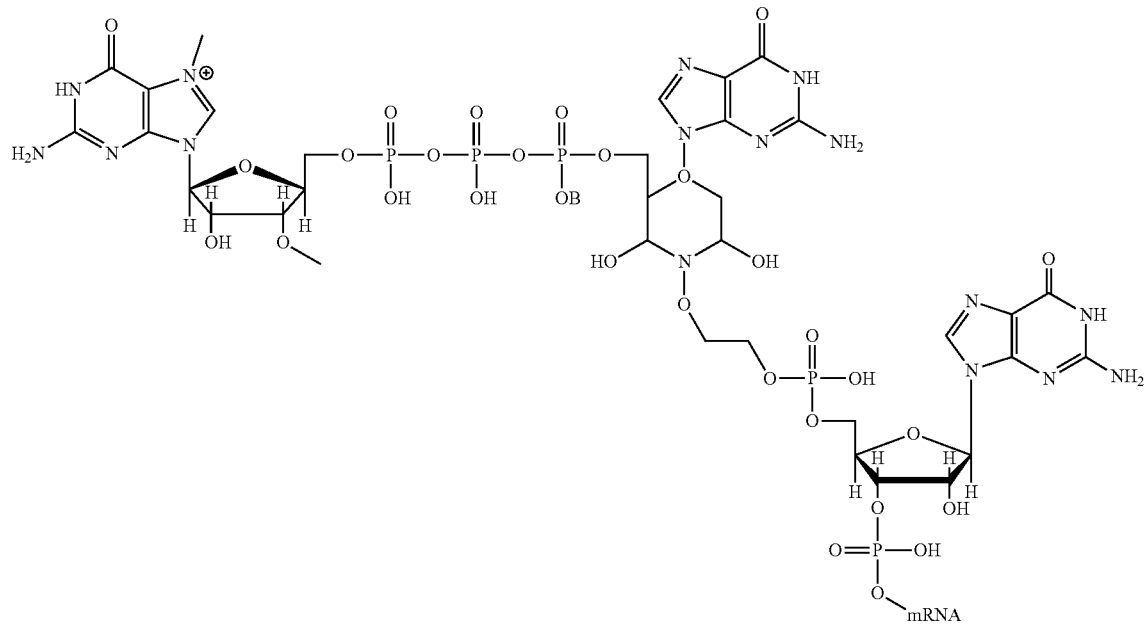
wherein mRNA is an mRNA molecule.
* * * * *